(12) United States Patent
Wakiyama et al.

(10) Patent No.: US 7,879,808 B2
(45) Date of Patent: Feb. 1, 2011

(54) LINCOMYCIN DERIVATIVES AND ANTIMICROBIAL AGENTS COMPRISING THE SAME AS ACTIVE INGREDIENT

(75) Inventors: Yoshinari Wakiyama, Tokyo-To (JP); Kou Kumura, Yokohama (JP); Satomi Masaki, Saitama (JP); Kazutaka Ueda, Kitakami (JP); Yasuo Sato, Hachioji (JP); Chika Kikuchi, Yokohama (JP); Eijirou Umemura, Chigasaki (JP); Yoko Hirai, Kawasaki (JP); Hiroshi Kondo, Yokohama (JP)

(73) Assignee: Meiji Seika Kaisha, Ltd., Tokyo-To (JP)

( * ) Notice: Subject to any disclaimer, the term of this patent is extended or adjusted under 35 U.S.C. 154(b) by 0 days.

(21) Appl. No.: 12/451,744

(22) PCT Filed: May 30, 2008

(86) PCT No.: PCT/JP2008/060042

§ 371 (c)(1),
(2), (4) Date: Mar. 1, 2010

(87) PCT Pub. No.: WO2008/146917

PCT Pub. Date: Dec. 4, 2008

(65) Prior Publication Data

US 2010/0210570 A1    Aug. 19, 2010

(30) Foreign Application Priority Data

May 31, 2007    (JP)    .............................. 2007-146192

(51) Int. Cl.
A01N 43/04    (2006.01)
A61K 31/70    (2006.01)
C07H 15/16    (2006.01)

(52) U.S. Cl. ...................... 514/24; 536/16.2; 536/16.3; 536/16.4; 536/16.5

(58) Field of Classification Search ........................ None
See application file for complete search history.

(56) References Cited

U.S. PATENT DOCUMENTS

| 3,418,414 | A |  | 12/1968 | Houtman et al. |
| 3,544,551 | A |  | 12/1970 | Kagan et al. |
| 3,689,474 | A |  | 9/1972 | Kagan et al. |
| 3,767,649 | A |  | 10/1973 | Bannister |
| 3,870,699 | A |  | 3/1975 | Bannister |
| 3,915,954 | A |  | 10/1975 | Bannister |
| 7,164,011 | B2 | * | 1/2007 | Lewis et al. ................. 536/16.5 |
| 7,199,105 | B2 | * | 4/2007 | Lewis et al. .................... 514/24 |
| 7,199,106 | B2 | * | 4/2007 | Lewis et al. .................... 514/24 |
| 7,256,177 | B2 | * | 8/2007 | Lewis et al. .................... 514/24 |
| 7,361,743 | B2 | * | 4/2008 | Lewis et al. ................. 536/16.3 |

FOREIGN PATENT DOCUMENTS

| DE | 2 229 950 | 12/1972 |
| JP | 2006-504673 | 2/2006 |
| WO | 2005/007665 | 1/2005 |
| WO | 2005/012320 | 2/2005 |
| WO | 2006/055070 | 5/2006 |
| WO | 2007/066805 | 6/2007 |

OTHER PUBLICATIONS

International Search Report issued Jul. 8, 2008 in International (PCT) Application No. PCT/JP2008/060042.
F. Sztaricskai et al., "Semisynthetic Modification of Antibiotic Lincomycin", The Journal of Antibiotics, vol. 49, No. 9, pp. 941-943, Sep. 1996.
R. D. Birkenmeyer et al., "Synthesis and Antimicrobial Activity of Clindamycin Analogues: Pirlimycin, a Potent Antibacterial Agent", J. Med. Chem., vol. 27, No. 2, pp. 216-223, 1984.
W. Schroeder et al., "Lincomycin. III. The Structure and Stereochemistry of the Carbohydrate Moiety", Journal of the American Chemical Society, vol. 89, No. 10, pp. 2448-2453, May 10, 1967.
R. Zhang et al., "Pseudo-A(1,3) Strain as a Key Conformational Control Element in the Design of Poly-L-proline Type II Peptide Mimics", J. Am. Chem. Soc., vol. 120, No. 16, pp. 3894-3902, 1998.
B. J. Magerlein et al., "Lincomycin. VIII. 4'-Alkyl-1'-demethyl-4'-depropylclindamycins. Potent Antibacterial and Antimalarial Agents", vol. 12, pp. 780-784, Sep. 1969.

(Continued)

Primary Examiner—Traviss C McIntosh, III
(74) Attorney, Agent, or Firm—Wenderoth, Lind & Ponack, L.L.P.

(57) ABSTRACT

An objective of the present invention is to provide compounds of formula (1) or their pharmacologically acceptable salts or solvates wherein A represents aryl; $R_1$ represents N-optionally substituted $C_{1-6}$ alkyl-N-optionally substituted $C_{1-6}$ alkylamino-$C_{1-6}$ alkyl; $R_2$ represents a hydrogen atom or optionally substituted $C_{1-6}$ alkyl; $R_3$ represents optionally substituted $C_{1-6}$ alkyl or $C_{3-6}$ cycloalkyl-$C_{1-4}$ alkyl; m is 1 to 3; n is 0; and p is 0 to 2. The compounds are novel lincomycin derivatives that have a potent activity against resistant *Streptococcus pneumoniae*, which have recently posed problems, in the treatment of infectious diseases. Further, the compounds are usable as antimicrobial agents and are useful for preventing or treating bacterial infectious diseases.

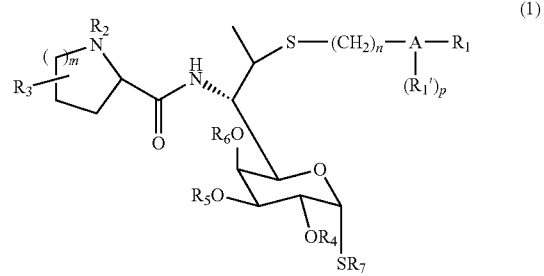

(1)

13 Claims, No Drawings

OTHER PUBLICATIONS

P. Gloanec et al., "Synthesis of benzyl (6S)-1,3-dichloro-4-oxo-4,6,7,8-tetrahydro-pyrrolo[1,2-β]pyrazine-6-carboxylic ester, a new conformationally constrained peptidomimetic derivative", Tetrahedron Letters, vol. 43, pp. 3499-3501, 2002.

C. Pedregal et al., "Highly Chemoselective Reduction of N-Boc Protected Lactams", Tetrahedron Letters, vol. 35, No. 13, pp. 2053-2056, 1994.

R. D. Birkenmeyer et al., "Lincomycin. XI. Synthesis and Structure of Clindamycin. a Potent Antibacterial Agent", Journal of Medicinal Chemistry, vol. 13, No. 4, pp. 616-619, 1970.

International Preliminary Report on Patentability (Chapter I) and Written Opinion of the International Searching Authority, issued Jan. 12, 2010 in International Application PCT/JP2008/060042 (with English translation).

* cited by examiner

LINCOMYCIN DERIVATIVES AND ANTIMICROBIAL AGENTS COMPRISING THE SAME AS ACTIVE INGREDIENT

This application is a U.S. national stage of International Application No. PCT/JP2008/060042 filed May 30, 2008.

CROSS-REFERENCE TO RELATED APPLICATIONS

This application is based upon and claims the benefit of priority from the prior Japanese Patent Application No. 146192/2007, filed on May 31, 2007, the entire contents of which are incorporated herein by reference.

BACKGROUND OF THE INVENTION

1. Field of the Invention

The present invention relates to novel lincomycin derivatives having antimicrobial activity or their pharmacologically acceptable salts thereof. The present invention also relates to antimicrobial agents comprising the compounds as active ingredient.

2. Related Art

Various compounds have hitherto been reported as lincomycin derivatives having antimicrobial activity. It is also disclosed that compounds having a structure similar to the compounds according to the present invention have antimicrobial activity. See, for example, (1) U.S. Pat. No. 3,915,954, (2) U.S. Pat. No. 3,870,699, (3) U.S. Pat. No. 3,767,649, (4) German Patent Laid-Open No. 2229950, (5) U.S. Pat. No. 3,689,474, (6) U.S. Pat. No. 3,544,551, (7) International Publication WO 2005/012320, (8) J. Antibiotics, 49, (1996), 941, and (9) Structure-Activity Relationships among the semisynthetic antibiotics, 601-651.

The compounds described in these documents, however, are ineffective against resistant pneumococci which have recently posed a clinical problem. Accordingly, the development of antimicrobial agents comprising lincomycin derivatives which are also effective against resistant pneumococci has been desired.

SUMMARY OF THE INVENTION

The present inventors have now found that a group of lincomycin derivatives represented by formula (I) have potent antimicrobial activity against resistant pneumococci against which lincomycin and clindamycin are ineffective. The present invention has been made based on such finding.

Accordingly, an object of the present invention is to provide novel lincomycin derivatives having potent activity against resistant pneumococci in the treatment of infectious diseases as a recent issue.

The compounds according to the present invention, that is, novel lincomycin derivatives according to the present invention are compounds of formula (I) or their pharmacologically acceptable salts or solvates:

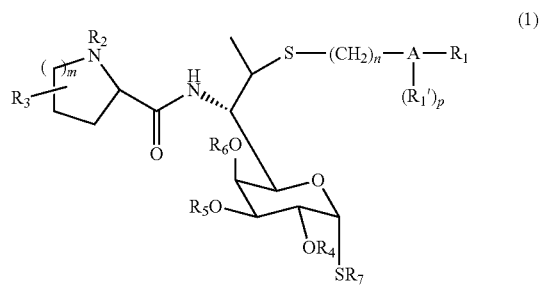

wherein
A represents
  aryl;
  cyclohexyl; or
  a four- to seven-membered heterocyclic group
    wherein the heterocyclic group is selected from the group consisting of pyridyl, piperidyl, pyridazyl, pyrimidinyl, pyrazinyl, thienyl, thiazolyl, 1,3,4-thiadiazolyl, azetidinyl, pyrrolidinyl, azepanyl, tetrahydropyridyl, dihydropyrrolyl, imidazolyl, 1,3,4-triazinyl, furyl, oxazolyl, 1,3,4-oxadiazolyl, and tetrahydroazepanyl, $R_1'$ represents
  a halide;
  nitro;
  amino;
  cyano;
  hydroxyl;
  $C_{1-6}$ alkyl;
  $C_{1-6}$ alkyloxy;
  $C_{1-6}$ alkylthio;
  $C_{1-6}$ alkylamino;
  di-$C_{1-6}$ alkylamino;
  $C_{1-6}$ alkyloxycarbonyl; or
  N,N-dialkyl substituted carbamoyl, and, when p is 2, $R_1$'s may be the same or different, $R_1$ represents
  amino-$C_{1-6}$ alkyl;
  N-(optionally substituted $C_{1-6}$ alkyl)amino-$C_{1-6}$ alkyl
    wherein the $C_{1-6}$ alkyl group in the optionally substituted $C_{1-6}$ alkyl group is optionally substituted by one or more groups, which may be the same or different, selected from the group consisting of hydroxyl, $C_{1-6}$ alkyloxy, and di- and $C_{1-6}$ alkylamino;
  N—$C_{3-6}$ cycloalkylamino-$C_{1-6}$ alkyl;
  N-optionally substituted $C_{1-6}$ alkyl-N-optionally substituted $C_{1-6}$ alkylamino-$C_{1-6}$ alkyl,
    wherein the $C_{1-6}$ alkyl group in the optionally substituted $C_{1-6}$ alkyl group is optionally substituted by one or more groups, which may be the same or different, selected from the group consisting of hydroxyl, $C_{1-6}$ alkyloxy, and di-$C_{1-6}$ alkylamino;
  N—$C_{1-6}$ alkyl-N—$C_{3-6}$ cycloalkylamino-$C_{1-6}$ alkyl;
  tri-$C_{1-6}$ alkylammonio-$C_{1-6}$ alkyl;
  1-(di-$C_{1-6}$ alkylamino-$C_{1-6}$ alkyl)vinyl;
  1-(amino-$C_{1-6}$ alkyl)vinyl;
  N—($C_{3-6}$ cycloalkyl-$C_{1-4}$ alkyl)-N—$C_{1-6}$ alkylamino-$C_{1-6}$ alkyl;
  1-formyl-2-di-$C_{1-6}$ alkylaminovinyl;
  amino-$C_{1-6}$ alkylamino-$C_{1-6}$ alkyl;

N—$C_{1-6}$ alkyl-N—(N',N'-di-$C_{1-6}$ alkylamino-$C_{1-6}$ alkyl)-amino-$C_{1-6}$ alkyl;
$C_{1-6}$ alkylamino-$C_{1-6}$ alkylamino-$C_{1-6}$ alkyl;
di-$C_{1-6}$ alkylamino-$C_{1-6}$ alkylamino-$C_{1-6}$ alkyl;
$C_{1-6}$ alkyl substituted by cyclic amino,
  wherein the cyclic amino group is selected from the group consisting of (1-, 2-, or 3-)pyrrolidinyl, (1-, 2-, or 3-)dihydropyrrolyl, 1-piperazinyl, 1-(4-methylpiperazinyl), 1-piperidino, 1-azetidinyl, 3-(1-methylazetidinyl), 3-azetidinyl, (1-, 2-, or 3-)azepanyl, (1-, 2-, or 3-)azepinyl, and 1H-pyrrolyl, and
  the cyclic amino group is optionally substituted by one or more groups, which may be the same or different, selected from the group consisting of $C_{1-6}$ alkyloxy, $C_{1-6}$ alkylamino, di-$C_{1-6}$ alkylamino, hydroxyl, $C_{2-6}$ alkenyloxy, hydroxy-$C_{1-6}$ alkyl, $C_{1-6}$ alkyloxy-$C_{1-6}$ alkyl, and di-$C_{1-6}$ alkylamino-$C_{1-6}$ alkyl;
amino-$C_{1-6}$ alkylcarbonyl;
N,N-di-$C_{1-6}$ alkylamino-$C_{1-6}$ alkylcarbonyl;
N,N-di-$C_{1-6}$ alkylamino-$C_{2-6}$ alkenyl;
N,N-di-$C_{1-6}$ alkylamino-$C_{2-6}$ alkynyl;
N,N-di-$C_{1-6}$ alkylamino-$C_{1-6}$ alkylamino;
N-N-di-$C_{1-6}$ alkylamino-$C_{1-6}$ alkoxy;
a group of formula (g-1):

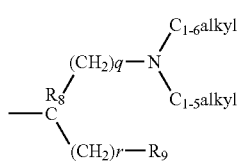

wherein
  $R_8$ represents a hydrogen atom, a halide, or $C_{1-6}$ alkyl,
  $R_9$ represents a hydrogen atom, hydroxyl, a halide, or $C_{1-6}$ alkyl optionally substituted by one or more halides, $C_{1-6}$ alkyloxy, $C_{1-6}$ alkyloxycarbonyl, or di-$C_{1-6}$ alkylamino, or, when r is 2 to 4, $R_8$ and $R_9$ may combine with each other and, together with the carbon atom to which $R_8$ is attached, represent $C_{3-6}$ cycloalkyl, and
  q and r, which may be the same or different, are an integer of 0 to 4; or
a group of formula (g-2):

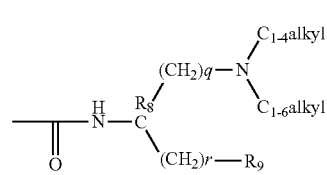

wherein $R_8$, $R_9$, q, and r are as defined in formula (g-1),
$R_2$ represents
  a hydrogen atom;
  optionally substituted $C_{1-6}$ alkyl;
  optionally substituted $C_{2-6}$ alkenyl;
  optionally substituted acyl; or
  optionally substituted $C_{1-6}$ alkyloxycarbonyl
  wherein the $C_{1-6}$ alkyl group, the $C_{2-6}$ alkenyl group, the acyl group, and the $C_{1-6}$ alkyloxycarbonyl group are optionally substituted by one or more groups that may be the same or different and are selected from the group consisting of heterocyclic rings, amino, hydroxy, and cyano that are optionally substituted by $C_{1-6}$ alkyl,
$R_3$ represents
  optionally substituted $C_{1-6}$ alkyl
    wherein the $C_{1-6}$ alkyl group is optionally substituted by one or more groups that are selected from the group consisting of halides; nitro; hydroxy; amino; $C_{1-6}$ alkyloxycarbonyl; carbamoyl; cyano; $C_{1-6}$ alkyloxy; oxo; heterocyclic rings; azide; $C_{1-6}$ alkylaminocarbonyl; di-$C_{1-6}$ alkylaminocarbonyl; and aryl optionally substituted by a halide, hydroxyl, or $C_{1-4}$ alkyl;
  $C_{3-6}$ cycloalkyl-$C_{1-4}$ alkyl; or
  $C_{2-6}$ alkenyl,
$R_4$, $R_5$, and $R_6$, which may be the same or different, represent
  a hydrogen atom;
  optionally substituted $C_{1-6}$ alkyl; or
  optionally substituted acyl
    wherein the $C_{1-6}$ alkyl group and hydrogen atoms on the acyl group are optionally substituted by one or more groups selected from the group consisting of halides; nitro; hydroxy; amino; $C_{1-6}$ alkyloxycarbonyl; carbamoyl; cyano; nitro halide; $C_{1-6}$ alkyloxy; oxo; heterocyclic rings; azide; $C_{1-6}$ alkylaminocarbonyl; di-$C_{1-6}$ alkylaminocarbonyl; and aryl optionally substituted by a halide, hydroxy or $C_{1-4}$ alkyl,
$R_7$ represents
  $C_{1-6}$ alkyl optionally substituted by one or more groups selected from the group consisting of halides and hydroxy,
m is 1 to 3,
n is 0 or 1, and
p is 0 to 2.

According to the present invention, there is provided a pharmaceutical composition comprising the compound of formula (I) or its pharmacologically acceptable salt or solvate and a pharmaceutically acceptable carrier. In a preferred embodiment of the present invention, there are provided pharmaceutical compositions comprising the above compound as an active ingredient together with an additive for a pharmaceutical preparation. These pharmaceutical compositions are useful for the prevention or treatment of microbisms (bacterial infectious diseases) (preferably microbisms in respiratory organs) and can be used as antimicrobial agents (that is, antimicrobial compositions).

According to another aspect of the present invention, there is provided an antimicrobial agent comprising the compound according to the present invention or its pharmacologically acceptable salt or solvate as active ingredient.

According to still another aspect of the present invention, there is provided a method for treating bacterial infectious diseases, comprising administering a therapeutically effective amount of the compound according to the present invention or its pharmacologically acceptable salt or solvate together with a pharmaceutically acceptable carrier to a mammal or a domestic fowl.

According to a further aspect of the present invention, there is provided use of the compound according to the present invention or its pharmacologically acceptable salt or solvate for the production of a pharmaceutical composition for preventing or treating bacterial infectious diseases. According to a still further aspect of the present invention, there is provided use of the compound according to the present invention or its pharmacologically acceptable salt or solvate as an active ingredient of an antimicrobial agent. In this case, the bacterial infectious diseases are preferably those in respiratory organs.

The lincomycin derivatives of formula (I) according to the present invention have potent antimicrobial activity against resistant pneumococci against which not only lincosamide-type antibiotics such as clindamycin but also other antibiotics such as macrolide antibiotics are ineffective. Accordingly, the compounds according to the present invention are expected to be excellent therapeutic agents for infectious diseases in respiratory organs.

DETAILED DESCRIPTION OF THE INVENTION

Compounds of Formula (I)

The term "$C_{1-6}$ alkyl" as used herein as a group or a part of a group means alkyl having 1 to 6 carbon atoms, which is of a straight chain or branched chain. $C_{1-6}$ alkyl is preferably $C_{1-4}$ alkyl, more preferably $C_{1-2}$ alkyl.

Examples of $C_{1-6}$ alkyl include methyl, ethyl, n-propyl, iso-propyl, n-butyl, iso-butyl, sec-butyl, tert-butyl, n-pentyl, and n-hexyl.

The alkenyl and the alkenyl moiety in the substituent containing the alkenyl group moiety may be, for example, vinyl, allyl, 1-propenyl, isopropenyl, 1-butenyl, 2-butenyl, propargyl, 1-butynyl, 1-pentynyl, or 2-butynyl which is of a straight chain, branched chain, or cyclic type or a combination thereof unless otherwise specified, preferably of a straight chain or branched chain type. The term "$C_{2-6}$ alkenyl" refers to alkenyl having 2 to 6 carbon atoms, preferably $C_{2-4}$ alkenyl. The number of double bonds contained in the alkenyl moiety is not particularly limited, and the double bond contained in the alkenyl moiety may be a Z configuration or an E configuration.

Acyl and the acyl moiety in the acyl moiety-containing substituent (for example, acyloxy such as acetoxy) as used herein refer to $C_2$ to $C_5$ straight-chain or branched-chain alkylcarbonyl or formyl, such as acetyl, propionyl, butyryl, isobutyryl, valeryl, or isovaleryl, unless otherwise specified.

The expression "alkyl optionally substituted by" as used herein refers to alkyl, wherein one or more hydrogen atoms on the alkyl group are substituted by one or more substituents which may be the same or different, and unsubstituted alkyl. It will be apparent to a person having ordinary skill in the art that the maximum number of substituents may be determined depending upon the number of substitutable hydrogen atoms on the alkyl group. This is true of groups containing substituents other than alkyl, for example, alkenyl, acyl, and aryl such as phenyl, and heterocyclic rings such as 1,3,4-thiadiazolyl.

The term "halide" (halogen atom) as used herein refers to a fluorine, chlorine, bromine, or iodine atom.

The term "halide" used herein, for example, in "alkyl halide" as a group or a part of a group means that one or more hydrogen atoms on each group have been substituted by a halogen atom.

The term "aryl" as used herein refers to a heteroatom-free six- to fourteen-membered (monocyclic to tricyclic, preferably monocyclic to bicyclic) aromatic ring, for example, phenyl, 1-naphthyl, 2-naphthyl, 1-anthryl, or 2-anthryl, unless otherwise specified. The six- to fourteen-membered aryl contains six to fourteen carbon atoms in the ring system.

Unless otherwise specified, the term "heterocyclic group" or "heterocyclic ring" as used herein may be a saturated, partially saturated, or unsaturated monocyclic or bicyclic heterocyclic ring which contains one to four heteroatoms selected from nitrogen, oxygen, and sulfur atoms with the remaining ring atoms being carbon atoms and wherein each ring is a four- to seven-membered (preferably 5- to 7-membered, more preferably five- or six-membered) ring. Examples of these heterocyclic groups include azetidino, pyrrolyl, pyrrolidinyl, pyrrolidino, furyl, thienyl, imidazolyl, isoxazolyl, oxazolyl, thiazolyl, isothiazolyl, triazolyl, thiadiazolyl, oxadiazolyl, tetrazolyl, pyridyl, pyrazolyl, pyrimidyl, pyrazinyl, piperazinyl, piperazino, piperidino, morpholinyl, morpholino, thiomorpholino, pyrazinyl, quinolyl, chromenyl, benzoxazolyl, benzothiazolyl, thiazolopyridyl, thiazolopyrimidinyl, and imidazothiazolyl wherein the binding position is not particularly limited.

Aryl represented by A is preferably phenyl.

The heterocyclic group represented by A is preferably pyridyl, piperidyl, pyrimidinyl, thienyl, thiazolyl, 1,3,4-thiadiazolyl, or imidazolyl, more preferably pyridyl, piperidyl or 1,3,4-thiadiazolyl.

A preferably represents phenyl.

The halide represented by $R_1'$ is preferably a fluorine atom or a chlorine atom.

$R_1'$ is preferably a halide, nitro, amino, $C_{1-6}$ alkyl, $C_{1-6}$ alkylamino, or di-$C_{1-6}$ alkylamino, more preferably a halide, nitro, amino, or di-$C_{1-6}$ alkylamino, still more preferably nitro, amino, di-$C_{1-6}$ alkylamino.

The substituent in the optionally substituted $C_{1-6}$ alkyl in "N-(optionally substituted $C_{1-6}$ alkyl)amino-$C_{1-6}$ alkyl" indicated by $R_1$ is preferably hydroxyl.

The substituent in optionally substituted $C_{1-6}$ alkyl in "N-optionally substituted $C_{1-6}$ alkyl-N-optionally substituted $C_{1-6}$ alkylamino-$C_{1-6}$ alkyl" indicated by $R_1$ is preferably hydroxyl or di-$C_{1-6}$ alkylamino.

Cyclic amino in "$C_{1-6}$ alkyl substituted by cyclic amino" indicated by $R_1$ is preferably 1-pyrrolidinyl, 1-dihydropyrrolyl, 1-(4-methylpiperazinyl), 1-piperidino, 1-azetidinyl, or 1H-pyrrolyl.

$R_1$ is preferably amino-$C_{1-6}$ alkyl, N-(optionally substituted $C_{1-6}$ alkyl)amino-$C_{1-6}$ alkyl, N—$C_{3-6}$ cycloalkylamino-$C_{1-6}$ alkyl, N-optionally substituted $C_{1-6}$ alkyl-N-optionally substituted $C_{1-6}$ alkylamino-$C_{1-6}$ alkyl, N—$C_{1-6}$ alkyl-N—$C_{3-6}$ cycloalkylamino-$C_{1-6}$ alkyl, 1-(di-$C_{1-6}$ alkylamino-$C_{1-6}$ alkyl)vinyl, 1-formyl-2-di-$C_{1-6}$ alkylaminovinyl, di-$C_{1-6}$ alkylamino-$C_{1-6}$ alkylamino-$C_{1-6}$ alkyl, $C_{1-6}$ alkyl substituted by cyclic amino in which $R_3$ preferably represents $C_{3-6}$ cycloalkyl-$C_{1-4}$ alkyl, amino-$C_{1-6}$ alkylcarbonyl, N,N-di-$C_{1-6}$ alkylamino-$C_{1-6}$ alkylcarbonyl, N,N-di-$C_{1-6}$ alkylamino-$C_{2-6}$ alkenyl, alkylamino-$C_{2-6}$ alkynyl, a group of formula (g-1), or a group of formula (g-2), more preferably N-optionally substituted $C_{1-6}$ alkyl-N-optionally substituted $C_{1-6}$ alkylamino-$C_{1-6}$ alkyl, a group of formula (g-1), or $C_{1-6}$ alkyl substituted by substituted cyclic amino, in which the cyclic amino group is preferably (1-, 2-, or 3-) pyrrolidinyl, still more preferably N-optionally substituted $C_{1-6}$ alkyl-N-optionally substituted $C_{1-6}$ alkylamino-$C_{1-6}$ alkyl or a group of formula (g-1).

$R_2$ is preferably a hydrogen atom or optionally substituted $C_{1-6}$ alkyl, more preferably a hydrogen atom or $C_{1-6}$ alkyl.

$R_3$ is preferably optionally substituted $C_{1-6}$ alkyl or $C_{3-6}$ cycloalkyl-$C_{1-4}$ alkyl, more preferably $C_{1-6}$ alkyl or $C_{3-6}$ cycloalkyl-$C_{1-4}$ alkyl, still more preferably $C_{3-6}$ cycloalkyl-$C_{1-4}$ alkyl, particularly preferably cyclopropylmethyl.

The substituent in "optionally substituted $C_{1-6}$ alkyl" or "optionally substituted acyl" indicated by $R_4$, $R_5$, and $R_6$ is preferably $C_{1-6}$ alkyloxycarbonyl.

Preferably, $R_4$, $R_5$, and $R_6$, which may be the same or different, are a hydrogen atom, $C_{1-4}$ alkyl, or acyl, more preferably a hydrogen atom or acyl, still more preferably each a hydrogen atom.

$R_7$ is preferably $C_{1-6}$ alkyl, more preferably $C_{1-4}$ alkyl, still more preferably methyl or ethyl, particularly preferably methyl.

m is preferably 1 or 2.

n is preferably 0.

p is preferably 0 or 1, more preferably 0.

In formula (g-1) or formula (g-2), $R_8$ is preferably a hydrogen atom.

In formula (g-1) or formula (g-2), $R_9$ is preferably a hydrogen atom, hydroxyl, or di-$C_{1-6}$ alkylamino, more preferably hydroxyl or di-$C_{1-6}$ alkylamino.

In formula (g-1) or formula (g-2), q is preferably 1 to 3.

In formula (g-1) or formula (g-2), r is preferably 1.

Asymmetric carbon, to which —S—$(CH_2)_n$-A-$((R_1')_p)R_1$ in formula (1) is bonded, is present in the molecule of the compound of formula (1) according to the present invention, and the present invention includes any isolated substance in the stereoisomers and a mixture of the stereoisomers. The carbon preferably has an S configuration.

Further, asymmetric carbon, to which —CONH in formula (1) is bonded, is present in the molecule of the compound of formula (1) according to the present invention, and the present invention includes any isolated substance in the stereoisomers and a mixture of the stereoisomers. The carbon preferably has an S configuration. In a preferred embodiment of the present invention, there are provided a group of compounds of formula (4) and pharmacologically acceptable salts thereof:

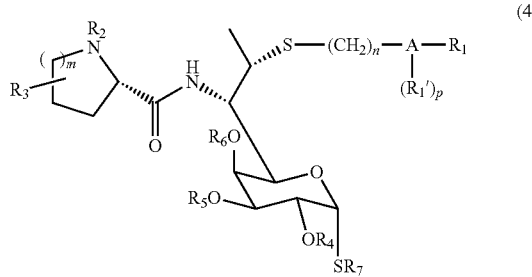

(4)

wherein A, $R_1$, $R_1'$, $R_2$, $R_3$, $R_4$, $R_5$, $R_6$, $R_7$, m, n, and p are as defined in formula (1).

According to another aspect of the present invention, there are provided compounds of formula (I) or their pharmacologically acceptable salts or solvates, wherein A, $R_1$, $R_1'$, $R_2$, $R_3$, $R_4$, $R_5$, $R_6$, $R_7$, m, n, and p are as defined below.

Specifically, in formula (1),

A represents aryl;

cyclohexyl; or a four- to seven-membered heterocyclic group
  wherein the heterocyclic group is selected from the group consisting of pyridyl, piperidyl, pyridazyl, pyrimidinyl, pyrazinyl, thienyl, thiazolyl, 1,3,4-thiadiazolyl, azetidinyl, pyrrolidinyl, azepanyl, tetrahydropyridyl, dihydropyrrolyl, imidazolyl, 1,3,4-triazinyl, furyl, oxazolyl, 1,3,4-oxadiazolyl, and tetrahydroazepanyl, $R_1'$ represents a group selected from the group consisting of
a halide;
nitro;
amino;
cyano;
hydroxyl;
$C_{1-6}$ alkyl;
$C_{1-6}$ alkyloxy;
$C_{1-6}$ alkylthio;
$C_{1-6}$ alkylamino;
di-$C_{1-6}$ alkylamino;
$C_{1-6}$ alkyloxycarbonyl; or
N,N-dialkyl substituted carbamoyl, $R_1$ represents
amino-$C_{1-6}$ alkyl;
N-(optionally substituted $C_{1-6}$ alkyl)amino-$C_{1-6}$ alkyl in which the $C_{1-6}$ alkyl groups are optionally substituted by one or more substituents which may be the same or different and selected from hydroxyl, $C_{1-6}$ alkyloxy, and di-$C_{1-6}$ alkylamino;
N—$C_{3-6}$ cycloalkylamino-$C_{1-6}$ alkyl;
N-optionally substituted $C_{1-6}$ alkyl-N-optionally substituted $C_{1-6}$ alkylamino-$C_{1-6}$ alkyl in which the $C_{1-6}$ alkyl groups are optionally substituted by one or more substituents which may be the same or different and selected from hydroxyl, $C_{1-6}$ alkyloxy, and di-$C_{1-6}$ alkylamino;
N—$C_{1-6}$ alkyl-N—$C_{3-6}$ cycloalkylamino-$C_{1-6}$ alkyl;
tri-$C_{1-6}$ alkylammonio-$C_{1-6}$ alkyl;
1-(di-$C_{1-6}$ alkylamino-$C_{1-6}$ alkyl)vinyl;
1-formyl-2-di-$C_{1-6}$ alkylaminovinyl;
amino-$C_{1-6}$ alkylamino-$C_{1-6}$ alkyl;
N—$C_{1-6}$ alkylamino-$C_{1-6}$ alkyl)-amino-$C_{1-6}$ alkyl;
$C_{1-6}$ alkylamino-$C_{1-6}$ alkylamino-$C_{1-6}$ alkyl;
di-$C_{1-6}$ alkylamino-$C_{1-6}$ alkylamino-$C_{1-6}$ alkyl;
$C_{1-6}$ alkyl substituted by cyclic amino,
  wherein the cyclic amino group is selected from the group consisting of (1-, 2-, or 3-)pyrrolidinyl, (1-, 2-, or 3-)dihydropyrrolyl, 1-piperazinyl, 1-(4-methylpiperazinyl), 1-piperidino, 1-azetidinyl, 3-(1-methylazetidinyl), 3-azetidinyl, (1-, 2-, or 3-)azepanyl, (1-, 2-, or 3-)azepinyl, and 1H-pyrrolyl, and the cyclic amino group is optionally substituted by one or more groups, which may be the same or different, selected from the group consisting of $C_{1-6}$ alkyloxy, $C_{1-6}$ alkylamino, di-$C_{1-6}$ alkylamino, hydroxyl, or $C_{2-6}$ alkenyloxy;
amino-$C_{1-6}$ alkylcarbonyl;
N,N-di-$C_{1-6}$ alkylamino-$C_{1-6}$ alkylcarbonyl;
N,N-di-$C_{1-6}$ alkylamino-$C_{2-6}$ alkenyl;
N,N-di-$C_{1-6}$ alkylamino-$C_{2-6}$ alkynyl;
N,N-di-$C_{1-6}$ alkylamino-$C_{1-6}$ alkylamino;
N,N-di-$C_{1-6}$ alkylamino-$C_{1-6}$ alkoxy;
a group of formula (g-1):

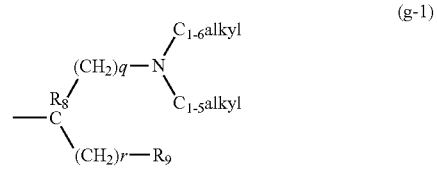

(g-1)

wherein
$R_8$ represents a hydrogen atom, a halide, or $C_{1-6}$ alkyl, $R_9$ represents a hydrogen atom, hydroxyl, a halide, or $C_{1-6}$ alkyl, $C_{1-6}$ alkyloxy, $C_{1-6}$ alkyloxycarbonyl, or di-$C_{1-6}$ alkylamino optionally substituted by one or more halides, or, when r is 2 to 4, $R_8$ and $R_9$ may combine with each other and, together with the carbon atom to which $R_8$ is attached, represent $C_{3-6}$ cycloalkyl, and q and r, which may be the same or different, are an integer of 0 to 4; or a group of formula (g-2):

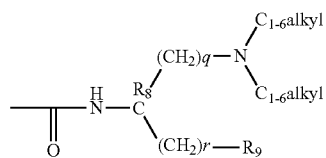

wherein $R_8$, $R_9$, q, and r are as defined above, $R_2$ represents a hydrogen atom;
optionally substituted $C_{1-6}$ alkyl;
optionally substituted $C_{2-6}$ alkenyl;
optionally substituted acyl; or
optionally substituted $C_{1-6}$ alkyloxycarbonyl
wherein the $C_{1-6}$ alkyl group, the $C_{2-6}$ alkenyl group, the acyl group, and the $C_{1-6}$ alkyloxycarbonyl group are optionally substituted by one or more groups selected from the group consisting of heterocyclic rings, amino, hydroxy, and cyano that are optionally substituted by $C_{1-6}$ alkyl, $R_3$ represents
optionally substituted $C_{1-6}$ alkyl
wherein the $C_{1-6}$ alkyl group is optionally substituted by one or more groups that are selected from the group consisting of halides; nitro; hydroxy; amino; $C_{1-6}$ alkyloxycarbonyl; carbamoyl; cyano; $C_{1-6}$ alkyloxy; oxo; heterocyclic rings; azide; $C_{1-6}$ alkylaminocarbonyl; di-$C_{1-6}$ alkylaminocarbonyl; and aryl optionally substituted by a halide, hydroxy, or $C_{1-4}$ alkyl;
$C_{3-6}$ cycloalkyl-$C_{1-4}$ alkyl; or
$C_{2-6}$ alkenyl, $R_4$, $R_5$, and $R_6$, which may be the same or different, represent
a hydrogen atom;
optionally substituted $C_{1-6}$ alkyl; or
optionally substituted acyl
wherein the $C_{1-6}$ alkyl group and hydrogen atoms on the acyl group are optionally substituted by one or more groups selected from the group consisting of halides; nitro; hydroxy; amino; $C_{1-6}$ alkyloxycarbonyl; carbamoyl; cyano; nitro halide; $C_{1-6}$ alkyloxy; oxo; heterocyclic rings; azide; $C_{1-6}$ alkylaminocarbonyl; di-$C_{1-6}$ alkylaminocarbonyl; and aryl optionally substituted by a halide, hydroxy or $C_{1-4}$ alkyl, $R_7$ represents
$C_{1-6}$ alkyl optionally substituted by one or more groups selected from the group consisting of halides and hydroxy,
m is 1 to 3,
n is 0 or 1, and
p is 0 to 2.

In a preferred embodiment of the present invention, in formula (1), when $R_1$ represents $C_{1-6}$ alkyl substituted by cyclic amino, $R_3$ represents $C_{3-6}$ cycloalkyl-$C_{1-4}$ alkyl.

In a more preferred embodiment of the present invention, in formula (1), n is 0.

In another more preferred embodiment of the present invention, in formula (1), A represents aryl, more preferably phenyl.

In another preferred embodiment of the present invention, in formula (1),
A represents aryl,
$R_3$ represents $C_{3-6}$ cycloalkyl-$C_{1-4}$ alkyl, and
n is 0.

In a further preferred embodiment of the present invention, in formula (1),
A represents aryl,
$R_1$ represents
N-optionally substituted $C_{1-6}$ alkyl-N-optionally substituted $C_{1-6}$ alkylamino-$C_{1-6}$ alkyl or
a group of formula (g-1)
$R_2$ represents
a hydrogen atom or
optionally substituted $C_{1-6}$ alkyl,
$R_3$ represents
optionally substituted $C_{1-6}$ alkyl or
$C_{3-6}$ cycloalkyl-$C_{1-4}$ alkyl,
m is 1 to 3,
n is 0, and
p is 0 to 2.

In another preferred embodiment of the present invention, in formula (1),
A represents
aryl or
a four- to seven-membered heterocyclic group,
$R_1$ represents
amino-$C_{1-6}$ alkyl;
N-(optionally substituted $C_{1-6}$ alkyl)amino-$C_{1-6}$ alkyl;
N—$C_{3-6}$ cycloalkylamino-$C_{1-6}$ alkyl;
N-optionally substituted $C_{1-6}$ alkyl-N-optionally substituted $C_{1-6}$ alkylamino-$C_{1-6}$ alkyl;
N—$C_{1-6}$ alkyl-N—$C_{3-6}$ cycloalkylamino-$C_{1-6}$ alkyl;
1-(di-$C_{1-6}$ alkylamino-$C_{1-6}$ alkyl)vinyl;
1-formyl-2-di-$C_{1-6}$ alkylaminovinyl;
di-$C_{1-6}$ alkylamino-$C_{1-6}$ alkylamino-$C_{1-6}$ alkyl;
$C_{1-6}$ alkyl substituted by cylic amino;
amino-$C_{1-6}$ alkylcarbonyl;
N,N-di-$C_{1-6}$ alkylamino-$C_{1-6}$ alkylcarbonyl;
N,N-di-$C_{1-6}$ alkylamino-$C_{2-6}$ alkenyl;
N,N-di-$C_{1-6}$ alkylamino-$C_{2-6}$ alkynyl;
a group of formula (g-1); or
a group of formula (g-2),
$R_2$ represents
a hydrogen atom or
optionally substituted $C_{1-6}$ alkyl,
$R_3$ represents
optionally substituted $C_{1-6}$ alkyl or
$C_{3-6}$ cycloalkyl-$C_{1-4}$ alkyl,
$R_4$, $R_5$, and $R_6$ each represent a hydrogen atom,
$R_7$ represents $C_{1-6}$ alkyl,
m is 1 to 3,
n is 0, and
p is 0 to 2.

In still another preferred embodiment of the present invention, in formula (1),
A represents
phenyl or
a five- or six-membered heterocyclic group
$R_1'$ represents
a halide;
nitro;
amino; or
di-$C_{1-6}$ alkylamino, R₁ represents
amino-$C_{1-6}$ alkyl;
N-(optionally substituted $C_{1-6}$ alkyl)amino-$C_{1-6}$ alkyl;
N—$C_{3-6}$ cycloalkylamino-$C_{1-6}$ alkyl;
N-optionally substituted $C_{1-6}$ alkyl-N-optionally substituted $C_{1-6}$ alkylamino-$C_{1-6}$ alkyl;
N—$C_{1-6}$ alkyl-N—$C_{3-6}$ cycloalkylamino-$C_{1-6}$ alkyl;
1-(di-$C_{1-6}$ alkylamino-$C_{1-6}$ alkyl)vinyl;
1-formyl-2-di-$C_{1-6}$ alkylaminovinyl;
di-$C_{1-6}$ alkylamino-$C_{1-6}$ alkylamino-$C_{1-6}$ alkyl;
$C_{1-6}$ alkyl substituted by cyclic amino
  wherein R₃ represents $C_{3-6}$ cycloalkyl-$C_{1-4}$ alkyl;
amino-$C_{1-6}$ alkylcarbonyl;
N,N-di-$C_{1-6}$ alkylamino-$C_{1-6}$ alkylcarbonyl;
N,N-di-$C_{1-6}$ alkylamino-$C_{2-6}$ alkenyl;
N,N-di-$C_{1-6}$ alkylamino-$C_{2-6}$ alkynyl;
a group of formula (g-1); or
a group of formula (g-2),
R₂ represents
a hydrogen atom, or
$C_{1-6}$ alkyl,
R₃ represents
$C_{1-6}$ alkyl or
$C_{3-6}$ cycloalkyl-$C_{1-4}$ alkyl
R₄, R₅, and R₆ each represent a hydrogen atom,
R₇ represents $C_{1-6}$ alkyl,
m is 1 to 3,
n is 0, and
p is 0 to 2.

The compounds according to the present invention may form pharmacologically acceptable salts thereof. Preferred examples of such salts include: alkali metal or alkaline earth metal salts such as sodium salts, potassium salts, or calcium salts; hydrohalogenic acid salts such as hydrofluoride salts, hydrochloride salts, hydrobromide salts, or hydroiodide salts; inorganic acid salts such as nitric acid salts, perchloric acid salts, sulfuric acid salts, or phosphoric acid salts; lower alkylsulfonic acid salts such as methanesulfonic acid salts, trifluoromethanesulfonic acid salts, or ethanesulfonic acid salts; arylsulfonic acid salts such as benzenesulfonic acid salts or p-toluenesulfonic acid salts; organic acid salts such as fumaric acid salts, succinic acid salts, citric acid salts, tartaric acid salts, oxalic acid salts, maleic acid salts, acetic acid salts, malic acid salts, lactic acid salts, or ascorbic acid salts; and amino acid salts such as glycine salts, phenylalanine salts, glutamic acid salts, or aspartic acid salts.

The compounds according to the present invention may form solvates. Such solvates include, for example, hydrates, alcoholates, for example, methanolates and ethanolates, and etherates, for example, diethyl etherates.

Use of Compounds/Pharmaceutical Composition

The compounds according to the present invention can inhibit the growth of bacteria, particularly resistant pneumococci, in vitro and actually exhibit antimicrobial activity (see Test Example 1).

The compounds according to the present invention are lincomycin derivatives having a very high level of antimicrobial activity, for example, against various bacteria, for example, resistant bacteria-containing pneumococci (*S. pneumoniae*). The compounds according to the present invention are lincosamide derivatives and thus have antimicrobial activity against various bacteria, which have hitherto been reported, and, at the same time, have potent antimicrobial activity against resistant pneumococci which pose a clinical problem. Accordingly, the compounds according to the present invention can be said to be very useful for the prevention or treatment of various microbisms including infectious diseases in respiratory organs.

Accordingly, the compounds according to the present invention can be used for the prevention or treatment of microbisms. Such microbisms include, for example, pneumonia, chronic bronchitis, acute otitis media, and acute sinusitis.

According to the present invention, there is provided a pharmaceutical composition comprising the compound according to the present invention or its pharmacologically acceptable salt or solvate and a pharmaceuticially acceptable carrier. In a preferred embodiment of the present invention, there are provided pharmaceutical compositions comprising the above compound as an active ingredient together with an additive for a pharmaceutical preparation. These pharmaceutical compositions are useful for the prevention or treatment of microbisms (preferably microbisms in respiratory organs) and can be used as antimicrobial agents (that is, antimicrobial compositions).

According to another aspect of the present invention, there is provided an antimicrobial agent comprising the compound according to the present invention or its pharmacologically acceptable salt or solvate as active ingredient.

According to still another aspect of the present invention, there is provided a method for treating bacterial infectious diseases, comprising administering a therapeutically effective amount of the compound according to the present invention or its pharmacologically acceptable salt or solvate together with a pharmaceutically acceptable carrier to a mammal.

According to a further aspect of the present invention, there is provided use of the compound according to the present invention or its pharmacologically acceptable salt or solvate for the production of a pharmaceutical composition for treating bacterial infectious diseases. According to a still further aspect of the present invention, there is provided use of the compound according to the present invention or its pharmacologically acceptable salt or solvate as an active ingredient of an antimicrobial agent.

In this case, the bacterial infectious diseases are preferably those in respiratory organs.

The term "treatment" as used herein generally means the attainment of desired pharmacological effect and/or physiological effect. The effect is prophylactical in that a disease and/or a symptom is completely or partly prevented, and is therapeutical in that a disease and/or an adverse effect caused by a disease is partly or completely cured. The term "treatment" as used herein includes any treatment of diseases of mammals, particularly humans and, for example, include the following treatments (a) to (c):

(a) preventing the onset of a disease or a symptom in a patient who may have a predisposition for a disease or a symptom but not diagnosed as having the disease or symptom;

(b) inhibiting a symptom of a disease, that is, inhibiting or delaying the progress of the symptom; and (c) alleviating a symptom of a disease, that is, causing the regression of a disease or a symptom or the reversal of the progress of a symptom.

The compounds according to the present invention can be administered to human and non-human animals orally or parenterally by administration routes, for example, intravenous administration, intramuscular administration, subcutaneous administration, rectal administration, or percutaneous administration.

Therefore, the pharmaceutical composition comprising a compound according to the present invention may be formulated into suitable dosage forms according to the administration routes. Specifically, oral preparations include tablets, capsules, powders, granules, pills, subtilized granules, troches, and syrups. Parenteral preparations include injections such as intravenous injections or intramuscular injections, suppositories, tapes, and ointments.

These various preparations may be prepared by conventional methods, for example, with pharmaceutically acceptable additives (carriers), that is, commonly used excipients, extenders, disintegrants, binders, lubricants, colorants, diluents, wetting agents, surfactants, dispersants, buffer agents, preservatives, solubilizers, antiseptics, flavoring agents, soothing agents, and stabilizers.

Excipients include, for example, lactose, fructose, glucose, corn starch, sorbit, and crystalline cellulose. Disintegrants include, for example, starch, sodium alginate, gelatin powder, calcium carbonate, calcium citrate, and dextrin. Binders include, for example, dimethylcellulose or its salts, polyvinyl alcohol, polyvinyl ether, methylcellulose, ethylcellulose, gum arabic, gelatin, hydroxypropylcellulose, and polyvinyl pyrrolidone. Lubricants include, for example, talc, magnesium stearate, polyethylene glycol, and hydrogenated vegetable oils. Other nontoxic additives usable herein include, for example, syrup, vaseline, lanoline, glycerin, ethanol, propylene glycol, citric acid, sodium chloride, sodium sulfite, sodium phosphate, β-cyclodextrin, hydroxypropyl-β-cyclodextrin, and Tween 80.

In preparing the above injections, if necessary, for example, buffering agents, pH adjustors, stabilizers, tonicity adjusting agents, and preservatives may be added.

The content of a compound according to the present invention in the pharmaceutical composition according to the present invention may vary according to the dosage form. The content, however, is generally 10 to 95% by weight, preferably 30 to 80% by weight, based on the whole composition.

The dose may be appropriately determined in consideration of particular conditions, for example, the age, weight, sex, type of disease, and severity of condition of patients. For example, for the treatment of infectious diseases induced by pneumococci, the pharmaceutical composition can be administered, for example, through an oral route at a dose of about 1 to 2000 mg, preferably 10 to 1000 mg per adult per day, in terms of the weight of the compound according to the present invention. This dose may be administered at a time daily or divided doses of two to six times daily depending upon the symptom.

Compounds according to the present invention may be administered in combination with other medicaments, for example, other antimicrobial agents, for example, penicillin, carbapenem, and quinolone. The administration can be carried out simultaneously or sequentially. The kind, administration interval and the like of other medicaments can be determined by taking into consideration the kind of symptoms and the conditions of the patient.

Production of Compounds of Formula (I)

The compounds of general formula (1) according to the present invention may be produced according to production processes which will be described later. The production process of the compound according to the present invention is not limited to these production processes. The compounds of the present invention are not limited to the compounds produced by the following production processes. Specific examples of the production process of compounds according to the present invention are described in the working examples of the present specification. Accordingly, all the compounds of formula (1) can easily be produced by a person having ordinary skill in the art by properly selecting starting compounds, reaction conditions, reagents and the like while referring to the following general description of production process and detailed description of the working examples and, if necessary, by conducting proper modification or improvement. The production process of the present invention includes all of processes for producing compounds based on the properties of the compounds clarified by the present invention by conventional means.

In the following description, characters of A, $R_1$ to $R_9$, $R_1'$, m, n, p, q, and r in structural formulae are as defined in formula (1). It should be noted that B, D, $R_{11}$ to $R_{18}$, and P mean a partial structure in $R_1$ and thus are not beyond the range defined in formula (1). Regarding additional characters, other than those in formula (1), which appear as needed, the meaning will be defined in each case, and, when the defined character appears after that, the definition is applied. Further, it should be noted that, in all the following reaction steps, the reaction step identified with the same number (is carried out under) the same reaction conditions.

At the outset, a group of compounds of formula (1), wherein $R_2$ represents methyl (hereinafter abbreviated to "Me"), $R_3$ represents propyl (hereinafter abbreviated to "Pr"), $R_4$, $R_5$, and $R_6$ represent a hydrogen atom (hereinafter abbreviated to "H"), and m is 1, can be produced, for example, by the following general process.

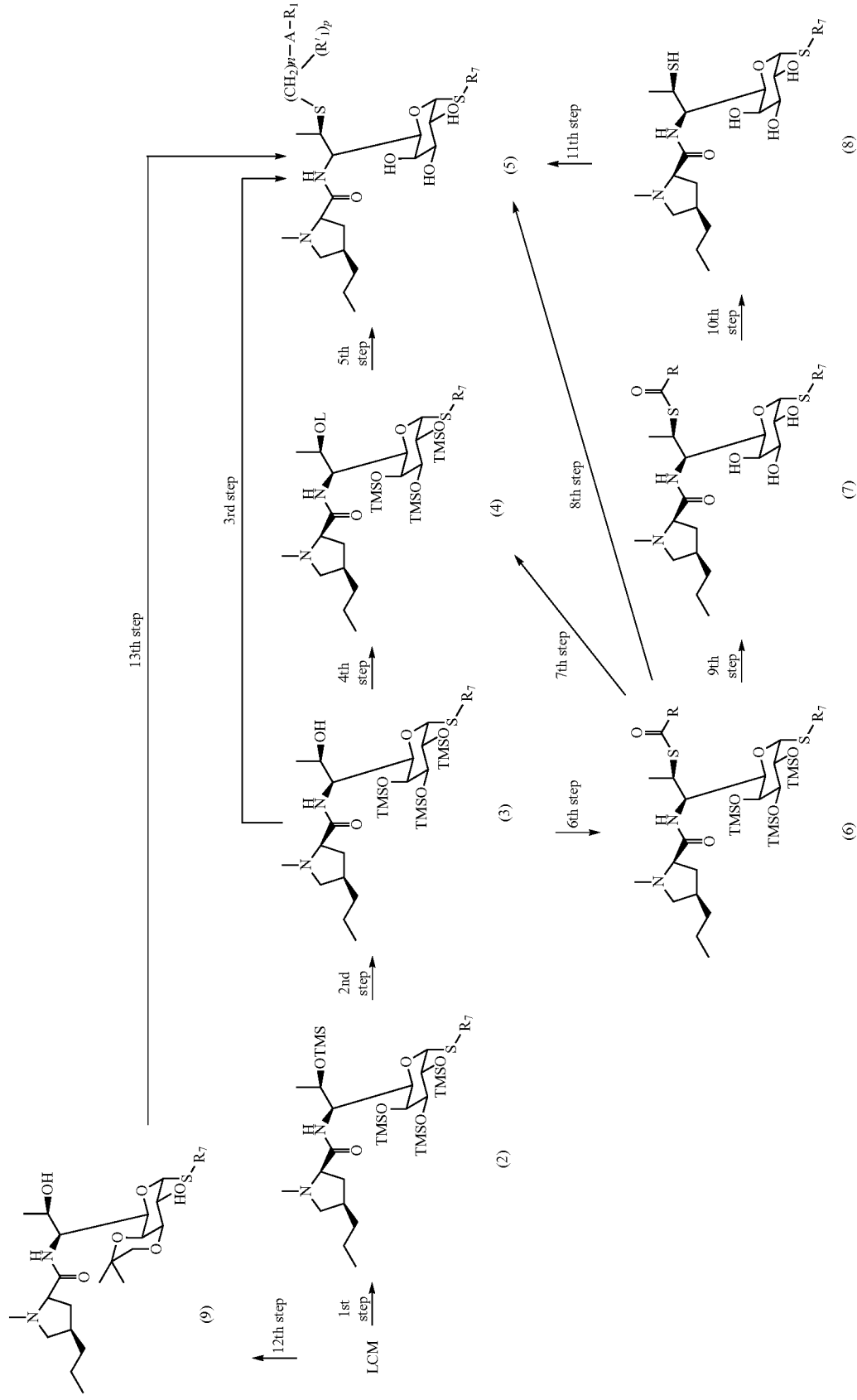

In formula (4), L represents $C_{1-6}$ alkylsulfonyl or arylsulfonyl. In formula (6), R represents $C_{1-6}$ alkyl or aryl, and TMS represents trimethylsilyl.

In the first and second steps, the conversion of lincomycin (hereinafter abbreviated to "LCM") to a compound of formula (2) and the conversion of the compound of formula (2) to a compound of formula (3) can be carried out by a process described, for example, in U.S. Pat. No. 3,418,414.

In the third step, the conversion of the compound of formula (3) to the compound of formula (5) can be carried out, for example, by properly selecting either process (i) or process (ii) depending upon whether the reaction reagent used is thiol (HS—(CH$_2$)n-A-(R$_1$')pR$_1$) or disulfide (R$_1$(R$_1$')p-A-(CH$_2$)n-S—S—(CH$_2$)n-A-(R$_1$')pR$_1$). (i) The compound of formula (5) can be produced by conducting a reaction using 1 to 10 equivalents of either the above thiol or the above disulfide in the presence of the compound of formula (3), triphenylphosphine, and diethyl azodicarboxylate in a tetrahydrofuran solution and then removing the trimethylsilyl group, for example, using a diluted hydrochloric acid-methanol solution. Regarding the reaction solvent in this reaction, in addition to tetrahydrofuran, conventional reaction solvents may be used, and preferred examples thereof include benzene, toluene, trifluoromethyl benzene, and acetonitrile. The phosphine reagent may be any phospine reagent commonly known in literatures and the like in addition to triphenylphosphine, preferably o-tolylphosphine, tri-n-butylphosphine, tri-tert-butylphosphine and the like, and the amount of the phosphine reagent is preferably 1 to 5 equivalents. The azo reagent may be any azo reagent commonly known in literatures and the like in addition to diethyl azodicarboxylate, preferably diisopropyl azodicarboxylate, 1,1'-(azodicarbonyl)dipiperidine and the like, and the amount of the azo reagent is preferably 1 to 5 equivalents. The reaction temperature is 0 to 50° C., and the reaction time is 0.5 to 24 hr. (ii) The compound of formula (5) can be produced by reacting the above thiol in the presence of the compound of formula (3) and cyanomethylene tri-n-butylphosphorane in a benzene solution and then removing the trimethylsilyl group, for example, using a dilute hydrochloric acid-methanol solution. Regarding the reaction solvent in this reaction, in addition to benzene, conventional reaction solvents may be used, and preferred examples thereof include tetrahydrofuran, toluene, trifluoromethyl benzene, and acetonitrile. The reaction accelerator may be, for example, phosphinylide commonly known in literatures and the like in addition to cyanomethylene tri-n-butylphosphorane, and preferred examples thereof include cyanomethylenetrimethyiphosphorane. The amount of the reaction accelerator is preferably 1 to 5 equivalents. The reaction temperature is 0 to 150° C., and the reaction time is 0.5 to 24 hr.

In the fourth step, the conversion of the compound of formula (3) to the compound of formula (4) can be carried out, for example, by the following process. Specifically, the compound of formula (4) can be produced by reacting the compound of formula (3) with a sulfonylating agent in a chloroform solvent in the presence of a base. The reaction solvent in this reaction may be a conventional reaction solvent in addition to chloroform, and preferred examples thereof include halogenic solvents such as methylene chloride and carbon tetrachloride, and polar solvents such as dimethylsulfoxide, pyridine, and 1-methylpyrrolidone. The base is a commonly known inorganic base or organic base, and preferred examples thereof include potassium carbonate, sodium hydrogencarbonate, triethylamine, diisopropylethylamine, and pyridine. The amount of the base is preferably 1 to 10 equivalents. The sulfonylating agent refers to conventional sulfonylating agents, that is, alkylsulfonyl chloride, arylsulfonyl chloride, or sulfonic anhydride, and preferred examples thereof include methanesulfonyl chloride, toluenesulfonyl chloride, and trifluoromethanesulfonic anhydride. The amount of the sulfonylating agent is preferably 1 to 10 equivalents. The reaction temperature is −10 to 50° C., and the reaction time is 0.5 to 24 hr.

In the fifth step, the conversion of the compound of formula (4) to the compound of formula (5) can be carried out, for example, by the following process. Specifically, the compound of formula (5) can be produced by reacting the compound of formula (4) with 1 to 10 equivalents of the above thiol in an N,N-dimethylformamide solvent in the presence of a base and then removing the trimethylsilyl group, for example, using a diluted hydrochloric acid-methanol solution. The reaction solvent in this reaction may be a conventional reaction solvent in addition to N,N-dimethylformamide, and preferred examples thereof include polar solvents such as dimethylsulfoxide, pyridine, and 1-methylpyrrolidone. The base is a commonly known inorganic base or organic base, and preferred examples thereof include potassium carbonate, sodium hydrogencarbonate, triethylamine, diisopropylamine, and pyridine. The amount of the base is preferably 1 to 10 equivalents. The reaction temperature is −10 to 120° C., and the reaction time is 0.5 to 24 hr.

In the sixth step, the conversion of the compound of formula (3) to the compound of formula (6) can be carried out, for example, in the same manner as in the third step except that the thiol is changed to 1 to 10 equivalents of a commonly known alkylthio carboxylic acid or a commonly known arylthio carboxylic acid, preferably, for example, thioacetic acid, thiopropionic acid, or thiobenzoic acid.

In the seventh step, for example, the conversion of the compound of formula (4) to the compound of formula (6) can be carried out, for example, in the same manner as in the fifth step except that the thiol is changed to 1 to 10 equivalents of a commonly known alkylthio carboxylic acid or its salt or a commonly known arylthio carboxylic acid or its salt, preferably thioacetic acid, thiopropionic acid or its potassium salt, sodium salt or the like, or thiobenzoic acid or its potassium salt, sodium salt or the like.

In the eighth step, the conversion of the compound of formula (6) to the compound of formula (5) can be carried out, for example, by the following process.

Specifically, the compound of formula (5) can be produced by removing the acyl group in the system in a methanol solvent in the presence of a base, reacting this compound, for example, with 1 to 10 equivalents of an alkyl halide, aryl halide, or a heterocyclic halide, and then removing the trimethylsilyl group, for example, using a diluted hydrochloric acid-methanol solution. The reaction solvent in this reaction may be a conventional polar solvent in addition to methanol, and preferred solvents include ethanol, propanol, butanol, N,N-dimethylformamide, dimethylsulfoxide, and 1-methylpyrrolidone. The base is a commonly known inorganic base, an alkali metal methoxide, or an alkali metal ethoxide, and preferred examples thereof include sodium hydrogencarbonate, potassium carbonate, calcium carbonate, sodium methoxide, and sodium ethoxide. The amount of the base is preferably 1 to 10 equivalents. The reaction temperature is 0 to 120° C., and the reaction time is 0.5 to 24 hr.

In the ninth step, the conversion of the compound of formula (6) to the compound of formula (7) can be carried out, for example, by the following process.

Specifically, the compound of formula (7) can be produced by removing the trimethylsilyl group in the compound of formula (6), for example, using a diluted hydrochloric acid-methanol solution in a methanol solvent. The reaction solvent in this reaction may be a conventional polar solvent in addition to methanol, and preferred examples thereof include ethanol, propanol, butanol, N,N-dimethylformamide, dimethylsulfoxide, and 1-methylpyrrolidone. The reaction temperature is 0 to 40° C., and the reaction time is 0.5 to 24 hr.

In the tenth step, the compound of formula (7) can be converted to the compound of formula (8), for example, by the following method. Specifically, the compound of formula (8) can be produced by deprotecting the acyl group in the compound of formula (7) with a base in a methanol solvent. The reaction solvent in this reaction may be a conventional polar solvent in addition to methanol, and preferred examples thereof include ethanol, propanol, butanol, N,N-dimethylformamide, dimethylsulfoxide, and 1-methylpyrrolidone. The base may be a commonly known inorganic base, an alkali metal methoxide, or an alkali metal ethoxide, and preferred examples thereof include sodium hydroxide, potassium hydroxide, sodium methoxide, and sodium ethoxide. The amount of the base is preferably 1 to 10 equivalents. The reaction temperature is 0 to 40° C., and the reaction time is 0.5 to 24 hr.

In the eleventh step, the conversion of the compound of formula (8) to the compound of formula (5) can be carried out, for example, by properly selecting either process (i) or process (ii). (i) The compound of formula (5) can be produced by reacting the compound of formula (8) with 1 to 10 equivalents of a reactant of $X_1$—$(CH_2)n$-A-$(R_1')pR_1$, wherein $X_1$ represents an $RSO_2$ group or a halide, in an N,N-dimethylformamide solvent in the presence of a base. The reaction solvent in this reaction may be a conventional reaction solvent in addition to N,N-dimethylformamide, and preferred examples thereof include dimethylsulfoxide, tetrahydrofuran, diethyl ether, and 1-methylpyrrolidone. The base may be a commonly known inorganic base or organic base, and preferred examples thereof include sodium hydrogencarbonate, sodium carbonate, potassium phosphate, sodium tert-butoxide, potassium tert-butoxide, 1,5-diazabicyclo[4.3.0]-5-nonene, 1,8-diazabicyclo[5.4.0]-7-undecene, 7-methyl-1,5,7-triazabicyclo[4.4.0]-5-decene, diisopropylethylamine, and triethylamine. The amount of the base is preferably 1 to 10 equivalents. The reaction temperature may be room temperature to 150° C., and the reaction time is 1 to 24 hr. (ii) The compound of formula (5) can be produced by allowing the compound of formula (8) to react in a dioxane solvent in the presence of a base, a reactant of $X_2$—$(CH_2)n$-A-$(R_1')p$, wherein $X_2$ represents I, Br, Cl, OTf, or OTs wherein Tf represents trifluoromethanesulfonyl and Ts represents tosyl, an additive, and a conventional palladium catalyst. The reaction solvent in this reaction may be a conventional reaction solvent in addition to dioxane, and preferred examples thereof include N,N-dimethylformamide, benzene, toluene, cyclopentyl methyl ether, tetrahydrofuran, butanol, and dimethylsulfoxide. The base may be a commonly known inorganic base or organic base, and preferred examples thereof include sodium carbonate, potassium phosphate, potassium fluoride, cesium fluoride, sodium tert-butoxide, potassium tert-butoxide, diisopropylethylamine, and triethylamine. The amount of the base is preferably 1 to 10 equivalents. The additive may be a conventional phosphine ligand, and preferred examples thereof include 4,5-bis(diphenylphosphino)-9,9-dimethylsantene, 2,2'-bis(diphenylphosphino)-1,1'-binaphthyl, triphenylphosphine, and tri-tert-butylphosphine. The amount of the additive is preferably 0.01 to 0.5 equivalent. Preferred examples of palladium catalysts which are generaly used herein include tris(dibenzylideneacetone)dipalladium, palladium acetate, and dichlorobis(diphenylphosphino)ferrocene palladium. In addition to the palladium catalyst, metallic catalysts such as copper catalysts may be used, and the amount of the catalyst is preferably 0.01 to 0.5 equivalent. The reaction temperature is room temperature to 150° C., and the reaction time is 1 to 48 hr.

In the twelfth step, LCM can be converted to the compound of formula (9), for example, by the process described in J. Med. Chem.,13 (1970), 616.

In the thirteenth step, the compound of formula (9) can be converted to the compound of formula (5), for example, by introducing an —S—$(CH_2)n$-A-$(R_1')pR_1$ group in the same manner as in the third step and then removing 3,4-o-isopropylidene as a protective group of the hydroxyl group, for example, with a diluted hydrochloric acid-methanol solution or trifluoroacetic acid.

Secondly, among a group of compounds of formula (5) wherein $R_1$ represents (—B—$NH_2$), (—B—$N(R_{11})R_{12}$) or (—B—$N(R_{11})H$) wherein B, $R_{11}$ and $R_{12}$ represents a group not beyond the scope of $R_1$, a group of compounds (formula (11), formula (12), and formula (15)) cannot be efficiently produced without difficulties by the process shown in scheme 1, for example, for production or purification reasons. The group of compounds (formula (11), formula (12), and formula (15)) can also be produced by an alternative process, for example, by producing the compound of formula (10), formula (13) or formula (14) as a precursor of the compound of formula (11), formula (12), or formula (15) by the process shown in scheme 1 and then subjecting the precursor to the following process.

Scheme 2

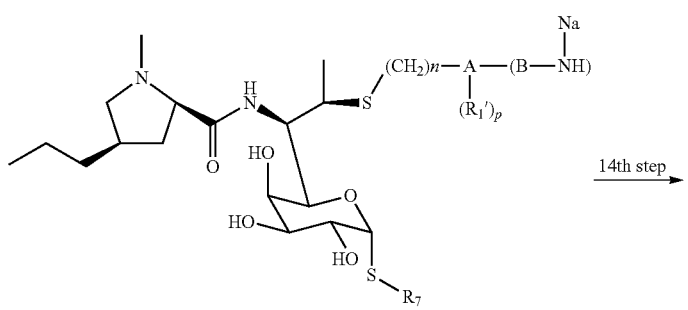

(10)

14th step

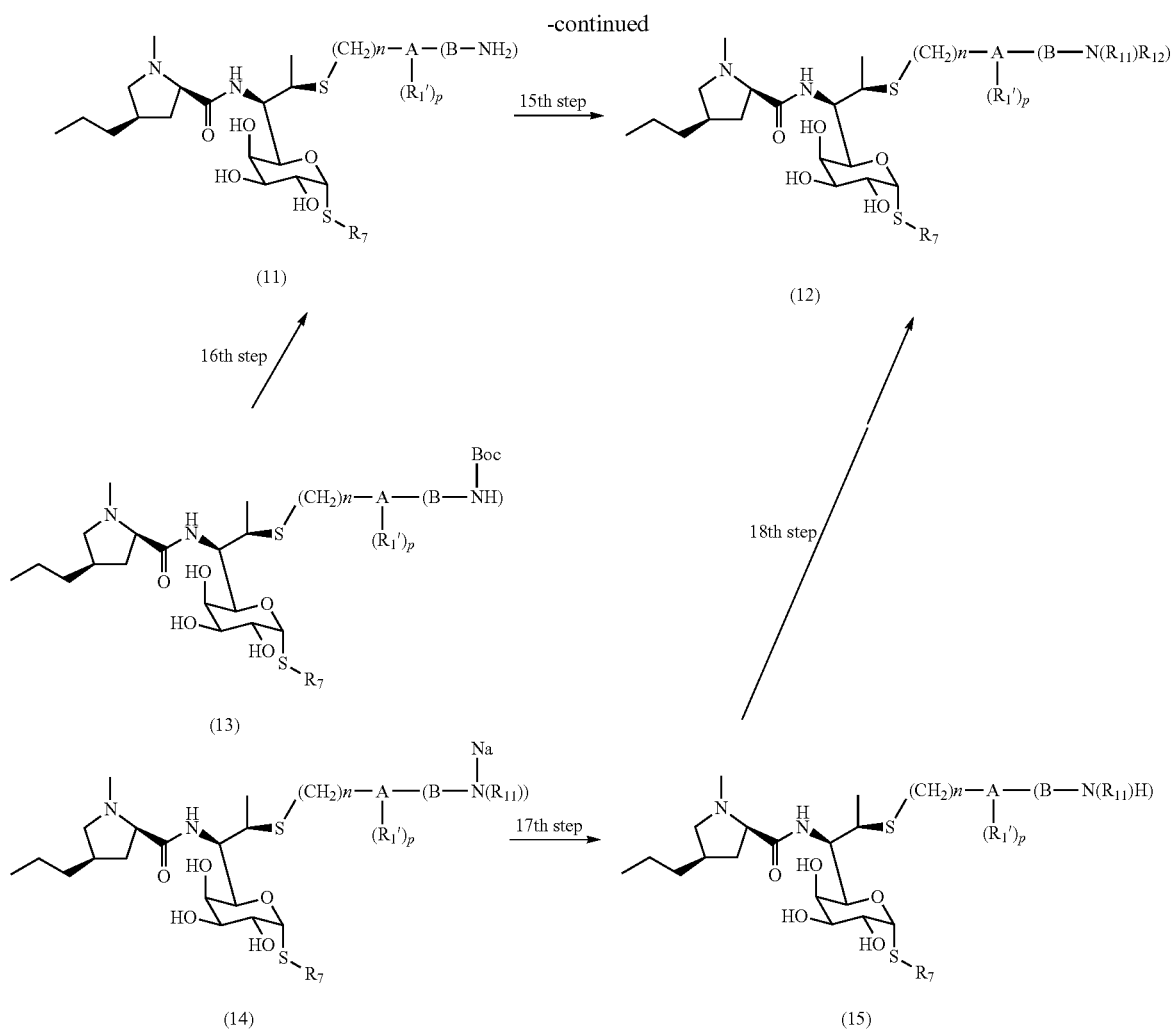

Ns in formula (10) or (14) represents o-nitrobenzenesulfonyl or p-nitrobenzenesulfonyl, and Boc in formula (13) represents a protective group for tert-butoxycarbonyl.

In the fourteenth step, the compound of formula (10) can be converted to the compound of formula (11), for example, by reacting the compound of formula (10) with 1 to 10 equivalents of thiol in an N,N-dimethylformamide solvent in the presence of a base. In this reaction, in addition to N,N-dimethylformamide, a conventional reaction solvent may be used. Preferred reaction solvents include polar solvents such as N,N-dimethylformamide, dimethylsulfoxide, 1-methylpyrrolidone, and acetonitrile. The base may be a commonly known inorganic base or organic base, and preferred examples thereof include potassium carbonate, sodium hydroxide, potassium hydroxide, sodium hydrogencarbonate, sodium tert-butoxide, pottasium tert-butoxide, 1,5-diazabicyclo[4.3.0]-5-nonene, 1,8-diazabicyclo[5.4.0]-7-undecene, and 7-methyl-1,5,7-triazabicyclo[4.4.0]-5-decene. The amount of the base is preferably 1 to 10 equivalents. The thiol may be a conventionally known thiol, and preferred examples thereof include benzenethiol and 4-bromobenzenethiol. The reaction temperature is room temperature to 100° C., and the reaction time is 1 to 24 hr.

In the fifteenth step, the compound of formula (11) can be converted to the compound of formula (12) properly by selecting processes (i) and (ii). For example, in process (i), the compound of formula (12) can be produced by reacting the compound of formula (11) with 1 to 10 equivalents of a ketone or an aldehyde in a 1,2-dichloroethane solvent in the presence of an acid or a reducing agent. The reaction solvent in this reaction may be a conventional solvent in addition to 1,2-dichloroethane, and preferred examples thereof include solvents such as methylene chloride, chloroform, tetrahydrofuran, diethyl ether, methanol, ethanol, and butanol. The acid is preferably acetic acid, hydrochloric acid, sulfuric acid or the like. The reducing agent may be a commonly known reducing agent, and preferred examples thereof include sodium tri(acetoxy)borohydride or the like. The amount of the reducing agent is preferably 1 to 10 equivalents. The reaction temperature is 0 to 120° C., and the reaction time is 0.5 to 4 hr. In process (ii), the compound of formula (12) can be produced by reacting the compound of formula (11) with 1 to 10 equivalents of an alkyl halide in an acetonitrile solvent in the presence of a base. The reaction solvent in this reaction may be a conventional solvent in addition to acetonitrile, and preferred examples thereof include polar solvents such as N,N-dimethylformamide, dimethylsulfoxide, and 1-methylpyrrolidone. The base may be a commonly known inorganic base or organic base, and preferred examples thereof include potassium carbonate, sodium hydroxide, potassium hydroxide, triethylamine, and diisopropylethylamine. The amount of the base is preferably 1 to 10 equivalents. The reaction temperature is 0 to 50° C., and the reaction time is 0.5 to 24 hr.

In sixteenth step, the compound of formula (13) can be converted to the compound of formula (11), for example, by properly selecting processes (i) and (ii). In process (i), the compound of formula (13) can be produced by reacting the compound of formula (13) with in either a 95% aqueous trifluoroacetic acid solution or a 4 N hydrochloric acid-dioxane solution. The reaction temperature is −15° C. to room temperature, and the reaction time is 0.5 to 24 hr. In process (ii), the compound of formula (11) can be produced by reacting the compound of formula (13) with a 95% aqueous trifluoroacetic acid solution in a methylene chloride solvent. The reaction temperature is −20° C. to room temperature, and the reaction time is 0.5 to 24 hr.

In the seventeenth step, the compound of formula (14) can be converted to the compound of formula (15), for example, according to the process described in the fourteenth step.

In the eighteenth step, the compound of formula (15) can be converted to the compound of formula (12), for example, according to the process described in the fifteenth step.

Thirdly, among a group of the compounds of formula (5) wherein $R_1$ represents (—B—NHCH$_2$CH$_2$OH) wherein B represents a group not beyond the scope of $R_1$ and, when B represents a bond, N is bonded directly to A, a group of compounds (formula (17) and formula (18)) cannot be efficiently produced by the process shown in scheme 1, for example, for production or purification reasons. The group of these compounds (formula (17) and formula (18)) can also be produced by an alternative method, for example, by producing the compound of formula (16) as a precursor of the compound of formula (17) or formula (18) by the process shown in scheme 1 and then subjecting the compound of formula (16) to the following process.

Scheme 3

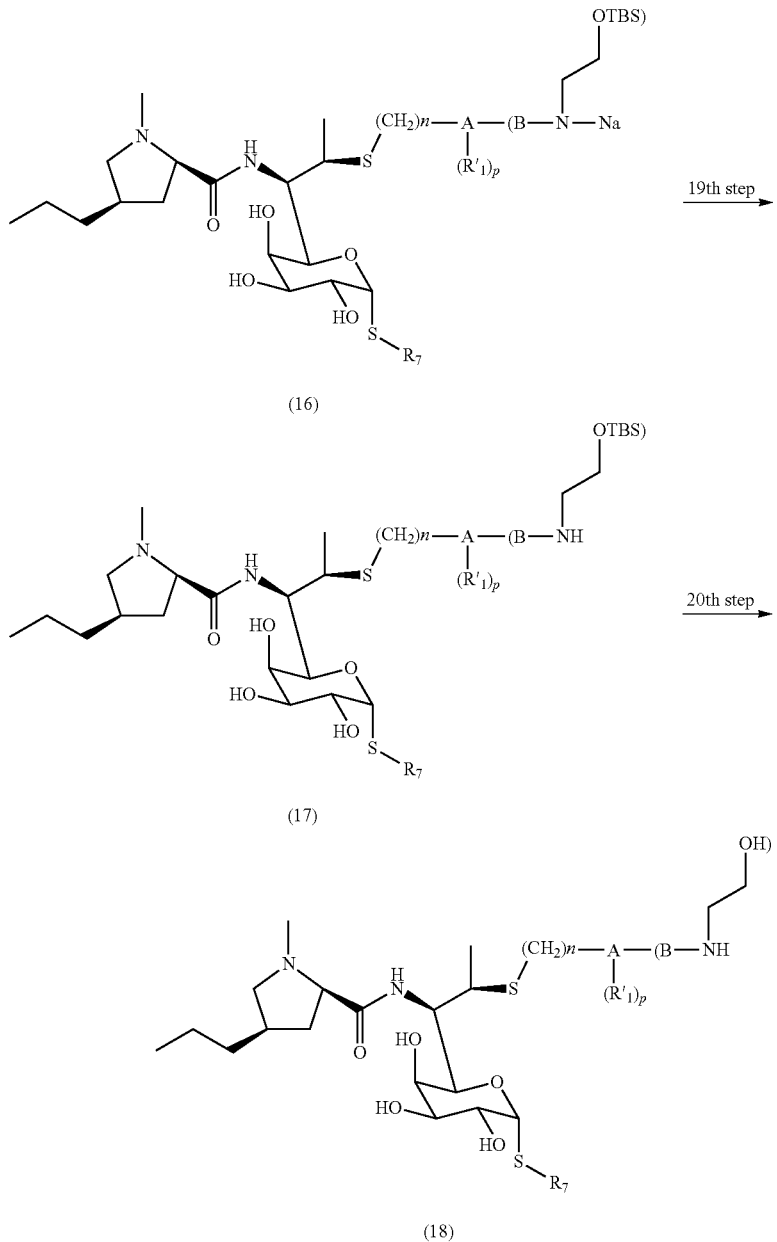

In nineteenth step, the compound of formula (16) can be converted to the compound of formula (17), for example, according to the process described in the fourteenth step.

In twentieth step, the compound of formula (17) can be converted to the compound of formula (18), for example, by the tert-butyldimethylsilyl group in the compound of formula (17) with a diluted hydrochloric acid or the like in a methanol solvent. The reaction solvent in this reaction may be a conventional polar solvent in addition to methanol, and preferred examples thereof include ethanol, propanol, butanol, N,N-dimethylformamide, dimethylsulfoxide, and 1-methylpyrrolidone. The reaction temperature is 0 to 40° C., and the reaction time is 0.5 to 24 hr.

Fourthly, among a group of the compounds of formula (5) wherein $R_1$ represents (-B-double bond-D-N$(R_{13})R_{14}$) wherein B, D, $R_{13}$ and $R_{14}$ represent a group not beyond the scope of $R_1$ and, when B represents a bond, the double bond is bonded directly to A, a group of compounds (formula (20) and formula (21)) cannot be efficiently produced by the process shown in scheme 1, for example, for production or purification reasons. The group of these compounds (formula (20) and formula (21)) can also be produced by an alternative method, for example, by producing the compound of formula (19) as a precursor of the compound of formula (20) or formula (21) by the process shown in scheme 1 and then subjecting the compound of formula (19) to the following process.

addition to methanol. The reaction temperature is 0 to 50° C., and the reaction time is 0.5 to 24 hr.

Fifthly, among a group of the compounds of formula (5) wherein $R_1$ represents $NH_2$ or $N(R_{15})R_{16}$ wherein $R_{15}$ and $R_{16}$ represent a group not beyond the scope of $R_1$, a group of compounds (formula (23) and formula (24)) cannot be efficiently produced by the process shown in scheme 1, for example, for production or purification reasons. The group of these compounds (formula (23) and formula (24)) can also be produced by an alternative method, for example, by producing the compound of formula (22) as a precursor of the compound of formula (23) or formula (24) by the process shown in scheme 1 and then subjecting the compound of formula (22) to the following process.

Scheme 5

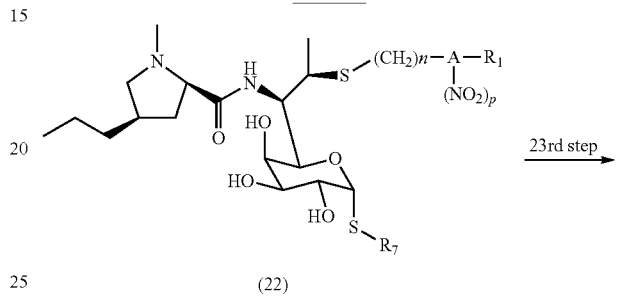

(22)

Scheme 4

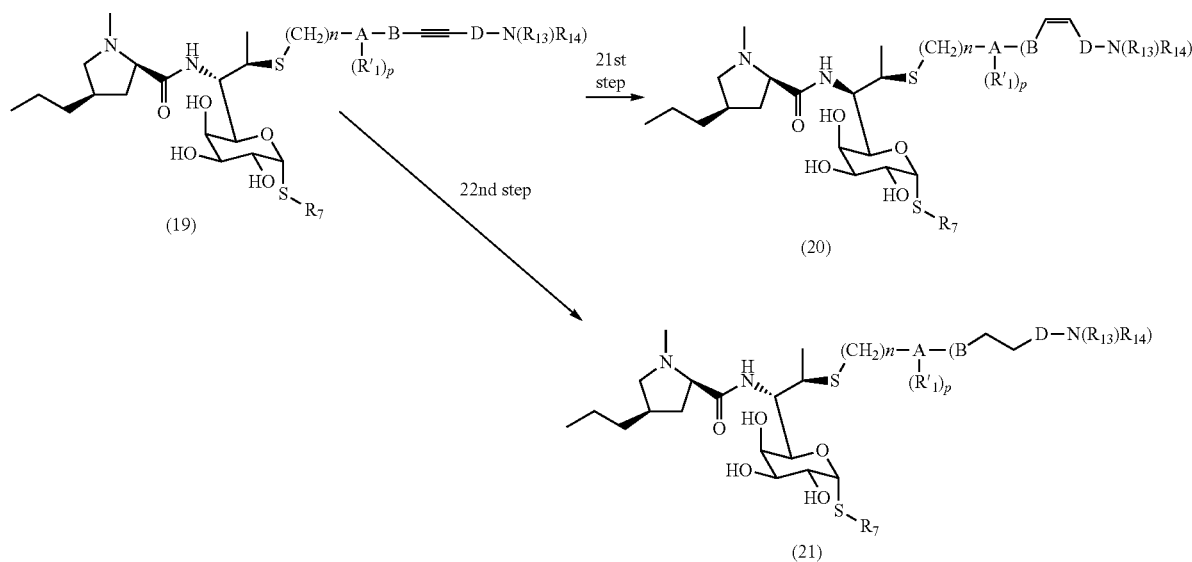

Specifically, in twenty-first step, the compound of formula (19) can be converted to the compound of formula (20), for example, by adding a Lindlar catalyst to the compound of formula (19) in an ethanol solvent and allowing a reaction to proceed in a hydrogen atmosphere (ordinary pressure). The reaction solvent in this reaction may be methanol in addition to ethanol. The reaction temperature is 0 to 50° C., and the reaction time is 0.5 to 24 hr.

Next, in twenty-second step, the compound of formula (19) can be converted to the compound of formula (21), for example, by adding a palladium-carbon catalyst to the compound of formula (19) in a methanol solvent and allowing a reaction to proceed in a hydrogen atmosphere (normal pressure). The reaction solvent in this reaction may be ethanol in -continued

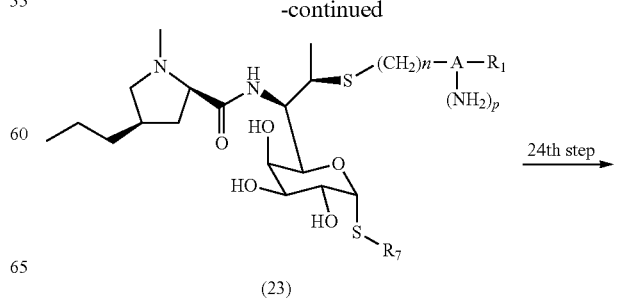

(23)

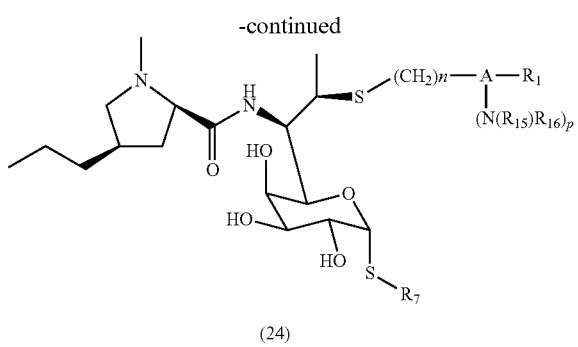

(24)

Specifically, in twenty-third step, the compound of formula (22) can be converted from the compound of formula (22) to the compound of formula (23), for example, according to the process described in the twenty-second step.

In twenty-fourth step, the compound of formula (23) can be converted to the compound of formula (24), for example, by adding a catalyst and an acid in a methanol solvent and reacting the compound of formula (23) with 1 to 10 equivalents of a ketone or an aldehyde in a hydrogen atmosphere. The reaction solvent in this reaction may be ethanol in addition to methanol. Preferably, the catalyst is a palladium-carbon catalyst, and the acid is hydrochloric acid. The reaction temperature is 0 to 100° C., and the reaction time is 0.5 to 4 hr.

Sixthly, among a group of the compounds of formula (5) wherein n=p=0, A represents piperidine and $R_1$ represents —CO—$CH_2N(R_{15})R_{16}$ or —CO—$CH_2NH_2$ wherein $R_{15}$ and $R_{16}$ represent a group not beyond the scope of $R_1$, a group of compounds (formula (27), formula (29) and formula (32)) cannot be efficiently produced by the process shown in scheme 1, for example, for production or purification reasons. The group of these compounds (formula (27), formula (29) and formula (32)) can also be produced by an alternative method, for example, by producing the compound of formula (18) as a precursor of the compound of formula (27), formula (29) or formula (32) by the process shown in scheme 1 and then subjecting the compound of formula (18) to the following process.

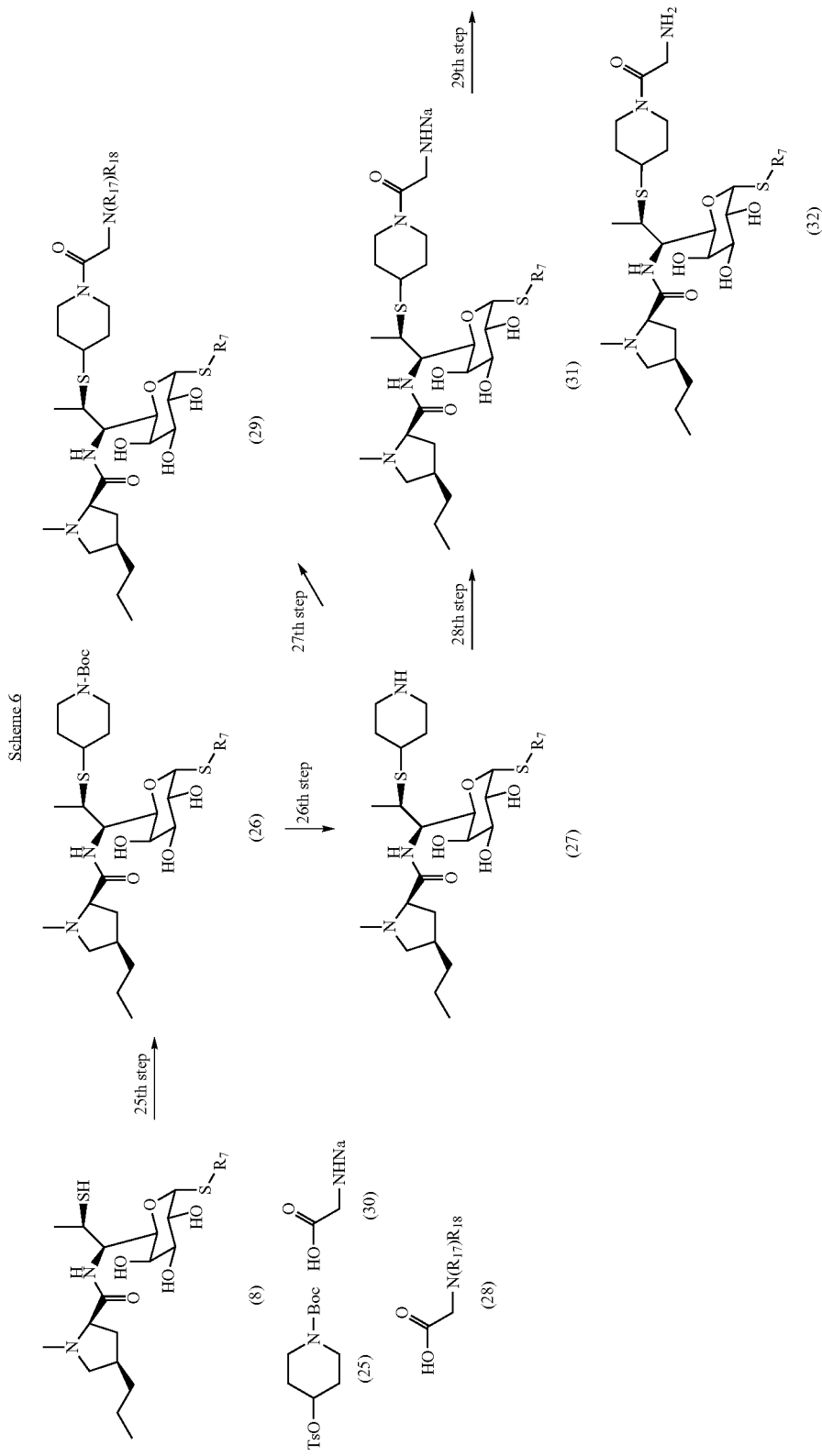

Ts in formula (25) represents toluenesulfonyl.

Specifically, in the twenty-fifth step, the compound of formula (8) can be converted to the compound of formula (26), for example, by reacting the compound of formula (8) with 1 to 3 equivalents of the compound of formula (25) in an N,N-dimethylformamide solvent in the presence of a base. The reaction solvent in this reaction may be a conventional reaction solvent in addition to N,N-dimethylformamide solvent, and preferred examples thereof include poloar solvents such as dimethylsulfoxide, 1-methylpyrrolidone, and acetonitrile. The base may be a conventional organic base or inorganic base and is preferably 1 to 2 equivalents of sodium hydride. The reaction temperature is room temperature to 100° C., and the reaction time is 1 to 24 hr.

In the twenty-sixth step, the compound of formula (27) can be converted to the compound of formula (29), for example, according to the process described in the twenty-seventh step.

In twenty-seventh step, the compound of formula (27) can be converted to the compound of formula (29) by properly selecting processes (i) and (ii). For example, in process (i), the compound of formula (29) can be produced by reacting the compound of formula (27) with 1 to 10 equivalents of the compound of formula (28) in an N,N-dimethylformamide solvent in the presence of 1-ethyl-3-(3-dimethylaminopropyl)carbodiimide hydrochloride and 1-hydroxybenzotriazole. The reaction solvent in this reaction may be a conventional solvent in addition to N,N-dimethylformamide, and preferred examples thereof include polar solvents such as tetrahydrofuran, diethyl ether, dimethylsulfoxide, and 1-methylpyrrolidone. The condensing agent may be a conventional condensing agent in addition to a combination of 1-ethyl-3-(3-dimethylaminopropyl)carbodiimide hydrochloride with 1-hydroxybenzotriazole. Preferably, 1 to 10 equivalents of a combination of 1-ethyl-3-(3-dimethylaminopropyl)carbodiimide hydrochloride and 3H-1,2,3-triazoro[4,5-b]pyridine-3-ol or the like. The reaction temperature is 0 to 120° C., and the reaction time is 0.5 to 24 hr. In process (ii), the compound of formula (27) is reacted with 1 to 10 equivalents of an acid chloride represented by $R_{18}(R_{17})NCH_2COCl$ in an N,N-dimethylformamide solvent in the presence of a base. The reaction solvent in this reaction may be a conventional solvent in addition to N,N-dimethylformamide, and preferred examples thereof include polar solvents such as tetrahydrofuran, diethyl ether, dimethylsulfoxide, and 1-methylpyrrolidone. The base may be a commonly known inorganic base or organic base, and preferred examples thereof include triethylamine, diisopropylethylamine, and 1,8-diazabicyclo[5.4.0]-7-undecene. The amount of the base is preferably 1 to 10 equivalents. The reaction temperature is 0 to 50° C., and the reaction time is 0.5 to 24 hr.

In twenty-eighth step, the compound of formula (27) can be converted to the compound of formula (31), for example, by converting the compound of formula (28) to the compound of formula (30) according to the process described in the twenty-seventh step.

In twenty-ninth step, the compound of formula (31) can be converted to the compound of formula (32), for example, according to the process described in the fourteenth step.

Seventhly, a group of compounds of formula (I), wherein $R_4$, $R_5$, and $R_6$ represent H and m is 1, 2 or 3, can be produced, for example, by the following general process.

Scheme 7
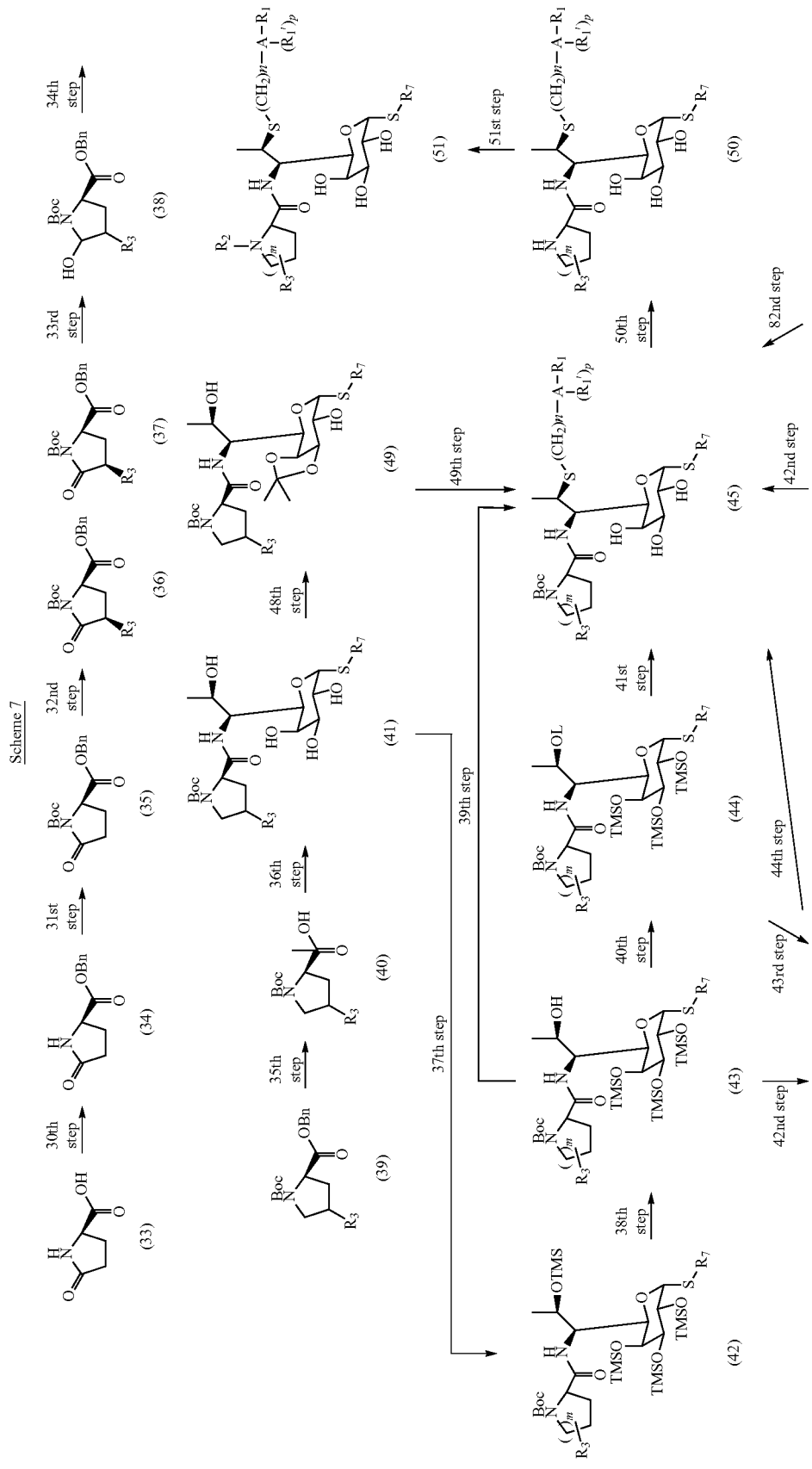

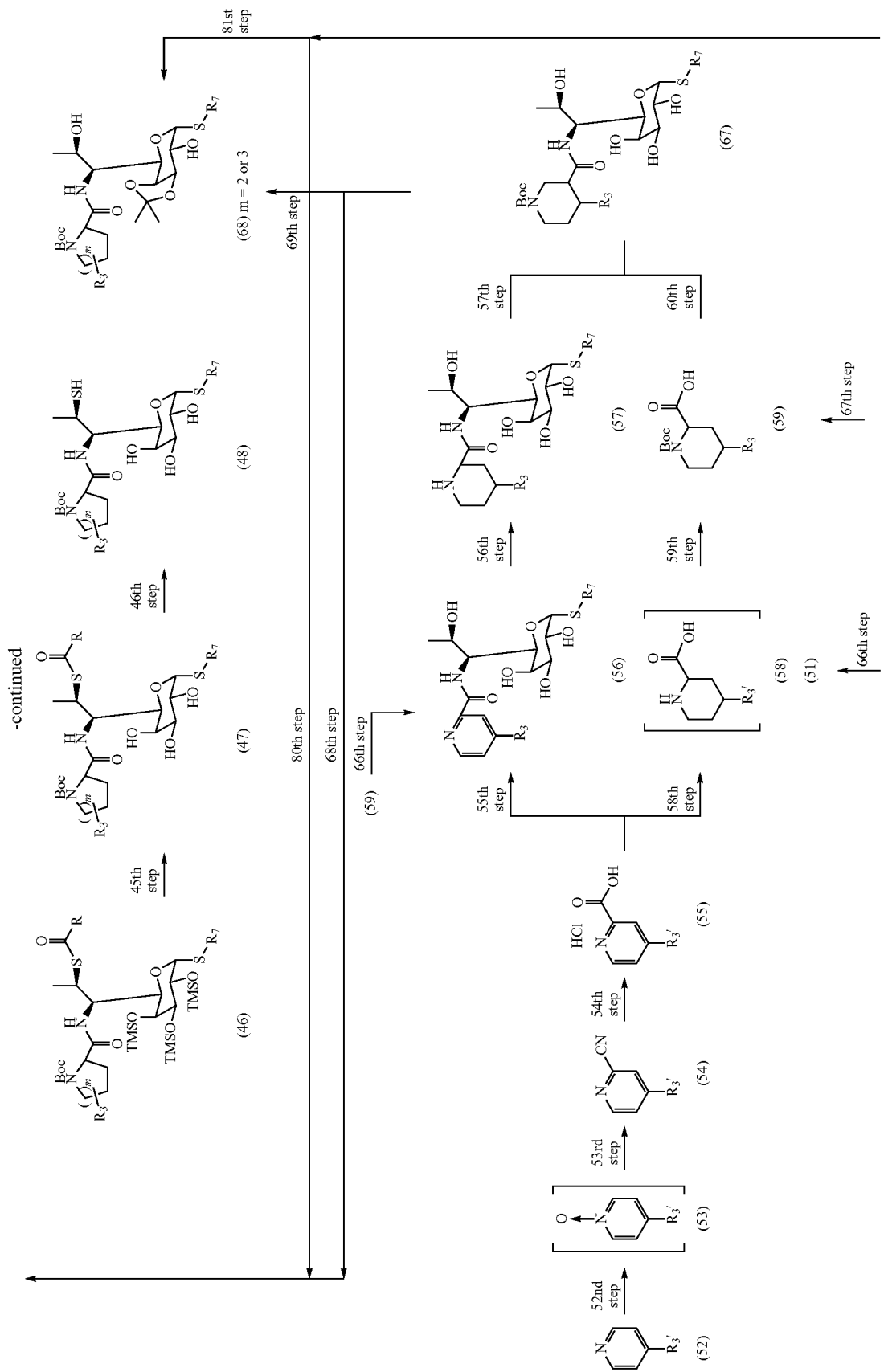

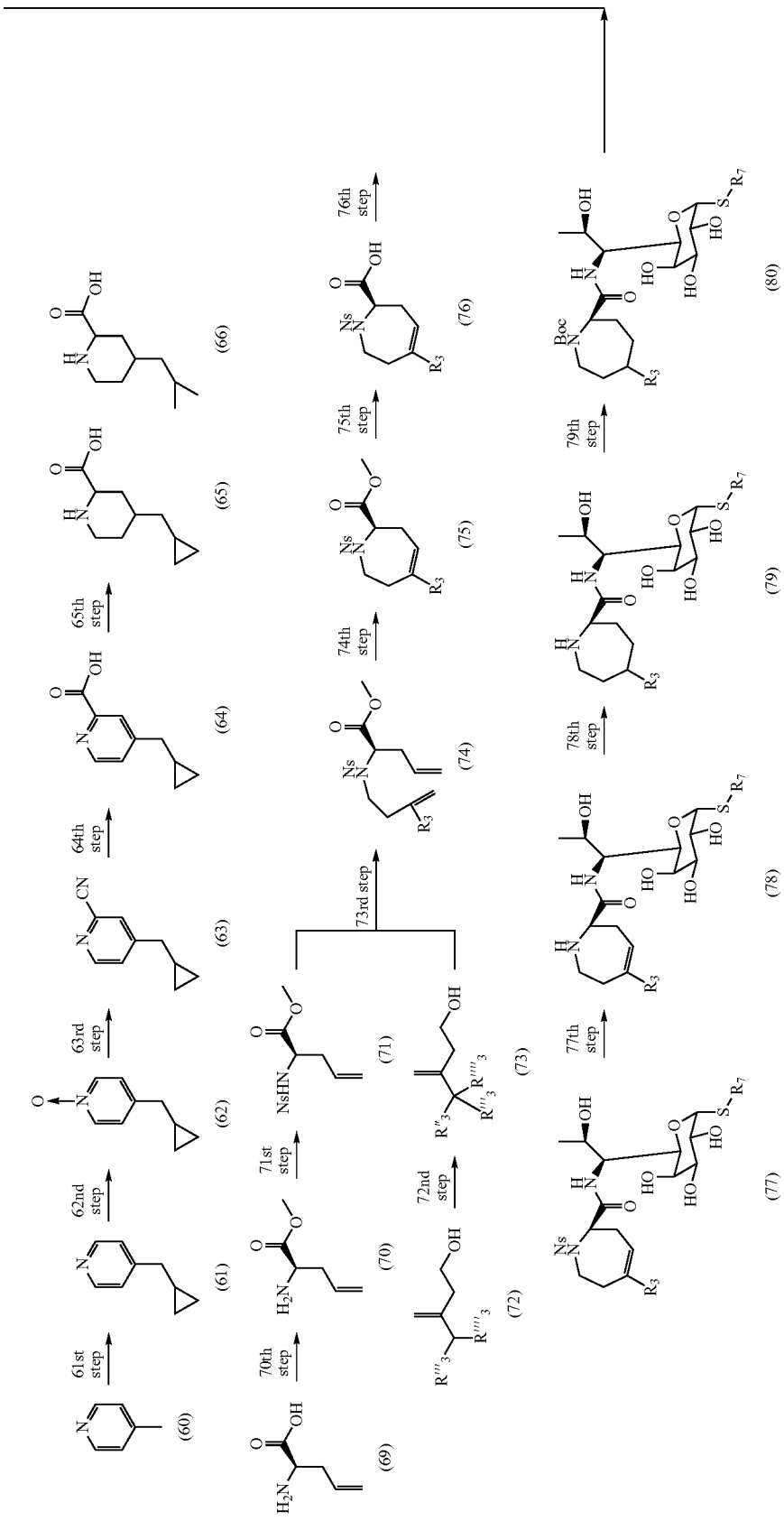

In scheme 7, $R_3$ represents $R''_3CR'''_3(R''''_3)$, and Ns represents o-nitrobenzenesulfonyl.

In thirtieth and thirty-first steps, the conversion of the compound of formula (33) to the compound of formula (34) and the conversion of the compound of formula (34) to the compound of formula (35) can be produced, for example, by the process described in Tetrahedron Lett., 43, (2002), 3499.

In the thirty-second, thirty-third, and thirty-fourth steps, the conversion of the compound of formula (37) to the compound of formula (38) and the compound of formula (37), the conversion of the compound of formula (36) and the compound of formula (37) to the compound of formula (38), and the conversion of the compound of formula (38) to the compound of formula (39) can be carried out, for example, according to the process described in Tetrahedron Lett., 35, (1994), 2053 and J. Am. Chem. Soc., 110, (1998), 3894.

Next, in thirty-fifth step, the conversion of the compound of formula (39) to the compound of formula (40) can be carried out by properly selecting whether, in $R_3$ in formula (40), the double bond (i) allows to remain unremoved or (ii) is removed and subjecting the compound of formula (39), for example, to the following process. For example, process (i), the compound of formula (40) can be produced by hydrolyzing the compound of formula (39) in a methanol solvent in the presence of a base. The reaction solvent in this reaction may be a conventional alcohol solvent in addition to methanol, and preferred examples thereof include ethanol, propanol, and butanol. The reaction temperature is 0 to 120° C., and the reaction time is 0.5 to 24 hr. In process (ii), the compound of formula (40) can be produced by the process described in J. Am. Chem. Soc., 110, (1998), 3894.

In thirty-sixth step, the conversion of the compound of formula (40) to the compound of formula (41) can be carried out, for example, by reacting the compound of formula (40) with 1 to 10 equivalents of $R_7$ 1-thio-α-lincosamide in an N,N-dimethylformamide solvent in the presence of 1-ethyl-3-(3-dimethylaminopropyl)carbodiimide hydrochloride and 1-hydroxybenzotriazole. The reaction solvent in this reaction may be a conventional solvent in addition to N,N-dimethylformamide, and preferred examples thereof include polar solvents such as tetrahydrofuran, diethyl ether, dimethylsulfoxide, and 1-methylpyrrolidone. The condensing agent may be a conventional condensing agent in addition to a combination of 1-ethyl-3-(3-dimethylaminopropyl)carbodiimide hydrochloride with 1-hydroxybenzotriazole. Preferably, 1 to 10 equivalents of, for example, a combination of dicyclohexylcarbodiimide with 4-dimethylaminopyridine is used. The reaction temperature is 0 to 120° C., and the reaction time is 0.5 to 24 hr.

In thirty-seventh step, the compound of formula (41) can be converted to the compound of formula (42), for example, according to the process described in the first step.

In thirty-eighth step, the compound of formula (42) can be converted to the compound of formula (43), for example, according to the process described in the second step.

In thirty-ninth step, the compound of formula (43) can be converted to the compound of formula (45), for example, according to the process described in the third step.

In fortieth step, the compound of formula (43) can be converted to the compound of formula (44), for example, according to the process described in the fourth step.

In forty-first step, the compound of formula (44) can be converted to the compound of formula (45), for example, according to the process described in the fifth step.

In forty-second step, the compound of formula (43) can be converted to the compound of formula (46), for example, according to the process described in the sixth step.

In forty-third step, the compound of formula (44) can be converted to the compound of formula (46), for example, according to the process described in the seventh step.

In forty-fourth step, the compound of formula (46) can be converted to the compound of formula (45), for example, according to the process described in the eighth step.

In forty-fifth step, the compound of formula (46) can be converted to the compound of formula (47), for example, according to the process described in the ninth step.

In forty-sixth step, the compound of formula (47) can be converted to the compound of formula (48), for example, according to the process described in the tenth step.

In forty-seventh step, the compound of formula (48) can be converted to the compound of formula (45), for example, according to the process described in the eleventh step.

In forty-eighth step, the compound of formula (41) can be converted to the compound of formula (49), for example, according to the process described in the twelfth step.

In forty-ninth step, the compound of formula (49) can be converted to the compound of formula (45), for example, according to the process described in the thirteenth step.

In fiftieth step, the compound of formula (45) can be converted to the compound of formula (50), for example, by reacting the compound of formula (45) with either a 95% aqueous trifluoroacetic acid solution or a 4 N hydrochloric acid-dioxane solution. The reaction temperature is −15° C. to room temperature, and the reaction time is 0.5 to 24 hr.

In the fifty-first step, the conversion of the compound of formula (50) to the compound of formula (51) can be carried out, for example, by properly selecting any one of processes (i), (ii), and (iii). For example, in process (i), the compound of formula (51) can be produced by reacting 1 to 10 equivalents of a ketone or an aldehyde with the compound of formula (50) in a 1,2-dichloroethane solvent in the presence of an acid and a reducing agent. The reaction solvent in this reaction may be a conventional solvent in addition to 1,2-dichloroethane, and preferred examples thereof include solvents such as methylene chloride, chloroform, tetrahydrofuran, diethyl ether, methanol, ethanol, and butanol. The acid is preferably acetic acid, hydrochloric acid, sulfuric acid or the like. The reducing agent may be a commonly known the reducing agent, and preferred examples thereof include sodium tri(acetoxy)borohydride. The amount of the reducing agent is preferably 1 to 10 equivalents. The reaction temperature is 0 to 120° C., and the reaction time is 0.5 to 4 hr. In process (ii), the compound of formula (51) can be produced by reacting the compound of formula (50) with 1 to 10 equivalents of an alkyl halide in an acetonitrile solvent in the presence of a base. The reaction solvent in this reaction may be a conventional solvent in addition to acetonitrile, and preferred examples thereof include polar solvents such as N,N-dimethylformamide, dimethylsulfoxide, and 1-methylpyrrolidone. The base may be a commonly known inorganic base or organic base, and preferred examples thereof include potassium carbonate, sodium hydroxide, potassium hydroxide, triethylamine, diisopropylethylamine, and 4-dimethylaminopyridine. The amount of the base is preferably 1 to 10 equivalents. The reaction temperature is 0 to 50° C., and the reaction time is 0.5 to 24 hr. In process (iii), the compound of formula (51) can be produced by reacting the compound of formula (50) with 1 to 10 equivalents of an alkylcarboxylic acid or an arylcarboxylic acid in an N,N-dimethylformamide solvent in the presence of 1-ethyl-3-(3-dimethylaminopropyl)carbodiimide hydrochloride and 1-hydroxybenzotriazole. The reaction solvent in this reaction may be a conventional solvent in addition to N,N-dimethylformamide, and preferred examples thereof include polar solvents such as dimethylsulfoxide and 1-methylpyrrolidone.

The condensing agent may be a conventional condensing agent in addition to a combination of 1-ethyl-3-(3-dimethylaminopropyl)carbodiimide hydrochloride with 1-hydroxybenzotriazole. Preferably, for example, 1 to 10 equivalents of a combination of dicyclohexylcarbodiimide with 4-dimethylaminopyridine or the like is used. The reaction temperature is 0 to 120° C., and the reaction time is 0.5 to 24 hr.

In the fifty-second, fifty-third, and fifty-fourth steps, the conversion of the compound of formula (52) to the compound of formula (53), the conversion of the compound of formula (53) to the compound of formula (54), and the conversion of the compound of formula (54) to the compound of formula (55) can be carried out, for example, according to the process described in J. Med. Chem., 32, (1989), 829.

In the fifty-fifth step, the conversion of the compound of formula (55) to the compound of formula (56) can be carried out, for example, according to the process in the thirty-sixth step.

In the fifty-sixth step, the conversion of the compound of formula (56) to the compound of formula (57) can be carried out, for example, by adding the compound of formula (56), an acid, and platinum oxide to a methanol-water mixed solvent and allowing a reaction to proceed under a hydrogen atmosphere (206850 to 689500 Pa). The reaction solvent in this reaction may be a conventional alcohol solvent in addition to the methanol-water mixed solvent, and preferred examples thereof include solvents such as methanol and ethanol. The acid may be a conventional acid, and preferred examples thereof include hydrochloric acid, sulfuric acid, and acetic acid. The amount of the acid is preferably 1 to 10 equivalents. The reaction temperature is 0° C. to room temperature, and the reaction time is 0.5 to 24 hr.

In fifty-seventh step, the conversion of the compound of formula (57) to the compound of formula (67) can be carried out, for example, by reacting the compound of formula (57) with 1 to 10 equivalents of di-tert-butyl dicarbonate in a dioxane solvent in the presence of a base. The reaction solvent in this reaction may be a conventional solvent in addition to dioxane, and preferred examples thereof include polar solvents such as tetrahydrofuran, diethyl ether, N,N-dimethylformamide, dimethylsulfoxide, and 1-methylpyrrolidone. The base may be a conventional organic base or inorganic base, and preferred examples thereof include 4-dimethylaminopyridine, sodium hydroxide, potassium hydroxide, and barium hydroxide. The base is used in an excessive amount. The reaction temperature is 0 to 50° C., and the reaction time is 0.5 to 24 hr.

In the fifty-eighth step, the conversion of the compound of formula (55) to the compound of formula (58) can be carried out, for example, by adding the compound of formula (55) and platinum oxide to an acetic acid solvent and allowing a reaction to proceed under a hydrogen atmosphere (ordinary pressure). The reaction temperature is 0 to 50° C., and the reaction time is 0.5 to 24 hr.

In the fifty-ninth step, the conversion of the compound of formula (58) to the compound of formula (59) can be carried out according to the process in the fifty-seventh step.

In the sixtieth step, the conversion of the compound of formula (59) to the compound of formula (67) can be carried out according to the process in the thirty-sixth step.

In the sixty-first step, the conversion of the compound of formula (60) to the compound of formula (61) can be carried out, for example, by reacting the compound of formula (60) with lithium diisopropylamine in a tetrahydrofuran solvent and then reacting the reaction product with 1 to 10 equivalents of cyclopropyl bromide. The reaction temperature is −78° C. to room temperature, and the reaction time is 1 to 24 hr.

In the sixty-second step, the compound of formula (61) can be converted to the compound of formula (62), for example, by reacting the compound of formula (61) with 1 to 10 equivalents of 3-chloroperbenzoic acid in a methylene chloride solvent. The reaction solvent in this reaction may be a halogenic solvent in addition to methylene chloride, and preferred examples thereof include chloroform, carbon tetrachloride, and 1,2-dichloroethane. The reaction temperature is 0 to 50° C., and the reaction time is 0.5 to 24 hr.

In the sixty-third step, the compound of formula (62) can be converted to the compound of formula (63), for example, by reacting the compound of formula (62) with an excessive amount of trimethylsilylcyanide and dimethylcarbamoylchloride in a methylene chloride solvent. The reaction solvent in this reaction may be a halogenic solvent in addition to methylene chloride, and preferred examples thereof include chloroform, carbon tetrachloride, and 1,2-dichloroethane. The reaction temperature is 0 to 50° C., and the reaction time is 0.5 to 24 hr.

In the sixty-fourth step, the compound of formula (63) can be converted to the compound of formula (64), for example, by reacting the compound of formula (63) with a base in a methanol solution. The base in this reaction is suitably a strong base. Preferably, sodium hydroxide, potassium hydroxide, barium hydroxide and the like are used in an excessive amount. The reaction temperature is 0 to 100° C., and the reaction time is 0.5 to 24 hr.

In the sixty-fifth step, the conversion of the compound of formula (64) to the compound of formula (65) or the conversion of the compound of formula (64) to the compound of formula (66) can be carried out, for example, according to the process described in the fifty-eighth step.

In the sixty-sixth step, the compound of formula (64) can be converted to the compound of formula (56), for example, according to the process described in the thirty-sixth step.

In the sixty-seventh step, the conversion of the compound of formula (65) to the compound of formula (59) and the conversion of the compound of formula (66) to the compound of formula (59) can be carried out according to the process described in the fifty-seventh step.

In the sixty-eighth step, the compound of formula (67) can be converted to the compound of formula (42), for example, according to the process described in the first step.

In the sixty-ninth step, the compound of formula (67) can be converted to the compound of formula (68), for example, according to the process described in the twelfth step.

In the seventieth step, the compound of formula (69) can be converted to the compound of formula (70) by either process (i) or process (ii). In process (i), the compound of formula (70) can be produced, for example, by reacting the compound of formula (69) in a methanol solvent in the presence of 1 to 10 equivalents of 4 N hydrochloric acid-dioxane. The acid in this reaction may be a conventional known strong acid in addition to hydrochloric acid. For example, sulfuric acid is preferred. The amount of the acid is preferably 1 to 10 equivalents. The reaction temperature is 0 to 50° C., and the reaction time is 0.5 to 120 hr. In process (ii), the compound of formula (70) can be produced by reacting the compound of formula (69) in a methanol solvent in the presence of 1 to 10 equivalents of thionylchloride. The reaction reagent in this reaction may be a commonly known carboxylic acid activating agent in addition to thionyl chloride, and preferred examples thereof include thionyl bromide, oxazalyl chloride, and dicyclohexylcarbodiimide-4-dimethylaminopyridine composite condensing agents. The amount of the reaction reagent is preferably 1 to 10 equivalents. The reaction temperature is 0 to 50° C., and the reaction time is 0.5 to 24 hr.

In the seventy-first step, the compound of formula (70) can be converted to the compound of formula (71), for example, by reacting the compound of formula (70) with 1 to 10 equivalents of o-nitrobenzenesulfonyl chloride in a diethyl ether solvent in the presence of a base. The reaction solvent in this reaction may be a conventional solvent in addition to diethyl ether. Preferred examples thereof include tetrahydrofuran, dimethylsulfoxide, 1-methylpyrrolidon, N,N-dimethylformamide, and methylene chloride. The base may be a conventional known inorganic base or organic base, and preferred examples thereof include sodium hydrogencarbonate, potassium carbonate, potassium phosphate, lithium hydroxide, sodium hydroxide, triethylamine, diisopropylethylamine, and 1,8-diazabicyclo[5.4.0]-7-undecene. The amount of the base is preferably 1 to 10 equivalents. The reaction temperature is 0 to 50° C., and the reaction time is 0.5 to 24 hr.

In the seventy-second step, the compound of formula (72) can be converted to the compound of formula (73), for example, by reacting the compound of formula (72) with 3-methyl-3-buten-1-ol at 0° C. in a diethyl ether solvent in the presence of N,N,N',N'-tetramethylethylenediamine and n-butyllithium, then adding 1 to 5 equivalents of an alkyl bromide represented by $R''_3Br$ at −78° C., and raising the temperature of the reaction system to room temperature. The reaction solvent in this reaction may be a conventional ether solvent in addition to diethyl ether, and preferred examples thereof include tetrahydrofuran. The reaction temperature is −78° C. to room temperature, and the reaction time is 15 to 36 hr.

In the seventy-third step, the compound of formula (71) and the compound of formula (73) can be converted to the compound of formula (74), for example, by reacting 1 to 10 equivalents of the compound of formula (71) in a tetrahydrofuran solution in the presence of the compound of formula (73) triphenylphosphine and diisopropyl azodicarboxylate. The reaction solvent in this reaction may be a conventional reaction solvent in addition to tetrahydrofuran, and preferred examples thereof include benzene, toluene, trifluoromethylbenzene, and acetonitrile. The phosphine reagent may be a conventional phosphine reagent commonly known in literatures and the like in addition to triphenylphosphine, and preferred examples thereof include o-tolylphosphine and tri-n-butylphosphine. The amount of the phosphine reagent is preferably 1 to 5 equivalents. The azo reagent may be a conventional azo reagent commonly known in literatures and the like in addition to diisopropyl azodicarboxylate, and preferred examples thereof include diethyl azodicarboxylate and 1,1'-(azodicarbonyl)dipiperidine. The amount of the azo reagent is preferably 1 to 5 equivalents. The reaction temperature is 0 to 50° C., and the reaction time is 0.5 to 24 hr.

In the seventy-fourth step, the compound of formula (74) can be converted to the compound of formula (75), for example, by ring-closing the compound of formula (74) in a methylene chloride solvent in the presence of 0.01 to 0.1 equivalent of benzylidene[1,3-bis(2,4,6-trimethylphenyl)-2-imidazolidinylidene]dichloro(tricyclohexylphosphine)-ruthenium. The reaction solvent in this reaction may be a conventional halogenic solvent in addition to the methylene chloride solvent, and preferred examples thereof include chloroform, carbon tetrachloride, and 1,2-dichloroethane. The reaction temperature is room temperature to 100° C., and the reaction time is 0.5 to 24 hr.

In the seventy-fifth step, the compound of formula (75) can be converted to the compound of formula (76), for example, by hydrolyzing the compound of formula (75) in a dioxane-water mixed solvent in the presence of a base. The reaction solvent in this reaction may be a conventional alcohol-water mixed solvent in addition to the dioxane-water mixed solvent, and a mixed solvent composed of methanol, ethanol, propanol, or butanol with water is preferred. The base may be a commonly known inorganic base, and preferred examples thereof include lithium hydroxide, sodium hydroxide, potassium hydroxide, and barium hydroxide. The amount of the base is preferably 1 to 10 equivalents. The reaction temperature is 0 to 120° C., and the reaction time is 0.5 to 24 hr.

In the seventy-sixth step, the compound of formula (76) can be converted to the compound of formula (77), for example, according to the process described in the thirty-sixth step.

In the seventy-seventh step, the compound of formula (77) can be converted to the compound of formula (78), for example, by reacting the compound of formula (77) with 1 to 10 equivalents of benzenethiol in an N,N-dimethylformamide solvent in the presence of a base. The reaction solvent in this reaction may be a conventional solvent in addition to N,N-dimethylformamide, and preferred examples thereof include tetrahydrofuran, dimethylsulfoxide, 1-methylpyrrolidone, and diethyl ether. The base may be a commonly known inorganic base or organic base, and preferred examples thereof include potassium carbonate, sodium hydroxide, triethylamine, diisopropylethylamine, 1,8-diazabicyclo[5.4.0]-7-undecene, and 7-methyl-1,5,7-triazabicyclo-[4,4,0]dec-5-ene. The amount of the base is preferably 1 to 10 equivalents. The thiol may be a commonly known alkylthiol or arylthiol in addition to benzenethiol, and preferred examples thereof include 4-bromobenzenethiol and 4-t-butylbenzenethiol. The amount of the thiol is preferably 1 to 10 equivalents. The reaction temperature is 0 to 50° C., and the reaction time is 0.5 to 24 hr.

In the seventy-eighth step, the conversion of the compound of formula (78) to the compound of formula (79) can be carried out, for example, by allowing a reaction to proceed in a methanol solvent in the presence of a metallic catalyst under a hydrogen atmosphere. The metallic catalyst in this reaction may be a metallic catalyst commonly used in hydrogen reduction, and preferred examples thereof include Raney nickel, palladium/carbon, and palladium hydroxide/carbon. The reaction temperature is 0 to 50° C., and the reaction time is 0.5 to 24 hr.

In the seventy-ninth step, the compound of formula (79) can be converted to the compound of formula (80), for example, according to the process described in the fifty-seventh step.

In the eightieth step, the compound of formula (80) can be converted to the compound of formula (42), for example, according to the process described in the first step.

In the eighty-first step, the compound of formula (80) can be converted to the compound of formula (68), for example, according to the process described in the twelfth step.

In the eighty-second step, the compound of formula (68) can be converted to the compound of formula (45), for example, according to the process described in the thirteenth step.

Eighthly, among a group of compounds of formula (1), wherein $R_2$ represents Me, $R_3$ represents Pr, $R_4$, $R_5$ and $R_6$ represent H, and m is 1, that can be produced according to the process described in schemes 1 to 7, a group of compounds (formula (5)) cannot be efficiently produced, for example, for production or purification reasons. The group of compounds of (formula (5)) corresponding to compounds of formula (51) can also be produced by an alternative process, for example, by N-methylation in the fifty-first step using the process described in scheme 7.

Ninthly, among a group of compounds of formula (1), wherein $R_4$, $R_5$, and $R_6$ represent H and m is 1 or 2, that can be produced, for example, according to the process described in schemes 1 to 7, a group of compounds (formula (50) and formula (51)) cannot be efficiently produced, for example, for production or purification reasons. The group of compounds (formula (50) and formula (51)) can also be produced by an alternative process, for example, by producing the compound of formula (45) according to the process described in scheme 8 and then producing the compound of formula (50) and the compound of formula (51) by the fiftieth step and the fifty-first step in scheme 7.

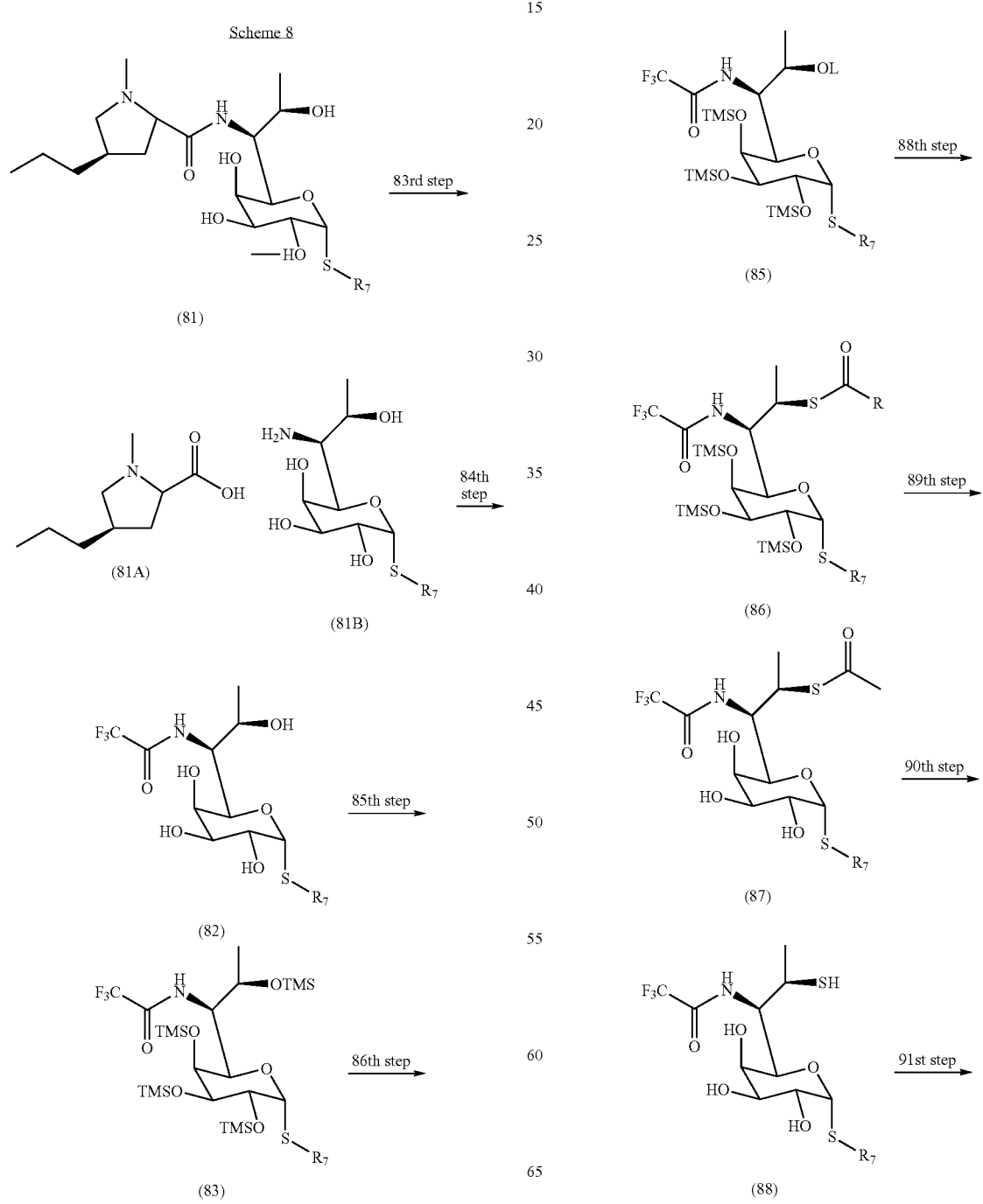

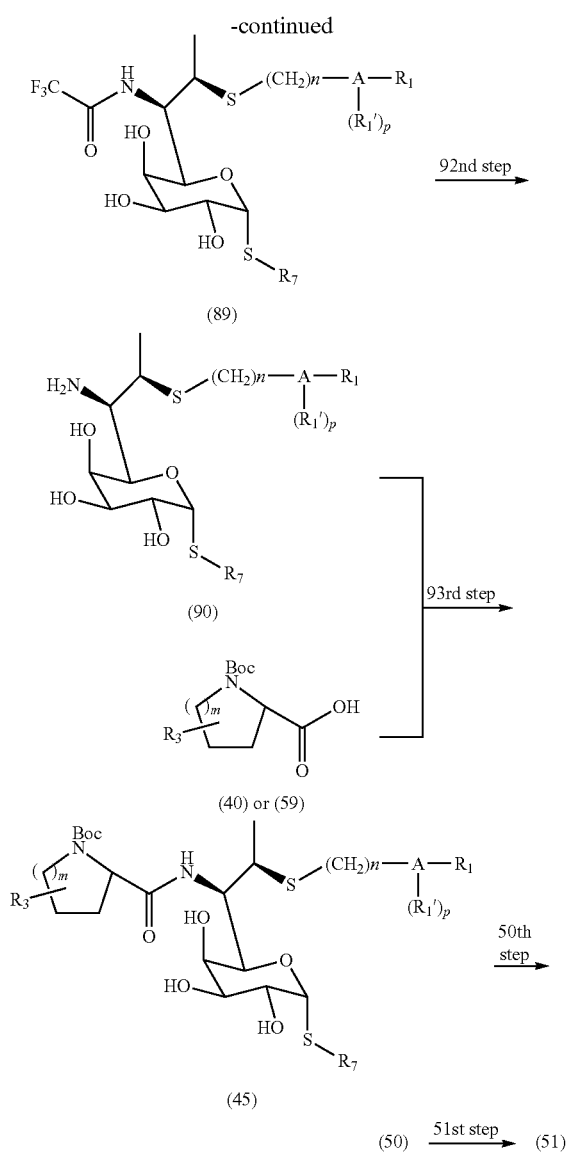

Specifically, in the eighty-third step, the compound of formula (81) can be converted to the compound of formula (81A) and the compound of formula (81B), for example, according to the process described in J. Am. Chem. Soc., (1967), 89, 2448-2453.

In the eighty-fourth step, the compound of formula (81B) can be converted to the compound of formula (82), for example, by reacting the compound of formula (81B) with 5 to 15 equivalents of ethyl trifluoroacetate in a methanol solvent in the presence of a base. The reaction solution in this reaction may be a conventional solvent in addition to methanol, and preferred examples thereof include ethanol, propanol, tetrahydrofuran, dimethylsulfoxide, 1-methylpyrrolidone, diethyl ether, and N,N-dimethylformamide. The base may be a conventional inorganic base or organic base, and preferred examples thereof include potassium carbonate, sodium hydroxide, triethylamine, diisopropylethylamine, and 1,8-diazabicyclo[5.4.0]-7-undecene. The amount of the base is preferably 1 to 10 equivalents. The reaction temperature is 0 to 150° C., and the reaction time is 1 to 24 hr.

In the eighty-fifth step, the compound (82) can be converted to the compound of formula (83), for example, according to the process described in the first step.

In the eighty-sixth step, the compound (83) can be converted to the compound of formula (84), for example, according to the process described in the second step.

In the eighty-seventh step, the compound (84) can be converted to the compound of formula (85), for example, according to the process described in the fourth step.

In the eighty-eighth step, the compound (85) can be converted to the compound of formula (86), for example, according to the process described in the seventh step.

In the eighty-ninth step, the compound (86) can be converted to the compound of formula (87), for example, by reacting the compound of formula (86) with an acid in a methanol solvent. The reaction solvent in this reaction may be a conventional solvent in addition to methanol, and preferred examples thereof include ethanol, propanol, tetrahydrofuran, dimethylsulfoxide, 1-methylpyrrolidone, diethyl ether, and N,N-dimethylformamide. The acid may be a conventional known strong acid, and preferred examples thereof include hydrochloric acid and sulfuric acid. The amount of the acid is preferably 1 to 10 equivalents. The reaction temperature is 0° C. to room temperature, and the reaction time is 1 to 24 hr.

In the ninety step, the compound of formula (87) can be converted to the compound of formula (88), for example, by reacting the compound of formula (87) with a base in a methanol solvent. The reaction solvent in this reaction may be a conventional polar solvent in addition to methanol, and preferred examples thereof include ethanol, propanol, butanol, N,N-dimethylformamide, dimethylsulfoxide, and 1-methylpyrrolidone. The base may be a conventional known inorganic base, alkali metal methoxide, or alkali metal ethoxide, and preferred examples thereof include sodium hydroxide, potassium hydroxide, sodium methoxide, and sodium ethoxide. The amount of the base is preferably 1 to 10 equivalents. The reaction temperature is 0 to 40° C., and the reaction time is 0.5 to 24 hr.

In the ninety-first step, the compound of formula (88) can be converted to the compound of formula (89), for example, according to the process described in the eleventh step.

In the ninety-second step, the compound of formula (89) can be converted to the compound of formula (90), for example, by reacting the compound of formula (89) with a base in a methanol solvent. The reaction solvent in this reaction may be a conventional polar solvent in addition to methanol, and preferred examples thereof include ethanol, propanol, butanol, N,N-dimethylformamide, dimethylsulfoxide, and 1-methylpyrrolidone. The base may be a conventional known inorganic base and preferred examples thereof include sodium hydroxide, potassium hydroxide, and potassium carbonate. The amount of the base is preferably 1 to 10 equivalents. The reaction temperature is 0 to 100° C., and the reaction time is 1 to 24 hr.

In the ninety-third step, the compound of formula (90) can be converted to the compound of formula (45), for example, according to the process described in the thirty-sixth step.

Tenthly, in scheme 7, in the conversion of the compound of formula (72) to the compound of formula (73), a group of compounds (formula (73)) cannot be efficiently produced, for example, for production or purification reasons. The group of compounds (formula (73)) can also be produced by an alternative process, for example, by producing the compound of formula (99) corresponding to the compound of formula (73) according to the process described in scheme 9., The compound of formula (74) can be produced by reacting the compound of formula (99) with the compound of formula (71).

The compound of formula (50) and the compound of formula (51) can be produced from the compound of formula (74) in the same manner as described in scheme 7.,

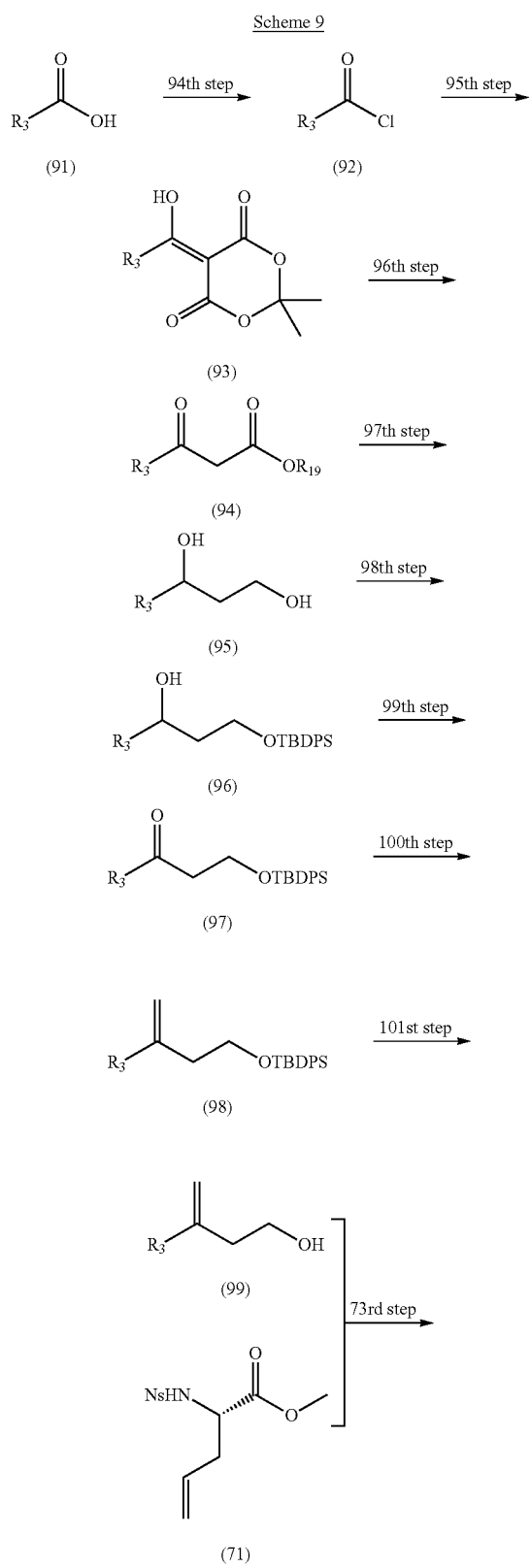

Scheme 9

(91) → 94th step → (92) → 95th step → (93) → 96th step → (94) → 97th step → (95) → 98th step → (96) → 99th step → (97) → 100th step → (98) → 101st step → (99) + (71) → 73rd step →

(74) → Scheme 7 → (50) → 51st step → (51)

In scheme 9, $R_{19}$ represents a commonly used protective group for a carbonxylic acid, for example, alkyl, aryl, or benzyl.

In the ninety-fourth step, the compound of formula (91) can be converted to the compound of formula (92), for example, by reacting the compound of formula (91) with 1 to 10 equivalents of thionyl chloride in a methylene chloride solvent in the presence of a base. The reaction solvent in this reaction may be a conventional halogenic solvent in addition to methylene chloride, and preferred examples thereof include chloroform, carbon tetrachloride, and 1,2-dichloroethane. The base may be a conventional known organic base, and preferred examples thereof include triethylamine, diisopropylethylamine, and 1,8-diazabicyclo[5.4.0]-7-undecene. The amount of the base is preferably 1 to 10 equivalents. The reaction temperature is –50° C. to room temperature, and the reaction time is 1 to 24 hr.

In the ninety-fifth step, the compound of formula (92) can be converted to the compound of formula (93), for example, by reacting 2,2-dimethyl-1,3-dioxane-4,6-dione with the compound of formula (92) in a methylene chloride-pyridine mixed solvent. The reaction solvent in this reaction may be a combination of a conventional halogenic solvent with an organic base in addition to the methylene chloride-pyridine mixed solvent, and preferred examples thereof include a mixture of solvents selected from chloroform, carbon tetrachloride, 1,2-dichloroethane, triethylamine, diisopropylethylamine, 1,8-diazabicyclo[5.4.0]-7-undecene, 2,6-dimethylpyridine, 2,4,6-trimethylpyridine and the like. The reaction temperature is –50° C. to room temperature, and the reaction time is 1 to 24 hr.

In the ninety-sixth step, the compound of formula (93) can be converted to the compound of formula (94), for example, by reacting the compound of formula (93) with a commonly used alcohol represented by $R_{19}OH$ in a N,N-dimethyl formamide solvent in the presence of an acid. The reaction solvent in this reaction may be a conventional polar solvent in addition to N,N-dimethylformamide, and preferred examples thereof include dimethylsulfoxide, 1-methylpyrrolidone, tetrahydrofuran, and diethyl ether. The acid may be a conventional known acid, and preferred examples thereof include hydrochloric acid, sulfuric acid, nitric acid, acetic acid, and formic acid. The amount of the acid is preferably 1 to 10 equivalents. The alcohol may be a conventional known alcohol, and preferred examples thereof include methanol, ethanol, propanol, butanol, benzylalcohol, and phenol. The reaction temperature is room temperature to 150° C., and the reaction time is 0.5 to 24 hr.

In the ninety-seventh step, the compound of formula (94) can be converted to the compound of formula (95), for example, by reacting the compound of formula (94) with a 1 to 5 equivalents of a reducing agent in a tetrahydrofuran solvent. The reaction solvent in this reaction may be a conventional ether solvent in addition to tetrahydrofuran, and preferred examples thereof include diethyl ether, 1,4-dioxane, and 1,2-dimethoxyethane. The reducing agent may be a conventional known reducing agent (that can reduce an ester and a keton), and preferred examples thereof include lithium aluminum hydride and sodium (bis-2-methoxyethoxy)aluminum hydride. The amount of the reducing agent is preferably 1 to 10 equivalents. The reaction temperature is −50° C. to room temperature, and the reaction time is 1 to 24 hr.

In the ninety-eighth step, the compound of formula (95) can be converted to the compound of formula (96), for example, by reacting the compound of formula (95) with 1 to 5 equivalents of tert-butylchlorodiphenylsilane in an N,N-dimethylformamide solvent in the presence of a base. The reaction solvent in this reaction may be a conventional polar solvent or halogenic solvent, excluding an alcoholic solvent, in addition to N,N-dimethylformamide, and preferred examples thereof include dimethylsulfoxide, 1-methylpyrrolidone, pyridine, tetrahydrofuran, diethyl ether, 1,4-dioxane, 1,2-dimethoxyethane, chloroform, carbon tetrachloride, and 1,2-dichloroethane. The base may be a conventional known organic base, and preferred examples thereof include triethylamine, diisopropylethylamine, 1,8-diazabicyclo [5.4.0]-7-undecene, imidazole, and pyridine. The amount of the base is preferably 1 to 10 equivalents. The reaction temperature is 0 to 50° C., and the reaction time is 0.25 to 24 hr.

In the ninety-ninth step, the compound of formula (96) can be converted to the compound of formula (97), for example, by reacting the compound of formula (96) with 1 to 10 equivalents of an oxidizing agent in a methylene chloride solvent. The reaction solvent in this reaction may be a conventional solvent in addition to methylene chloride, and preferred examples thereof include chloroform, carbon tetrachloride, 1,2-dichloroethane, dimethylsulfoxide, 1-methylpyrrolidone, tetrahydrofuran, diethyl ether, 1,4-dioxane, and 1,2-dimethoxyethane. The oxidizing agent may be a conventional known oxidizing agent, and preferred examples thereof include 1,1,1-tris(acetyloxy)-1,1-dihydro-1,2-benziodoxol-3-(1H)-one (Dess-Martin periodinane). The amount of the oxidizing agent is preferably 1 to 10 equivalents. The reaction temperature is 0° C. to room temperature, and the reaction time is 0.5 to 24 hr.

In the one hundredth step, the compound of formula (97) can be converted to the compound of formula (98), for example, by reacting the compound of formula (97) with an ylide agent prepared from methyltriphenyl phosphonium bromide and butyllithium in a tetrahydrofuran solvent. The reaction solvent in this reaction may be a conventional ether solvent in addition to tetrahydrofuran, and preferred examples thereof include diethyl ether, 1,4-dioxane, and 1,2-dimethoxyethane. The reaction temperature is 0° C. to room temperature, and the reaction time is 1 to 24 hr.

In the one hundred and first step, the compound of formula (98) can be converted to the compound of formula (99), for example, by reacting the compound of formula (98) with 1 to 10 equivalents of tetrabutyl ammonium fluoride in a tetrahydrofuran solvent. The reaction solvent in this reaction may be a conventional solvent in addition to tetrahydrofuran, and preferred examples thereof include dimethylsulfoxide, 1-methylpyrrolidone, N,N-dimethylformamide, diethyl ether, 1,4-dioxane, chloroform, carbon tetrachloride, and 1,2-dichloroethane. The reaction temperature is 0° C. to room temperature, and the reaction time is 1 to 24 hr.

Eleventhly, among a group of compounds of formula (1), wherein $R_4$, $R_5$, and $R_6$ represent H and m is 3, that can be produced according to the process described in schemes 7 and 9, a group of compounds (formula (50) and formula (51)) cannot be efficiently produced, for example, for production or purification reasons. The group of compounds (formula (50) and formula (51)) can also be produced by an alternative process, for example, by producing the compound of formula (103) according to the process described in scheme 10 and then reacting the resultant compound with the compound of formula (90) in scheme 8. The compound of formula (50) and the compound of formula (51) can be produced from the compound of formula (45) by the fiftieth step and the fifty-first step in the same manner as described in scheme 7. Further, a compound of formula (104) corresponding to the compound of formula (80) in scheme 7 can be produced by reacting the compound of formula (103) with $R_7$ 1-thio-α-lincosamide.

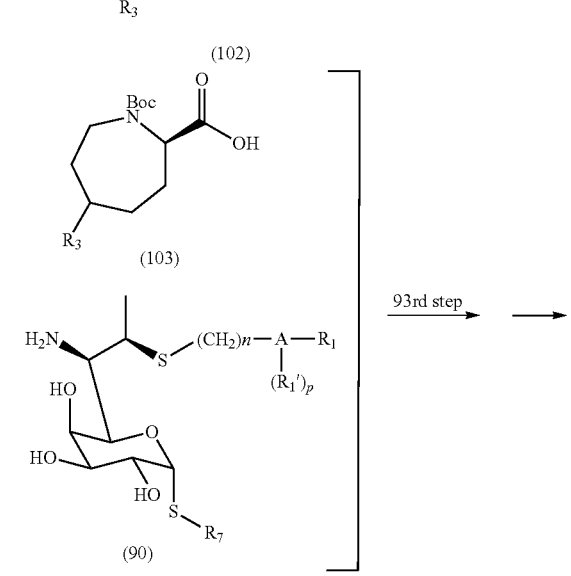

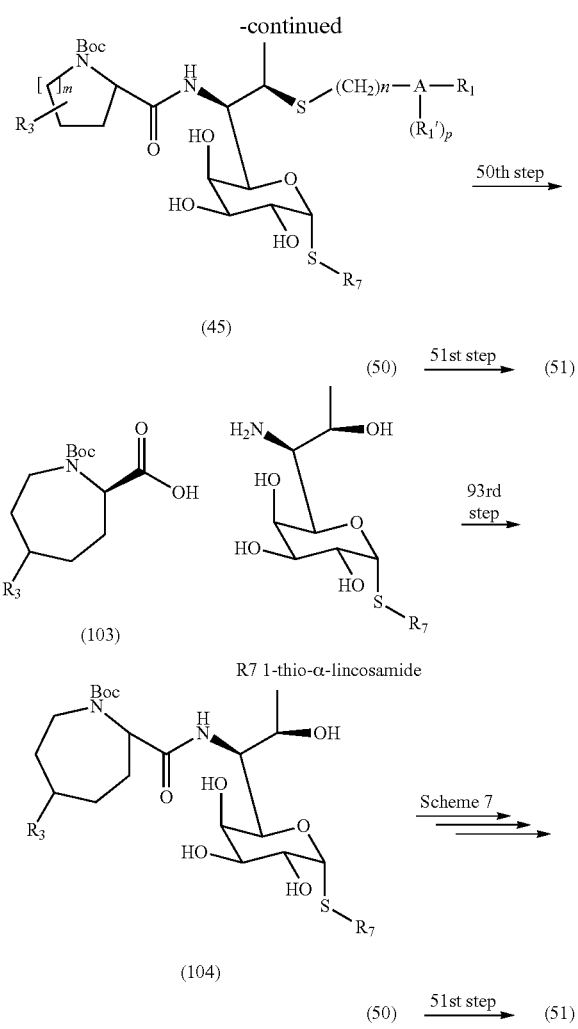

formula (100), for example, according to the process described in the seventy-seventh step.

In the one hundred and third step, the compound of formula (100) can be converted to the compound of formula (101), for example, by adding rhodium-carbon to the compound of formula (100) in a methanol solvent and allowing a reaction to proceed in a hydrogen atmosphere (0.7 MPa). The reaction solvent in this reaction may be a conventional alcohol solvent in addition to methanol, and preferred examples thereof include ethanol. The reaction temperature is 0° C. to room temperature, and the reaction time is 0.5 to 24 hr.

In the one hundred and fourth step, the compound of formula (101) can be converted to the compound of formula (102), for example, by reacting the compound of formula (101) with 1 to 10 equivalents of di-tert-butyl dicarbonate in a dioxane-water mixed solvent in the presence of a base. The reaction solvent in this reaction may be a conventional solvent in addition to the dioxane-water mixed solvent. A combination of a polar solvent such as tetrahydrofuran, diethyl ether, N,N-dimethylformamide, dimethylsulfoxide, or 1-methylpyrrolidone with water is preferred. The base may be a conventional organic base or an inorganic base, and preferred examples thereof include 7-methyl-1-5-7-triazabicyclo[4,4,0]-5-decene and lithium hydroxide. The base is preferably used in an excessive amount. The reaction temperature is 0 to 50° C., and the reaction time is 0.5 to 24 hr.

In the one hundred and fifth step, the compound of formula (102) can be converted to the compound of formula (103), for example, according to the process described in the seventy-fifth step.

Twelfthly, the processes described in schemes 2 to 6 are an example in which m=1. This is true of the compound of formula (45) or the compound of formula (51) wherein m=2 or 3.

Thirteenthly, a group of compounds of formula (1) wherein $R_5$ and $R_6$ represent H and m=1 to 3 can be produced, for example, by producing the compound of formula (41), the compound of formula (67), the compound of formula (80), and the compound of formula (104) according to the process described in scheme 7 or scheme 10, then subjecting the compounds to the forty-eighth step to give the compound of formula (105) and subjecting the compound to the following process.

Specifically, in the one hundered and second step, the compound of formula (75) can be converted to the compound of Scheme 11

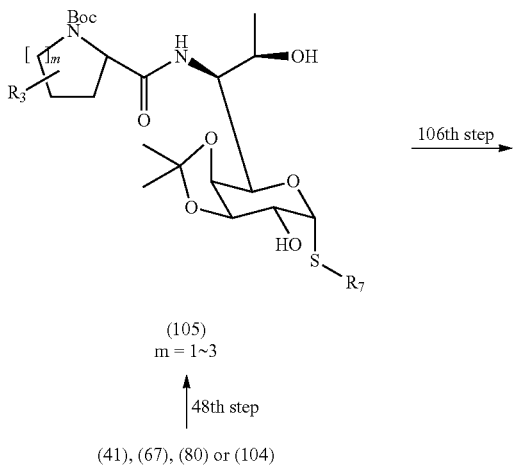

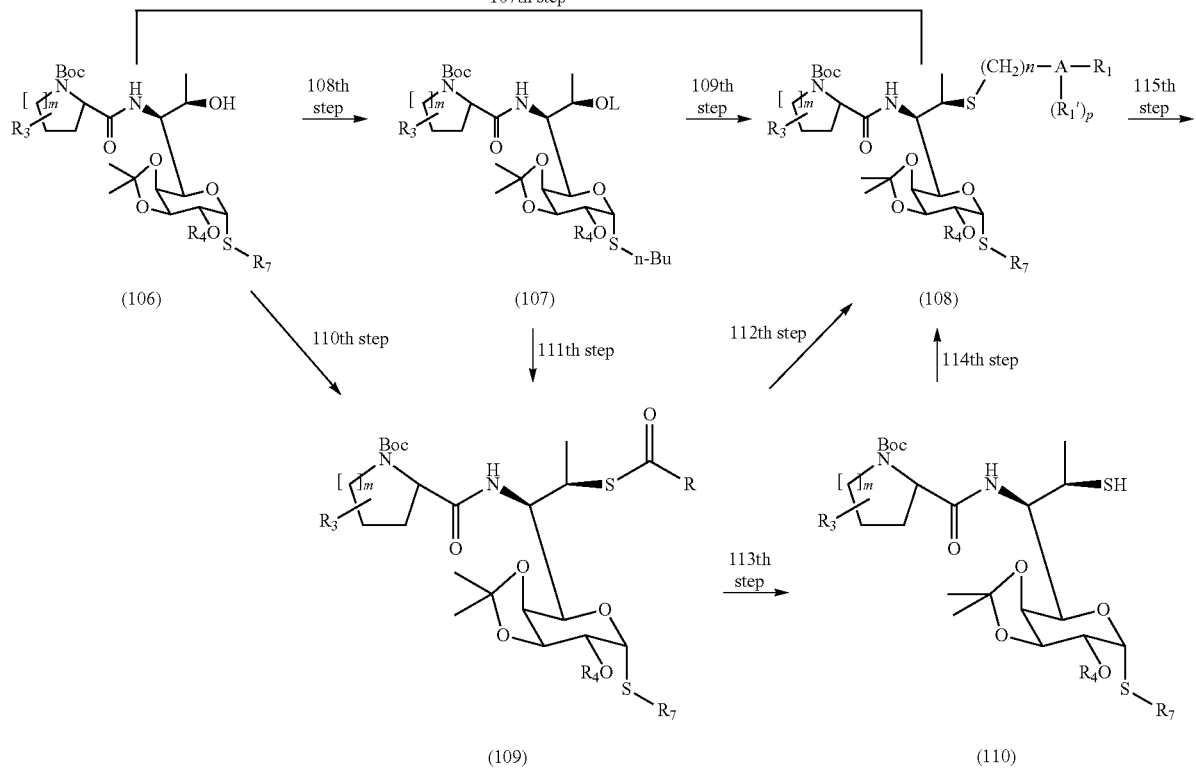
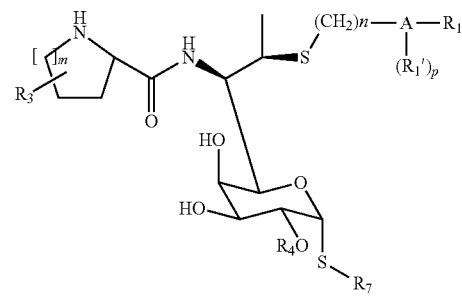
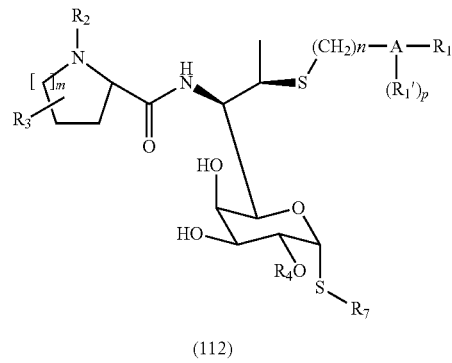

Specifically, in the one hundred and sixth step, the compound of formula (105) can be converted to the compound of formula (106), for example, by reacting the compound of formula (105) with 1 to 10 equivalents of a reagent represented by $R_4X$, wherein X represents a halide, in a benzene solvent in the presence of a base. The reaction solvent in this reaction may be a conventional solvent in addition to benzene, and preferred examples thereof include toluene, tetrahydrofuran, diethyl ether, dimethylsulfoxide, 1-methylpyrrolidone, and dimethylformamide. The base may be a conventional inorganic base, and preferred examples thereof include potassium tert-butoxide, sodium tert-butoxide, sodium hydroxide, potassium hydroxide, and sodium hydride. The base is preferably used in an excessive amount. The reaction temperature is 0 to 50° C., and the reaction time is 0.5 to 24 hr. A method may also be adopted in which the reaction is carried out with the addition of 1 to 10 equivalents of tetra n-butylammonium iodide, tetra-n-butylammonium hydrogen sulfate or the like as an additive.

In the one hundred and seventh step, the compound of formula (106) can be converted to the compound of formula (108), for example, according to the process described in the thirty-ninth step.

In the one hundred and eighth step, the compound of formula (106) can be converted to the compound of formula (107), for example, according to the process described in the fortieth step.

In the one hundred and ninth step, the compound of formula (107) can be converted to the compound of formula (108), for example, according to the process described in the forty-first step.

In the one hundred and tenth step, the compound of formula (106) can be converted to the compound of formula (109), for example, according to the process described in the forty-second step.

In the one hundred and eleventh step, the compound of formula (107) can be converted to the compound of formula (109), for example, according to the process described in the forty-third step.

In the one hundred and twelfth step, the compound of formula (109) can be converted to the compound of formula (108), for example, according to the process described in the forty-fourth step.

In the one hundred and thirteenth step, the compound of formula (109) can be converted to the compound of formula (110), for example, according to the process described in the forty-sixth step.

In the one hundred and fourteenth step, the compound of formula (110) can be converted to the compound of formula (108), for example, according to the process described in the forty-seventh step.

In the one hundred and fifteenth step, the compound of formula (108) can be converted to the compound of formula (111), for example, according to the process described in the fiftieth step.

In the one hundred and sixteenth step, the compound of formula (111) can be converted to the compound of formula (112), for example, according to the process described in the fifty-first step.

Fourteenthly, a group of compounds of formula (1) wherein $R_4$, $R_5$ and $R_6$ represent (i) optionally substituted acyl or (ii) optionally substituted $C_{1-6}$ alkyl can be produced, for example, by producing the compound of formula (45) or the compound of formula (51) according to the process described in scheme 7 and then subjecting the resultant compound to the following process.

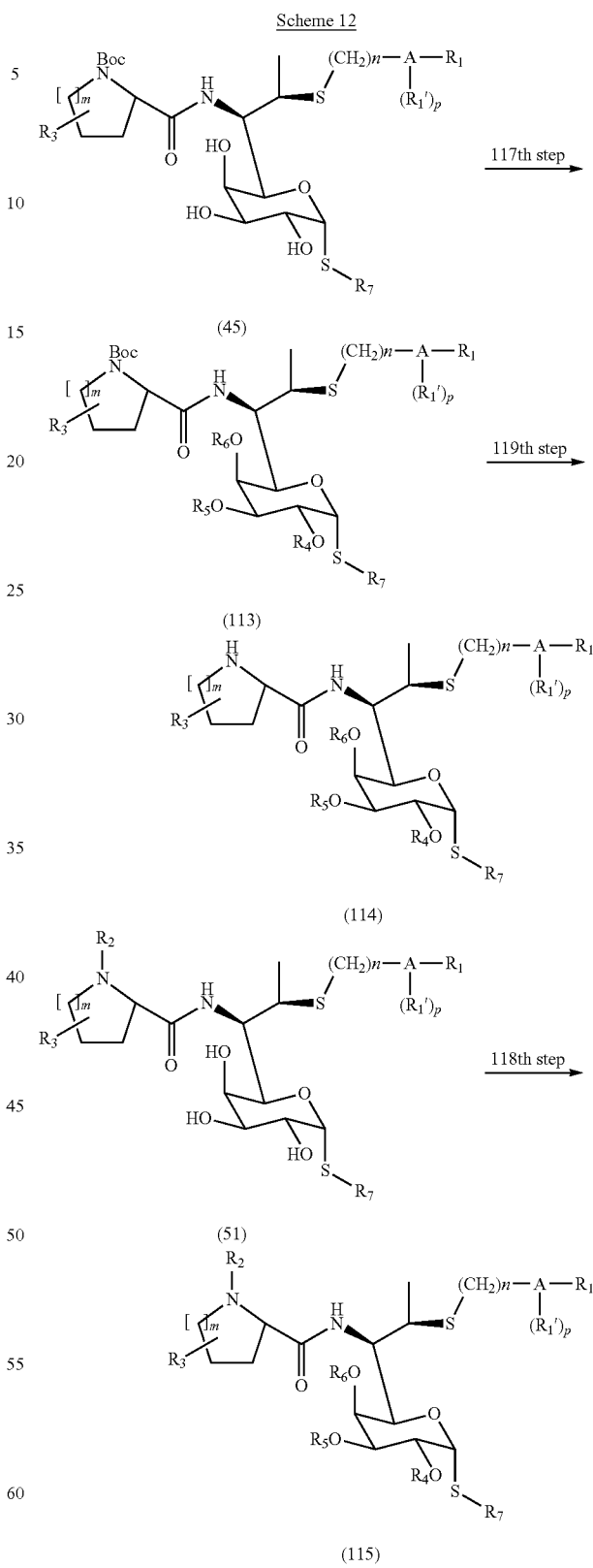

In the one hundred and seventeenth step and one hundred and eighteenth step, the conversion of the compound of formula (45) to the compound of formula (113) and the conversion of the compound of formula (51) to the compound of formula (115) can be carried out, for example, by process (i) in which the compound of formula (45) or formula (51) is reacted with 1 to 10 equivalents of an optionally substituted acid anhydride or acyl halide in a pyridine solvent in the presence of a base. The reaction solvent in this reaction may be a conventional polar solvent in addition to pyridine, and preferred examples thereof include tetrahydrofuran, dimethylsulfoxide, 1-methylpyrrolidone, and dimethylformamide. The base may be a conventional organic base or inorganic base, and preferred examples thereof include dimethylaminopyridine and triethylamine. The amount of the base is preferably an excessive amount. The reaction temperature is 0 to 100° C., and the reaction time is 0.5 to 24 hr. In process (ii), the comtemplated compound can be produced according to the process described in the one hundred and sixth step.

In the one hundred and nineteenth step, the compound of formula (113) can be converted to the compound of formula (114), for example, according to the process described in the fiftieth step.

EXAMPLES

Reference Examples and Examples for producing the compounds of the present invention and physicochemical properties of the compounds of the present invention will be described. However, it should be noted that the Examples are not intended as a limitation of the invention and the present invention includes all of methods for synthesizing, producing, extracting, and purifying the compounds by applying not only modification means of the Examples but also conventional means based on the properties of the compounds elucidated by the present invention.

Compounds synthesized by Reference Examples were used in the Examples.

Step (i) of Reference Example 1

2-(4-Bromophenyl)-N,N-dimethylethanamine

Formaldehyde (0.58 ml, 6.927 mmol) and 0.4 ml (6.927 mmol) of acetic acid were added in that order to a solution of 231 mg (1.154 mmol) of 2-(4-bromophenyl)ethanamine in methanol (5 ml). Sodium tri(acetoxy)borohydride (1.47 g, 6.927 mmol) was then added thereto, and the mixture was stirred at room temperature for one hr. A saturated aqueous sodium hydrogencarbonate solution was added, and the mixture was then extracted with ethyl acetate. The organic layer was dried over anhydrous sodium sulfate and was then filtered. The filtrate was concentrated under the reduced pressure, and the residue was purified by preparative thin-layer chromatography (chloroform:methanol:28% aqueous ammonia=10:2:0.2) to give 244 mg (yield 93%) of the title compound.

$^1$H-NMR (400 MHz, CDCl$_3$) δ: 2.28 (6H, s), 2.47-2.53 (2H, m), 2.69-2.76 (2H, m), 7.07 (2H, d, =8.3 Hz), 7.39 (2H, d, J=8.5 Hz).

Separately, the procedure of step (i) of Reference Example 1 was repeated, except that 2-amino-1-(4-bromophenyl)ethanol was used instead of 2-(4-bromophenyl)ethanamine. The following compound thus synthesized was used in the Examples.

1-(4-Bromophenyl)-2-(dimethylamino)ethanol

Step (i) of Reference Example 2

1-(4-Bromobenzyl)-2,5-dihydro-1H-pyrrole

Triethylamine (0.135 ml, 0.958 mmol) and 60 µl (0.760 mmol) of methanesulphonyl chloride were added to a solution of 70.5 mg (0.377 mmol) of 4-bromobenzylalcohol in dichloromethane (2 ml) under ice cooling, and the mixture was stirred for 1.5 hr. The reaction solution was diluted with 10 ml of ethyl acetate, and the diluted solution was washed with an 8% aqueous sodium hydrogencarbonate solution. The aqueous layer was extracted twice with 3 ml of ethyl acetate. The organic layers were combined, were washed with 25% brine, and were dried over anhydrous sodium sulfate, followed by filtration. The filtrate was concentrated under the reduced pressure. The residue was dissolved in 1.8 ml of N,N-dimethylformamide, 87 µl of 2,5-dihydro-1H-pyrrole (70% purity, 0.793 mmol) was added to the solution, and the mixture was stirred at 80° C. for 3 hr. The reaction solution was diluted with 10 ml of ethyl acetate, and the diluted solution was washed thrice with 5 ml of water. The aqueous layer was extracted twice with 5 ml of ethyl acetate. The organic layers were combined, were washed with 25% brine, and were dried over anhydrous sodium sulfate, followed by filtration. The filtrate was concentrated under the reduced pressure, and the residue was purified by preparative thin-layer chromatography (chloroform:methanol=18:1) to give 63.8 mg (yield 71%) of the title compound.

$^1$H-NMR (300 MHz, CDCl$_3$) δ: 3.47 (4H, s), 3.76 (2H, s), 5.78 (2H, s), 7.24 (2H, d, J=8.4 Hz), 7.44 (2H, d, J=8.4 Hz).

MS (FAB) m/z 238 [M+H]$^+$.

The procedure of step (i) of Reference Example 2 was repeated, except that various amines were used instead of 2,5-dihydro-1H-pyrrole. The following compounds thus synthesized were used in the Examples.

1-(4-Bromophenyl)-N,N-dimethylmethanamine
1-(4-Bromobenzyl)-4-methylpiperazine
1-(4-Bromobenzyl)piperidine
$N^1$-(4-Bromobenzyl)-$N^2$,$N^2$-dimethylethane-1,2-diamine
1-(4-Bromobenzyl)azetidine
1-(4-Bromobenzyl)pyrrolidine
N-(4-Bromobenzyl)-N-methylethanamine
1-(4-Bromobenzyl)-1H-pyrrole
N-(4-Bromobenzyl)cyclopropanamine
N-(4-Bromobenzyl)butan-1-amine
N-(4-Bromobenzyl)propan-1-amine
N-(4-Bromobenzyl)-2-methoxyethanamine
N-(4-Bromobenzyl)-N-ethylethanamine The procedure of step (i) of Reference Example 2 was repeated, except that 4-bromophenethyl alcohol was used instead of 4-bromobenzylalcohol and various amines were used instead of 2,5-dihydro-1H-pyrrole. The following compounds thus synthesized were used in the Examples.

1-(4-Bromophenethyl)pyrrolidine
$N^1$-(4-Bromophenethyl)-$N^2$,$N^2$-dimethylethane-1,2-diamine
1-(4-Bromophenethyl)-4-methylpiperazine
2-(4-Bromophenethylamino)ethanol
N-(4-Bromophenethyl)cyclopropanamine
2-(4-Bromophenyl)-N-ethyl-N-methylethanamine
2-(4-Bromophenyl)-N,N-diethylethanamine

Step (ii) of Reference Example 2

$N^1$-(4-Bromophenethyl)-$N^1$,$N^2$,$N^2$-trimethylethane-1,2-diamine

The title compound (100.0 mg, yield 81%) was produced in the same manner as in step (i) of Reference Example 1, except that 117.0 mg (0.431 mmol) of $N^1$-(4-bromophenethyl)-$N^2$,$N^2$-dimethylethane-1,2-diamine produced in step (i) of Reference Example 2 was used.

$^1$H-NMR (400 MHz, CDCl$_3$) δ: 2.24 (6H, s), 2.31 (3H, s), 2.37-2.42 (2H, m), 2.50-2.55 (2H, m), 2.57-2.63 (2H, m), 2.71-2.76 (2H, m), 7.07 (2H, d, J=8.3 Hz), 7.39 (2H, d, J=8.3 Hz).

The following compound was synthesized in the same manner as in step (ii) of Reference Example 2, except that 2-(4-bromophenethylamino)ethanol produced in the same manner as in step (i) of Reference Example 2 was used. The compound thus synthesized was used in the Examples.

2-((4-Bromophenethyl)(methyl)amino)ethanol

N-(4-Bromobenzyl)-N-methylcyclopropanamine was synthesized in the same manner as in step (ii) of Reference Example 2, except that N-(4-bromobenzyl)cyclopropanamine produced in the same manner as in step (i) of Reference Example 2 was used. The compound thus synthesized was used in the Examples.

N-(4-Bromobenzyl)-N-methylbutan-1-amine was synthesized in the same manner as in step (ii) of Reference Example 2, except that N-(4-bromobenzyl)butan-1-amine produced in the same manner as in step (i) of Reference Example 2 was used. The compound thus synthesized was used in the Examples.

N-(4-Bromobenzyl)-N-methylpropan-1-amine was synthesized in the same manner as in step (ii) of Reference Example 2, except that N-(4-bromobenzyl)propan-1-amine produced in the same manner as in step (i) of Reference Example 2 was used. The compound thus synthesized was used in the Examples.

N-(4-Bromobenzyl)-2-methoxy-N-methylethanamine was synthesized in the same manner as in step (ii) of Reference Example 2, except that N-(4-bromobenzyl)-2-methoxyethanamine produced in the same manner as in step (i) of Reference Example 2 was used. The compound thus synthesized was used in the Examples.

Step (iii) of Reference Example 2

1-(4-Bromophenyl)-2-(dimethylamino)ethanone

A 2.0 M solution of dimethylamine (0.5 mmol) in methanol was added to a solution of 2-bromo-1-(4-bromophenyl)ethanone (114.5 mg, 0.41 mmol) in tetrahydrofuran (2 ml), and the mixture was stirred at room temperature for 15 min. The solvent was removed by distillation, and the residue was then purified by column chromatography on silica gel (hexane:ethyl acetate=10:1 to 0:100) to give 84.7 mg (yield 86%) of the title compound.

$^1$H-NMR (400 MHz, CDCl$_3$) δ: 2.41 (6H, s), 3.77 (2H, s), 7.60 (2H, ddd, J=8.8, 2.1, 2.1 Hz), 7.87 (2H, ddd, J=8.8, 2.1, 2.1 Hz).

MS (GC) m/z 241 [M]$^+$

Step (iv) of Reference Example 2

(R)-1-(4-Bromobenzyl)pyrrolidin-3-ol

Diisopropylethylamine (1.57 ml, 9.00 mmol) was added to a solution (15 ml) of 1.50 g (6.00 mmol) of 4-bromobenzyl bromide and 1.11 g (9.00 mmol) of (R)-pyrrolidin-3-ol hydrochloride in dimethylformamide and the mixture was stirred at room temperature for one hr. The solvent was removed by distillation under the reduced pressure. Water and 1 N hydrochloric acid were then added to the residue, and the mixture was washed with ethyl acetate. A 5 N aqueous sodium hydroxide solution and an aqueous sodium hydrogencarbonate solution were added thereto, and the mixture was extracted with ethyl acetate. The extract was dried over anhydrous sodium sulfate and was then filtered. The filtrate was concentrated under the reduced pressure to give 1.09 g (yield 71%) of the title compound.

$^1$H-NMR (400 MHz, CDCl$_3$) δ: 1.68-1.79 (1H, m), 2.14-2.33 (2H, m), 2.52 (1H, dd, J=10.0, 5.1 Hz), 2.60-2.68 (1H, m), 3.34 (1H, dt, J=4.9, 8.8 Hz), 3.57 (2H, s), 4.30-4.37 (1H, m), 7.20 (2H, d, J=8.3 Hz), 7.44 (2H, d, J=8.3 Hz).

Separately, the following compounds were synthesized in the same manner as in step (iv) of Reference Example 2, except that various amines were used instead of (R)-pyrrolidin-3-ol. The following compounds thus synthesized were used in the Examples.

(R)-(1-(4-Bromobenzyl)pyrrolidin-2-yl)methanol
(S)-(1-(4-Bromobenzyl)pyrrolidin-2-yl)methanol
(S)-1-(4-Bromobenzyl)pyrrolidin-3-ol
(R)-1-(4-Bromobenzyl)-2-(methoxymethyl)pyrrolidine
(S)-1-(4-Bromobenzyl)-2-(methoxymethyl)pyrrolidine

Step (v) of Reference Example 2

(R)-1-(4-Bromobenzyl)-3-methoxypyrrolidine

Sodium hydride (55% in paraffin liquid) (61.1 mg, 1.40 mmol) and 0.0874 ml (1.40 mmol) of methyl iodide were added to a solution of 300 mg (1.17 mmol) of the title compound in step (iv) of Reference Example 2 in tetrahydrofuran (3 ml), and the mixture was stirred at room temperature for one hr. Water was added to the reaction solution, and the mixture was extracted with ethyl acetate. The organic layer was dried over anhydrous sodium sulfate and was then filtered. The filtrate was concentrated under the reduced pressure, and the residue was purified by column chromatography on silica gel (chloroform:methanol=97:3) to give 108 mg (yield 34%) of the title compound.

$^1$H-NMR (400 MHz, CDCl$_3$) δ: 1.77-1.85 (1H, m), 2.02-2.13 (1H, m), 2.42-2.49 (1H, m), 2.54 (1H, dd, J=10.2, 3.4 Hz), 2.62-2.74 (2H, m), 3.27 (3H, s), 3.54 (1H, d, J=12.9 Hz), 3.58 (1H, d, J=12.9 Hz), 3.88-3.96 (1H, m), 7.21 (2H, d, J=8.3 Hz), 7.43 (2H, d, J=8.3 Hz).

MS (FAB) m/z 270 [M+H]$^+$.

(S)-1-(4-Bromobenzyl)-3-methoxypyrrolidine was synthesized in the same manner as in step (v) of Reference Example 2, except that (S)-1-(4-bromobenzyl)pyrrolidin-3-ol produced in the same manner as in step (iv) of Reference Example 2 was used. The compound thus synthesized was used in the Examples.

Step (vi) of Reference Example 2

(S)-1-(1-(4-Bromobenzyl)pyrrolidin-2-yl)-N,N-dimethylmethanamine

Thionyl chloride (0.433 ml, 5.93 mmol) was added under ice cooling to a solution of 534 mg (1.98 mmol) of (S)-(1-(4-bromobenzyl)pyrrolidin-2-yl)methanol in chloroform (5 ml) produced in the same manner as in step (iv) of Reference Example 2, and the mixture was stirred with heating under reflux for 2 hr 20 min. The reaction solution was cooled to room temperature and was then concentrated under the reduced pressure. A 100 mg portion of the residue (668 mg) was dissolved in 0.2 ml of dimethylformamide. Dimethylamine (a 2 M tetrahydrofuran solution, 1.5 ml) was added to the solution. The mixture was treated with a microwave reaction apparatus at 100° C. for 30 min and then at 120° C. for 4 hr. The reaction solution was concentrated under the reduced pressure, and the residue was purified by column chromatography on silica gel (chloroform:methanol:concentrated aqueous ammonia=9:0.6:0.06) to give 53 mg of the title compound.

$^1$H-NMR (400 MHz, CDCl$_3$) δ: 1.58-1.75 (3H, m), 1.94-2.04 (1H, m), 2.06-2.14 (1H, m), 2.24 (6H, s), 2.25-2.31 (1H, m), 2.42 (1H, dd, J=4.1, 12.1 Hz), 2.53-2.60 (1H, m), 2.85-2.91 (1H, m), 3.22 (1H, d, J=13.2 Hz), 4.08 (1H, d, J=13.2 Hz), 7.20 (2H, d, J=8.3 Hz), 7.42 (2H, d, J=8.3 Hz).

MS (EI) m/z 296 M$^+$.

Step (vii) of Reference Example 2

1-(4-Bromophenyl)-N-methylmethanamine

4-Bromobenzyl bromide (200 mg, 0.800 mmol) was added slowly to a 2 M solution (4 ml) of methanamine in tetrahydrofuran, and the solution was stirred at room temperature for 24 hr. The reaction solution was adjusted to pH 3 by the addition of 1 N hydrochloric acid and was then washed twice with diethyl ether. A saturated aqueous sodium hydrogencarbonate solution was added to the aqueous layer, and the mixture was extracted with ethyl acetate. The extract was dried over anhydrous sodium sulfate and was then filtered. The filtrate was concentrated under the reduced pressure to give 136.1 mg (yield 85%) of the title compound.

$^1$H-NMR (400 MHz, CD$_3$OD) δ: 2.35 (3H, s), 3.78 (2H, s), 7.24 (2H, d, J=8.4 Hz), 7.47 (2H, d, J=8.4 Hz).

Step (viii) of Reference Example 2

N-(4-Bromobenzyl)-1-cyclopropyl-N-methylmethanamine

The title compound (71.0 mg, yield 88%) was produced in the same manner as in step (i) of Reference Example 1, except that 63.7 mg (0.318 mmol) of the title compound in step (vii) of Reference Example 2 was used and cyclopropanaldehyde was used instead of formaldehyde.

$^1$H-NMR (400 MHz, CDCl$_3$) δ: 0.06-0.12 (2H, m), 0.48-0.56 (2H, m), 0.84-0.96 (1H, m), 2.27 (2H, d, J=6.5 Hz), 2.28 (3H, s), 3.49 (2H, s), 7.21 (2H, d, J=8.3 Hz), 7.43 (2H, d, J=8.3 Hz).

Step (i) of Reference Example 3

2-(4-Bromophenyl)-3-(dimethylamino)acrylaldehyde

The title compound (171 mg, yield 76%) was produced in the same manner as in step (i) of Reference Example 1, except that a solution (2.64 ml) of 200 mg (0.881 mmol) of 2-(4-bromophenyl)malonaldehyde and 2 M dimethylamine (5.28 mmol) in methanol was used.

$^1$H-NMR (400 MHz, CDCl$_3$) δ: 2.20-3.50 (6H, br), 6.70-6.90 (1H, br), 7.06 (2H, ddd, J=2.0, 2.4, 8.3 Hz), 7.46 (2H, ddd, J=2.0, 2.4, 8.3 Hz), 9.07 (1H, s).

Step (i) of Reference Example 4

N-(4-Bromophenethyl)-2-nitrobenzenesulfonamide

Triethylamine 0.7 ml (5.0 mmol) was added to a solution of 500 mg (2.5 mmol) of 2-(4-bromophenyl)ethanamine in tetrahydrofuran (5 ml). 2-Nitrobenzenesulfonyl chloride (664.6 mg, 3.0 mmol) was then added thereto, and the mixture was stirred at room temperature for one hr. Thereafter, a saturated aqueous sodium hydrogencarbonate solution was added thereto, and the mixture was then extracted with ethyl acetate. The organic layer was dried over anhydrous sodium sulfate and was then filtered. The filtrate was concentrated under the reduced pressure. The residue was purified by column chromatography on silica gel (hexane:ethyl acetate=3:1) to give 915 mg (yield 95%) of the title compound.

$^1$H-NMR (400 MHz, CDCl$_3$) δ: 2.80 (2H, t, J=6.8 Hz), 3.40 (2H, dt, J=5.9, 6.8 Hz), 5.34 (1H, t, J=5.8 Hz), 6.97 (2H, ddd, J=1.9, 2.7, 8.3 Hz), 7.31 (2H, ddd, J=1.9, 2.7, 8.3 Hz), 7.70 (1H, dt, J=1.7, 7.6 Hz), 7.74 (1H, dt, J=1.7, 7.6 Hz), 7.81-7.86 (1H, m), 8.01-8.05 (1H, m).

Step (ii) of Reference Example 4

N-(4-Bromophenethyl)-N-methyl-2-nitrobenzenesulfonamide

Potassium carbonate (270 mg, 1.95 mmol) and 122 μl (1.95 mmol) of methyl iodide were added to a solution of 500 mg (1.30 mmol) of the title compound in step (i) of Reference Example 4 in N,N-dimethylformamide (4 ml), and the mixture was stirred at room temperature for 2.3 hr. The reaction solution was diluted with ethyl acetate. The diluted solution was washed with 10% brine and was then dried over anhydrous sodium sulfate. The filtrate was concentrated to give 520 mg (yield 100%) of the title compound.

$^1$H-NMR (400 MHz, CDCl$_3$) δ: 2.86 (2H, t, J=7.6 Hz), 2.93 (3H, s), 3.47 (2H, t, J=7.6 Hz), 7.04-7.09 (2H, m), 7.34-7.38 (2H, m), 7.58-7.72 (3H, m), 7.88-7.92 (1H, m).

MS (FAB) m/z 399 [M+H]$^+$.

The following compound was synthesized in the same manner as in step (ii) of Reference Example 4. The following compound thus synthesized was used in the Examples.

N-(4-Bromophenethyl)-N-propyl-2-nitrobenzenesulfonamide

Step (iii) of Reference Example 4

N-(4-Bromophenethyl)-N-(2-(tert-butyldimethylsilyloxy)ethyl)-2-nitrobenzenesulfonamide Sodium hydride (55% in paraffin liquid) (22.7 mg, 0.52 mmol) was added to a solution of 100 mg (0.260 mmol) of the title compound in step (i) of Reference Example 4 in N,N-dimethylformamide (1.0 ml), and the mixture was stirred at room temperature for 30 min. Thereafter, 186.3 mg (0.779 mmol) of (2-bromoethoxy)(tert-butyl)dimethylsilane was added thereto, and the mixture was stirred at 100° C. for 1.5 hr. The reaction solution was cooled to room temperature, a saturated aqueous sodium hydrogencarbonate solution was added thereto, and the mixture was extracted with ethyl acetate. The organic layer was dried over anhydrous sodium sulfate and was then filtered. The filtrate was concentrated under the reduced pressure. The residue was purified by column chromatography on silica gel (hexane:ethyl acetate=2:1) to give 118 mg (yield 84%) of the title compound.
$^1$H-NMR (400 MHz, CDCl$_3$) δ: 0.03 (6H, s), 0.86 (9H, s), 2.84 (2H, t, J=7.8 Hz), 3.49 (2H, t, J=5.6 Hz), 3.60 (2H, t, J=7.8 Hz), 3.75 (2H, t, J=5.6 Hz), 7.00 (2H, d, J=8.4 Hz), 7.31 (2H, d, J=8.4 Hz), 7.58-7.62 (2H, m), 7.65-7.91 (1H, m), 7.91-7.93 (1H, m).
MS (FAB) m/z 543 [M+H]$^+$ Step (i) of Reference Example 5

Tert-butyl 2-(4-bromophenyl)-2-oxoethylcarbamate

Sodium hydrogencarbonate (844.6 mg, 10 mmol) was added to an aqueous methanol solution (28 ml, methanol:water=1:1) of 1.0 g (4.0 mmol) of 2-amino-1-(4-bromophenyl)ethanone hydrochloride. Di-tert-butyl dicarbonate (1.28 ml, 6 mmol) was then added thereto, and the mixture was stirred at room temperature overnight. The reaction solution was poured into iced water, and the mixture was filtered. The residue was then washed with water to give 1.068 mg (yield 84%) of the title compound.
$^1$H-NMR (400 MHz, CDCl$_3$) δ: 1.48 (9H, s), 4.62 (2H, brd, J=4.6 Hz), 7.64 (2H, ddd, J=8.7, 2.0, 2.0 Hz), 7.82 (2H, ddd, J=8.7, 2.0, 2.0 Hz).
MS (FAB) m/z 314 [M+H]$^+$ Step (i) of Reference Example 6

4-Bromo-2-nitrophenethyl acetate (title compound 1 in the Reference Example)
4-Bromo-3-nitrophenethyl acetate (title compound 2 in the Reference Example)

4-Bromophenethyl alcohol (500 mg, 2.5 mmol) was dissolved in acetic anhydride (4 ml), and a mixed solution composed of 940 mg (15.2 mmol) of nitric acid (d=1.42) and 0.5 ml of sulfuric acid was added dropwise thereto at 4° C. under ice cooling. After the dropwise addition, the mixture was stirred at room temperature for 16 hr. The reaction solution was poured into 10 ml of iced water and was neutralized with potassium carbonate and sodium hydrogencarbonate. The resultant precipitate was dissolved in 20 ml of ethyl acetate, and the solution was dried over anhydrous sodium sulfate. After filtration, the filtrate was concentrated under the reduced pressure, and the residue was purified by column chromatography on silica gel (ethyl acetate:hexane=1:2) to give 277 mg (yield 39%) of the title compound 1 in the Reference Example and 245 mg (yield 34%) of the title compound 2 in the Reference Example.
(Title Compound 1 in the Reference Example)
$^1$H-NMR (400 MHz, CD$_3$OD) δ: 2.03 (3H, s), 2.98 (2H, t, J=6.6 Hz), 4.30 (2H, t, J=6.6 Hz), 7.30 (1H, m), 7.67 (1H, m), 7.72 (1H, m).
MS (API) m/z 288 [M+H]$^+$.
(Title Compound 2 in the Reference Example)
$^1$H-NMR (400 MHz, CD$_3$OD) δ: 2.02 (3H, s), 3.21 (2H, t, J=6.6 Hz), 4.35 (2H, t, J=6.6 Hz), 7.28 (1H, m), 7.68 (1H, m), 8.10 (1H, m).
MS (API) m/z 288 [M+H]$^+$.

Step (ii) of Reference Example 6

2-(4-Bromo-2-nitrophenyl)ethanol

4-Bromo-2-nitrophenethyl acetate (270 mg, 0.96 mmol) was dissolved in 4 ml of methanol. A 5 N aqueous NaOH solution (0.97 ml, 4.82 mmol) was added to the solution at room temperature with stirring, and the mixture was stirred at room temperature for 2 hr. A 10% aqueous ammonium chloride solution (5 ml) was added to the reaction solution, and the mixture was neutralized with a 1 N aqueous HCl solution. The resultant precipitate was dissolved in 20 ml of ethyl acetate, and the solution was dried over anhydrous sodium sulfate. After filtration, the filtrate was concentrated under the reduced pressure, and the residue was purified by column chromatography on silica gel (ethyl acetate:hexane=1:1) to give 198 mg (yield 83%) of the title compound.
$^1$H-NMR (400 MHz, CDCl$_3$) δ: 2.90 (2H, m,), 3.91 (2H, m), 7.32 (1H, m), 7.67 (1H, m), 7.74 (1H, m).
MS (API) m/z 246 [M+H]$^+$.
In the same manner as described above, 245 mg (0.85 mmol) of 4-bromo-3-nitrophenethyl acetate was treated to give 155 mg (yield 74%) of 2-(4-bromo-3-nitrophenyl)ethanol.
$^1$H-NMR (400 MHz, CDCl$_3$) δ: 3.13 (2H, m), 3.94 (2H, m), 7.32 (1H, m), 7.67 (1H, m), 8.08 (1H, m).
MS (API) m/z 246 [M+H]$^+$.

Step (iii) of Reference Example 6

2-(4-Bromo-2-nitrophenyl)-N,N-dimethylethanamine

The title compound was produced in the same manner as in step (i) of Reference Example 2, except that the title compound in step (ii) of Reference Example 6 was used.

Step (iv) of Example 6

5-Bromo-2-(2-(dimethylamino)ethyl)-N,N-dimethylaniline

The title compound (42 mg, 0.15 mmol) in step (iii) of Example 6 was dissolved in 2 ml of methanol. A 1 N aqueous HCl solution (1 ml) and 0.46 ml of a 37% formalin solution were added to the solution. Sulfidated Pt/C (40 mg) was added to the reaction solution, and was stirred in a hydrogen atmosphere at room temperature for 4 hr. The catalyst was removed by filtration from the reaction solution and was concentrated under the reduced pressure. The residue was purified by NH column chromatography on silica gel (chloroform:methanol:aqueous ammonia=20:1:0.1) to give 20 mg (yield 50%) of the title compound.
$^1$H-NMR (400 MHz, CDCl$_3$) δ: 2.24 (6H, s), 2.46 (2H, m), 2.60 (6H, m), 2.76 (2H, m), 6.98 (1H, m), 7.06 (1H, m), 7.19 (1H, m).
MS (API) m/z 287 [M+H]$^+$.

Step (i) of Reference Example 7

4-Bromo-N-(2-(dimethylamino)ethyl)benzamide

4-Bromophenylcarboxylic acid (100.0 mg, 0.497 mmol), 100.8 mg (0.746 mmol) of 1-hydroxybenzotriazole, 143.0 mg (0.746 mmol) of 1-ethyl-3-(3-dimethylaminopropyl)carbodiimide hydrochloride, and N,N-dimethylformamide (1.0 ml) were added in that order, and the mixture was stirred at room temperature for 20 min. Thereafter, 0.080 ml (0.746 mmol) of N$^1$,N$^1$-dimethylethane-1,2-diamine was added thereto, and the mixture was stirred at room temperature for one hr. A saturated aqueous sodium hydrogencarbonate solution was added thereto, and the mixture was then extracted with ethyl acetate. The extract was dried over anhydrous sodium sulfate and was then filtered. The filtrate was concentrated under the reduced pressure, and the residue was purified by preparative thin-layer chromatography (chloroform:methanol:28% aqueous ammonia=9:2:0.2) to give 127 mg (yield 94%) of the title compound.

$^1$H-NMR (400 MHz, CDCl$_3$) δ: 2.31 (6H, s), 2.57 (2H, t, J=6.8 Hz), 3.52 (2H, t, J=6.8 Hz), 7.62 (2H, ddd, J=2.0, 2.2, 8.6 Hz), 7.75 (2H, ddd, J=1.9, 2.2, 8.8 Hz).

Step (i) of Reference Example 8

2-(5-Bromopyridin-2-yl)-N,N-dimethylethanamine

A vinylboronic acid anhydride pyridine complex (86.2 mg (0.36 mmol), 39.3 mg (0.05 mmol) of a [1,1'-bis(diphenylphosphino)ferrocene]palladium(II) dichloride dichloromethane complex, and 209.0 mg (1.5 mmol) of potassium carbonate were added to a solution of 241.2 mg (1.0 mmol) of 2,5-dibromopyridine in dioxane-water (4 ml, 3:1), and the mixture was stirred at 80° C. for 3 hr. A saturated aqueous sodium hydrogencarbonate solution was added thereto, and the mixture was extracted with ethyl acetate. The organic layer was washed with saturated brine and was then dried over anhydrous sodium sulfate. The solvent was removed by distillation to give 208.4 mg of a crude product of 5-bromo-2-vinylpyridine. A 2.0 M dimethylamine methanol solution (5 ml, 10 mmol) was added to a solution of 208.4 mg of the crude product of 5-bromo-2-vinyl pyridine in acetic acid (1.4 ml), and the mixture was stirred at 80° C. overnight and at 90° C. for two nights. A saturated aqueous sodium hydrogencarbonate solution was added, and the mixture was extracted with ethyl acetate. The extract was dried over anhydrous sodium sulfate. The solvent was removed by distillation, and the residue was then purified by column chromatography on silica gel (hexane:ethyl acetate=10:1, chloroform:methanol=10:1) to give 49.7 mg (two steps, yield 22%) of the title compound.

$^1$H-NMR (400 MHz, CDCl$_3$) δ: 2.29 (6H, s), 2.66-2.70 (2H, m), 2.90-2.94 (2H, m), 7.10 (1H, d, J=8.3 Hz), 7.71 (1H, dd, J=8.3, 2.4 Hz), 8.58 (1H, d, J=2.4 Hz)

Step (ii) of Reference Example 8

2-(6-Bromopyridin-3-yl)-N,N-dimethylethanamine 2-(6-Bromopyridin-3-yl)ethanol (40 mg, 0.20 mmol) was dissolved in dichloroethane (3 ml), 200 mg of triethylamine was added to the solution, and the mixture was stirred at 4° C. under ice cooling. Mesyl chloride (68 mg, 0.60 mmol) was added to the reaction solution. After the dropwise addition, the mixture was stirred at 4° C. for 1 hr under ice cooling and was further stirred at room temperature for 30 min. The reaction solution was poured into 10 ml of iced water, was extracted with ml of ethyl acetate, and the extract was dried over anhydrous sodium sulfate. After filtration, the filtrate was concentrated under the reduced pressure. The residue was dissolved in DMF (2 ml), and the solution was stirred at room temperature. A 2 M solution (1 ml) of dimethylamine (2 mmol) in methanol was added thereto, and the mixture was stirred at 5.0° C. for 4 hr. The reaction solution was poured into 10 ml of iced water and was extracted with 20 ml of ethyl acetate. The extract was dried over anhydrous sodium sulfate. After filtration, the filtrate was concentrated under the reduced pressure, and the residue was purified by column chromatography on silica gel (ethyl acetate:methanol=10:1) to give 12 mg (yield 28.1%) of the title compound.

$^1$H-NMR (400 MHz, CDCl$_3$) δ: 2.27 (6H, s), 2.44 (2H, t, J=8.0 Hz), 2.66 (2H, t, J=8.0 Hz), 7.33 (2H, m), 8.15 (1H, m).

MS (API) m/z 228 [M+H]$^+$.

Step (iii) of Reference Example 8

1-(6-Bromopyridin-3-yl)-N,N-dimethylethanamine 1-(6-Bromopyridin-3-yl)ethanol (100 mg, 0.54 mmol) was dissolved in dichloroethane (4 ml), 200 mg of triethylamine was added thereto, and the mixture was stirred at 4° C. under ice cooling. Mesyl chloride (68 mg, 0.60 mmol) was added to the reaction solution. After the dropwise addition, the mixture was stirred at 4° C. under ice cooling and was further stirred at room temperature for 30 min. The reaction solution was poured into 10 ml of iced water and was extracted with 20 ml of ethyl acetate. The extract was dried over anhydrous sodium sulfate. After filtration, the filtrate was concentrated under the reduced pressure. The residue was dissolved in DMF (2 ml), and the solution was stirred at room temperature. A 2 M solution (1 ml) of dimethylamine (2 mmol) in methanol was added thereto, and the mixture was stirred at 50° C. for 4 hr. The reaction solution was poured into 10 ml of iced water and was extracted with 20 ml of ethyl acetate. The extract was dried over anhydrous sodium sulfate. After filtration, the filtrate was concentrated under the reduced pressure, and the residue was purified by column chromatography on silica gel (ethyl acetate:hexane=1:2) to give 15 mg (yield 33.1%) of the title compound.

$^1$H-NMR (400 MHz, CDCl$_3$) δ: 1.26 (3H, d, J=7.2 Hz), 2.12 (6H, s), 3.22 (1H, q, J=7.2 Hz), 7.37 (1H, m), 7.47 (1H, m), 8.21 (1H, m).

MS (API) m/z 228 [M+H]$^+$.

Step (i) of Reference Example 9

5-(2-(Dimethylamino)ethyl)-1,3,4-thiadiazol-2-amine

A solution of 2.00 ml (17.7 mmol) of 3-(dimethylamino)propanenitrile and 1.70 g (18.6 mmol) of thiosemicarbazide in trifluoroacetic acid (5 ml) was heated at 80° C. for 6 hr. The reaction solution was cooled to room temperature and was then diluted with water. The diluted solution was rendered weakly basic by the addition of a 10% aqueous potassium carbonate solution. The solution was extracted with chloroform, and the extract was dried over anhydrous sodium sulfate. The filtrate was concentrated, and the residue was washed with diethyl ether-ethyl acetate to give 1.00 g (yield 33%) of the title compound.

$^1$H-NMR (400 MHz, CDCl$_3$) δ: 2.29 (6H, s), 2.61 (2H, t, J=6.8 Hz), 3.06 (2H, t, J=6.8 Hz), 5.21 (2H, br).

MS (FAB) m/z 173 [M+H]$^+$.

The following compound was synthesized in the same manner as in step (i) of Reference Example 9, except that 4-(dimethylamino)butanenitrile was used instead of 3-(dimethylamino)propanenitrile.

5-(3-(Dimethylamino)propyl)-1,3,4-thiadiazol-2-amine

The following compound was synthesized in the same manner as in step (i) of Reference Example 9, except that 2-(dimethylamino)acetonitrile was used instead of 3-(dimethylamino)propanenitrile.

5-(3-(Dimethylamino)propyl)-1,3,4-thiadiazol-2-amine

Step (ii) of Reference Example 9

2-(5-Chloro-1,3,4-thiadiazol-2-yl)-N,N-dimethylethanamine

Tert-butyl nitrite (331 μl, 2.79 mmol) and 442 mg (4.46 mmol) of copper(II) chloride were added to a solution of 400 mg (2.23 mmol) of the title compound in step (i) of Reference Example 9 in acetonitrile (10 ml), and the mixture was stirred at room temperature for one hr. The reaction solution was diluted with ethyl acetate, and the insolubles were then removed by filtration. A 10% aqueous potassium carbonate solution was added to the filtrate. The mixture was extracted with ethyl acetate, and the extract was dried over anhydrous sodium sulfate. After filtration, the filtrate was concentrated to give 45.0 mg (yield 11%) of the title compound.

$^1$H-NMR (400 MHz, CDCl$_3$) δ: 2.31 (6H, s), 2.61 (2H, t, J=6.2 Hz), 3.20 (2H, t, J=6.2 Hz).

MS (FAB) m/z 192 [M+H]$^+$.

The following compounds were synthesized in the same manner as in step (ii) of Reference Example 9, except that 5-(3-(dimethylamino)propyl)-1,3,4-thiadiazol-2-amine and 5-(3-(dimethylamino)propyl)-1,3,4-thiadiazol-2-amine produced in the same manner as in step (i) of Reference Example 9 were used. The compounds thus synthesized were used in the Examples.

3-(5-Chloro-1,3,4-thiadiazol-2-yl)-N,N-dimethylpropan-1-amine 1-(5-Chloro-1,3,4-thiadiazol-2-yl)-N,N-dimethylethanamine Step (i) of Reference Example 10

3-(4-Bromophenyl)-N,N-dimethylprop-2-yn-1-amine

Copper(I) iodide (17.4 mg, 0.0913 mmol), 0.113 ml (1.06 mmol) of N,N-dimethylprop-2-yn-1-amine, and 67.8 mg (0.0966 mmol) of bistriphenyl phosphine palladium dichloride were added in that order to a solution of 280.8 mg (0.993 mmol) of 1-bromo-4-iodobenzene in diisopropylamine (2 ml), and the mixture was stirred at room temperature for 50 min. The reaction solution was filtered through Celite. The solvent was removed by distillation, and the residue was then purified by column chromatography on silica gel (hexane:ethyl acetate=2:1 to 0:100) to give 248.4 mg (yield 99%) of the title compound.

$^1$H-NMR (400 MHz, CDCl$_3$) δ: 2.37 (6H, s), 3.45 (2H, s), 7.29 (2H, ddd, J=8.6, 2.1, 2.1 Hz), 7.43 (2H, ddd, J=8.6, 2.1, 2.1 Hz).

MS (FAB) m/z 238 [M+H]$^+$.

The following compound was synthesized in the same manner as in step (i) of Reference Example 10, except that 1-bromo-3-iodobenzene was used instead of 1-bromo-4-iodobenzene. The compound thus synthesized was used in the Examples.

3-(3-Bromophenyl)-N,N-dimethylprop-2-yn-1-amine

Step (i) of Reference Example 11

5-(2-(Dimethylamine)ethyl)-1H-imidazole-2-thiol

Chlorothionoformate (0.456 ml, 3.30 mmol) was added dropwise to a solution of 180 mg (1.30 mmol) of 2-(1H-imidazol-5-yl)-N,N-dimethylethanamine and 657 mg (7.82 mmol) of sodium hydrogencarbonate in tetrahydrofuran-water (1:1, 8 ml) over a period of 10 min. The reaction solution was stirred at 80° C. for 17 hr. Brine was added thereto, and the mixture was extracted with a chloroform-isopropanol mixed solvent. The organic layer was dried over anhydrous sodium sulfate and was then filtered. The filtrate was concentrated under the reduced pressure, and the residue was purified by column chromatography on silica gel (chloroform:methanol:28% aqueous ammonia=90:10:0.1) to give 26.3 mg (yield 12%) of the title compound.

$^1$H-NMR (400 MHz, CDCl$_3$) δ: 2.30 (6H, s), 2.50-2.65 (2H, m), 6.45 (1H, s).

MS (FAB) m/z 172 (M+H)$^+$.

Step (i) of Reference Example 12

2-(4-Bromophenyl)propane-1,3-diol

Sodium borohydride (433 mg, 11.5 mmol) was added slowly to a solution of 2.0 g (8.81 mmol) of 2-(4-bromophenyl)malonaldehyde in tetrahydrofuran (20 ml) under ice cooling, and the mixture was stirred for 1.5 hr. A saturated aqueous sodium hydrogencarbonate solution was added thereto. The mixture was extracted with ethyl acetate, and the extract was dried over anhydrous sodium sulfate. The solvent was removed by distillation, and the residue was then purified by column chromatography on silica gel (hexane:ethyl acetate=1:1 to 1:4) to give 1.35 g (yield 66%) of the title compound.

$^1$H-NMR (400 MHz, CD$_3$OD) δ: 2.92 (1H, quin, J=6.6 Hz), 3.74 (2H, dd, J=6.6, 10.9 Hz), 3.83 (2H, dd, J=6.6, 10.9 Hz), 7.19 (2H, d, J=8.4 Hz), 7.44 (2H, d, J=8.4 Hz).

Step (ii) of Reference Example 12

2-(4-Bromophenyl)-N$^1$,N$^1$,N$^3$,N$^3$-tetramethylpropane-1,3-diamine

Triethylamine (525.2 mg, 5.19 mmol) was added to a solution of 200 mg (0.865 mmol) of the title compound in step (i) of Reference Example 12 in chloroform (2 ml), and the mixture was stirred at room temperature for 10 min. Thereafter, 396.6 mg (3.46 mmol) of methanesulfonyl chloride was added thereto, and the mixture was stirred for 30 min. A saturated aqueous sodium hydrogencarbonate solution was added thereto, the mixture was extracted with chloroform, and the extract was dried over anhydrous sodium sulfate. The solvent was removed by distillation, and the residue was dried. A 2 M solution (1.73 ml) of dimethylamine in tetrahydrofuran was then added thereto, and a reaction was allowed to proceed at 70° C. for 2 hr. A 2 M solution (2 ml) of dimethylamine in methanol was then added thereto, and the mixture was stirred at 70° C. for 26 hr. The reaction solution was then cooled to room temperature, and the solvent was removed by distillation. The residue was purified by preparative thin-layer chromatography (chloroform:methanol:28% aqueous ammonia=9:1:0.1) to give 74 mg (yield 30%) of the title compound.

$^1$H-NMR (400 MHz, CDCl$_3$) δ: 2.19 (12H, s), 2.43 (2H, dd, J=8.3, 12.4 Hz), 2.54 (2H, dd, J=6.6, 12.4 Hz), 2.92-3.03 (1H, m), 7.09 (2H, d, J=8.3 Hz), 7.42 (2H, d, J=8.3 Hz).

Step (i) of Reference Example 13

Tert-butyl 2-(4-bromophenyl)allyl(4-nitrophenylsulfonyl)carbamate

Triphenylphosphine (731.8 mg, 2.79 mmol) was added to a solution of 161.0 mg (0.697 mmol) of the title compound in step (i) of Reference Example 12 in tetrahydrofuran (6.8 ml), and the mixture was stirred at room temperature for 5 min. Thereafter, 364.3 mg (2.091 mmol) of diethylazodicarboxylate and tert-butyl 4-nitrophenylsulfonyl carbamate were added thereto, and the mixture was stirred at room temperature for 14 hr. A saturated aqueous sodium hydrogencarbonate solution was added thereto, and the mixture was extracted with ethyl acetate. The extract was dried over anhydrous sodium sulfate. The solvent was removed by distillation, and the residue was purified by column chromatography (hexane:ethyl acetate=2:1) to give 67 mg (yield 19%) of the title compound.

$^1$H-NMR (400 MHz, CDCl$_3$) δ: 1.36 (9H, s), 4.84 (2H, brs), 5.20-5.23 (1H, m), 5.42 (1H, brs), 7.27 (2H, d, J=8.5 Hz), 7.49 (2H, d, J=8.5 Hz), 8.04 (2H, d, J=9.1 Hz), 8.32 (2H, d, J=9.1 Hz).

Step (ii) of Reference Example 13

Tert-butyl 2-(4-bromophenyl)allylcarbamate

Potassium carbonate (27.9 mg, 0.202 mmol) was added to a solution of 67 mg (0.135 mmol) of the title compound in step (i) of Reference Example 13 in N,N-dimethylformamide (1 ml). 4-Bromobenzenethiol (38.2 mg, 0.202 mmol) was then stirred at room temperature for 3 hr. A saturated aqueous sodium hydrogencarbonate solution was added to the reaction solution, and the mixture was extracted with ethyl acetate. The extract was dried over anhydrous sodium sulfate. The solvent was removed by distillation, and the residue was purified by preparative thin-layer chromatography (hexane:ethyl acetate=3:1) to give 34 mg (yield 81%) of the title compound.

$^1$H-NMR (400 MHz, CDCl$_3$) δ: 1.43 (9H, s), 4.16 (2H, brd, J=5.6 Hz), 4.65 (1H, brs), 5.25 (1H, d, J=0.7 Hz), 5.47 (1H, s), 7.29 (2H, d, J=8.3 Hz), 7.46 (2H, d, J=8.3 Hz).

Step (i) of Reference Example 14

Tert-butyl 2-(4-bromophenyl)-3-hydroxypropyl(4-nitrophenylsulfonyl)carbamate

Triphenylphosphine (170.5 mg, 0.650 mmol) was added to a solution of 100.0 mg (0.433 mmol) of the title compound in step (i) of Reference Example 12 in tetrahydrofuran (4.2 ml), and the mixture was stirred at room temperature for 5 min. Thereafter, 0.120 ml (0.65 mmol) of diethyl azodicarboxylate and tert-butyl 4-nitrophenylsulfonylcarbamate were added thereto, and the mixture was stirred at room temperature for 13 hr. A saturated aqueous sodium hydrogencarbonate solution was added thereto, and the mixture was extracted with ethyl acetate. The extract was dried over anhydrous sodium sulfate. The solvent was removed by distillation, and the residue was purified by preparative thin-layer chromatography (hexane:ethyl acetate=2:1) to give 103 mg (yield 46%) of the title compound.

$^1$H-NMR (400 MHz, CDCl$_3$) δ: 1.33 (9H, s), 3.25-3.35 (1H, m), 4.07 (2H, dd, J=6.8, 14.6 Hz), 4.23 (2H, dd, J=8.0, 14.6 Hz), 7.24 (2H, d, J=8.4 Hz), 7.47 (2H, d, J=8.4 Hz), 7.92 (2H, d, J=8.9 Hz), 8.31 (2H, d, J=8.9 Hz).

Step (ii) of Reference Example 14

Tert-butyl 2-(4-bromophenyl)-3-hydroxypropylcarbamate

The title compound (18.0 mg, yield 46%) was produced in the same manner as in step (ii) of Reference Example 13, except that 61.0 mg (0.118 mmol) of the title compound in step (i) of Reference Example 14 was used.

$^1$H-NMR (400 MHz, CD$_3$OD) δ: 1.38 (9H, s), 2.89-2.98 (1H, m), 3.22-3.29 (1H, m), 3.35-3.42 (1H, m), 3.72 (2H, d, J=6.3 Hz), 7.17 (2H, d, J=8.4 Hz), 7.44 (2H, d, J=8.4 Hz).

Step (iii) of Reference Example 14

2-(4-Bromophenyl)-3-(dimethylamino)propan-1-ol

Trifluoroacetic acid (0.2 ml) cooled to 0° C. was added to 18.0 mg (0.0545 mmol) of the title compound in step (ii) of Reference Example 14, and the mixture was stirred for 45 min. Trifluoroacetic acid was removed by distillation under the reduced pressure. Formaldehyde (0.0136 ml, 0.164 mmol) and 0.0107 ml (0.164 mmol) of acetic acid were added in that order to a solution of the residue in methanol (0.5 ml). After 5 min from the addition, 69.3 mg (0.327 mmol) of sodium triacetoxy borohydride was added thereto, and the mixture was stirred at room temperature for 30 min. The solvent was removed by distillation, and the residue was purified by preparative thin-layer chromatography (chloroform:methanol:28% aqueous ammonia=9:2:0.2) to give 10.9 mg (yield 78%) of the title compound.

$^1$H-NMR (400 MHz, CD$_3$OD) δ: 2.33 (6H, s), 2.73 (1H, dd, J=7.6, 12.6 Hz), 2.91 (1H, dd, J=7.1, 12.6 Hz), 3.03-3.13 (1H, m), 3.67 (1H, dd, J=5.8, 10.7 Hz), 3.74 (1H, dd, J=7.3, 10.7 Hz), 7.20 (2H, d, J=8.5 Hz), 7.47 (2H, d, J=8.5 Hz).

Step (i) of Example S1

2,3,4-Tris-O-trimethylsilyl lincomycin

Trimethylsilyl chloride (90 ml, 71 mmol) and 65 ml (60 mmol) of hexamethyldisilazane were added to a solution of 50 g (122 mmol) of lincomycin in pyridine (200 ml) under ice cooling, and the mixture was stirred at room temperature for 2 hr. The solvent was removed by distillation, and the residue was diluted with hexane, followed by washing twice with water. The solvent was removed by distillation. An 80% aqueous acetic acid solution (22.5 ml) was added to a solution of the residue in methanol (150 ml), and the mixture was stirred at room temperature for 16 hr. A saturated aqueous sodium hydrogencarbonate solution (30 ml) was added to the reaction solution. The solvent was removed by distillation, and the residue was then diluted with hexane, followed by washing twice with water. The solvent was removed by distillation to give 69.5 g (yield 91%) of the title compound.

$^1$H-NMR (400 MHz, CDCl$_3$) δ: 0.10-0.20 (27H, m), 0.84-0.92 (3H, m), 1.13 (3H, d, J=6.3 Hz), 1.21-1.35 (4H, m), 1.75-2.07 (4H, m), 2.08 (3H, s), 3.38 (3H, s), 2.96-3.03 (1H, m), 3.05-3.20 (2H, m), 3.58 (1H, dd, J=2.2, 9.5 Hz), 3.79 (1H, d, J=2.2 Hz), 4.00 (1H, d, J=9.5 Hz), 4.10 (1H, dq, J=4.9, 6.3 Hz), 4.14 (1H, dd, J=5.6, 9.5 Hz), 4.33 (1H, ddd, J=4.9, 9.5, 10.0 Hz), 5.20 (1H, d, J=5.6 Hz), 7.43 (1H, d, J=10.0 Hz).

Step (ii) of Example S1

7-O-Methylsulfonyl-2,3,4-tris-O-trimethylsilyl lincomycin

Triethylamine (2.45 ml, 16.1 mmol) and 0.99 ml (12.8 mmol) of methanesulfonyl chloride were added to a solution of 4.0 g (6.42 mmol) of the title compound in step (i) of Example S1 in chloroform (20 ml) under ice cooling, and the mixture was stirred at room temperature for 3 hr. The reaction solution was diluted with 150 ml of chloroform. A 10% aqueous sodium hydrogencarbonate solution (150 ml) was then added to the diluted solution for washing. The organic layer was dried over anhydrous sodium sulfate. After filtration, the filtrate was concentrated, and the residue was purified by column chromatography on silica gel (hexane:ethyl acetate=100:0 to 75:25) to give 4.2 g (yield 93%) of the title compound.

$^1$H-NMR (400 MHz, CDCl$_3$) δ: 0.09-0.20 (27H, m), 0.84-0.94 (3H, m), 1.20-1.35 (4H, m), 1.40 (3H, d, J=6.8 Hz), 1.78-2.13 (7H, m), 2.40 (3H, s), 2.95-3.02 (1H, m), 3.09 (3H, s), 3.03-3.21 (1H, m), 3.52 (1H, dd, J=2.2, 9.5 Hz), 3.75 (1H, d, J=2.2 Hz), 3.90 (1H, d, J=9.7 Hz), 4.15 (1H, dd, J=5.6, 9.5 Hz), 4.74-4.79 (1H, m), 5.08-5.19 (2H, m), 7.60 (1H, d, J=11.0 Hz).

Step (iii) of Example S1

7-Acetylthio-7-deoxy-7-epi-2,3,4-tris-O-trimethylsilyl lincomycin

Potassium thioacetate (163 mg, 1.43 mmol) was added to a solution of 200 mg (0.285 mmol) of the title compound in step (ii) of Example S1 in N,N-dimethylformamide (0.65 ml), and the mixture was stirred at 60° C. for 4 hr. The reaction solution was diluted with 50 ml of ethyl acetate, and 50 ml of a 10% aqueous sodium hydrogencarbonate solution was then added to the diluted solution for washing. The organic layer was dried over anhydrous sodium sulfate. After filtration, the filtrate was concentrated, and the residue was purified by column chromatography on silica gel (hexane:ethyl acetate=100:0 to 75:25) to give 170 mg (yield 88%) of the title compound.

$^1$-NMR (400 MHz, CDCl$_3$) δ: 0.09-0.20 (27H, m), 0.84-0.93 (3H, m), 1.20-1.47 (7H, m), 1.76-1.87 (1H, m), 1.90-2.09 (6H, m), 2.31 (3H, s), 2.40 (3H, s), 2.93-3.02 (1H, m), 3.12-3.20 (1H, m), 3.56 (1H, dd, J=2.4, 9.5 Hz), 3.72 (1H, d, J=2.4 Hz), 3.94 (1H, d, J=10.0 Hz), 4.07 (1H, dt, J=2.2, 7.1 Hz), 4.15 (1H, dd, J=5.6, 9.5 Hz), 4.55 (1H, ddd, J=2.2, 10.0, 10.7 Hz), 5.18 (1H, d, J=5.6 Hz), 7.34 (1H, d, J=10.7 Hz).

MS (EI) m/z 681 M$^+$.

Step (iv) of Example S1

7-Acetylthio-7-deoxy-7-epilincomycin

To a solution of 10.6 g (15.6 mmol) of the title compound in step (iii) of Example S1 in methanol (50 ml) was added 38.9 ml of 2 N hydrochloric acid. The mixture was stirred at room temperature for 10 min. A 10% aqueous sodium hydrogencarbonate solution (30 ml) was added to the reaction solution, and methanol was removed by distillation under the reduced pressure. Ethyl acetate (250 ml) and 250 ml of 10% brine were added to the residue to perform extraction. The organic layer was dried over anhydrous sodium sulfate. After filtration, the filtrate was concentrated, and the residue was purified by column chromatography on silica gel (ethyl acetate:methanol=100:0 to 95:5) to give 7.05 g (yield 97%) of the title compound.

$^1$H-NMR (400 MHz, CDCl$_3$) δ: 0.88-0.95 (3H, m), 1.22-1.42 (7H, m), 1.82-2.13 (7H, m), 2.35-2.44 (7H, m), 2.72 (1H, d, J=10.0 Hz), 3.05 (1H, dd, J=4.6, 10.5 Hz), 3.19-3.28 (1H, m), 3.46-3.56 (1H, m), 3.61 (1H, br), 3.94 (1H, d, J=10.2 Hz), 4.11 (1H, dd, J=4.6, 10.5 Hz), 4.17 (1H, dq, J=2.4, 7.1 Hz), 4.25 (1H, ddd, J=2.4, 9.5, 10.2 Hz), 5.07 (1H, d, J=2.9 Hz), 5.31 (1H, d, J=5.6 Hz), 7.79 (1H, d, J=9.5. Hz).

Step (v) of Example S1

7-Deoxy-7-epi-7-mercaptolincomycin

Sodium methoxide (2.46 g, 45.5 mmol) was added to a solution of 7.05 g (15.2 mmol) of the title compound in step (iv) of Example S1 in methanol (50 ml), and the mixture was stirred at room temperature for 20 min. The reaction solution was neutralized by the addition of a saturated aqueous ammonium chloride solution, and methanol was then removed by distillation under the reduced pressure. A 10% aqueous sodium hydrogencarbonate solution (300 ml) was added to the residue, and the mixture was extracted with 300 ml of ethyl acetate. The organic layer was dried over anhydrous sodium sulfate. After filtration, the filtrate was concentrated, and the residue was purified by column chromatography on silica gel (chloroform:methanol:28% aqueous ammonia=95:5:0.1) to give 6.06 g (yield 94%) of the title compound.

$^1$H-NMR (400 MHz, CDCl$_3$) δ: 0.86-0.95 (3H, m), 1.22-1.36 (8H, m), 1.83-2.00 (2H, m), 2.04-2.13 (2H, m), 2.23 (3H, s), 2.38 (1H, d, J=5.1 Hz), 2.42 (3H, s), 2.72 (1H, d, J=10.0 Hz), 3.05 (1H, dd, J=4.6, 10.5 Hz), 3.19-3.28 (1H, m), 3.52-3.60 (1H, m), 3.61-3.67 (1H, m), 3.70-3.80 (1H, m), 3.90 (1H, d, J=10.2 Hz), 4.06-4.15 (2H, m), 5.15 (1H, d, J=3.7 Hz), 5.34 (1H, d, J=5.6 Hz), 8.16 (1H, d, J=9.3 Hz).

MS (FAB) m/z 422 [M+H]$^+$.

Step (vi) of Example S1

7-Deoxy-7-(4-(2-(dimethylamino)ethyl)phenylthio)-7-epilincomycin (Compound 1)

4-Bromo(2-(dimethylamino)ethyl)benzene (124.4 mg, 0.50 mmol) and 0.064 ml (0.37 mmol) of diisopropylethylamine were added to a solution of 106.0 mg (0.25 mmol) of the title compound in step (v) of Example S1, 15.8 mg (0.027 mmol) of 4,5-bis(diphenylphosphino)-9,9-dimethylsantene, and 12.9 mg (0.014 mmol) of tris(dibenzylideneacetone)dipalladium in dioxane (3 ml), and the mixture was then heated under reflux overnight. The reaction solution was filtered through Celite, and the residue was then purified by preparative thin-layer chromatography (chloroform:methanol:28% aqueous ammonia=10:1:0.1) to give 85.7 mg (yield 60%) of the title compound.

$^1$H-NMR (400 MHz, CD$_3$OD) δ: 0.90-0.95 (3H, m), 1.26 (3H, d, J=6.8 Hz), 1.30-1.38 (4H, m), 1.80-1.90 (1H, m), 1.96-2.04 (4H, m), 2.06-2.20 (2H, m), 2.40 (3H, s), 2.50 (6H, s), 2.70-2.90 (4H, m), 3.00 (1H, dd, J=10.7, 4.7 Hz), 3.20-3.28 (1H, m), 3.57 (1H, dd, J=10.3, 3.5 Hz), 3.73-3.75 (1H, m), 3.85 (1H, qd, J=7.0, 2.6 Hz), 4.10 (1H, dd, J=10.2, 5.6 Hz), 4.34 (1H, d, J=9.8 Hz), 4.40 (1H, dd, J=9.7, 2.4 Hz), 5.26 (1H, d, J=5.6 Hz), 7.22 (2H, d, J=8.3 Hz), 7.38 (2H, d, J=8.3 Hz).

MS (FAB) m/z 570 [M+H]$^+$

Compound 2 (26.9 mg, yield 31%) was produced in the same manner as in step (vi) of Example S1, except that 63.0 mg (0.149 mmol) of the title compound in step (v) of Example S1 was used and, further, 43.8 mg (0.182 mmol) of 1-(4-bromophenyl)-2-(dimethylamino)ethanone was used instead of 4-bromo(2-(dimethylamino)ethyl)benzene.

Compound 3 (59.4 mg, yield 66%) was produced in the same manner as in step (vi) of Example S1, except that 66.2 mg (0.157 mmol) of the title compound in step (v) of Example S1 was used and, further, 42.5 mg (0.179 mmol) of 3-(4- bromophenyl)-N,N-dimethylprop-2-yn-1-amine was used instead of 4-bromo(2-(dimethylamino)ethyl)benzene.

Compound 4 (64.8 mg, yield 98%) was produced in the same manner as in step (vi) of Example S1, except that 42.0 mg (0.099 mmol) of the title compound of step (v) of Example 51 was used and, further, 57.2 mg (0.268 mmol) of 1-(4-bromophenyl)-N,N-dimethylmethanamine was used instead of 4-bromo(2-(dimethylamino)ethyl)benzene.

Compound 5 (31.7 mg, yield 55%) was produced in the same manner as in step (vi) of Example S1, except that 42.5 mg (0.101 mmol) of the title compound in step (v) of Example S1 was used and, further, 52.4 mg (0.221 mmol) of 3-(3-bromophenyl)-N,N-dimethylprop-2-yn-1-amine was used instead of 4-bromo(2-(dimethylamino)ethyl)benzene.

Compound 6 (82 mg, yield 70%) was produced in the same manner as in step (vi) of Example S1, except that 83.0 mg (0.2 mmol) of the title compound in step (v) of Example S1 was used and, further, 50.0 mg (0.2 mmol) of 1-(4-bromophenethyl)pyrrolidine was used instead of 4-bromo(2-(dimethylamino)ethyl)benzene.

Compound 7 (35 mg, yield 54%) was produced in the same manner as in step (vi) of Example S1, except that 45.1 mg (0.107 mmol) of the title compound in step (v) of Example S1 was used and, further, 34.7 mg (0.128 mmol) of $N^1$-(4-bromophenethyl)-$N^2$,$N^2$-dimethylethane-1,2-diamine was used instead of 4-bromo(2-(dimethylamino)ethyl)benzene.

Compound 8 (60 mg, yield 72%) was produced in the same manner as in step (vi) of Example S1, except that 57.4 mg (0.136 mmol) of the title compound in step (v) of Example S1 was used and, further, 44.2 mg (0.163 mmol) of 4-bromo-N-(2-(dimethylamino)ethyl)benzamide was used instead of 4-bromo(2-(dimethylamino)ethyl)benzene.

Compound 9 (89 mg, yield 67%) was produced in the same manner as in step (vi) of Example S1, except that 90.0 mg (0.21 mmol) of the title compound in step (v) of Example S1 was used and, further, 60.0 mg (0.21 mmol) of 1-(4-bromophenethyl)-4-methylpiperazine was used instead of 4-bromo(2-(dimethylamino)ethyl)benzene.

Compound 10 (43 mg, yield 73%) was produced in the same manner as in step (vi) of Example S1, except that 40.0 mg (0.0947 mmol) of the title compound in step (v) of Example S1 was used and, further, 32.4 mg (0.114 mmol) of $N^1$-(4-bromophenethyl)-$N^1$,$N^2$,$N^2$-trimethylethane-1,2-diamine was used instead of 4-bromo(2-(dimethylamino)ethyl)benzene.

Compound 11 (184 mg, yield 66%) was produced in the same manner as in step (vi) of Example S1, except that 203.1 mg (0.48 mmol) of the title compound in step (v) of Example 51 was used and, futher, 150.0 mg (0.625 mmol) of N-(4-bromophenethyl)cyclopropanamine was used instead of 4-bromo(2-(dimethylamino)ethyl)benzene.

Compound 12 (50 mg, yield 77%) was produced in the same manner as in step (vi) of Example S1, except that 46 mg (0.11 mmol) of the title compound in step (v) of Example S1 was used and, further, 30 mg (0.11 mmol) of 2-(4-bromo-2-nitrophenyl)-N,N-dimethylethanamine was used instead of 4-bromo(2-(dimethylamino)ethyl)benzene.

Compound 13 (133 mg, yield 92%) was produced in the same manner as in step (vi) of Example S1, except that 100 mg (0.237 mmol) of the title compound in step (v) of Example S1 was used and, further, 144.2 mg (0.536 mmol) of 1-(4-bromobenzyl)-4-methylpiperazine was used instead of 4-bromo(2-(dimethylamino)ethyl)benzene.

Compound 14 (123 mg, yield 89%) was produced in the same manner as in step (vi) of Example S1, except that 98.1 mg (0.232 mmol) of the title compound in step (v) of Example S1 was used and, further, 95.4 mg (0.375 mmol) of 1-(4-bromobenzyl)piperidine was used instead of 4-bromo(2-(dimethylamino)ethyl)benzene.

Compound 15 (106 mg, yield 77%) was produced in the same manner as in step (vi) of Example S1, except that 99.5 mg (0.235 mmol) of the title compound in step (v) of Example S1 was used and, further, 85.5 mg (0.353 mmol) of 2-(4-bromophenyl)-N-ethyl-N-methylethanamine was used instead of 4-bromo(2-(dimethylamino)ethyl)benzene.

Compound 16 (116 mg, yield 86%) was produced in the same manner as in step (vi) of Example S1, except that 97.5 mg (0.231 mmol) of the title compound in step (v) of Example S1 was used and, further, 89.8 mg (0.374 mmol) of 1-(4-bromobenzyl)pyrrolidine was used instead of 4-bromo(2-(dimethylamino)ethyl)benzene.

Compound 17 (17 mg, yield 61%) was produced in the same manner as in step (vi) of Example S1, except that 19.6 mg (0.0465 mmol) of the title compound in step (v) of Example S1 was used and, further, 12.0 mg (0.0465 mmol) of 2-((4-bromophenethyl)(methyl)amino)ethanol was used instead of 4-bromo(2-(dimethylamino)ethyl)benzene.

Compound 18 (48.6 mg, yield 47%) was produced in the same manner as in step (vi) of Example S1, except that 77.3 mg (0.183 mmol) of the title compound in step (v) of Example S1 was used and, further, 46.5 mg (0.203 mmol) of 2-(5-bromopyridin-2-yl)-N,N-dimethylethanamine was used instead of 4-bromo(2-(dimethylamino)ethyl)benzene.

Compound 19 (55 mg, yield 78%) was produced in the same manner as in step (vi) of Example S1, except that 50.0 mg (0.118 mmol) of the title compound in step (v) of Example S1 was used and, further, 39.1 mg (0.154 mmol) of (E)-2-(4-bromophenyl)-3-(dimethylamino)acrylaldehyde was used instead of 4-bromo(2-(dimethylamino)ethyl)benzene.

Compound 20 (95.7 mg, yield 68%) was produced in the same manner as in step (vi) of Example S1, except that 99.1 mg (0.235 mmol) of the title compound in step (v) of Example S1 was used and, further, 95.3 mg (0.371 mmol) of $N^1$-(4-bromobenzyl)-$N^2$,$N^2$-dimethylethane-1,2-diamine was used instead of 4-bromo(2-(dimethylamino)ethyl)benzene.

Compound 21 (84.0 mg, yield 76%) was produced in the same manner as in step (vi) of Example S1, except that 81.1 mg (0.192 mmol) of the title compound in step (v) of Example S1 was used and, further, 64.0 mg (0.269 mmol) of 1-(4-bromobenzyl)-2,5-dihydro-1H-pyrrole was used instead of 4-bromo(2-(dimethylamino)ethyl)benzene.

Compound 22 (50.0 mg, yield 54%) was produced in the same manner as in step (vi) of Example S1, except that 76.0 mg (0.180 mmol) of the title compound in step (v) of Example S1 was used and, further, 41.0 mg (0.150 mmol) of 2-(4-bromo-2-nitrophenyl)-N,N-dimethylethanamine was used instead of 4-bromo(2-(dimethylamino)ethyl)benzene.

Compound 23 (45.5 mg, yield 42%) was produced in the same manner as in step (vi) of Example S1, except that 80.3 mg (0.190 mmol) of the title compound in step (v) of Example S1 was used and, further, 85.1 mg (0.376 mmol) of 1-(4-bromobenzyl)azetidine was used instead of 4-bromo(2-(dimethylamino)ethyl)benzene.

Compound 24 (5 mg, yield 11%) was produced in the same manner as in step (vi) of Example S1, except that 34 mg (0.08 mmol) of the title compound in step (v) of Example S1 was used and, further, 20.0 mg (0.070 mmol) of 5-bromo-2-(2-(dimethylamino)ethyl)-N,N-dimethylaniline was used instead of 4-bromo(2-(dimethylamino)ethyl)benzene.

Compound 59 (20 mg, yield 54%) was produced in the same manner as in step (vi) of Example S1, except that 41 mg (0.098 mmol) of the title compound in step (v) of Example S1 was used and, further, 15 mg (0.065 mmol) of 1-(6-bromopyridin-3-yl)-N,N-dimethylethanamine was used instead of 4-bromo(2-(dimethylamino)ethyl)benzene.

Compound 60 (94.3 mg, yield 67%) was produced in the same manner as in step (vi) of Example S1, except that 100 mg (0.237 mmol) of the title compound in step (v) of Example S1 was used and, further, 94 mg (0.41 mmol) of N-(4-bromobenzyl)-N-methylethanamine was used instead of 4-bromo(2-(dimethylamino)ethyl)benzene.

Compound 61 (80.7 mg, yield 59%) was produced in the same manner as in step (vi) of Example S1, except that 100 mg (0.237 mmol) of the title compound in step (v) of Example S1 was used and, further, 117 mg (0.496 mmol) of 1-(4-bromobenzyl)-1H-pyrrole was used instead of 4-bromo(2-(dimethylamino)ethyl)benzene.

Compound 62 (101 mg, yield 73%) was produced in the same manner as in step (vi) of Example S1, except that 100 mg (0.237 mmol) of the title compound in step (v) of Example S1 was used and, further, 115 mg (0.479 mmol) of N-(4-bromobenzyl)-N-methylcyclopropanamine was used instead of 4-bromo(2-(dimethylamino)ethyl)benzene.

Compound 63 (106 mg, yield 75%) was produced in the same manner as in step (vi) of Example S1, except that 100 mg (0.237 mmol) of the title compound in step (v) of Example S1 was used and, further, 140 mg (0.546 mmol) of N-(4-bromobenzyl)-N-methylbutan-1-amine was used instead of 4-bromo(2-(dimethylamino)ethyl)benzene.

Compound 64 (75.0 mg, yield 76%) was produced in the same manner as in step (vi) of Example S1, except that 70.0 mg (0.166 mmol) of the title compound in step (v) of Example S1 was used and, further, 85.0 mg (0.332 mmol) of (R)-1-(4-bromobenzyl)pyrrolidin-3-ol was used instead of 4-bromo(2-(dimethylamino)ethyl)benzene.

Compound 65 (71.0 mg, yield 70%) was produced in the same manner as in step (vi) of Example S1, except that 70.0 mg (0.166 mmol) of the title compound in step (v) of Example S1 was used and, further, 67.3 mg (0.249 mmol) of (R)-1-(4-bromobenzyl)-3-methoxypyrrolidine was used instead of 4-bromo(2-(dimethylamino)ethyl)benzene.

Compound 66 (8.0 mg, yield 48%) was produced in the same manner as in step (vi) of Example S1, except that 18 mg (0.042 mmol) of the title compound in step (v) of Example S1 was used and, further, 8 mg (0.035 mmol) of 2-(6-bromopyridin-3-yl)-N,N-dimethylethanamine was used instead of 4-bromo(2-(dimethylamino)ethyl)benzene.

Compound 67 (113.7 mg, yield 93%) was produced in the same manner as in step (vi) of Example S1, except that 85.1 mg (0.200 mmol) of the title compound in step (v) of Example Si was used and, further, 117.1 mg (0.380 mmol) of (R)-(1-(4-bromobenzyl)pyrrolidin-2-yl)methanol was used instead of 4-bromo(2-(dimethylamino)ethyl)benzene.

Compound 68 (119.7 mg, yield 98%) was produced in the same manner as in step (vi) of Example S1, except that 85.3 mg (0.200 mmol) of the title compound in step (v) of Example Si was used and, further, 124.2 mg (0.400 mmol) of (R)-(1-(4-bromobenzyl)pyrrolidin-2-yl)methanol was used instead of 4-bromo(2-(dimethylamino)ethyl)benzene.

Compound 69 (69 mg, yield 83%) was produced in the same manner as in step (vi) of Example S1, except that 56.1 mg (0.133 mmol) of the title compound in step (v) of Example S1 was used and, further, 45.4 mg (0.159 mmol) of 2-(4-bromophenyl)-$N^1,N^1,N^3,N^3$-tetramethylpropane-1,3-diamine was used instead of 4-bromo(2-(dimethylamino)ethyl) benzene.

Compound 70 (112 mg, yield 81%) was produced in the same manner as in step (vi) of Example S1, except that 100 mg (0.237 mmol) of the title compound in step (v) of Example S1 was used and, further, 91 mg (0.376 mmol) of N-(4-brombenzyl)-N-methylpropan-1-amine was used instead of 4-bromo(2-(dimethylamino)ethyl)benzene.

Compound 71 (98.0 mg, yield 69%) was produced in the same manner as in step (vi) of Example S1, except that 100 mg (0.237 mmol) of the title compound in step (v) of Example S1 was used and, further, 136 mg (0.527 mmol) of N-(4-bromobenzyl)-2-methoxy-N-methylethanamine was used instead of 4-bromo(2-(dimethylamino)ethyl)benzene.

Compound 72 (46.8 mg, yield 66%) was produced in the same manner as in step (vi) of Example S1, except that 50 mg (0.118 mmol) of the title compound in step (v) of Example S1 was used and, further, 45.5 mg (0.178 mmol) of (S)-1-(4-bromobenzyl)pyrrolidin-3-ol was used instead of 4-bromo(2-(dimethylamino)ethyl)benzene.

Compound 73 (54.0 mg, yield 80%) was produced in the same manner as in step (vi) of Example S1, except that 49.0 mg (0.116 mmol) of the title compound in step (v) of Example S1 was used and, further, 34.0 mg (0.139 mmol) of 1-(4-bromophenyl)-2-(dimethylamino)ethanol was used instead of 4-bromo(2-(dimethylamino)ethyl)benzene.

Compound 74 (59.0 mg, yield 82%) was produced in the same manner as in step (vi) of Example S1, except that 50 mg (0.118 mmol) of the title compound in step (v) of Example S1 was used and, further, 48.1 mg (0.178 mmol) of (S)-1-(4-bromobenzyl)-3-methoxypyrrolidine was used instead of 4-bromo(2-(dimethylamino)ethyl)benzene.

Compounds (compounds 2 to 24 and 59 to 74) produced in the same manner as in step (vi) of Example S1 and $^1$H-NMR data and MS data for these compounds are shown in Tables 2, 3, 19 and 20.

Step (vii) of Example S1

7-Deoxy-7-(4-(((R)-3-(dimethylamino)pyrrolidin-1-yl)methyl)phenylthio)-7-epilincomycin (Compound 75)

(R)-N,N-Dimethylpyrrolidin-3-amine (56.9 mg, 4.98 mmol) was added to a solution (0.8 ml) of 83 mg (0.332 mmol) of 4-bromobenzyl bromide in dimethylformamide, and the mixture was stirred at room temperature for 20 min. The title compound (70 mg, 0.166 mmol) in step (v) of Example S1, 7.6 mg (0.0083 mmol) of tris(dibenzylideneacetone)dipalladium, 9.61 mg (0.0166 mmol) of 4,5-bis(diphenylphosphino)-9,9-dimethylsantene, and 0.0578 ml (0.322 mmol) of diisopropylethylamine were added to the reaction solution, and the mixture was stirred with a microwave reaction apparatus at 130° C. for 20 min. The reaction solution was diluted with ethyl acetate, and the diluted solution was then washed with an aqueous sodium hydrogencarbonate solution, was dried over anhydrous sodium sulfate, and was then filtered. The filtrate was concentrated under the reduced pressure, and the residue was purified by column chromatography on silica gel (chloroform:methanol:28% aqueous ammonia=90:10:1) to give 41 mg (yield 20%) of the title compound.

$^1$H-NMR (400 MHz, CD$_3$OD) δ: 0.89-0.97 (3H, m), 1.28 (3H, d, J=6.8 Hz), 1.30-1.40 (4H, m), 1.67-1.77 (1H, m), 1.80-1.91 (1H, m), 1.95-2.24 (13H, m), 2.27-2.35 (1H, m), 2.40 (3H, s), 2.47-2.55 (1H, m), 2.69-2.89 (3H, m), 2.99 (1H, dd, J=10.5, 4.6 Hz), 3.25 (1H, dd, J=8.3, 5.6 Hz), 3.56 (1H, d, J=12.7 Hz), 3.58 (1H, dd, J=10.0, 3.4 Hz), 3.63 (1H, d, J=12.7 Hz), 3.74 (1H, d, J=3.4 Hz), 3.85 (1H, dq, J=2.4, 6.8 Hz), 4.10 (1H, dd, J=10.0, 5.6 Hz), 4.34 (1H, d, J=9.7 Hz), 4.40 (1H, dd, J=10.0, 2.4 Hz), 5.26 (1H, d, J=5.6 Hz), 7.29 (2H, d, J=8.3 Hz), 7.39 (2H, d, J=8.3 Hz)

MS (FAB) m/z 625 [M+H]$^+$

Compound 76 (52.0 mg, yield 50%) was produced in the same manner as in step (vii) of Example S1, except that 70.0 mg (0.166 mmol) of the title compound in step (v) of Example S1 was used and, further, 56.9 mg (0.498 mmol) of (S)-N,N-dimethylpyrrolidin-3-amine was used instead of (R)-N,N-dimethylpyrrolidin-3-amine.

Compound 77 (48.9 mg, yield 47%) was produced in the same manner as in step (vii) of Example S1, except that 70.0 mg (0.166 mmol) of the title compound in step (v) of Example S1 was used and, further, 46.4 mg (0.403 mmol) of (R)-2-(methoxymethyl)pyrrolidine was used instead of (R)-N,N-dimethylpyrrolidin-3-amine.

Compound 78 (61.0 mg, yield 59%) was produced in the same manner as in step (vii) of Example S1, except that 70.0 mg (0.166 mmol) of the title compound in step (v) of Example S1 was used and, further, 46.4 mg (0.403 mmol) of (S)-2-(methoxymethyl)pyrrolidine was used instead of (R)—N,N-dimethylpyrrolidin-3-amine.

Compounds (76 to 78) produced in the same manner as in step (vii) of Example S1 and $^1$H-NMR data and MS data for these compounds are shown in Table 21.

Step (i) of Example S2

7-Deoxy-7-(4-(2-(2-nitrophenylsulfonamide)ethyl)phenylthio)-7-epilincomycin

The title compound (72.0 mg, yield 60%) was produced in the same manner as in step (vi) of Example S1, except that 70.0 mg (0.166 mmol) of the title compound in step (v) of Example S1, 9.6 mg (0.0166 mmol) of 4,5-bis(diphenylphosphino)-9,9-dimethylsantene, 7.6 mg (0.0083 mmol) of tris(dibenzylideneacetone)dipalladium, 76.7 mg (0.199 mmol) of N-(4-bromophenethyl)-2-nitrobenzenesulfonamide, 0.058 ml (0.332 mmol) of diisopropylethylamine, and dioxane (1 ml) were used.

$^1$H-NMR (400 MHz, CD$_3$OD) δ: 0.88-0.96 (3H, m), 1.25 (3H, d, J=6.8 Hz), 1.28-1.40 (4H, m), 1.86 (1H, dt, J=10.5, 12.6 Hz), 1.96-2.23 (3H, m), 2.00 (3H, s), 2.40 (3H, s), 2.78 (2H, t, J=7.3 Hz), 3.01 (1H, dd, J=4.6, 10.5 Hz), 3.24 (1H, dd, J=5.8, 8.3 Hz), 3.30 (2H, t, J=7.8 Hz), 3.59 (1H, dd, J=3.4, 10.3 Hz), 3.75 (1H, d, J=3.2 Hz), 3.78 (1H, dq, J=2.4, 6.8 Hz), 4.11 (1H, dd, J=5.6, 10.3 Hz), 4.34 (1H, d, J=9.7 Hz), 4.39 (1H, dd, J=2.5, 9.8 Hz), 5.27 (1H, d, J=5.6 Hz), 7.11 (2H, d, J=8.3 Hz), 7.28 (2H, d, J=8.3 Hz), 7.72-7.84 (3H, m), 7.98-8.02 (1H, m).

Step (ii) of Example S2

7-(4-(2-Aminoethyl)phenylthio)-7-deoxy-7-epilincomycin (Compound 25)

Potassium carbonate (20.6 mg, 0.149 mmol) was added to a solution of 72 mg (0.099 mmol) of the title compound in step (i) of Example S2 in N,N-dimethylformamide (1 ml). Thereafter, 28.1 mg (0.149 mmol) of 4-bromobenzenethiol was added thereto, and the mixture was stirred at room temperature for 18 hr. The reaction solvent was then removed by distillation under the reduced pressure, and the residue was purified by preparative thin-layer chromatography (chloroform:methanol:28% aqueous ammonia=9:2:0.2) to give 46.8 mg (yield 87%) of the title compound.

$^1$H-NMR (400 MHz, CD$_3$OD) δ: 0.88-0.97 (3H, m), 1.27 (3H, d, J=6.9 Hz), 1.29-1.39 (4H, m), 1.85 (1H, dt, J=10.4, 12.8 Hz), 1.99 (1H, ddd, J=4.8, 8.4, 12.8 Hz), 2.01 (3H, s), 2.08 (1H, dd, J=8.4, 10.0 Hz), 2.10-2.22 (1H, m), 2.39 (3H, s), 2.72-2.79 (2H, m), 2.84-2.93 (2H, m), 2.98 (1H, dd, J=4.6, 10.5 Hz), 3.23 (1H, dd, J=3.2, 10.3 Hz), 3.74 (1H, d, J=3.2 Hz), 3.81 (1H, dq, J=2.4, 6.8 Hz), 4.11 (1H, dd, J=5.7, 10.3 Hz), 4.34 (1H, d, J=10.0 Hz), 4.39 (1H, d, J=2.4, 9.8 Hz), 5.27 (1H, d, J=5.6 Hz), 7.20 (2H, d, J=8.1 Hz), 7.38 (2H, d, J=8.3 Hz).

MS (FAB) m/z 542 [M+H]$^+$

Step (i) of Example S3

7-Deoxy-7-(4-(2-(tert-butoxycarbonylamino)acetyl)phenylthio)-7-epilincomycin

1-Bromo-4-(2-(tert-butoxycarbonylamino)acetylbenzene (187.4 mg, 0.60 mmol) and 0.128 ml (0.75 mmol) of diisopropylethylamine were added to a solution of 213.9 mg (0.51 mmol) of the title compound in step (v) of Example S1, 31.3 mg (0.054 mmol) of 4,5-bis(diphenylphosphino)-9,9-dimethylsantene, and 24.1 mg (0.026 mmol) of tris(dibenzylideneacetone)dipalladium in dioxane (3 ml), and the mixture was then heated under reflux overnight. The reaction solution was filtered through Celite, and the residue was purified by preparative thin-layer chromatography (chloroform:methanol:28% aqueous ammonia=10:1:0.1) to give 276.6 mg (yield 83%) of the title compound.

$^1$H-NMR (400 MHz, CD$_3$OD) δ: 0.90-0.97 (3H, m), 1.30-1.45 (7H, m), 1.46 (9H, s), 1.82 (3H, s), 1.82-1.90 (1H, m), 1.98-2.26 (3H, m), 2.40 (3H, s), 2.99 (1H, dd, J=10.5, 4.9 Hz), 3.23-3.30 (1H, m), 3.57 (1H, dd, J=10.2, 3.2 Hz), 3.78 (1H, d, J=3.2 Hz), 4.03-4.14 (2H, m), 4.37 (1H, d, J=9.8 Hz), 4.50 (2H, s), 4.54 (1H, d, J=9.8, 3.0 Hz), 5.24 (1H, d, J=5.6 Hz), 7.47 (2H, d, J=8.5 Hz), 7.92 (2H, d, J=8.5 Hz)

MS (FAB) m/z 656 [M+H]$^+$.

7-(4-(3-Tert-butoxycarbonylaminopropen-2-yl)phenylthio)-7-deoxy-7-epilincomycin (46.0 mg, yield 72%) was produced in the same manner as in step (i) of Example S3, except that 38.4 mg (0.0908 mmol) of the title compound in step (v) of Example S1 was used and, further, 34.0 mg (0.109 mmol) of tert-butyl 2-(4-bromophenyl)allylcarbamate was used instead of 1-bromo-4-(2-(tert-butoxycarbonylamino)acetylbenzene.

Step (ii) of Example S3

7-(4-(2-Aminoacetyl)phenylthio)-7-deoxy-7-epilincomycin (Compound 26)

Trifluoroacetic acid (0.8 ml) was added at −20° C. to a solution of 263.3 mg (0.4 mmol) of the title compound in step (i) of Example S3 in methylene chloride (2 ml), and the temperature of the mixture was gradually raised to room temperature. The mixture was then stirred at room temperature for 3 hr. The solvent was removed by distillation, and the residue was purified by preparative thin-layer chromatography (chloroform:methanol:28% aqueous ammonia=10:1:0.1) to give 34.4 mg (yield 15%) of the title compound.

$^1$H-NMR (400 MHz, CD$_3$OD) δ: 0.95 (3H, t, J=7.3 Hz), 1.28-1.52 (7H, m), 1.78 (3H, s), 2.15-2.37 (3H, m), 2.88 (1H, t, J=10.7 Hz), 2.94 (3H, s), 3.55-3.59 (1H, m), 3.77 (1H, dd, J=10.9, 6.7 Hz), 3.86 (1H, d, J=3.2 Hz), 4.06-4.18 (3H, m), 4.46 (1H, d, J=10.3 Hz), 4.55 (2H, s), 4.75 (1H, dd, J=10.0, 2.4 Hz), 5.25 (1H, d, J=5.6 Hz), 7.48 (2H, d, J=6.7 Hz), 7.95 (2H, d, J=6.7 Hz).

MS (FAB) m/z 556 [M+H]$^+$.

Compound 79 (31.0 mg, yield 80%) was produced in the same manner as in step (ii) of Example S3, except that 46.0 mg (0.0703 mmol) of 7-(4-(3-tert-butoxycarbonylaminopropen-2-yl)phenylthio)-7-deoxy-7-epilincomycin was used.

Compound 79 produced in the same manner as in step (ii) of Example S3 and ¹H-NMR data and MS data for the compound are shown in Table 22.

Step (iii) of Example S3

7-Deoxy-7-(4-(3-(dimethylamino)propen-2-yl)phenylthio)-7-epilincomycin (Compound 80)

Acetic acid (54.0 µl, 0.0951 mmol), 8.0 µl of formalin, and 40.3 mg (0.1902 mmol) of sodium tri(acetoxy)borohydride were added to a solution of 19.0 mg (0.0317 mmol) of (compound 79) in methanol (1.0 ml), and the mixture was stirred at room temperature for 90 min. The reaction solution was diluted with ethyl acetate. The diluted solution was washed with a 10% aqueous sodium hydrogencarbonate solution, was dried over anhydrous sodium sulfate, and was filtered. The filtrate was then concentrated, and the residue was purified by column chromatography on silica gel (chloroform:methanol:28% aqueous ammonia=9:2:0.2) to give 11.0 mg (yield 60%) of the title compound.

¹H-NMR (400 MHz, $CD_3OD$) δ: 0.90-0.96 (3H, m), 1.31 (3H, d, J=6.8 Hz), 1.33-1.39 (4H, m), 1.61-1.83 (1H, m), 2.00 (3H, s), 1.91-2.10 (1H, m), 2.13-2.29 (1H, m), 2.29-2.45 (1H, m), 2.30 (6H, s), 2.41 (3H, s), 3.02 (1H, dd, J=4.8, 10.6 Hz), 3.26 (1H, dd, J=5.5, 8.4 Hz), 3.51 (2H, s), 3.59 (1H, dd, J=3.4, 10.2 Hz), 3.75 (1H, d, J=3.4 Hz), 3.88 (1H, dq, J=2.7, 6.8 Hz), 4.11 (1H, dd, J=5.7, 10.2 Hz), 4.37 (1H, d, J=9.7 Hz), 4.44 (1H, dd, J=2.7, 9.7 Hz), 5.27 (1H, d, J=5.7 Hz), 5.32 (1H, d, J=1.0 Hz), 5.54 (1H, d, J=1.0 Hz), 7.41 (2H, d, J=8.6 Hz), 7.47 (2H, d, J=8.6 Hz)

MS (FAB) m/z 582 [M+H]⁺.

Step of Example S4

7-(4-(2-(Cyclopropyl(methyl)amino)ethyl)phenylthio)-7-deoxy-7-epilincomycin (Compound 27)

Acetic acid (26.0 µl, 0.454 mmol), 38.0 0 of formalin, and 192.0 mg (0.906 mmol) of sodium tri(acetoxy)borohydride were added to a solution of 88.0 mg (0.151 mmol) of 7-deoxy-7-(4-(2-(cyclopropylamino)ethyl)phenylthio)-7-epilincomycin in step (vi) of Example S1 in methanol (1 ml), and the mixture was stirred at room temperature for 30 min. After filtration, the filtrate was concentrated, and the residue was purified by preparative thin-layer chromatography (chloroform:methanol:28% aqueous ammonia=20:1:1) to give 68.0 mg (yield 76%) of the title compound.

¹H-NMR (400 MHz, $CD_3OD$) δ: 0.40-0.45 (2H, m), 0.51-0.57 (2H, m), 0.89-0.96 (3H, m), 1.27 (3H, d, J=6.8 Hz), 1.31-1.39 (4H, m), 1.74-1.80 (1H, m), 1.85 (1H, dt, J=10.4, 12.4 Hz), 2.00 (1H, ddd, J=5.2, 7.6, 12.8 Hz), 2.01 (3H, s), 2.06-2.12 (1H, m), 2.10-2.23 (1H, m), 2.39 (3H, s), 2.42 (3H, s), 2.74-2.86 (4H, m), 3.00 (1H, dd, J=4.6, 10.5 Hz), 3.25 (1H, dd, J=5.6, 8.0 Hz), 3.58 (1H, dd, J=3.4, 10.2 Hz), 3.74 (1H, d, J=3.1 Hz), 3.80 (1H, dq, J=2.5, 6.8 Hz), 4.10 (1H, dd, J=5.6, 10.2 Hz), 4.34 (1H, d, J=10.2 Hz), 4.39 (1H, dd, J=2.5, 10.0 Hz), 5.26 (1H, d, J=5.6 Hz), 7.19 (2H, d, J=8.0 Hz), 7.37 (2H, d, J=8.3 Hz).

MS (FAB) m/z 596 [M+H]⁺.

Compound 28 (45.1 mg, yield 91%) was produced in the same manner as in step (i) of Example S4, excep that 48.7 mg (0.0813 mmol) of compound 20 was used.

Compound 28 produced in the same manner as in step (i) of Example S4 and ¹H-NMR data and MS data for the compound are shown in Table 4.

Step (i) of Example S5

7-Deoxy-7-epi-7-(4-(2-(2-nitro-N-propylphenylsulfonamide)ethyl)phenylthio)lincomycin The title compound (128 mg, yield 88%) was produced in the same manner as in step (vi) of Example S1, except that 80.0 mg (0.189 mmol) of the title compound in step (v) of Example S1, 97.1 mg (0.227 mmol) of N-(4-bromophenethyl)-2-nitro-N-propylbenzene benzenesulfonamide, 8.65 mg (0.00945 mmol) of tris(dibenzylideneacetone)dipalladium, 10.9 mg (0.0189 mmol) of 4,5-bis(diphenylphosphino)-9,9-dimethylsantene, dioxane (0.8 ml), and 65.8 µl (0.378 mmol) of diisopropylethylamine were used and the reaction conditions were changed to a temperature of 100° C. and a reaction time of 5 hr.

¹H-NMR (400 MHz, $CDCl_3$) δ: 0.70 (3H, t, J=7.3 Hz), 0.78-0.93 (3H, m), 1.22 (3H, d, J=6.8 Hz), 1.29-1.48 (4H, m), 1.50-1.62 (2H, m), 1.85-1.99 (2H, m), 2.05-2.12 (2H, m), 2.15 (3H, s), 2.32-2.40 (4H, m), 2.72 (1H, br), 2.83-2.91 (2H, m), 3.04 (1H, dd, J=4.6, 10.5 Hz), 3.21-3.32 (3H, m), 3.45-3.54 (2H, m), 3.57-3.68 (2H, m), 3.93 (1H, dq, J=1.9, 7.3 Hz), 4.13 (1H, dd, J=5.6, 10.5 Hz), 4.19-4.28 (2H, m), 5.28 (1H, br), 5.38 (1H, d, =5.6 Hz), 7.15 (2H, d, J=8.0 Hz), 7.34 (2H, d, J=8.0 Hz), 7.59-7.72 (3H, m), 7.97-8.02 (1H, m), 8.11 (1H, d, J=8.3 Hz).

MS (FAB) m/z 769 [M+H]⁺.

7-Deoxy-7-epi-7-(4-(2-(N-methyl-2-nitrophenylsulfonamide)ethyl)phenylthio)lincomycin (72 mg, yield 82%) was produced in the same manner as in step (i) of Example S5, except that 56.7 mg (0.142 mmol) of N-(4-bromophenethyl)-N-methyl-2-nitrobenzenesulfonamide was used instead of N-(4-bromophenethyl)-2-nitro-N-propylbenzenesulfonamide.

Step (ii) of Example S5

7-Deoxy-7-epi-7-(4-(2-(propylamino)ethyl)phenylthio)lincomycin (Compound 29)

4-Bromothiophenol (58.0 mg, 0.307 mmol) and 68.6 µl (0.459 mmol) of 1,8-diazabicyclo[5.4.0]-7-undecene were added to a solution of 118 mg (0.153 mmol) of the title compound in step (i) of Example S5 in N,N-dimethylformamide (1.5 ml), and the mixture was stirred at room temperature for 19 hr. The reaction solution was diluted with ethyl acetate, and the diluted solution was then washed with a 10% aqueous sodium hydrogencarbonate solution and was dried over anhydrous sodium sulfate. After filtration, the filtrate was concentrated, and the residue was purified by column chromatography on silica gel (chloroform:methanol:28% aqueous ammonia=95:5:1) to give 84 mg (yield 94%) of the title compound.

¹H-NMR (400 MHz, $CD_3OD$) δ: 0.88-0.96 (6H, m), 1.27 (3H, d, J=7.1 Hz), 1.30-1.40 (4H, m), 1.52 (2H, tq, J=7.6, 7.6 Hz), 1.80-1.90 (1H, m), 1.95-2.23 (6H, m), 2.38 (3H, s), 2.38 (3H, s), 2.52-2.59 (2H, m), 2.79 (4H, s), 2.98 (1H, dd, J=4.9, 10.4 Hz), 3.34 (1H, dd, J=5.6, 8.0 Hz), 3.58 (1H, dd, J=3.2, 10.2 Hz), 3.73 (1H, d, J=3.2 Hz), 3.82 (1H, dq, J=2.4, 7.1 Hz), 4.10 (1H, dd, J=5.6, 10.2 Hz), 4.33 (1H, d, J=10.0 Hz), 4.38 (1H, dd, J=2.4, 10.0 Hz), 5.26 (1H, d, J=5.6 Hz), 7.20 (2H, d, J=8.3 Hz), 7.35 (2H, d, J=8.3 Hz).

MS (FAB) 584 [M+H]⁺.

Compound 30 (39 mg, yield 72%) was produced in the same manner as in step (ii) of Example S5, except that 72.0 mg (0.0972 mmol) of 7-deoxy-7-epi-7-(4-(2-(N-methyl-2-nitrophenylsulfonamide)ethyl)phenylthio)lincomycin was used.

Step (iii) of Example S5

7-Deoxy-7-epi-7-(4-(2-(methyl(propyl)amino)ethyl) phenylthio)lincomycin (Compound 31)

Acetic acid (28.2 µl, 0.493 mmol), 20.6 µl of formalin, and 52.3 mg (0.247 mmol) of sodium tri(acetoxy)borohydride were added to a solution of 48.0 mg (0.082 mmol) of the title compound in step (ii) of Example S5 in methanol (0.4 ml), and the mixture was stirred at room temperature for 50 min. The reaction solution was diluted with ethyl acetate. The diluted solution was then washed with a 10% aqueous sodium hydrogencarbonate solution, was dried over anhydrous sodium sulfate, and was filtered. The filtrate was concentrated, and the residue was purified by column chromatography on silica gel (chloroform:methanol:28% aqueous ammonia=95:5:1) to give 42.0 mg (yield 85%) of the title compound.

$^1$H-NMR (400 MHz, CD$_3$OD) δ: 0.88-0.97 (6H, m), 1.26 (3H, d, J=6.8 Hz), 1.29-1.40 (4H, m), 1.48-1.59 (2H, m), 1.80-1.90 (1H, m), 1.94-2.22 (6H, m), 2.32 (3H, s), 2.35-2.44 (5H, m), 2.58-2.65 (2H, m), 2.75-2.81 (2H, m), 2.98 (1H, dd, J=4.6, 10.5 Hz), 3.23 (1H, dd, J=5.6, 8.1 Hz), 3.58 (1H, dd, J=3.2, 10.3 Hz), 3.73 (1H, d, J=3.2 Hz), 3.80 (1H, dq, J=2.4, 6.8 Hz), 4.10 (1H, dd, J=5.4, 10.2 Hz), 4.33 (1H, d, J=9.8 Hz), 4.38 (1H, dd, J=2.4, 9.8 Hz), 5.26 (1H, d, J=5.6 Hz), 7.19 (2H, d, J=8.3 Hz), 7.36 (2H, d, J=8.3 Hz).

MS (FAB) m/z 598 [M+H]$^+$.

Compound 30 produced in the same manner as in Example S5 and $^1$H-NMR data and MS data for the compound are shown in Table 5.

Step of Example S6

7-(4-(2-(N-(2-(Tert-butyldimethylsilyloxy)ethyl)-2-nitrophenylsulfonamide)ethyl)phenylthio)-7-deoxy-7-epilincomycin The title compound (35.0 mg, yield 64%) was produced in the same manner as in step (vi) of Example S1, except that 26.1 mg (0.0618 mmol) of the title compound in step (v) of Example S1, 7.2 mg (0.0124 mmol) of 4,5-bis(diphenylphosphino)-9,9-dimethylsantene, 5.7 mg (0.00618 mmol) of tris(dibenzylideneacetone)dipalladium, 40.3 mg (0.0741 mmol) of N-(4-bromophenethyl)-N-(2-(tert-butyldimethylsilyloxy) ethyl)-2-nitrobenzenesulfonamide, 0.022 ml (0.124 mmol) of diisopropylethylamine, and dioxane (1 ml) were used.

$^1$H-NMR (400 MHz, CD$_3$OD) δ: 0.00 (6H, s), 0.83 (9H, s), 0.87-0.93 (3H, m), 1.22 (3H, d, J=6.8 Hz), 1.27-1.35 (4H, m), 1.82 (1H, dt, J=10.7, 12.9 Hz), 1.92-2.00 (1H, m), 1.96 (3H, s), 2.05-2.20 (1H, m), 2.06 (1H, dd, J=8.2, 10.3 Hz), 2.36 (3H, s), 2.83 (2H, t, J=8.0 Hz), 2.98 (1H, dd, J=4.6, 10.7 Hz), 3.21 (1H, dd, J=5.6, 8.3 Hz), 3.45 (2H, t, J=5.6 Hz), 3.55 (1H, dd, J=3.2, 10.2 Hz), 3.58 (2H, t, J=8.0 Hz), 3.70 (2H, t, J=5.4 Hz), 3.71 (1H, d, J=1.8 Hz), 3.77 (1H, dq, J=2.4, 6.8 Hz), 4.07 (1H, dd, J=5.6, 10.2 Hz), 4.31 (1H, d, J=10.0 Hz), 4.36 (1H, dd, J=2.4, 9.8 Hz), 5.23 (1H, d, J=5.6 Hz), 7.11 (2H, d, J=8.3 Hz), 7.29 (2H, d, J=8.3 Hz), 7.69-7.79 (3H, m), 7.96-8.01 (1H, m).

MS (FAB) m/z 885 [M+H]$^+$.

Step (ii) of Example S6

7-Deoxy-7-epi-7-(4-(2-(2-hydroxyethylamino)ethyl) phenylthio)lincomycin (Compound 32)

7-Methyl-1,5,7-triazabicyclo[4.4.0]dec-5-ene (0.011 ml, 0.079 mmol) was added to a solution of 35 mg (0.0395 mmol) of the title compound in step (i) of Example S6 in N,N-dimethylformamide (1 ml). 4-Bromobenzenethiol (15.0 mg, 0.079 mmol) was then added thereto, and the mixture was stirred at room temperature for 15 hr. Methanol (1 ml) and 1 N hydrochloric acid (1 ml) were then added to the reaction solution, and the mixture was stirred for 30 min. The solvent was removed by distillation under the reduced pressure, and the residue was purified by preparative thin-layer chromatography (chloroform:methanol:28% aqueous ammonia=9:2:0.2) to give 8 mg (two steps, yield 35%) of the title compound.

$^1$H-NMR (400 MHz, CD$_3$OD) δ: 0.91-0.97 (3H, m), 1.27 (3H, d, J=7.1 Hz), 1.31-1.39 (4H, m), 1.85 (1H, dt, J=1.0, 12.8 Hz), 1.96-2.03 (1H, m), 2.00 (3H, s), 2.09 (1H, dd, J=8.4, 10.4 Hz), 2.10-2.25 (1H, m), 2.40 (3H, s), 2.83-2.90 (2H, m), 2.86 (2H, t, J=5.6 Hz), 2.93-3.01 (3H, m), 3.24 (1H, dd, J=5.3, 8.2 Hz), 3.57 (1H, dd, J=3.2, 10.2 Hz), 3.69 (2H, t, J=5.6 Hz), 3.74 (1H, d, J=2.5 Hz), 3.82 (1H, dq, J=2.7, 7.1 Hz), 4.10 (1H, dd, J=5.6, 10.3 Hz), 4.33 (1H, d, J=10.4 Hz), 4.40 (1H, dd, J=2.7, 9.8 Hz), 5.26 (1H, d, J=5.6 Hz), 7.22 (2H, d, J=8.3 Hz), 7.39 (2H, d, J=8.2 Hz).

MS (FAB) m/z 586 [M+H]$^+$.

Step (i) of Example S7

7-Deoxy-7-(4-(3-(dimethylamino)propyl)phenylthio)-7-epilincomycin (Compound 33)

Palladium-carbon (12.5 mg) was added to a solution of 21.4 mg (0.037 mmol) of compound 3 in step (vi) of Example S1 in methanol (1 ml), and the mixture was stirred in a hydrogen atmosphere under the atmospheric pressure overnight. The solvent was removed by distillation, and the residue was purified by preparative thin-layer chromatography (chloroform:methanol:28% aqueous ammonia=10:1:0.1) to give 13.7 mg (yield 64%) of the title compound.

$^1$H-NMR (400 MHz, CD$_3$OD) δ: 0.91-0.95 (3H, m), 1.26 (3H, d, J=6.8 Hz), 1.35-1.40 (4H, m), 1.75-1.89 (3H, m), 1.96-1.99 (1H, m), 2.01 (3H, s), 2.06-2.19 (2H, m), 2.23 (6H, s), 2.31-2.35 (2H, m), 2.39 (3H, s), 2.62 (2H, t, J=7.7 Hz), 2.98 (1H, dd, J=10.8, 4.7 Hz), 3.22-3.25 (1H, m), 3.57 (1H, dd, J=10.3, 3.4 Hz), 3.73 (1H, d, J=3.1 Hz), 3.80 (1H, qd, J=7.0, 2.5 Hz), 4.10 (1H, dd, J=10.2, 5.6 Hz), 4.33 (1H, d, J=9.9 Hz), 4.37 (1H, dd, J=9.7, 2.4 Hz), 5.26 (1H, d, J=5.6 Hz), 7.18 (2H, d, J=8.2 Hz), 7.36 (2H, d, J=8.2 Hz).

MS (FAB) m/z 584 [M+H]$^+$

Compound 34 (40.7 mg, yield 64%) was produced in the same manner as in step (i) of Example S7, except that 63.4 mg (0.11 mmol) of compound 5 was used instead of compound 3.

Compound 34 produced in the same manner as in step (i) of Example S7 and $^1$H-NMR data and MS data for the compound are shown in Table 6.

Step (i) of Example S8

7-Deoxy-7-(3-(Z)-(3-(dimethylamino)-1-propenyl) phenylthio)-7-epilincomycin (Compound 35)

A lindlar catalyst (7.5 mg) was added to a solution of 23.6 mg (0.04 mmol) of 7-deoxy-7-(3-(3-(dimethylamino)-1-propynyl)phenylthio)-7-epilincomycin (compound 5) synthesized as described in step (vi) of Example S1 in methanol (1 ml), and the mixture was stirred in a hydrogen atmosphere under the atmospheric pressure for 3.5 hr. The solvent was removed by distillation, and the residue was purified by preparative thin-layer chromatography (chloroform:methanol:28% aqueous ammonia=10:1:0.1) to give 15.4 mg (yield 66%) of the title compound.

¹H-NMR (400 MHz, CD₃OD) δ: 0.91-0.94 (3H, m), 1.30-1.39 (7H, m), 1.83-1.88 (1H, m), 1.95 (3H, s), 1.97-2.10 (3H, m), 2.24 (6H, s), 2.39 (3H, s), 2.98 (1H, dd, J=10.6, 4.8 Hz), 3.22-3.25 (1H, m), 3.57 (1H, dd, J=10.3, 3.2 Hz), 3.75 (1H, d, J=3.2 Hz), 3.87 (1H, qd, J=6.8, 2.7 Hz), 4.10 (1H, dd, J=10.2, 5.6 Hz), 4.36 (1H, d, J=10.0 Hz), 4.43 (1H, dd, J=9.8, 2.7 Hz), 5.26 (1H, d, J=5.6 Hz), 5.80 (1H, dt, J=11.9, 6.5 Hz), 6.61 (1H, d, J=11.9 Hz), 7.13-7.15 (1H, m), 7.29-7.33 (3H, m).

MS (FAB) m/z 582 [M+H]⁺

Step of Example S9

7-(2-Amino-4-(2-dimethylanninoethyl)phenylthio)-7-deoxy-7-epilincomycin (Compound 36)

7-Deoxy-7-(4-(2-dimethylaminoethyl)-6-nitrophenylthio)-7-epilincomycin (compound 12) (46 mg, 0.073 mmol) was dissolved in methanol (4 ml), and 50 mg of Pd/C (wet, 50% by weight) was added to the solution. The mixture was stirred at room temperature in a hydrogen atmosphere for 16 hr. The catalyst was removed by filtration from the reaction solution and was concentrated under the reduced pressure. The residue was purified by NH column chromatography on silica gel (ethyl acetate:methanol=10:1) to give 20 mg (yield 47%) of the title compound.

¹H-NMR (400 MHz, CD₃OD) δ: 0.90-0.95 (3H, m), 1.10-1.20 (3H, m), 1.30-1.40 (4H, m), 1.70-2.10 (4H, m), 2.18 (3H, s), 2.20-2.40 (9H, m), 2.58 (2H, m), 2.69 (2H, m), 2.93 (1H, m), 3.21 (1H, m), 3.55-3.70 (2H, m), 3.73 (1H, m), 4.10 (1H, dd, J=5.6, 10.2 Hz), 4.32 (2H, m), 5.26 (1H, d, J=5.8 Hz), 6.52 (1H, m), 7.01 (1H, m), 7.32 (1H, m).

MS (API) m/z 585 [M+1]⁺.

7-Deoxy-7-(4-(2-dimethylaminoethyl)-3-aminophenylthio)-7-epilincomycin (compound 37) (11 mg, yield 25%) was produced in the same manner as in step (i) of Example S9, except that 46 mg (0.073 mmol) of compound 22 was used instead of compound 12.

Step (ii) of Example S9

7-Deoxy-7-(4-(2-dimethylaminoethyl)-2-dimethylaminophenylthio)-7-epilincomycin (Compound 38)

Aqueous formalin solution (0.5 ml), 0.5 ml of a 1 N aqueous hydrochloric acid solution, and 30 mg of Pd/C (wet, 50% by weight) were added to a solution (2 ml) of 16 mg (0.027 mmol) of 7-deoxy-7-(4-(2-dimethylaminoethyl)-2-aminophenylthio)-7-epilincomycin (compound 36) in methanol. The mixture was stirred in a hydrogen atmosphere at room temperature for 2 hr. The catalyst was removed by filtration from the reaction solution, and the filtrate was concentrated under the reduced pressure. The residue was purified by NH column chromatography on silica gel (chloroform:methanol:aqueousammonia=20:1:0.1) to give 15 mg (yield 90%) of the title compound.

¹H-NMR (400 MHz, CD₃OD) δ: 0.90-0.95 (3H, m), 1.29 (3H, d, J=6.8 Hz), 1.30-1.40 (4H, m), 1.80-2.30 (4H, m), 1.82 (3H, s), 2.32 (6H, s), 2.38 (3H, s), 2.58 (2H, m), 2.78 (6H, m), 2.88 (2H, m), 2.98 (1H, m), 3.26 (1H, m), 3.51 (1H, m), 3.73 (1H, m), 3.79 (1H, m), 4.07 (1H, dd, J=5.6, 10.0 Hz), 4.26 (1H, m), 4.36 (1H, m), 5.19 (1H, d, J=5.6 Hz), 6.91 (1H, m), 6.69 (1H, m), 7.26 (1H, m).

MS (API) m/z 613 [M+1]⁺.

Compound 37 produced in the same manner as in Example S9 and ¹H-NMR data and MS data for the compound are shown in Table 7.

Step (i) of Example S10

7-(4-(1-Tert-butoxycarbonyl)piperidylthio)-7-deoxy-7-epilincomycin

Sodium hydride (60 mg, 1.54 mmol) is added to a solution of 651 mg (1.54 mmol) of 7-deoxy-7-epi-7-mercaptolincomycin in N,N-dimethylformamide (8 ml) at 4° C. under ice cooling. The mixture was stirred at 4° C. under ice cooling for 30 min and at room temperature for one hr. A solution of 1-tert-butoxycarbonyl-4-(p-toluenesulfonyl)oxypiperidine (660 mg, 1.86 mmol) in N,N-dimethylformamide (2 ml) was added to the reaction solution, and the mixture was stirred at 60° C. for 16 hr. The reaction solution was diluted with 15 ml of ethyl acetate. The diluted solution was then washed with 15 ml of a 10% aqueous sodium hydrogencarbonate solution, and the organic layer was dried over anhydrous sodium sulfate. After filtration, the filtrate was concentrated, and the residue was purified by column chromatography on silica gel (ethyl acetate) to give 360 mg (yield 39%) of the title compound.

¹H-NMR (400 MHz, CDCl₃) δ: 0.85-0.95 (3H, m), 1.25-1.40 (7H, m), 1.46 (9H, s), 1.50-1.65 (4H, m), 1.80-2.15 (4H, m), 2.26 (3H, s), 2.40 (3H, s), 2.70-3.05 (5H, m), 3.23 (1H, m), 3.50-3.65 (3H, m), 3.90-4.05 (2H, m), 4.05-4.20 (2H, m), 5.30-5.40 (1H, m), 8.07 (1H, m).

MS (API) m/z 606 [M+1]⁺.

Step (ii) of Example S10

7-Deoxy-7-epi-7-(4-piperidylthio)lincomycin

Water (0.1 ml) was added to a solution of 360 mg (0.60 mmol) of 7-(4-(1-tert-butoxycarbonyl)piperidylthio)-7-deoxy-7-epilincomycin in methylene chloride (5 ml). Further, 1 ml of trifluoroacetic acid was added thereto at 4° C. under ice cooling, and the mixture was stirred for 3 hr. The reaction solution was concentrated under the reduced pressure. Toluene (5 ml) was added to the residue, and the mixture was again concentrated. The residue was purified by NH column chromatography on silica gel (ethyl acetate:methanol=8:2) to give 275 mg (yield 92%) of the title compound.

¹H-NMR (400 MHz, CDCl₃) δ: 0.85-0.95 (3H, m), 1.20-1.40 (7H, m), 1.45-1.60 (2H, m), 1.80-1.95 (1H, m), 1.95-2.20 (5H, m), 2.22 (3H, s), 2.41 (3H, s), 2.55-2.70 (2H, m), 2.95-3.10 (4H, m), 3.23 (1H, m), 3.47 (1H, m), 3.55 (1H, m), 3.69 (1H, m), 4.05-4.50 (4H, m), 5.23 (1H, d, J=5.6 Hz).

MS (API) m/z 506 [M+1]⁺.

Step (iii) of Example S10

7-Deoxy-7-(1-(2-dimethylaminoacetyl)piperidin-4-ylthio)-7-epilincomycin (Compound 39)

1-Ethyl-3-(3-dimethylaminopropyl)carbodiimide hydrochloride (8.4 mg, 0.0438 mmol), 6.5 mg (0.0471 mmol) of 1-hydroxybenzotriazole, and 10.0 mg (0.0198 mmol) of the title compound in step (ii) of Example S10 were added to a solution of 5.2 mg (0.0489 mmol) of N, N-dimethylglycine in N,N-dimethylformamide (0.5 ml), and the mixture was stirred at room temperature for 21 hr. The reaction solution was diluted with 10 ml of ethyl acetate. The diluted solution was washed with an 8% aqueous sodium hydrogencarbonate solution. The aqueous layer was extracted twice with 3 ml of ethyl acetate. The organic layers were combined and were washed with 25% brine. The organic layers were dried over anhydrous sodium sulfate and was then filtered, and the filtrate was concentrated under the reduced pressure. The residue was purified by chromatography (chloroform:methanol=40:1 to 20:1) to give 4.3 mg (yield 37%) of the title compound.

$^1$H-NMR (300 MHz, CD$_3$OD) δ: 0.88-0.96 (3H, m), 1.28-1.38 (4H, m), 1.35 (3H, d, J=6.9 Hz), 1.43-1.62 (2H, m), 1.78-1.91 (1H, m), 1.94-2.20 (5H, m), 2.22 (3H, s), 2.28 (6H, s), 2.40 (3H, s), 2.88-3.02 (1H, m), 2.97 (1H, dd, J=4.5, 10.2 Hz), 3.10-3.26 (3H, m), 3.22 (2H, s), 3.48 (1H, dq, J=2.7, 7.2 Hz), 3.54 (1H, dd, J=3.3, 10.2 Hz), 3.70 (1H, d, J=2.7 Hz), 3.91-4.02 (1H, m), 4.09 (1H, dd, J=5.7, 10.2 Hz), 4.15 (1H, d, J=9.6 Hz), 4.19-4.32 (1H, m), 4.25 (1H, dd, J=2.4, 9.6 Hz), 5.23 (1H, d, J=5.1 Hz).

MS (FAB) m/z 591 [M+1]$^+$.

Step (i) of Example S11

7-Deoxy-7-epi-7-(1-(2-(2-nitrophenylsulfonamide)acetyl)piperidin-4-ylthio)lincomycin The title compound (34.7 mg, yield 39%) was produced from 60.4 mg (0.119 mmol) of the title compound in step (ii) of Example S10 in the same manner as in step (iii) of Example S10, except that N-nosylglycine was used instead of N,N-dimethylglycine.

$^1$H-NMR (300 MHz, CD$_3$OD) δ: 0.86-0.95 (3H, m), 1.25-1.38 (4H, m), 1.33. (3H, d, J=6.6 Hz), 1.43-1.64 (1H, m), 1.80-2.16 (6H, m), 2.19 (3H, d, J=7.5 Hz), 2.41 (3H, s), 2.82-2.95 (1H, m), 3.01 (1H, dd, J=4.5, 10.5 Hz), 3.07-3.26 (3H, m), 3.40-3.51 (1H, m), 3.54 (1H, dd, J=2.4, 10.2 Hz), 3.70 (1H, d, J=3.0 Hz), 4.06 (2H, s), 4.09 (1H, dd, J=5.7, 10.5 Hz), 4.14 (1H, d, J=9.6 Hz), 4.25 (1H, dd, J=1.8, 9.6 Hz), 5.22 (1H, d, J=1.8, 5.4 Hz), 7.77-7.83 (2H, m), 7.85-7.90 (1H, m), 8.07-8.11 (1H, m).

MS (API) m/z 748 [M+1]$^+$.

Step (ii) of Example S11

7-(1-(2-Aminoacetyl)piperidin-4-ylthio)-7-deoxy-7-epilincomycin (Compound 40)

The title compound (13.4 mg, yield 51%) was produced from 34.7 mg (0.0464 mmol) of the title compound in step (i) of Example S11 in the same manner as in step (ii) of Example S2.

$^1$H-NMR (300 MHz, CD$_3$OD) δ: 0.88-0.94 (3H, m), 1.28-1.38 (4H, m), 1.35 (3H, d, J=6.9 Hz), 1.40-1.62 (2H, m), 1.84 (1H, dt, J=9.9, 12.6 Hz), 1.94-2.15 (5H, m), 2.21 (3H, s), 2.40 (3H, s), 2.92-3.03 (1H, m), 2.97 (1H, dd, J=4.5, 10.5 Hz), 3.10-3.26 (3H, m), 3.45 (2H, s), 3.47 (1H, dq, J=2.1, 7.2 Hz), 3.54 (1H, dd, J=3.3, 10.2 Hz), 3.70 (1H, d, J=3.3 Hz), 3.68-3.80 (1H, m), 4.09 (1H, dd, J=5.7, 10.2 Hz), 4.14 (1H, d, J=9.6 Hz), 4.20-4.32 (1H, m), 4.25 (1H, dd, J=2.4, 9.6 Hz), 5.23 (1H, d, J=5.4 Hz).

MS (FAB) m/z 563 [M+1]$^+$.

Step of Example S12

7-Deoxy-7-(5-(2-(dimethylamino)ethyl)-1,3,4-thiadiazol-2-ylthio)-7-epilincomycin (Compound 41)

2-(5-Chloro-1,3,4-thiadiazol-2-yl)-N,N-dimethylethanamine (45.0 mg, 0.235 mmol) and 70.3 μl (0.470 mmol) of 1,8-diazabicyclo[5.4.0]-7-undecene were added to a solution of 99.2 mg (0.235 mmol) of the title compound in step (v) of Example S1 in N,N-dimethylformamide (2.0 ml), and the mixture was stirred at room temperature for 18 hr. The reaction solution was diluted with chloroform. The diluted solution was then washed with a 10% aqueous sodium hydrogencarbonate solution and was dried over anhydrous sodium sulfate. After filtration, the filtrate was concentrated. The residue was purified by column chromatography on silica gel (chloroform:methanol:28% aqueous ammonia=94:6:1) to give 71.0 mg (yield 52%) of the title compound.

$^1$H-NMR (400 MHz, CD$_3$OD) δ: 0.87-0.97 (3H, m), 1.26-1.40 (4H, m), 1.50 (3H, d, J=7.1 Hz), 1.78-1.88 (1H, m), 1.95-2.09 (5H, m), 2.13-2.25 (1H, m), 2.30 (6H, s), 2.36 (3H, s), 2.68 (2H, t, J=6.6 Hz), 2.98 (1H, dd, J=5.0, 10.5 Hz), 3.17-3.30 (3H, m), 3.55 (1H, dd, J=3.3, 10.1 Hz), 3.79 (1H, d, J=3.3 Hz), 4.10 (1H, dd, J=5.6, 10.1 Hz), 4.34 (1H, dq, J=3.2, 7.1 Hz), 4.38 (1H, d, J=10.0 Hz), 4.55 (1H, dd, J=3.2, 10.0 Hz), 5.25 (1H, d, J=5.6 Hz).

MS (FAB) m/z 578 [M+1]$^+$.

Compound 42 (129 mg, yield 75%) was produced in the same manner as in step (i) of Example S12, except that 60.0 mg (0.291 mmol) of 3-(5-chloro-1,3,4-thiadiazol-2-yl)-N,N-dimethylpropan-1-amine was used instead of 2-(5-chloro-1,3,4-thiadiazol-2-yl)-N,N-dimethylethanamine.

Compound 81 (83 mg, yield 65%) was produced in the same manner as in step (i) of Example S12, except that 60.0 mg (0.291 mmol) of 1-(5-chloro-1,3,4-thiadiazol-2-yl)-N,N-dimethylethanamine was used instead of 2-(5-chloro-1,3,4-thiadiazol-2-yl)-N,N-dimethylethanamine.

Compounds 42 and 81 produced in the same manner as in Example S12 and $^1$H-NMR data and MS data for the compounds are shown in Tables 8 and 23.

Step of Example S13

7-Deoxy-7-(4-((dimethylamino)ethyl)imidazol-2-ylthio)-7-epilincomycin (Compound 82)

Triphenylphosphine (39.9 mg, 0.152 mmol), 27.6 μl (0.152 mol) of diethyl azodicarboxylate, and 26 mg (0.152 mmol) of 5-(2-(dimethylamino)ethyl)-1H-imidazole-2-thiol were added in that order to a solution of 72.9 mg (0.117 mmol) of the title compound in step (i) of Example 1 in tetrahydrofuran (0.45 ml), and the mixture was stirred at room temperature for 5 hr. The reaction solution was concentrated under the reduced pressure, and the residue was purified by column chromatography on silica gel (chloroform:methanol=88:12) to give a residue containing the title compound protected by TMS. Methanol (1 ml) and 1 ml of 1 N hydrochloric acid were added to the residue, and the mixture was stirred for 10 min. The solvent was removed by distillation, and the residue was purified by preparative thin-layer chromatography (chloroform:methanol:28% aqueous ammonia=9:2:0.2) to give 10 mg (yield 16%) of the title compound.

$^1$H-NMR (400 MHz, CD$_3$OD) δ: 0.82-0.96 (3H, m), 1.24 (3H, d, J=7.1 Hz), 1.27-1.39 (4H, m), 1.71-1.82 (1H, m), 1.90-2.10 (5H, m), 2.23 (1H, br), 2.29 (3H, s), 2.32 (6H, s), 2.58-2.67 (2H, m), 2.74-2.82 (2H, m), 2.96 (1H, dd, J=10.2, 5.3 Hz), 3.17-3.24 (1H, m), 3.55-3.66 (2H, m), 3.82 (1H, d, J=3.2 Hz), 4.09 (1H, dd, J=10.2, 5.6 Hz), 4.31 (1H, dd, J=9.3, 3.8 Hz), 4.39 (1H, d, J=9.3 Hz), 5.24 (1H, d, J=5.24 Hz), 6.93 (1H, s)

MS (FAB) m/z 560 [M+1]$^+$.

Step (i) of Example T1

Benzyl (S)-1-N-tert-butoxycarbonyl-5-oxopyrrolidine-2-carboxylate

The title compound (two steps, 200 g, yield 94%) was produced from (S)-5-oxopyrrolidine-2-carboxylic acid in the same manner as in Tetrahedron Lett., 43, (2002), 3499.

Step (ii) of Example T1

Benzyl (2S,4R)-4-allyl-1-N-tert-butoxycarbonylpyrrolidine-2-carboxylate

The title compound (three steps, 95.1 g, yield 51%) was produced in the same manner as in Tetrahedron Lett., 35, (1994), 2053 and J. Am. Chem. Soc., 110, (1998), 3894, except that the title compound in step (i) of Example T1 was used.

$^1$H-NMR (400 MHz, CDCl$_3$) δ: 1.34 (9H, d, J=49.2 Hz), 1.81-1.95 (1H, m), 2.02-2.20 (3H, m), 2.29-2.42 (1H, m), 3.02 (1H, ddd, J=8.8, 10.0, 26.4 Hz), 3.69 (1H, ddd, J=8.0, 10.4, 32.0 Hz), 4.36 (1H, ddd, J=2.4, 9.2, 48.8 Hz), 4.99-5.27 (4H, m), 5.72 (ddt, J=6.8, 10.0, 17.2 Hz), 7.28-7.45 (5H, m).

Step (iii) of Example T1

(2S,4R)-4-Propyl-1-N-tert-butoxycarbonylpyrrolidine-2-carboxylic acid

Pd—C (5 g) was added to a solution of 30.2 g (87.4 mmol) of the title compound in step (ii) of Example T1 in methanol (350 ml) in an argon atmosphere. The mixture was then stirred in a hydrogen atmosphere at room temperature for 7.5 hr. The insolubles were removed by filtration through Celite, and the filtrate was concentrated under the reduced pressure to give the title compound.

$^1$H-NMR (400 MHz, CD$_3$OD) δ: 0.76-0.90 (3H, s), 0.14-0.44 (13H, m), 1.70-1.89 (1H, m), 1.96-2.05 (1H, m), 2.18 (1H, br), 2.80-2.88 (1H, m), 3.50-3.60 (1H, m), 2.78-2.89 (1H, m), 3.50-3.61 (1H, m), 4.07-4.21 (1H, m).

Step (iv) of Example T1

1'-Tert-butoxycarbonyl-1'-demethyl-lincomycin

1-Hydroxybenzotriazole (17.7 g, 131.1 mmol), 27.1 g (131.1 mmol) of dicyclohexylcarbodiimide, and 33.2 g (131.1 mmol) of methyl 1-thio-α-lincosamide were added in that order to a solution of the residue containing the title compound in step (iii) of Example T1 in pyridine (207 ml), and the mixture was stirred at room temperature for 16 hr. Water was added to the reaction solution. The resultant precipitate was removed by filtration, and the filtrate was concentrated to dryness to give the title compound.

$^1$H-NMR (400 MHz, CD$_3$OD) δ: 0.85 (3H, br), 1.05-1.43 (16H, m), 1.61-1.76 (1H, m), 1.90-2.06 (4H, m), 2.32 (1H, br), 2.82 (1H, t, J=10.1 Hz), 3.42-3.62 (2H, m), 3.64-4.38 (6H, m), 5.13 (1H, d, J=5.4 Hz).

Step (v) of Example T1

1'-Tert-butoxycarbonyl-1'-demethyl-2,3,4-tris-O-trimethylsilyl lincomycin

The title compound (18.2 g) (four steps) was produced in the same manner as in step (i) of Example S1, except that the half amount of the residue obtained in step (iv) of Example T1 was used.

$^1$H-NMR (400 MHz, CD$_3$OD) δ: 0.10-0.25 (27H, m), 0.88-0.98 (3H, m), 1.09-1.95 (18H, m), 1.98-2.38 (5H, m), 2.95 (1H, br), 3.59-4.02 (3H, m), 4.06-4.42 (4H, m), 5.19 (1H, d, J=5.4 Hz).

Step (vi) of Example T1

1'-N-Tert-butoxycarbonyl-1'-demethyl-7-O-methanesulphonyl-2,3,4-tris-O-trimethylsilyl lincomycin A crude product of the title compound was produced from 500 mg (0.706 mmol) of the title compound in step (v) of Example T1 in the same manner as in step (ii) of Example S1.

Step (vii) of Example T1

7-Acetylthio-1'-N-tert-butoxycarbonyl-1'-demethyl-7-deoxy-7-epi-2,3,4-tris-O-trimethylsilyl lincomycin The title compound (two steps, 218 mg, yield 40%) was produced from a crude product of the title compound in step (vi) of Example T1 in the same manner as in step (iii) of Example S1.

$^1$H-NMR (300 MHz, CDCl$_3$) δ: 0.13 (18H, s), 0.16 (9H, s), 0.80-1.00 (3H, m), 1.18-1.42 (4H, m), 1.34 (3H, d, J=6.6 Hz), 1.65-2.48 (3H, m), 1.99 (3H, s), 2.29 (3H, s), 2.80-3.13 (1H, m), 3.45-3.60 (1H, m), 3.55 (1H, dd, J=2.4, 9.6 Hz), 3.69 (1H, s), 3.89 (1H, d, J=9.9 Hz), 4.02 (1H, dq, J=2.4, 6.6 Hz), 4.10-4.17 (1H, m), 4.25-4.40 (1H, m), 4.50-4.70 (1H, m), 5.16 (1H, d, J=5.4 Hz), 6.81 (1H, d, J=8.7 Hz).

MS (API) m/z 767 [M+1]$^+$.

Step (viii) of Example T1

7-Acetylthio-1'-N-tert-butoxycarbonyl-1'-demethyl-7-deoxy-7-epilincomycin

The title compound (137 mg, yield 88%) was produced from 218 mg (0.284 mmol) of the title compound in step (vii) of Example T1 in the same manner as in step (iv) of Example S1.

$^1$H-NMR (300 MHz, CD$_3$OD) δ: 0.87-0.96 (3H, m), 1.26-1.40 (4H, m), 1.31 (3H, d, J=7.2 Hz), 1.47 (9H, s), 1.76-1.93 (1H, m), 1.97-2.16 (1H, m), 2.01 (3H, s), 2.20-2.36 (1H, m), 2.32 (3H, s), 2.95 (1H, t, =9.9 Hz), 3.51 (1H, dd, J=3.0, 10.2 Hz), 3.66 (1H, dd, J=7.5, 10.2 Hz), 3.91 (1H, d, J=2.7 Hz), 3.96 (1H, dq, J=2.4, 6.9 Hz), 4.06 (1H, dd, J=5.4, 10.2 Hz), 4.16-4.36 (1H, m), 4.19 (1H, d, J=9.6 Hz), 4.46 (1H, dd, J=3.0, 9.6 Hz), 5.21 (1H, d, J=5.7 Hz).

MS (API) m/z 551 [M$^+$+1].

Step (ix) of Example T1

1'-N-Tert-butoxycarbonyl-1'-demethyl-7-deoxy-7-epi-7-mercaptolincomycin

The title compound (120 mg, yield 95%) was produced from the title compound (137 mg, 0.249 mmol) in step (viii) of Example T1 in the same manner as in step (v) of Example S1.

$^1$H-NMR (300 MHz, CD$_3$OD) δ: 0.89-0.97 (3H, m), 1.29 (3H, d, J=6.3 Hz), 1.29-1.41 (4H, m), 1.47 (9H, s), 1.82-1.94 (1H, m), 2.06-2.18 (1H, m), 2.15 (3H, s), 2.21-2.35 (1H, br), 2.97 (1H, t, J=9.9 Hz), 3.40-3.52 (1H, m), 3.54 (1H, dd, J=3.0, 10.2 Hz), 3.66 (1H, dd, J=7.5, 10.2 Hz), 3.82-3.89 (1H, br), 4.08 (1H, dd, J=6.0, 10.2 Hz), 4.13 (1H, d, J=9.9 Hz), 4.27-4.45 (2H, m), 5.25 (1H, d, J=5.7 Hz).

MS (FAB) m/z 509 [M+H]$^+$.

Step (x) of Example T1

1'-N-Tert-butoxycarbonyl-1'-demethyl-7-deoxy-7-(4-(2-(dimethylamino)ethyl)phenylthio)-7-epilincomycin The title compound (33.0 mg, yield 85%) was produced in the same manner as in step (vi) of Example S1, except that 30.0 mg (0.059 mmol) of the title compound in step (ix) of Example T1, 6.8 mg (0.0118 mmol) of 4,5-bis(diphenylphosphino)-9,9-dimethylsantene, 5.4 mg (0.0059 mmol) of tris (dibenzylideneacetone)dipalladium, 25.4 mg (0.111 mmol) of 2-(4-bromophenyl)-N,N-dimethylethanamine, 0.021 ml (0.118 mmol) of diisopropylethylamine, and dioxane (0.5 ml) were used.

$^1$H-NMR (400 MHz, CD$_3$OD) δ: 0.89-0.98 (3H, m), 1.24-1.43 (4H, m), 1.26 (3H, d, J=7.1 Hz), 1.48 (9H, s), 1.80-1.91 (1H, m), 1.97 (3H, s), 2.07-2.20 (1H, m), 2.24-2.38 (1H, m), 2.34 (6H, s), 2.57-2.65 (2H, m), 2.74-2.84 (2H, m), 2.96 (1H, t, J=9.3 Hz), 3.58 (1H, dd, J=3.4, 10.2 Hz), 3.67 (1H, dd, J=7.5 Hz), 3.72-3.81 (1H, m), 3.90-3.98 (1H, m), 4.08 (1H, dd, J=5.4, 10.2 Hz), 4.28-4.54 (3H, m), 5.26 (1H, d, J=5.6 Hz), 7.18 (2H, d, J=7.8 Hz), 7.35 (2H, d, J=8.0 Hz).

MS (FAB) m/z 656 [M+H]$^+$.

Step (xi) of Example T1

1'-Demethyl-7-(4-(2-dimethylaminoethyl)phenylthio)-7-deoxy-7-epilincomycin (Compound 43)

Ice cooled trifluoroacetic acid was added to 33.0 mg (0.0503 mmol) of the title compound in step (x) of Example T1, and the mixture was then stirred at room temperature for 40 min. Trifluoroacetic acid was removed by distillation under the reduced pressure, and the residue was purified by preparative thin-layer chromatography (chloroform : methanol : 28% aqueous ammonia=9:2:0.2) to give 21 mg (yield 75%) of the title compound.

$^1$H-NMR (400 MHz, CD$_3$OD) δ: 0.89-1.00 (3H, m), 1.24 (3H, d, J=6.9 Hz), 1.26-1.45 (4H, m), 1.85 (1H, dd, J=3.7, 9.5 Hz), 1.99 (3H, s), 2.04-2.16 (2H, m), 2.48 (6H, s), 2.65 (1H, dd, J=8.2, 10.3 Hz), 2.73-2.89 (4H, m), 3.27 (1H, dd, J=7.5, 10.3 Hz), 3.57 (1H, dd, J=3.2, 10.2 Hz), 3.78 (1H, d, J=3.2 Hz), 3.80 (1H, d, J=2.5, 6.9 Hz), 3.93 (1H, dd, J=3.7, 9.3 Hz), 4.09 (1H, dd, J=5.6, 10.2 Hz), 4.37 (1H, d, J=10.0 Hz), 4.47 (1H, dd, J=2.4, 10.0 Hz), 5.27 (1H, d, J=5.6 Hz), 7.21 (2H, d, J=8.2 Hz), 7.37 (2H, d, J=8.0 Hz).

MS (FAB) m/z 556 [M+H]$^+$.

Step (i) of Example U1

4-Propylpiperidine-2-carboxylic acid

Platinum(IV) oxide (79.8 mg, 0.35 mmol) was added to a solution of 1.05 g (5.22 mmol) of 4-propylpyridine-2-carboxylic acid hydrochloride synthetized according to a literature (J. Med. Chem. 1984, 27, 216.) in acetic acid (8 ml), and the mixture was stirred in a hydrogen atmosphere under the atmospheric pressure overnight. The reaction solution was filtered through Celite, and the solvent was then removed by distillation to give 9.90 g (yield 90%) of the title compound as acetate.

$^1$H-NMR (400 MHz, CD$_3$OD) δ: 0.71 (3H, t, J=7.2 Hz), 1.02-1.22 (6H, m), 1.43-1.55 (1H, m), 1.65-1.74 (1H, m), 2.06-2.15 (1H, m), 2.78 (1H, td, J=13.4, 3.2 Hz), 3.15-3.22 (1H, m), 3.66 (1H, dd, J=12.8, 3.3 Hz)

MS (FAB) m/z 172 [M+H]$^+$.

Step (ii) of Example U1

1-(Tert-butoxycarbonyl)-4-propylpiperidine-2-carboxylic acid

Di-tert-butyl dicarbonate (11.9 ml, 52 mmol) and 43 ml of a 2 N aqueous sodium hydroxide solution were added in that order to a solution of 9.9 g (43 mmol) of the compound synthesized in step (i) of Example U1 in tert-butanol (40 ml), and the mixture was stirred at room temperarure overnight. The solvent was removed by distillation. Water and ether were then added to the residue. Ethyl acetate and 2 N hydrochloric acid were added to the aqueous layer, and the mixture was extracted with ethyl acetate. The organic layer was washed with saturated brine and was then dried over anhydrous sodium sulfate. The solvent was removed by distillation to give 7.9 g (yield 68%) of the title compound.

$^1$H-NMR (400 MHz, CDCl$_3$) δ: 0.88 (3H, t, J=6.9 Hz), 1.26-1.40 (4H, m), 1.45 (9H, s), 1.45-1.50 (1H, m), 1.55-1.70 (1H, m), 1.70-1.85 (2H, m), 1.95-2.05 (1H, m), 3.35-3.43 (1H, m), 3.49-3.60 (1H, m), 4.30 (1H, t, J=6.9 Hz)

MS (EI): 271 [M]$^+$.

Step (iii) of Example U1

Methyl 6-N-((2S,4R)-1-(tert-butoxycarbonyl)-4-propylpiperidine-2-carbonyl)-1-thio-α-lincosamide The title compound and methyl 6-N-((2R,4S)-1-(tert-butoxycarbonyl)-4-propyl)piperidine-2-carbonyl)-1-thio-α-lincosamide were obtained as a mixture (1:1) (2.67 g, yield quant.) in the same manner as in step (iv) of Example T1, except that 969.9 mg (3.58 mmol) of the compound synthesized in step (ii) of Example U1, 1.35g (5.35 mmol) of methylthio lincosamide, 1.11 g (5.38 mmol) of dicyclohexylcarbodiimide, 725.0 mg (5.37 mmol) of 1-hydroxybenzotriazole, and 8 ml of N,N-dimethylformamide were used.

Step (iv) of Example U1

Methyl 6-N-((2S,4R)-4-propylpiperidine-2-carbonyl)-1-thio-2,3,4-tris-O-trimethylsilyl-α-lincosamide The title compound (0.8 g, yield 41%) was produced in the same manner as in step (v) of Example T1, except that 1.35 g (2.68 mmol) of the compound synthesized in step (iii) of Example U1, 2.72 ml (21.4 mmol) of trimethylchlorosilane, 4.52 ml (21.4 mol) of hexamethyldisilazane, 13.4 ml of pyridine, 18.7 ml of methanol, and 0.75 ml of 6 N acetic acid were used.

$^1$H-NMR (400 MHz, CDCl$_3$) δ: 0.14 (18H, s), 0.19 (9H, s), 0.58 (3H, t, J=6.8 Hz), 1.15 (3H, d, J=5.6 Hz), 1.23-1.34 (4H, m), 1.46 (9H, s), 1.47-1.53 (1H, m), 1.57 (1H, s), 1.78-1.91 (1H, m), 1.91-2.06 (4H, m), 2.91-2.95 (1H, m), 3.33-3.53 (2H, m), 3.59 (1H, dd, J=8.6, 2.5 Hz), 3.88 (1H, brd), 3.93-4.01 (1H, m), 4.04 (1H, d, J=8.3 Hz), 4.08-4.15 (3H, m), 4.28-4.38 (1H, m), 5.16 (1H, d, J=5.4 Hz), 6.33 (1H, d, J=8.7 Hz).

Step (v) of Example U1

Methyl 6-N-((2S,4R)-1-(N-tert-butoxycarbonyl)-4-propylpiperidine-2-carbonyl)-7-O-methanesulphonyl-1-thio-2,3,4-tris-O-trimethylsilyl-α-lincosamide Triethylamine (291 µl, 2.08 mmol) and 107 µl (1.39 mmol) of methanesulphonyl chloride were added to a solution of 500 mg (0.693 mmol) of the title compound in step (iv) of Example U1 in dichloromethane (2 ml), and the mixture was stirred at room temperature for one hr. The reaction solution was diluted with ethyl acetate, and the diluted solution was then washed with a 10% aqueous sodium hydrogencarbonate solution and was dried over anhydrous sodium sulfate. After filtration, the filtrate was then concentrated to give 530 mg (yield 95%) of the title compound.

$^1$H-NMR (400 MHz, CDCl$_3$) δ: 0.09-0.22 (27H, m), 0.83-0.92 (3H, m), 1.03-1.73 (18H, m), 1.78-1.99 (2H, m), 2.06 (3H, s), 2.62 (1H, br), 3.07 (3H, s), 3.15-3.25 (1H, m), 3.58 (1H, dd, J=2.3, 9.7 Hz), 3.66 (1H, br), 3.90-4.04 (2H, m), 4.10 (1H, dd, J=5.6, 9.7 Hz), 4.26-4.46 (1H, m), 4.46-4.69 (1H, m), 4.91-5.00 (1H, m), 5.12 (1H, d, J=5.6 Hz), 6.80 (1H, br).

Step (vi) of Example U1

Methyl 7-acetylthio-6-N-((2S,4R)-1-(N-tert-butoxycarbonyl)-4-propylpiperidine-2-carbonyl)-7-deoxy-7-epi-1-thio-2,3,4-tris-O-trimethylsilyl-α-lincosamide Potassium thioacetate (396 mg, 3.47 mmol) was added to a solution of 530 mg (0.693 mmol) of the title compound in step (v) of Example U1 in N,N-dimethylformamide (3.0 ml), and the mixture was stirred at 80° C. for 2 hr. The reaction solution was diluted with ethyl acetate, and the diluted solution was then washed with a 10% aqueous sodium hydrogencarbonate solution and 10% brine. The washed solution was dried over anhydrous sodium sulfate. After filtratin, the filtrate was concentrated, and the residue was purified by column chromatography on silica gel (hexane:ethyl acetate=100:0-85:15) to give 357 mg (yield 69%) of the title compound.

$^1$-NMR (400 MHz, CDCl$_3$) δ: 0.09-0.21 (27H, m), 0.83-0.92 (3H, m), 1.10-1.58 (19H, m), 1.82-2.07 (5H, m), 2.29 (3H, s), 3.10 (1H, br), 3.57 (1H, dd, J=2.2, 9.5 Hz), 3.64-3.82 (2H, m), 3.91 (1H, d, J=9.3 Hz), 3.94-4.02 (1H, m), 4.12 (1H, dd, J=5.6, 9.5 Hz), 4.24-4.32 (1H, m), 4.56 (1H, dt, J=3.2, 9.5 Hz), 5.15 (1H, d, J=5.6 Hz), 6.19 (1H, br).

MS (EI) m/z 781 [M+H]$^+$.

Step (vii) of Example U1

Methyl 7-acetylthio-6-N-((2S,4R)-1-(N-tert-butoxycarbonyl)-4-propylpiperidine-2-carbonyl)-7-deoxy-7-epi-1-thio-α-lincosamide 1 N Hydrochloric acid (2.5 ml) was added to a solution of 341 mg (0.436 mmol) of the title compound in step (vi) of Example U1 in methanol (4 ml), and the mixture was stirred at room temperature for 5 min. A 10% aqueous sodium hydrogencarbonate solution was added to the reaction solution. The mixture was concentrated under the reduced pressure to about half amount, and the residue was extracted with ethyl acetate. The extract was dried over anhydrous sodium sulfate. After filtration, the filtrate was concentrated to give 250 mg (yield quant) of the title compound.

$^1$H-NMR (400 MHz, CDCl$_3$) δ: 0.86-0.93 (3H, m), 1.21-1.37 (6H, m), 1.44 (3H, d, J=7.3 Hz), 1.46 (9H, s), 1.60-1.72 (1H, m), 1.78-1.90 (1H, m), 1.95-2.06 (1H, m), 2.15 (3H, s), 2.33 (1H, d, J=5.6 Hz), 2.36 (3H, s), 2.63 (1H, d, J=10.0 Hz), 3.40 (1H, br), 3.50 (1H, dt, J=3.2, 9.7 Hz), 3.62 (1H, br), 3.84-3.95 (2H, m), 3.99 (1H, d, J=10.0 Hz), 4.05-4.12 (1H, m), 4.20 (1H, br), 4.32 (1H, dt, J=3.3, 10.0 Hz), 4.90 (1H, d, J=3.2 Hz), 5.29 (1H, d, J=5.6 Hz), 6.90 (1H, br).

MS (FAB) m/z 565 [M+H]$^+$.

Step (viii) of Example U1

Methyl 6-N-((2S,4R)-1-(N-tert-butoxycarbonyl)-4-propylpiperidine-2-carbonyl)-7-deoxy-7-epi-7-mercapto-1-thio-α-lincosamide A 28% sodium methoxide-methanol solution (251 µl) was added to a solution of 244 mg (0.432 mmol) of the title compound in step (vii) of Example U1 in methanol (2.5 ml), and the mixture was stirred at room temperature for 20 min. The reaction solution was diluted with ethyl acetate. The diluted solution was then washed with a 10% aqueous ammonium chloride solution and a 10% aqueous sodium hydrogencarbonate solution and was dried over anhydrous sodium sulfate. After filtration, the filtrate was concentrated, and the residue was purified by column chromatography on silica gel (chloroform:methanol=100:0 to 96:4) to give 234 mg (yield 96%) of the title compound.

$^1$H-NMR (400 MHz, CDCl$_3$) δ: 0.86-0.94 (3H, m), 1.21-1.38 (8H, m), 1.44 (1H, d, J=4.6 Hz), 1.45 (9H, s), 1.55-1.64 (1H, m), 1.65-1.75 (1H, m), 1.80-1.91 (1H, m), 1.95-2.03 (1H, m), 2.22 (3H, s), 2.38 (1H, d, J=5.1 Hz), 2.64 (1H, d, J=10.2 Hz), 3.27 (1H, br), 3.55 (1H, dt, J=3.4, 10.0 Hz), 3.59-3.78 (2H, m), 3.82-3.90 (2H, m), 4.07-4.18 (2H, m), 4.22-4.30 (1H, m), 4.84 (1H, d, J=3.6 Hz), 5.32 (1H, d, J=5.6 Hz), 6.69 (1H, d, J=9.0 Hz).

MS (FAB) m/z 523 [M+H]$^+$.

Step (ix) of Example U1

Methyl 6-N-((2S,4R)-1-(N-tert-butoxycarbonyl)-4-propylpiperidine-2-carbonyl)-7-deoxy-7-(4-(2-(dimethylamino)ethyl)phenylthio)-7-epi-1-thio-α-lincosamide The title compound (123.0 mg, yield 96%) was produced in the same manner as in step (vi) of Example S1, except that 100 mg (0.191 mmol) of the title compound in step (viii) of Example U1, 11.1 mg (0.0191 mmol) of 4,5-bis(diphenylphosphino)-9,9-dimethylsantene, 8.7 mg (0.00096 mmol) of tris(dibenzylideneacetone)dipalladium, 56.7 mg (0.249 mmol) of 2-(4-bromophenyl)-N,N-dimethylethanamine, 0.067 ml (0.382 mmol) of diisopropylethylamine, and dioxane (1.4 ml) were used.

$^1$H-NMR (400 MHz, CD$_3$OD) δ: 0.91 (3H, t, J=6.6 Hz), 1.22-1.42 (6H, m), 1.28 (3H, d, J=7.1 Hz), 1.46 (9H, s), 1.51-1.68 (2H, m), 1.76-1.87 (1H, m), 1.97 (3H, s), 2.34 (6H, s), 2.55-2.65 (2H, m), 2.75-2.84 (2H, m), 3.24-3.70 (1H, br), 3.58 (1H, dd, J=3.4, 10.2 Hz), 3.74 (1H, dq, J=2.7, 6.9 Hz), 3.92-4.30 (2H, br), 4.07 (1H, dd, J=5.6, 10.2 Hz), 4.43 (1H, d, J=9.2 Hz), 4.47 (1H, dd, J=2.4, 9.2 Hz), 5.25 (1H, d, J=5.6 Hz), 7.18 (2H, d, J=8.3 Hz), 7.36 (2H, d, J=8.3 Hz).

MS (FAB) m/z 670 [M+H]$^+$.

Step (x) of Example U1

Methyl 7-deoxy-7-(4-(2-dimethylaminoethyl)phenylthio)-7-epi-6-N-(((2S,4R)-4-propyl)piperidine-2-carbonyl)-1-thio-α-lincosamide (Compound 44)

The title compound (66.0 mg, yield 63%) was produced from 123 mg (0.184 mmol) of the title compound in step (ix) of Example U1 in the same manner as in step (xi) of Example T1.

$^1$H-NMR (400 MHz, CD$_3$OD) δ: 0.94 (3H, t, J=7.3 Hz), 1.06-1.20 (2H, m), 1.23-1.45 (4H, m), 1.26 (3H, d, J=6.9 Hz), 1.52-1.67 (1H, m), 1.77 (1H, d, J=13.0 Hz), 1.97 (3H, s), 2.05

(1H, d, J=12.7 Hz), 2.40 (6H, s), 2.62-2.70 (2H, m), 2.74 (1H, dt, J=2.9, 12.9 Hz), 2.76-2.86 (2H, m), 3.19-3.26 (1H, m), 3.46 (1H, dd, J=2.9, 12.1 Hz), 3.58 (11-I, dd, J=3.4, 10.3 Hz), 3.77 (1H, dq, J=2.4, 6.9 Hz), 3.86 (1H, d, J=3.4 Hz), 4.09 (1H, dd, J=5.6, 10.2 Hz), 4.43 (1H, d, J=10.0 Hz), 4.55 (1H, dd, J=2.4, 1.0 Hz), 5.27 (1H, d, J=5.6 Hz), 7.19 (2H, d, J=8.3 Hz), 7.35 (2H, d, J=8.2 Hz).

MS (FAB) m/z 570 [M+H]$^+$.

Step (xi) of Example U1

Methyl 7-deoxy-7-(4-(2-dimethylaminoethyl)phenylthio)-7-epi-6-N-((2S,4R)-1-methyl-4-propylpiperidine-2-carbonyl)-1-thio-α-lincosamide (Compound 45)

Formaldehyde (0.020 ml, 0.237 mmol) and 0.014 ml (0.237 mmol) of acetic acid were added in that order to a solution of 45 mg (0.0790 mmol) of compound 44 in methanol (1 ml). Sodium tri(acetoxy)borohydride (100.5 mg, 0.474 mmol) was then added thereto, and the mixture was stirred at room temperature for one hr. The solvent was removed by distillation, and the residue was purified by preparative thin-layer chromatography (chloroform:methanol:28% aqueous ammonia=10:2:0.2) to give 34 mg (yield 74%) of the title compound.

$^1$H-NMR (400 MHz, CD$_3$OD) δ: 0.91 (3H, t, J=7.2 Hz), 1.16-1.39 (10H, m), 1.71 (1H, d, J=12.5 Hz), 1.86 (1H, d, J=12.5 Hz), 1.99 (3H, s), 2.08-2.14 (1H, m), 2.25 (3H, s), 2.35 (6H, s), 2.57-2.62 (3H, m), 2.77-2.81 (2H, m), 2.95 (1H, ddd, J=11.2, 7.4, 7.4 Hz), 3.58 (1H, dd, J=10.0, 3.4 Hz), 3.78-3.82 (2H, m), 4.11 (1H, dd, J=10.2, 5.6 Hz), 4.40 (1H, d, J=10.0 Hz), 4.54 (1H, dd, J=10.0, 2.7 Hz), 5.27 (1H, d, J=5.6 Hz), 7.18 (2H, d, J=8.3 Hz), 7.35 (2H, d, J=8.3 Hz).

MS (FAB) m/z 584 [M+H]$^+$.

Step (i) of Example W1

4-Cyclopropylmethylpyridine

A solution of 19.5 ml (200 mmol) of 4-picoline in tetrahydrofuran (120 ml) was cooled to −78° C. Lithium diisopropylamide (2 M heptane, tetrahydrofuran, ethylbenzene solution) (200 ml) was added dropwise to the cooled solution over a period of 20 min. The mixture was then stirred at -40° C. for 20 min and was cooled to −78° C. Cyclopropylbromide (16.0 ml, 200 mmol) was added dropwise to the reaction solution over a period of 25 min, and the mixture was stirred at −78° C. for one hr. The reaction solution was then added to 300 ml of a saturated aqueous ammonium chloride solution, and the mixture was satisfactorily washed with 100 ml of water. The solution was extracted twice with 200 ml of ethyl acetate, and the extract was dried over anhydrous sodium sulfate. After filtration, the filtrate was concentrated, and the residue was distilled under the reduced pressure (8 mmHg, 86 to 87° C.). The distillation residue was purified by column chromatography on silica gel (hexane:ethyl acetate=70:30) to give 17.6 g (yield 66%) of the title compound.

$^1$H-NMR (400 MHz, CDCl$_3$) δ: 0.19-0.25 (2H, m), 0.55-0.61 (2H, m), 0.93-1.04 (1H, m), 2.54 (2H, d, J=7.1 Hz), 7.17-7.22 (2H, m), 8.47-8.52 (2H, m).

MS (FAB) m/z 134 [M+H]$^+$.

Step (ii) of Example W1

4-Cyclopropylmethylpyridine-N-oxide

Methachloroperbenzoic acid (42.7 g, purity: >65%) was added to a solution of 21.4 g (161 mmol) of the title compound in step (i) of Example W1 in dichloromethane (240 ml), and the mixture was stirred at room temperature for 1 hr 20 min. A 20% sodium thiosulfate pentahydrate solution (120 ml) was added to the reaction solution, and the mixture was stirred at room temperature for one hr. A saturated aqueous sodium hydrogencarbonate solution (200 ml) and 50 ml of a saturated aqueous potassium carbonate solution were added to the reaction solution, and the mixture was extracted thrice with a mixed solution composed of chloroform and isopropanol (8: 1, 450 ml). The extract was dried over anhydrous sodium sulfate. After filtration, the filtrate was concentrated to give 23.9 g (yield 100%) of the title compound.

$^1$H-NMR (400 MHz, CDCl$_3$) δ: 0.19-0.27 (2H, m), 0.58-0.66 (2H, m), 0.90-1.02 (1H, m), 2.54 (2H, d, J=7.1 Hz), 7.21 (2H, d, J=6.8 Hz), 8.15 (2H, d, J=6.8 Hz).

Step (iii) of Example W1

2-Cyano-4-cyclopropylmethylpyridine

Trimethylsilyl cyanide (25.8 ml, 0.193 mmol) was added to a solution of 23.9 g (160 mmol) of the title compound In step (ii) of Example W1 in dichloromethane (300 ml). Dimethylcarbamic acid chloride (17.8 ml, 193 mmol) was added in three divided portions at intervals of 20 min. The mixture was stirred at room temperature for 24 hr. A 10% (w/v) aqueous potassium carbonate solution (300 ml) was added to the reaction solution, and the mixture was stirred for 30 min. Dichloromethane (100 ml) was then added to the reaction solution for extraction. Dichloromethane (200 ml) was added to the aqueous layer for extraction. The organic layers were combined and were dried over anhydrous sodium sulfate. After filtration, the filtrate was concentrated, and the residue was purified by column chromatography on silica gel (hexane: ethyl acetate=100:0 to 85:15) to give 22.6 g (yield 89%) of the title compound.

$^1$H-NMR (400 MHz, CDCl$_3$) δ: 0.22-0.29 (2H, m), 0.62-0.68 (2H, m), 0.93-1.04 (1H, m), 2.61 (2H, d, J=7.1 Hz), 7.41-7.45 (1H, m), 7.63-7.66 (1H, m), 8.58-8.62 (1H, m).

MS (EI) m/z 158 M$^+$.

Step (iv) of Example W1

4-(Cyclopropylmethyl)picolinic acid

A 5 N aqueous sodium hydroxide solution (250 ml) was added to a solution of 25.5 g (161 mmol) of the title compound in step (iii) of Example W1 in methanol (250 ml), and the mixture was stirred at 50° C. for 8 hr. 5 N hydrochloric acid (250 ml) was added to the reaction solution under ice cooling. The mixture was rendered weakly acidic by the addition of 1 N hydrochloric acid. The adjusted solution was extracted seven times with a mixed solution composed of chloroform and isopropanol (5:1, 600 ml). The combined organic layers were dried over anhydrous sodium sulfate. After filtration, the filtrate was concentrated to give 27.6 g (yield 97%) of the title compound.

$^1$H-NMR (400 MHz, CDCl$_3$) δ: 0.24-0.30 (2H, m), 0.60-0.67 (2H, m), 0.98-1.08 (1H, m), 2.67 (2H, d, J=7.1 Hz), 7.48-7.53 (1H, m), 8.15-8.19 (1H, m), 8.52-8.56 (1H, m).

MS (FAB) m/z 178 [M+H]$^+$.

Step (v) of Example W1

Cis-4-(cyclopropylmethyl)piperidine-2-carboxylic acid trifluoroacetate

Platinum oxide (1.5 g, 6.6 mmol) was added to a solution of 23.4 g (132 mmol) of the title compound in step (iv) of Example W1 in acetic acid-water (9:1, 187 ml), and the mixture was stirred in a hydrogen atmosphere for 3 days. The reaction solution was filtered through Celite, and the filtrate was concentrated to give 25.5 g of a 5:1 mixture composed of the title compound and 4-isobutyl pipecolic acid. Trifluoroacetic acid (1 ml) was added to a solution of 500 mg of the mixture in methanol (20 ml). The mixture was concentrated, and the residue was purified by column chromatography on ODS (methanol:water:trifluoroacetic acid=88:12:0.1) to give 658 mg of the title compound.

$^1$H-NMR (400 MHz, D$_2$O) δ: −0.05-0.04 (2H, m), 0.35-0.45 (2H, m), 0.62-0.75 (1H, m), 1.14-1.47 (4H, m), 1.75-1.88 (1H, m), 2.00 (1H, d, J=14.6 Hz), 2.23-2.45 (1H, m), 3.11 (1H, dt, J=2.9, 13.2 Hz), 3.47 (1H, ddd, J=2.2, 4.1, 12.9 Hz), 3.94 (1H, dd, J=3.3, 12.9 Hz).

MS (FAB) m/z 184 [M+H]$^+$.

Step (vi) of Example W1

Cis-1-(tert-butoxycarbonyl)-4-(cyclopropylmethyl)piperidine-2-carboxylic acid

A 2 N aqueous sodium hydroxide solution (6 ml, 12.0 mmol) and 1.00 ml (4.36 mmol) of di-tert-butyl dicarbonate were added to a solution of 1.08 g (3.63 mmol) of the title compound in step (v) of Example W1 in dioxane (8 ml), and the mixture was stirred at room temperature for 3 hr. The reaction solution was concentrated to about half amount under the reduced pressure. The residue was rendered weakly alkaline by the addition of a 1 N aqueous sodium hydroxide solution. The adjusted solution was then washed with ethyl acetate and was rendered weakly acidic by the addition of 1 N hydrochloric acid. The adjusted solution was then extracted with ethyl acetate. After filtration, the filtrate was dried over anhydrous sodium sulfate and was then concentrated to give 968 mg (yield 94%) of the title compound.

$^1$H-NMR (400 MHz, CDCl$_3$) δ: −0.01-0.04 (2H, m), 0.39-0.46 (2H, m), 0.62-0.73 (1H, m), 1.14-1.28 (2H, m), 1.38-1.49 (10H, m), 1.69-1.88 (3H, m), 2.05-2.14 (1H, m), 3.38-3.58 (2H, m), 4.25-4.33 (1H, m).

Step (vii) of Example W1

Methyl 6-N-((2S,4R)-1-(tert-butoxycarbonyl)-4-(cyclopropylmethyl)piperidine-2-carbonyl)-1-thio-α-lincosamide 1-Hydroxybenzotriazole (28.6 g, 187 mmol), 35.8 g (187 mmol) of dicyclohexylcarbodiimide, and 33.2 g (187 mmol) of methyl 1-thio-α-lincosamide were added to a solution of 44.2 g (156 mmol) of the title compound in step (vi) of Example W1 in N,N-dimethylformamide (300 ml), and the mixture was stired at room temperature for 13 hr. Ethyl acetate (150 ml) and 150 ml of acetone were added to the reaction solution, and the mixture was filtered. Ethyl acetate (800 ml) was added to the filtrate, and the mixture was washed with 800 ml of saturated aqueous sodium hydrogencarbonate solution. The organic layer was dried over anhydrous sodium sulfate. After filtration, the filtrate was concentrated. Toluene was added to the residue, and the insolubles were filtered to give 35.0 g (yield 71%) of the title compound.

MS (FAB) m/z 519 (M+H)$^+$.

Step (viii) of Example W1

Methyl 6-N-((2S,4R)-1-(tert-butoxycarbonyl)-4-(cyclopropylmethyl)piperidine-2-carbonyl)-1-thio-2,3,4-tris-O-trimethylsilyl-α-lincosamide Trimethylsilane chloride (43.1 ml, 337 mmol) and 70.6 ml (337 mmol) of hexamethyldisilazane were added to a solution of 35.0 g (67.5 mmol) of the title compound in step (vii) of Example W1 in pyridine (130 ml), and the mixture was stirred at room temperature for one hr. The reaction solution was added to 1L of a saturated aqueous sodium hydrogencarbonate solution, and the mixture was extracted with ethyl acetate. The organic layer was dried over anhydrous sodium sulfate. After filtration, the filtrate was concentrated. 6 N acetic acid (16.9 ml, 101 mmol) was added to a solution of the residue in methanol (350 ml), the mixture was stirred at room temperature for 2.3 hr. A saturated aqueous sodium hydrogencarbonate solution (100 ml) was added to the reaction solution, and the mixture was concentrated. Ethyl acetate was added to the residue, and the mixture was washed with 10% brine. The organic layer was dried over anhydrous sodium sulfate. After filtration, the filtrate was concentrated. The residue was purified by column chromatography on silica gel (hexane:ethyl acetate=85:15-82:18) to give 30.6 g (yield 62%) of the title compound.

$^1$H-NMR (400 MHz, CDCl$_3$) δ: −0.04-0.02 (2H, m), 0.13 (9H, s), 0.14 (9H, s), 0.19 (9H, s), 0.39-0.46 (2H, m), 0.62-0.72 (1H, m), 1.11-1.34 (6H, m), 1.47 (9H, s), 1.56-1.68 (2H, m), 1.82-1.92 (1H, m), 2.00-2.16 (4H, m), 2.86 (1H, d, J=6.6 Hz), 3.30-3.65 (3H, m), 3.88-4.23 (5H, m), 4.29-4.39 (1H, m), 5.17 (1H, d, J=5.4 Hz), 6.42 (1H, d, J=9.3 Hz).

MS (FAB) m/z 735 [M+H]$^+$.

Step (ix) of Example W1

Methyl 6-N-((2S,4R)-1-(tert-butoxycarbonyl)-4-(cyclopropylmethyl)piperidine-2-carbonyl)-7-O-methanesulphonyl-1-thio-2,3,4-tris-O-trimethylsilyl-α-lincosamide Triethylamine (571 μl, 4.08 mmol) and 211 μl (2.72 mmol) of methanesulphonyl chloride were added to a solution of 1.00 g (1.36 mmol) of the title compound in step (viii) of Example W1 in chloroform (7 ml), and the mixture was stirred at room temperature for 45 min. The reaction solution was diluted with ethyl acetate, and the diluted solution was washed with a 10% aqueous sodium hydrogencarbonate solution and 10% brine. The washed solution was dried over anhydrous sodium sulfate. After filtration, the filtrate was then concentrated to give 1.06 g (yield 96%) of the title compound.

MS (EI) m/z 813 [M+H]$^+$.

Step (x) of Example W1

Methyl 7-acetylthio-6-N-((2S,4R)-1-(tert-butoxycarbonyl)-4-(cyclopropylmethyl)piperidine-2-carbonyl)-7-deoxy-7-epi-1-thio-2,3,4-tris-O-trimethylsilyl-α-lincosamide Potassium thioacetate (6.14 g, 53.8 mmol) was added to a solution of 8.75 g (9.37 mmol) of the title compound in step (ix) of Example W1 in N,N-dimethylformamide (75 ml), and the mixture was stirred at 80° C. for 1.5 hr. The reaction solution was diluted with ethyl acetate. The diluted solution was washed with a 10% aqueous sodium hydrogencarbonate solution and 10% brine. The washed solution was dried over anhydrous sodium sulfate. After filtration, the filtrate was concentrated. The residue was purified by column chromatography on silica gel (hexane:ethyl acetate=100:0-85:15) to give 4.0 g (yield 54%) of the title compound.

$^1$H-NMR (400 MHz, CDCl$_3$) δ: −0.03-0.05 (2H, m), 0.13 (18H, m), 0.18 (9H, s), 0.38-0.46 (2H, m), 0.62-0.73 (1H, m), 1.17-1.29 (3H, m), 1.36 (3H, d, J=6.8 Hz), 1.50 (9H, s), 1.58-1.72 (2H, m), 1.87-2.17 (5H, m), 2.29 (3H, s), 3.11 (1H, br), 3.58 (1H, dd, =2.2, 9.5 Hz), 3.67-3.84 (2H, m), 3.88-4.03 (2H, m), 4.12 (1H, dd, =5.4, 9.5 Hz), 4.30-4.40 (1H, m), 4.52-4.62 (1H, m), 5.16 (1H, d, J=5.4 Hz), 6.27 (1H, br).

MS (EI) m/z 793 [M+H]$^+$.

Step (xi) of Example W1

Methyl 7-acetylthio-6-N-((2S,4R)-1-(tert-butoxycarbonyl)-4-(cyclopropylmethyl)piperidine-2-carbonyl)-7-deoxy-7-epi-1-thio-α-lincosamide 1 N Hydrochloric acid (26.2 ml, 26.2 mmol) was added to a solution of 5.20 g (6.55 mmol) of the title compound in step (x) of Example W1 in methanol (70 ml), and the mixture was stirred at room temperature for 5 min. A 10% aqueous sodium hydrogencarbonate solution was added to the reaction solution. The mixture was concentrated under the reduced pressure to about half amount. The residue was extracted with ethyl acetate. After filtration, the filtrate was dried over anhydrous sodium sulfate. The filtrate was then concentrated to give 4.7 g of a residue containing the title compound.

Step (xii) of Example W1

Methyl 6-N-((2S,4R)-1-(tert-butoxycarbonyl)-4-(cyclopropylmethyl)piperidine-2-carbonyl)-7-deoxy-7-epi-7-mercapto-1-thio-α-lincosamide The residue (4.7 g) containing the title compound in step (xi) of Example W1 was dissolved in 38 ml of methanol. A 28% sodium methoxide-methanol solution (3.79 ml) was then added to the solution, and the mixture was stirred at room temperature for 15 min. A 10% aqueous ammonium chloride solution was added to the reaction solution, the mixture was concentrated under the reduced pressure to about half amount, and the residue was extracted with ethyl acetate. The extract was dried over anhydrous sodium sulfate. After filtration, the filtrate was concentrated, and the residue was purified by column chromatography on silica gel (hexane:ethyl acetate=50:50-20:80) to give 3.45 g (two steps, yield 99%) of the title compound.

$^1$H-NMR (400 MHz, CDCl$_3$) δ: −0.02-0.07 (2H, m), 0.41-0.48 (2H, m), 0.63-0.74 (1H, m), 1.14-1.49 (6H, m), 1.44 (1H, d, J=4.9 Hz), 1.48 (9H, s), 1.65-1.78 (2H, m), 1.86-1.97 (1H, m), 2.02-2.12 (1H, m), 2.22 (3H, s), 2.39 (1H, d, J=5.1 Hz), 2.65 (1H, d, J=10.2 Hz), 3.31 (1H, br), 3.55 (1H, dt, J=3.7, 10.0 Hz), 3.63 (1H, br), 3.70-3.79 (H, m), 3.84-3.92 (2H, m), 4.06-4.19 (2H, m), 4.26 (1H, br), 4.85 (1H, d, J=3.7 Hz), 5.33 (1H, d, J=5.6 Hz), 6.69 (1H, d, J=9.0 Hz).

MS (FAB) m/z 535 [M+H]$^+$.

Step (xiii) of Example W1

Methyl 6-N-((2S,4R)-1-(tert-butoxycarbonyl)-(4-cyclopropylmethyl)piperidine-2-carbonyl)-7-deoxy-7-epi-7-(4-(2-(dimethylamino)ethyl)phenylthio)-1-thio-α-lincosamide The title compound (248.6 mg, yield 73%) was produced in the same manner as in step (vi) of Example S1, except that 270.9 mg (0.498 mmol) of the title compound in step (xii) of Example W1, 30.7 mg (0.0515 mmol) of 4,5-bis(diphenylphosphino)-9,9-dimethylsantene, 23.0 mg (0.0251 mmol) of tris(dibenzylideneacetone)dipalladium, 140.0 mg (0.614 mmol) of 2-(4-bromophenyl)-N,N-dimethylethanamine, 0.175 ml (1.008 mmol) of diisopropylethylamine, and dioxane(2 ml) were used.

$^1$H-NMR (400 MHz, CD$_3$OD) δ: −0.04-0.06 (2H, m), 0.36-0.48 (2H, m), 0.64-0.76 (1H, m), 1.09-1.54 (4H, m), 1.26 (3H, d, J=7.0 Hz), 1.44 (9H, s), 1.55-1.75 (2H, m), 1.77-1.88 (1H, m), 1.95 (3H, s), 2.00-2.12 (1H, m), 2.35 (6H, s), 2.57-2.67 (2H, m), 2.72-2.84 (2H, m), 3.15-3.70 (1H, br), 3.56 (1H, dd, J=3.2, 10.3 Hz), 3.71 (1H, dq, J=2.7, 6.8 Hz), 3.92-4.35 (2H, br), 4.41 (1H, d, J=9.0 Hz), 4.42-4.50 (1H, m), 5.24 (1H, d, J=5.6 Hz), 7.17 (2H, d, J=8.3 Hz), 7.34 (2H, d, J=8.3 Hz).

MS (API) m/z 682 [M+H]$^+$.

Methyl 6-N-((2S,4R)-1-(N-tert-butoxycarbonyl)-4-(cyclopropylmethyl)piperidine-2-carbonyl)-7-deoxy-7-(6-(2-(dimethylamino)ethyl)pyridin-3-ylthio)-7-epi-1-thio-α-lincosamide (85.1 mg, yield 62%) was produced in the same manner as in step (xiii) of Example W1, except that 107.6 mg (0.20 mmol) of the title compound in step (xii) of Example W1 was used, and 49.7 mg (0.22 mmol) of 2-(5-bromopyridin-2-yl)-N,N-dimethylethanamine was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-deoxy-7-epi-7-(4-(2-ethylmethylaminoethyl)phenylthio)-1-thio-α-lincosamide (92.0 mg, yield 80%) was produced in the same manner as in step (xiii) of Example W1, except that 96.5 mg (0.177 mmol) of the title compound in step (xii) of Example W1 was used and 85.5 mg (0.353 mmol) of 2-(4-bromophenyl)-N-ethyl-N-methylethanamine was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-(4-(2-(cyclopropyl(methyl)amino)ethyl)phenylthio)-7-deoxy-7-epi-1-thio-α-lincosamide (39.8 mg, yield 37%) was produced in step (xiii) of Example W1, except that 80.0 mg (0.150 mmol) of the title compound in step (xii) of Example W1 was used and 57.0 mg (0.224 mmol) of N-(4-bromophenethyl)-N-methylcyclopropanamine was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-deoxy-7-epi-7-(4-(pyrrolidin-1-ylmethyl)phenylthio)-1-thio-α-lincosamide (41.4 mg, yield 81%) was produced in the same manner as in step (xiii) of Example W1, except that 40.2 mg (0.0739 mmol) of the title compound in step (xii) of Example W1 was used and 64.6 mg (0.269 mmol) of 1-(4-bromobenzyl)pyrrolidine was used instead of 4-bromo(2-(dimethylamino)ethyl) benzene.

Methyl 6-N-((2S,4R)-1-(N-tert-butoxycarbonyl)-4-(cyclopropylmethyl)piperidine-2-carbonyl)-7-deoxy-7-epi-7-(4-(2-(pyrrolidin-1-yl)ethyl)phenylthio)-1-thio-α-lincosamide (21 mg, yield 63%) was produced in the same manner as in step (xiii) of Example W1, except that 30.0 mg (0.06 mmol)

of the title compound in step (xii) of Example W1 was used and 29 mg (0.12 mmol) of 1-(4-bromophenethyl)pyrrolidine was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-deoxy-7-epi-7-(4-(piperidin-1-ylmethyl)phenylthio)-1-thio-α-lincosamide (52.4 mg, yield 74%) was produced in the same manner as in step (xiii) of Example W1, except that 52.9 mg (0.100 mmol) of the title compound in step (xii) of Example W1 was used and 63.4 mg (0.250 mmol) of 1-(4-bromobenzyl)piperidine was used instead of 4-bromo(2-(dimethylamino)ethyl)benzene.

Methyl 7-(4-(azetidin-1-ylmethyl)phenylthio)-7-deoxy-7-epi-6-N-((2S,4R)-1-(N-tert-butoxycarbonyl)-4-(cyclopropylmethyl)piperidine-2-carbonyl)-1-thio-α-lincosamide (38.0 mg (yield 75%) was produced in step (xiii) of Example W1, except that 40 mg (0.0748 mmol) of the title compound in step (xii) of Example W1 and 34 mg (0.150 mmol) of 1-(4-bromobenzyl)azetidine was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-deoxy-7-epi-7-(4-(((R)-3-hydroxypyrrolidin-1-yl)methyl)phenylthio)-1-thio-α-lincosamide (27.8 mg, yield 70%) was produced in the same manner as in step (xiii) of Example W1, except that 30.0 mg (0.0561 mmol) of the title compound in step (xii) of Example W1 was used and 21.6 mg (0.0842 mmol) of (R)-1-(4-bromobenzyl)pyrrolidin-3-ol was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-(4-((cyclopropyl(methyl)amino)methyl)phenylthio)-7-deoxy-7-epi-1-thio-α-lincosamide (41.2 mg, yield 59%) was produced in the same manner as in step (xiii) of Example W1, except that 55.1 mg (0.100 mmol) of the title compound in step (xii) of Example W1 was used and 59.7 mg (0.249 mmol) of N-(4-bromobenzyl)-N-methylcyclopropanamine was used instead of 4-bromo(2-(dimethylamino)ethyl)benzene.

Methyl 7-(4-(1,3-bis(dimethylamino)propan-2-yl)phenylthio)-7-deoxy-7-epi-6-N-((2S,4R)-1-(N-tert-butoxycarbonyl)-4-(cyclopropylmethyl)piperidine-2-carbonyl)-1-thio-α-lincosamide (25.0 mg, yield 44%) was produced in the same manner as in step (xiii) of Example W1, except that 40.9 mg (0.0868 mmol) of the title compound in step (xii) of Example W1 was used and 29.7 mg (0.104 mmol) of 2-(4-bromophenyl)-$N^1,N^1,N^3,N^3$-tetramethylpropane-1,3-diamine was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-deoxy-7-(4-((2,5-dihydro-1H-pyrrol-1-yl)methyl)phenylthio)-7-epi-1-thio-α-lincosamide (25.2 mg, yield 50%) was produced in the same manner as in step (xiii) of Example W1, except that 39.1 mg (0.073 mmol) of the title compound in step (xii) of Example W1 and 66.8 mg (0.281 mmol) of 1-(4-bromobenzyl)-2,5-dihydro-1H-pyrrole was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-deoxy-7-epi-7-(4-(((R)-2-(hydroxymethyl)pyrrolidin-1-yl)methyl)phenylthio)-1-thio-α-lincosamide (42.6 mg, yield 78%) was produced in the same manner as in step (xiii) of Example W1, except that 40.0 mg (0.075 mmol) of the title compound in step (xii) of Example W1 was used and 68.1 mg (0.252 mmol) of (R)-(1-(4-bromobenzyl)pyrrolidin-2-yl)methanol was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-deoxy-7-epi-7-(4-(((S)-2-(hydroxymethyl)pyrrolidin-1-yl)methyl)phenylthio)-1-thio-α-lincosamide (45.7 mg, yield 84%) was produced in the same manner as in step (xiii) of Example W1, except that 40.2 mg (0.075 mmol) of the title compound in step (xii) of Example W1 was used and 74.1 mg (0.274 mmol) of (S)-(1-(4-bromobenzyl)pyrrolidin-2-yl)methanol was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-deoxy-7-epi-7-(4-(((S)-2-(methoxymethyl)pyrrolidin-1-yl)methyl)phenylthio)-1-thio-α-lincosamide (41.0 mg, yield 99%) was produced in the same manner as in step (xiii) of Example W1, except that 30.0 mg (0.0561 mmol) of the title compound in step (xii) of Example W1 and 23.9 mg (0.0842 mmol) of (S)-1-(4-bromobenzyl)-2-(methoxymethyl)pyrrolidine was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-deoxy-7-(4-(2-(diethylaminoethyl)phenylthio)-7-epi-1-thio-α-lincosamide (27.3 mg, yield 51%) was produced in the same manner as in step (xiii) of Example W1, except that 40 mg (0.0748 mmol) of the title compound in step (xii) of Example W1 was used and 38 mg (0.148 mmol) of 2-(4-bromophenyl)-N,N-diethylethanamine was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-deoxy-7-epi-7-(4-((ethyl(methyl)amino)methyl)phenylthio)-1-thio-α-lincosamide (21.0 mg, yield 44%) was produced in the same manner as in step (xiii) of Example W1, except that 37.5 mg (0.0701 mmol) of the title compound in step (xii) of Example W1 was used and 32 mg (0.140 mmol) of N-(4-bromobenzyl)-N-methylethanamine was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-deoxy-7-(4-(diethylaminomethyl)phenylthio)-7-epi-1-thio-α-lincosamide (12.4 mg, yield 34%) was produced in the same manner as in step (xiii) of Example W1, except that 35 mg (0.0655 mmol) of the title compound in step (xii) of Example W1 was used and 32 mg (0.132 mmol) of N-(4-bromobenzyl)-N-ethylethanamine was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-deoxy-7-(4-(((S)-2-(dimethylaminomethyl)pyrrolidin-1-yl)methyl)phenylthio)-7-epi-1-thio-α-lincosamide (67.0 mg, yield 95%) was produced in the same manner as in step (xiii) of Example W1, except that 50.0 mg (0.0935 mmol) of the title compound in step (xii) of Example W1 was used and 50.0 mg (0.168 mmol) of (S)-1-(1-(4-bromobenzyl)pyrrolidin-2-yl)-N,N-dimethylmethanamine was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-deoxy-7-(4-((2-(dimethylamino)-1-hydroxy)ethyl)phenylthio)-7-epi-1-thio-α-lincosamide (51.0 mg, yield 98%) was produced in the same manner as in step (xiii) of Example W1, except that 40 mg (0.0748 mmol) of the title compound in step (xii) of Example W1 was used and 21.9 mg (0.0898 mmol) of 1-(4-bromophenyl)-2-(dimethylamino)ethanol was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-deoxy-7-(4-(1-(dimethylamino)-3-hydroxypropan-2-yl)phenylthio)-7-epi-1-thio-α-lincosamide (16.0 mg, yield 64%) was produced in the same manner as in step (xiii) of Example W1, except that 18.8 mg (0.0351 mmol) of the title compound in step (xii) of Example W1 was used and 10.9 mg (0.0422 mmol) of 2-(4-bromophenyl)-3-(dimethylamino)propan-1-ol was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-(4-(((cyclopropylmethyl)(methyl)amino)methyl)phenylthio)-7-deoxy-7-epi-1-thio-α-lincosamide (65.0 mg, yield 94%) was produced in the same manner as in step (xiii) of Example W1, except that 52.4 mg (0.0980 mmol) of the title compound in step (xii) of Example W1 was used and 29.9 mg (0.118 mmol) of N-(4-bromobenzyl)-1-cyclopropyl-N-methylmethanamine was used instead of 4-bromo(2-(dimethylamino)ethyl)benzene.

Methyl 6-N-((2S,4R)-1-(N-tert-butoxycarbonyl)-4-(cyclopropylmethyl)piperidine-2-carbonyl)-7-deoxy-7-(4-(dimethylaminomethyl)phenylthio)-7-epi-1-thio-α-lincosamide (49 mg, yield 67%) was produced in the same manner as in step (xiii) of Example W1, except that 59 mg (0.11 mmol) of the title compound in step (xii) of Example W1 was used and 25 mg (0.11 mmol) of 1-(4-bromophenyl)-N,N-dimethylmethanamine was used instead of 4-bromo(2-(dimethylamino)ethyl)benzene.

Step (xiv) of Example W1

Methyl 6-N-((2S,4R)-4-(cyclopropylmethyl)piperidine-2-carbonyl)-7-deoxy-7-(4-(2-dimethylaminoethyl)phenylthio)-7-epi-1-thio-α-lincosamide (Compound 46)

The title compound (20 mg, yield 98%) was produced from 24 mg (0.0352 mmol) of the title compound in step (xiii) of Example W1 in the same manner as in step (xi) of Example T1.

$^1$H-NMR (400 MHz, CD$_3$OD) δ: −0.03-0.03 (2H, m), 0.40-0.47 (2H, m), 0.62-0.73 (1H, m), 1.08-1.16 (2H, m), 1.20 (3H, d, J=6.8 Hz), 1.21-1.33 (2H, m), 1.71-1.83 (1H, m), 1.85-1.98 (1H, m), 1.89 (3H, s), 2.28 (1H, d, J=13.9 Hz), 2.60 (6H, s), 2.82-2.98 (5H, m), 3.27-3.34 (1H, m), 3.52 (1H, dd, J=3.1, 10.3 Hz), 3.68-3.76 (2H, m), 3.81 (1H, d, J=3.2 Hz), 4.02 (1H, dd, J=5.6, 10.2 Hz), 4.37 (1H, d, J=10.0 Hz), 4.52 (1H, dd, J=2.5, 10.0 Hz), 5.20 (1H, d, J=5.6 Hz), 7.16 (2H, d, J=8.1 Hz), 7.29 (2H, d, J=8.3 Hz).

MS (FAB) m/z 582 [M+H]$^+$.

Compound 47 (38.6 mg, yield 53%) was produced in the same manner as in step (xiv) of Example W1, except that 85.1 mg (0.125 mmol) of methyl 6-N-((2S,4R)-1-(N-tert-butoxycarbonyl)-(4-cyclopropylmethyl)piperidine-2-carbonyl)-7-deoxy-7-(6-(2-(dimethylamino)ethyl)pyridin-3-ylthio)-7-epi-1-thio-α-lincosamide was used.

Compound 48 (62.8 mg, yield 80%) was produced in the same manner as in step (xiv) of Example W1, except that 92.0 mg (0.132 mmol) of methyl 6-N-((2S,4R)-1-(N-tert-butoxycarbonyl)-4-(cyclopropylmethyl)piperidine-2-carbonyl)-7-deoxy-7-epi-7-(4-(2-ethylmethylaminoethyl)phenylthio)-1-thio-α-lincosamide was used.

Compound 49 (29.6 mg, yield 87%) was produced in the same manner as in step (xiv) of Example W1, except that 39.8 mg (0.0562 mmol) of methyl 6-N-((2S,4R)-1-(N-tert-butoxycarbonyl)-4-(cyclopropylmethyl)piperidine-2-carbonyl)-7-(4-(2-(cyclopropyl(methyl)amino)ethyl)phenylthio)-7-deoxy-7-epi-1-thio-α-lincosamide was used.

Compound 50 (28.8 mg, yield 81%) was produced in the same manner as in step (xiv) of Example W1, except that 41.4 mg (0.0597 mmol) of methyl 6-N-((2S,4R)-1-(N-tert-butoxycarbonyl)-4-(cyclopropylmethyl)piperidine-2-carbonyl)-7-deoxy-7-epi-7-(4-(pyrrolidin-1-ylmethyl)phenylthio)-1-thio-α-lincosamide was used.

Compound 83 (8 mg, yield 28%) was produced in the same manner as in step (xiv) of Example W1, except that mg (0.028 mmol) of methyl 6-N-((2S,4R)-1-(N-tert-butoxycarbonyl)-4-(cyclopropylmethyl)piperidine-2-carbonyl)-7-deoxy-7-epi-7-(4-(2-(pyrrolidin-1-yl)ethyl)phenylthio)-1-thio-α-lincosamide was used.

Compound 84 (40.4 mg, yield 90%) was produced in the same manner as in step (xiv) of Example W1, except that 52.4 mg (0.074 mmol) of methyl 6-N-((2S,4R)-1-(N-tert-butoxycarbonyl)-4-(cyclopropylmethyl)piperidine-2-carbonyl)-7-deoxy-7-epi-7-(4-(piperidin-1-ylmethyl)phenylthio)-1-thio-α-lincosamide was used.

Compound 85 (22.1 mg, yield 70%) was produced in the same manner as in step (xiv) of Example W1, except that 37 mg (0.0544 mmol) of methyl 7-(4-(azetidin-1-ylmethyl)phenylthio)-7-deoxy-7-epi-6-N-((2S,4R)-1-(N-tert-butoxycarbonyl)-4-(cyclopropylmethyl)piperidine-2-carbonyl)-1-thio-α-lincosamide was used.

Compound 86 (19.0 mg, yield 82%) was produced in the same manner as in step (xiv) of Example W1, except that mg (0.0380 mmol) of methyl 6-N-((2S,4R)-1-(N-tert-butoxycarbonyl)-4-(cyclopropylmethyl)piperidine-2-carbonyl)-7-deoxy-7-epi-7-(4-(((R)-3-hydroxypyrrolidin-1-yl)methyl)phenylthio)-1-thio-α-lincosamide was used.

Compound 87 (32.8 mg, yield 94%) was produced in the same manner as in step (xiv) of Example W1, except that 41.2 mg (0.059 mmol) of methyl 6-N-((2S,4R)-1-(N-tert-butoxycarbonyl)-4-(cyclopropylmethyl)piperidine-2-carbonyl)-7-(4-((cyclopropyl(methyl)amino)methyl)phenylthio)-7-deoxy-7-epi-1-thio-a-lincosamide was used.

Compound 88 (7 mg, yield 32%) was produced in the same manner as in step (xiv) of Example W1, except that mg (0.0338 mmol) of methyl 7-(4-(1,3-bis(dimethylamino)propan-2-yl)phenylthio)-7-deoxy-7--epi-6-N-((2S,4R)-1-(N-tert-butoxycarbonyl)-4-(cyclopropylmethyl)piperidine-2-carbonyl)-1-thio-α-lincosamide was used.

Compound 89 (21.0 mg, yield 99%) was produced in the same manner as in step (xiv) of Example W1, except that 25.2 mg (0.036 mmol) of methyl 6-N-((2S,4R)-1-(N-tert-butoxycarbonyl)-4-(cyclopropylmethyl)piperidine-2-carbonyl)-7-deoxy-7-(4-((2,5-dihydro-1H-pyrrol-1-yl)methyl)phenylthio)-7-epi-1-thio-α-lincosamide was used.

Compound 90 (24.3 mg, yield 66%) was produced in the same manner as in step (xiv) of Example W1, except that 42.6 mg (0.059 mmol) of methyl 6-N-((2S,4R)-1-(N-tert-butoxycarbonyl)-4-(cyclopropylmethyl)piperidine-2-carbonyl)-7-deoxy-7-epi-7-(4-(((R)-2-(hydroxymethyl)pyrrolidin-1-yl)methyl)phenylthio)-1-thio-α-lincosamide was used.

Compound 91 (27.4 mg, yield 70%) was produced in the same manner as in step (xiv) of Example W1, except that 45.7 mg (0.063 mmol) of methyl 6-N-((2S,4R)-1-(N-tert-butoxycarbonyl)-4-(cyclopropylmethyl)piperidine-2-carbonyl)-7-deoxy-7-epi-7-(4-(((S)-2-(hydroxymethyl)pyrrolidin-1-yl)methyl)phenylthio)-1-thio-α-lincosamide was used.

Compound 92 (29.0 mg, yield 84%) was produced in the same manner as in step (xiv) of Example W1, except that 40.0 mg (0.0542 mmol) of methyl 6-N-((2S,4R)-1-(N-tert-butoxycarbonyl)-4-(cyclopropylmethyl)piperidine-2-carbonyl)-7-deoxy-7-epi-7-(4-(((S)-2-(methoxymethyl)pyrrolidin-1-yl)methyl)phenylthio)-1-thio-α-lincosamide was used.

Compound 93 (11.1 mg, yield 48%) was produced in the same manner as in step (xiv) of Example W1, except that 27 mg (0.0380 mmol) of methyl 6-N-((2S,4R)-1-(N-tert-butoxycarbonyl)-4-(cyclopropylmethyl)piperidine-2-carbonyl)-7-deoxy-7-(4-(2-diethylaminoethyl)phenylthio)-7-epi-1-thio-α-lincosamide was used.

Compound 94 (14.4 mg, yield 80%) was produced in the same manner as in step (xiv) of Example W1, except that mg (0.0308 mmol) of methyl 6-N-((2S,4R)-1-(N-tert-butoxycarbonyl)-4-(cyclopropylmethyl)piperidine-2-carbonyl)-7-deoxy-7-epi-7-(4-((ethyl(methyl)amino)methyl)phenylthio)-1-thio-α-lincosamide was used.

Compound 95 (5.7 mg, yield 43%) was produced in the same manner as in step (xiv) of Example W1, except that 12 mg (0.0224 mmol) of methyl 6-N-((2S,4R)-1-(N-tert-butoxycarbonyl)-4-(cyclopropylmethyl)piperidine-2-carbonyl)-7-deoxy-7-(4-(diethylaminomethyl)phenylthio)-7-epi-1-thio-α-lincosamide was used.

Compound 96 (46.0 mg, yield 79%) was produced in the same manner as in step (xiv) of Example W1, except that 67.0 mg (0.0892 mmol) of methyl 6-N-((2S,4R)-1-(N-tert-butoxycarbonyl)-4-(cyclopropylmethyl)piperidine-2-carbonyl)-7-deoxy-7-(4-(((S)-2-(dimethylaminomethyl)pyrrolidin-1-yl)methyl)phenylthio)-7-epi-1-thio-α-lincosamide was used.

Compound 97 (16.8 mg, yield 38%) was produced in the same manner as in step (xiv) of Example W1, except that 51.0 mg (0.0731 mmol) of methyl 6-N-((2S,4R)-1-(N-tert-butoxycarbonyl)-4-(cyclopropylmethyl)piperidine-2-carbonyl)-7-deoxy-7-(4-((2-(dimethylamino)-1-hydroxy)ethyl)phenylthio)-7-epi-1-thio-α-lincosamide was used.

Compound 98 (7.2 mg, yield 52%) was produced in the same manner as in step (xiv) of Example W1, except that 16.0 mg (0.0225 mmol) of methyl 6-N-((2S,4R)-1-(N-tert-butoxycarbonyl)-4-(cyclopropylmethyl)piperidine-2-carbonyl)-7-deoxy-7-(4-(1-(dimethylamino)-3-hydroxypropan-2-yl)phenylthio)-7-epi-1-thio-α-lincosamide was used.

Compound 99 (26.0 mg, yield 90%) was produced in the same manner as in step (xiv) of Example W1, except that 33.5 mg (0.0473 mmol) of methyl 6-N-((2S,4R)-1-(N-tert-butoxycarbonyl)-4-(cyclopropylmethyl)piperidine-2-carbonyl)-7-(4-(((cyclopropylmethyl)(methyl)amino)methyl)phenylthio)-7-deoxy-7-epi-1-thio-α-lincosamide was used.

Compound 100 (31 mg, yield 74%) was produced in the same manner as in step (xiv) of Example W1, except that mg (0.073 mmol) of methyl 6-N-((2S,4R)-1-(N-tert-butoxycarbonyl)-4-(cyclopropylmethyl)piperidine-2-carbonyl)-7-deoxy-7-(4-(dimethylaminomethyl)phenylthio)-7-epi-1-thio-α-lincosamide was used.

Step (xv) of Example W1

Methyl 6-N-(((2S,4R)-4-cyclopropylmethyl-1-methyl)piperidine-2-carbonyl)-7-deoxy-7-(4-(2-dimethylaminoethyl)phenylthio)-7-epi-1-thio-α-lincosamide (Compound 51)

The title compound (7.8 mg, yield 67%) was produced in the same manner as in step (xi) of Example U1, except that 11.4 mg (0.0196 mmol) of compound 46 was used.

$^1$H-NMR (400 MHz, CD$_3$OD) δ: −0.03-0.02 (2H, m), 0.39-0.45 (2H, m), 0.64-0.73 (1H, m), 1.15 (2H, dt, J=2.2, 6.8 Hz), 1.26 (3H, d, J=7.0 Hz), 1.27-1.35 (2H, m), 1.42-1.55 (1H, m), 1.74-1.82 (1H, m), 1.91-2.00 (1H, m), 1.97 (3H, s), 2.12 (1H, dt, J=2.4, 12.0 Hz), 2.24 (3H, s), 2.35 (6H, s), 2.58-2.65 (3H, m), 2.75-2.80 (2H, m), 2.92-2.98 (1H, m), 3.56 (1H, dd, J=3.2, 10.2 Hz), 3.77 (1H, dq, J=2.6, 7.0 Hz), 3.80 (1H, d, J=2.7 Hz), 4.08 (1H, dd, J=5.6, 10.3 Hz), 4.38 (1H, d, J=10.0 Hz), 4.52 (1H, dd, J=2.6, 10.0 Hz), 5.24 (1H, d, J=5.6 Hz), 7.17 (2H, d, J=8.3 Hz), 7.34 (2H, d, J=8.1 Hz).

MS (FAB) m/z 596 [M+H]$^+$.

Compound 52 (20.3 mg, yield 76%) was produced in the same manner as in step (xv) of Example W1, except that 26.2 mg (0.045 mmol) of compound 47 was used.

Compound 53 (28.7 mg, yield 81%) was produced in the same manner as in step (xv) of Example W1, except that 34.7 mg (0.0582 mmol) of compound 48 was used.

Compound 54 (21 mg, yield 85%) was produced in the same manner as in step (xv) of Example W1, except that 24.0 mg (0.0395 mmol) of compound 49 was used.

Compound 55 (14.7 mg, yield 88%) was produced in the same manner as in step (xv) of Example W1, except that 16.4 mg (0.0276 mmol) of compound 50 was used.

Compound 101 (5 mg, yield 82%) was produced in the same manner as in step (xv) of Example W1, except that 6 mg (0.01 mmol) of compound 83 was used.

Compound 102 (18.6 mg, yield 79%) was produced in the same manner as in step (xv) of Example W1, except that 22.8 mg (0.038 mmol) of compound 84 was used.

Compound 103 (15.8 mg, yield 82%) was produced in the same manner as in step (xv) of Example W1, except that 19 mg (0.0326 mmol) of compound 85 was used.

Compound 104 (12.0 mg, yield 81%) was produced in the same manner as in step (xv) of Example W1, except that 14.5 mg (0.0238 mmol) of compound 86 was used.

Compound 105 (17.1 mg, yield 69%) was produced in the same manner as in step (xv) of Example W1, except that 24.3 mg (0.041 mmol) of compound 87 was used.

Compound 106 (4 mg, yield 95%) was produced in the same manner as in step (xv) of Example W1, except that 4.1 mg (0.00642 mmol) of compound 88 was used.

Compound 107 (14.1 mg, yield 83%) was produced in the same manner as in step (xv) of Example W1, except that 16.7 mg (0.028 mmol) of compound 89 was used.

Compound 108 (12.2 mg, yield 58%) was produced in the same manner as in step (xv) of Example W1, except that 20.6 mg (0.033 mmol) of compound 90 was used.

Compound 109 (10.4 mg, yield 48%) was produced in the same manner as in step (xv) of Example W1, except that 21.1 mg (0.034 mmol) of compound 91 was used.

Compound 110 (13.2 mg, yield 81%) was produced in the same manner as in step (xv) of Example W1, except that 16.0 mg (0.0251 mmol) of compound 92 was used.

Compound 111 (7.7 mg, yield 83%) was produced in the same manner as in step (xv) of Example W1, except that 9 mg (0.0148 mmol) of compound 93 was used.

Compound 112 (10.1 mg, yield 76%) was produced in the same manner as in step (xv) of Example W1, except that 13 mg (0.0223 mmol) of compound 94 was used.

Compound 113 (2.4 mg, yield 78%) was produced in the same manner as in step (xv) of Example W1, except that 3 mg (0.00503 mmol) of compound 95 was used.

Compound 114 (25.3 mg, yield 93%) was produced in the same manner as in step (xv) of Example W1, except that 26.5 mg (0.0407 mmol) of compound 96 was used.

Compound 115 (9.3 mg, yield 61%) was produced in the same manner as in step (xv) of Example W1, except that 14.9 mg (0.0249 mmol) of compound 97) was used.

Compound 116 (3.8 mg, yield 60%) was produced in the same manner as in step (xv) of Example W1, except that 6.2 mg (0.0101 mmol) of compound 98 was used.

Compound 117 (20.0 mg, yield 79%) was produced in the same manner as in step (xv) of Example W1, except that 24.7 mg (0.0407 mmol) of compound 99 was used.

Compound 118 (11 mg, yield 90%) was produced in the same manner as in step (xv) of Example W1, except that 12 mg (0.018 mmol) of compound 100 was used.

Compounds (compounds 47 to 50, 52 to 55, 83 to 100, and 101 to 118) produced in the same manner as in steps (xiv) and (xv) of Example W1 and $^1$H-NMR data and MS data for these compounds are shown in Tables 9 and 24 to 27.

Step (i) of Example W2

Methyl 6-N-((2S,4R)-(1-tert-butoxycarbonyl-4-cyclopropylmethyl)piperidine-2-carbonyl)-7-deoxy-7-(5-((dimethylamino)ethyl)-1,3,4-thiadiazol-2-ylthio)-7-epi-1-thio-α-lincosamide 1,8-Diazabicyclo[5.4.0]undeca-7-ene (33.6 μl, 0.224 mmol) and 21.5 mg (0.112 mmol) of 2-(5-chloro-1,3,4-thiadiazol-2-yl)-N,N-dimethylethanamine were added to a solution of 60 mg (0.112 mmol) of the title compound in step (xii) of Example W1 in N,N-dimethylformamide (0.8 ml), and the mixture was stirred at room temperature for 20 min. The reaction solution was diluted with ethyl acetate. A saturated aqueous ammonium chloride solution was then added to the diluted solution. Thereafter, the mixture was washed with 15 ml of a 10% aqueous sodium hydrogencarbonate solution. The organic layer was dried over anhydrous sodium sulfate. After filtration, the filtrate was concentrated under the reduced pressure, and the residue was purified by preparative thin-layer chromatography (chloroform:methanol=96:4) to give 70 mg (yield 91%) of the title compound.

$^1$H-NMR (400 MHz, CD$_3$OD) δ: –0.04-0.05 (2H, m), 0.40-0.48 (2H, m), 0.65-0.77 (1H, m), 1.16-1.32 (3H, m), 1.35-1.46 (11H, m), 1.49 (3H, d, J=7.1 Hz), 1.55-1.92 (4H, m), 1.98 (3H, s), 2.08-2.15 (1H, m), 2.30 (6H, s), 2.68 (2H, t, J=6.8 Hz), 3.23 (2H, t, J=6.8 Hz), 3.55 (1H, dd, J=10.2, 3.2 Hz), 4.04 (1H, br), 4.07 (1H, m), 4.38 (1H, m), 4.47 (1H, m), 4.55 (1H, m), 5.26 (1H, d, J=5.60 Hz)

Step (ii) of Example W2

Methyl 6-N-((2S,4R)-(4-cyclopropylmethyl)piperidine-2-carbonyl)-7-deoxy-7-(5-((dimethylamino)ethyl)-1,3,4-thiadiazol-2-ylthio)-7-epi-1-thio-α-lincosamide (Compound 119)

A solution of 70 mg (0.112 mol) of the title compound in step (i) of Example W2 in dichloromethane (1.6 ml) was cooled to 0° C. Trifluoroacetic acid (0.8 ml) was added to the cooled solution, and the mixture was stirred under ice cooling for 10 min and was stirred at room temperature for one hr. The reaction solution was concentrated under the reduced pressure, and the residue was purified by preparative thin-layer chromatography (chloroform:methanol:aqueous ammonia=9:2:0.2) to give 26 mg (yield 44%) of the title compound.

$^1$H-NMR (400 MHz, CD$_3$OD) δ: –0.01-0.05 (2H, m), 0.41-0.48 (2H, m), 0.68-0.78 (1H, m), 1.07-1.26 (4H, m), 1.48 (3H, d, J=6.8 Hz), 1.70 (1H, m), 1.76-1.84 (1H, m), 1.96 (3H, s), 2.05-2.12 (1H, m), 2.30 (6H, s), 2.63-2.73 (3H, m), 3.14-3.20 (1H, m), 3.22 (2H, t, J=6.8 Hz), 3.34-3.38 (1H, m), 3.54 (1H, dd, J=10.2, 3.4 Hz), 3.86 (1H, dd, J=3.4, 1.0 Hz), 4.08 (1H, dd, J=10.2, 5.6 Hz), 4.31 (1H, dq, J=2.4, 6.8 Hz), 4.36 (1H, dd, J=10.2, 1.0 Hz), 4.61 (1H, dd, J=10.2, 2.4 Hz), 5.25 (1H, d, J=5.6 Hz)

MS (FAB) m/z 590 [M+H]$^+$.

Step (iii) of Example W2

Methyl 6-N-((2S,4R)-(4-cyclopropylmethyl-1-methyl)piperidine-2-carbonyl)-7-deoxy-7-(5-((dimethylamino)ethyl)-1,3,4-thiadiazol-2-ylthio)-7-epi-1-thio-α-lincosamide (Compound 120)

Acetic acid (6.1 μl, 0.107 mmol) and 8.7 μl (0.107 mmol) of 37% aqueous formaldehyde solution and 22.6 mg (0.107 mmol) of sodium tri(acetoxy)borohydride were added to a solution of 21.0 mg (0.0356 mmol) of the title compound in step (ii) of Example W2 in dichloromethane-ethanol (6:1, 0.7 ml), and the mixture was stirred at room temperature for 45 min. The reaction solution was diluted with chloroform. The diluted solution was washed with a saturated aqueous sodium bicarbonate solution. The organic layer was dried over anhydrous sodium sulfate. After filtration, the filtrate was concentrated under the reduced pressure, and the residue was purified by preparative thin-layer chromatography(chloroform:methanol:aqueous ammonia=9:1:0.1) to give 22.8 mg (yield quant.) of the title compound.

$^1$H-NMR (400 MHz, CD$_3$OD) δ: –0.04-0.05 (2H, m), 0.38-0.47 (2H, m), 0.64-0.75 (1H, m), 1.09-1.24 (2H, m), 1.25-1.38 (2H, m), 1.49 (3H, d, J=7.1 Hz), 1.52 (1H, br), 1.74-1.83 (1H, m), 1.90-1.99 (4H, m), 2.08-2.17 (1H, m), 2.24 (3H, s), 2.30 (6H, s), 2.59-2.71 (3H, m), 2.90-2.99 (1H, m), 3.22 (2H, t, J=6.8 Hz), 3.55 (1H, dd, J=10.2, 3.2 Hz), 3.84 (1H, d, J=3.2 Hz), 4.10 (1H, d, J=10.2, 5.6 Hz), 4.32 (1H, dq, J=2.7, 7.1 Hz), 4.39 (1H, d, J=10.2 Hz), 4.63 (1H, dd, J=10.2, 2.7 Hz), 5.25 (1H, d, J=5.60 Hz)

MS (FAB) m/z 604 [M+H]$^+$.

Step (i) of Example W3

Methyl 7-deoxy-7-(4-(2-(dimethylamino)ethyl)phenylthio)-7-epi-6-N-((2S,4R)-(4-cyclopropylmethyl-1-ethyl)piperidine-2-carbonyl)-1-thio-α-lincosamide (Compound 121)

The title compound (compound 46) (20 mg, 0.030 mmol) in step (xiv) of Example W1 was dissolved in anhydrous THF (4 ml). Triethylamine (0.5 ml) was added to the solution, and the mixture was stirred in an argon atmosphere. Ethyl iodide (24 mg, 0.15 mmol) was added thereto at room temperature, and the mixture was stirred for 4 hr. The reaction solution was concentrated under the reduced pressure, and the residue was purified by column chromatography on silica gel (chloroform:methanol:aqueous ammonia=10:1:0.1) to give 6 mg (yield 28.7%) of the title compound.

$^1$H-NMR (400 MHz, CD$_3$OD) δ: –0.05-0.10 (2H, m), 0.4-0.5 (2H, m), 0.7-0.8 (1H, m), 1.10-1.60 (4H, m), 1.20 (3H, t, J=7.1 Hz), 1.27 (3H, d, J=6.8Hz), 1.80-2.40 (4H, m), 1.91 (3H, s), 2.59 (6H, s), 2.80-3.15 (5H, m), 3.50-3.60 (2H, m), 3.75-3.90 (2H, m), 4.09 (1H, dd, J=5.6 Hz, 10.2 Hz), 4.39 (1H, m), 4.55 (1H, m), 5.26 (1H, d, J=5.4 Hz), 7.22 (2H, d, J=8.3 Hz), 7.36 (2H, d, J=8.3 Hz)

MS (FAB) m/z 610 [M+H]$^+$.

Step (i) of Example X1

(S)-Methyl 2-(2-nitrophenylsulfonamide)pent-4-enoate

L-2-amino 4-pentenoic acid was added to a solution of 3.18 ml (43.5 mmol) of thionylchloride in methanol (40 ml), which had been cooled to 0° C., and the mixture was then stirred at room temperature for 24 hr. The reaction solution was concentrated under the reduced pressure. The residue was then dried. A solution of the crude product in diethyl ether (26 ml) was cooled to 0° C. A saturated aqueous sodium hydrogencarbonate solution (26 ml) was then added to the cooled solution. 2-Nitrobenzenesulfonyl chloride (4.24 g, 19.14 mol) was added thereto, and the mixture was stirred at room temperature for 7 hr. Thereafter, the reaction solution was cooled to 0° C. N,N-Dimethylethylenediamine (2 ml) was added to the cooled solution, and the mixture was stirred at room temperature for 30 min. The organic layer was separated. The aqueous layer was adjusted to pH 3 by the addition of citric acid and was then extracted with diethyl ether. The combined organic layers were washed with a 3% aqueous citric acid solution, a saturated aqueous sodium hydrogencarbonate solution, and saturated brine in that order, were dried over anhydrous sodium sulfate, and were then filtered. The filtrate was concentrated under the reduced pressure, and the residue was then purified by column chromatography on silica gel (hexane:ethyl acetate=5:1) to give 4.52 g (yield 83%) of the title compound.

$^1$H-NMR (400 MHz, CDCl$_3$) δ: 2.58 (2H, dd, J=5.9, 6.8 Hz), 3.52 (3H, s), 4.30 (1H, dt, J=5.8, 8.8 Hz), 5.12-5.15 (1H, m), 5.17 (1H, s), 5.62-5.72 (1H, m), 6.09 (1H, d, J=8.7 Hz), 7.72-7.76 (2H, m), 7.91-7.96 (1H, m), 8.06-8.10 (1H, m).

MS (FAB) m/z 315 [M+H]$^+$.

Step (ii) of Example X1

3-Methylenehexan-1-ol

Butyllithium (a 2.66 M toluene solution) (82 ml, 218.2 mmol) was added to a solution of 39 ml (258 mmol) of N,N,N',N'-tetramethylethylenediamine in diethyl ether (148 ml), which had been cooled to 0° C., and the mixture was then stirred at room temperature for one hr. The reaction solution was cooled to 0° C. 3-Methyl-3-buten-1-ol 10.1 ml (99.2 mmol) was added to the cooled solution, and the mixture was then stirred at room temperature for 6 hr. The reaction solution was cooled to −78° C. A solution of 8.9 ml (119 mmol) of bromoethane in diethyl ether (29.2 ml) was added to the cooled solution. The mixture was gradually raised to room temperature and was stirred for 15 hr. A saturated aqueous ammonium chloride solution was added thereto, and the mixture was extracted with dithyl ether. The organic layer was washed with a 3% aqueous citric acid solution, a saturated aqueous sodium hydrogencarbonate solution, and saturated brine in that order, was dried over anhydrous magnesium sulfate, and was then filtered. The filtrate was concentrated under the reduced pressure, and the residue was then purified by distillation under the reduced pressure to give 1.4 g (yield 12%) of the title compound.

$^1$H-NMR (400 MHz, CDCl$_3$) δ: 0.80 (3H, t, J=7.3 Hz), 1.35 (2H, tq, J=7.3. 7.5 Hz), 1.89 (2H, t, J=7.5 Hz), 2.17 (2H, t, J=6.3 Hz), 3.59 (2H, dt, J=5.3, 6.1 Hz), 4.70 (1H, dd, J=0.7, 1.2 Hz), 4.74 (1H, d, J=1.5 Hz).

MS (GC) m/z 114 [M]$^+$.

Step (iii) of Example X1

(S)-Methyl 2-(N-(3-methylenehexyl)-2-nitrophenylsulfonamide)pent-4-enoate

Tetrahydrofuran (30.2 ml) was added to 2.27 g (7.22 mmol) of the title compound in step (i) of Example X1 and 1.07 g (9.39 mmol) of the title compound in step (ii) of Example X1. The mixture was cooled to 0° C. Ttriphenylphosphine (2.84 g, 10.8 mmol) was added thereto, and the mixture was stirred for 10 min. Diisopropyl azodicarboxylate (2.1 ml, 10.8 mmol) was added thereto. The temperature of the mixture was then gradually raised over a period of 2 hr, and the mixture was stirred for 19 hr. The solvent was removed under the reduced pressure, and the residue was then purified by column chromatography on silica gel (hexane:ethyl acetate=20:1) to give 2.42 g (yield 82%) of the title compound.

$^1$H-NMR (400 MHz, CDCl$_3$) δ: 0.90 (3H, t, J=7.3 Hz), 1.45 (2H, tq, J=7.3. 7.6 Hz), 1.99 (2H, t, J=7.5 Hz), 2.32 (1H, dt, J=5.1, 12.9 Hz), 2.44-2.55 (2H, m), 2.83 (1H, dtt, J=1.5, 6.0, 15.1 Hz), 3.25 (1H, ddd, J=5.1, 12.2, 15.4 Hz), 3.53 (1H, ddd, J=5.1, 12.0, 15.3 Hz), 3.58 (3H, s), 4.71-4.75 (2H, m), 4.79 (1H, d, J=1.4 Hz), 5.14 (1H, dq, J=1.5, 10.2 Hz), 5.20 (1H, dq, J=1.5, 17.1 Hz), 5.82 (ddt, J=6.8, 10.5, 17.0 Hz), 7.56-7.60 (1H, m), 7.67-7.74 (2H, m), 8.02-8.06 (1H, m).

MS (FAB) m/z 411 [M+H]$^+$.

Step (iv) of Example X1

(S,Z)-Methyl 1-(2-nitrophenylsulfonyl)-5-propyl-2,3,6,7-tetrahydro-1H-azepine-2-carboxylate Benzylidene-[1,3-bis(2,4,6-trimethylphenyl)-2-imidazolidinylidene]dichloro(tricyclohexylphosphine)ruthenium (250 mg, 0.295 mmmol) was added to a solution of 2.42 g (5.89 mmol) of the title compound in step (iii) of Example X1 in methylene chloride (295 ml), and the mixture was heated under reflux for one hr. The reaction solution was cooled to room temperature. The solvent was removed under the reduced pressure, and the residue was purified by column chromatography on silica gel (hexane:ethyl acetate=10:1) to give 1.84 g (yield 82%) of the title compound.

$^1$H-NMR (400 MHz, CDCl$_3$) δ: 0.82 (3H, t, J=7.3 Hz), 1.22-1.42 (2H, m), 1.91 (3H, t, J=7.3 Hz), 2.28 (1H, ddd, J=1.9, 6.1, 16.3 Hz), 2.38-2.47 (1H, m), 2.56-2.64 (1H, m), 2.79 (1H, dt, J=7.3, 14.9 Hz), 3.45 (1H, ddd, J=2.2, 10.5, 14.4 Hz), 3.62 (3H, s), 3.83 (1H, ddd, J=3.2, 6.3, 14.4 Hz), 4.90 (1H, dd, J=3.4, 6.8 Hz), 5.45 (1H, ddd, J=1.0, 5.3, 7.3 Hz), 7.61-7.65 (1H, m), 7.66-7.71 (2H, m), 8.05-8.10 (1H, m).

MS (ESI) m/z 383 [M+H]$^+$.

Step (v) of Example X1

(S,Z)-1-(2-Nitrophenylsulfonyl)-5-propyl-2,3,6,7-tetrahydro-1H-azepine-2-carboxylic acid Lithium hydroxidemonohydrate (164.6 mg, 3.92 mmol) was added to a solution of 500 mg (1.31 mmol) of the title compound in step (iv) of Example X1 in 1,4-dioxane:water=4:1 (7 ml), and the mixture was stirred at room temperature for 4 hr. Water and diethyl ether were added thereto for dilution. The diluted solution was then filtered through Celite. The organic layer was separated. A 3% aqueous citric acid solution was added to the aqueous layer, and the mixture was extracted with ethyl acetate. The combined organic layers were dried over anhydrous sodium sulfate and were then filtered. The filtrate was concentrated under the reduced pressure, and the residue was dried.

Step (vi) of Example X1

Methyl 6-N-((2S,Z)-1-(2-nitrophenylsulfonyl)-5-propyl(2,3,6,7-tetrahydro-1H-azepine-2-carbonyl))-1-thio-α-lincosamide The title compound (whole quantity) in step (v) of Example X1, 265.0 mg (1.96 mmol) of 1-hydroxybenzotriazole, 375.8 mg (1.96 mmol) of 1-ethyl-3-(3-dimethylaminopropyl)carbodiimide hydrochloride, and N,N-dimethylformamide (5.0 ml) were added in that order, and the mixture was stirred at room temperature for 20 min. Thereafter, 496.8 mg (1.96 mmol) of methyl 1-thio-α-lincosamide was added, and the mixture was stirred at room temperature for 13 hr. A saturated aqueous sodium hydrogencarbonate solution was added thereto, and the mixture was then extracted with ethyl acetate. The extract was dried over anhydrous sodium sulfate and was then filtered. The filtrate was concentrated under the reduced pressure, and the residue was then purified by column chromatography on silica gel (chloroform:methanol=50:1) to give 660 mg (two steps, yield 84%) of the title compound.

$^1$H-NMR (400 MHz, CD$_3$OD) δ: 0.83 (3H, t, J=7.3 Hz), 1.15 (3H, d, J=6.3 Hz), 1.26-1.34 (2H, m), 1.80 (2H, t, J=7.3 Hz), 2.05 (3H, s), 2.25-2.55 (3H, m), 2.75 (1H, dt, J=7.5, 15.8 Hz), 3.58 (1H, dd, J=3.4, 10.2 Hz), 3.75-3.83 (3H, m), 4.03-4.11 (3H, m), 4.38 (1H, d, J=5.8 Hz), 5.22 (1H, d, J=5.6 Hz), 5.37-5.42 (1H, m), 7.74-7.78 (1H, m), 7.79-7.86 (2H, m), 8.09-8.14 (1H, m).

MS (FAB) m/z 604 [M+H]$^+$.

Step (vii) of Example X1

Methyl 6-N-((2S,Z)-5-propyl(2,3,6,7-tetrahydro-1H-azepine-2-carbonyl))-1-thio-α-lincosamide 4-Bromobenzenethiol (413.4 mg, 2.19 mmol) was added to a solution of 660 mg (1.09 mmol) of the title compound in step (vi) of Example X1 in N,N-dimethylformamide (5 ml), and the mixture was cooled to 0° C. 1,3,4,6,7,8-Hexahydro-1-methyl-2H-pyrimido[1,2-a]pyrimidine was added to the solution, and the mixture was stirred for 6 hr. The solvent was removed under the reduced pressure, and the residue was purified by column chromatography on silica gel (hexane:ethyl acetate=1:1, chloroform:methanol=10:1)

Step (viii) of Example X1

Methyl 6-N-((2S,5S)-5-propylazepane-2-carbonyl)-1-thio-α-lincosamide

Raney nickel (1 g) was added to a solution of 475 mg of the title compound in step (vii) of Example X1 in methanol (5 ml), and the mixture was stirred in a hydrogen atmosphere for 37 hr. The reaction solution was filtered through Celite, and the filtrate was removed under the reduced pressure. The residue was purified by column chromatography on silica gel (chloroform:methanol:28% aqueous ammonia=20:1:0.1) to give 130 mg (yield 28%) of the title compound.

$^1$H-NMR (400 MHz, CD$_3$OD) δ: 0.90 (3H, t, J=7.3 Hz), 1.18 (3H, d, J=6.6 Hz), 1.19-1.42 (7H, m), 1.61-1.71 (1H, m), 1.80-1.86 (1H, m), 1.95-2.03 (2H, m), 2.08 (3H, s), 2.74-2.82 (1H, m), 3.03 (1H, ddd, J=2.4, 5.6, 14.2 Hz), 3.57 (1H, dd, J=3.4, 10.2 Hz), 3.59 (1H, t, J=5.6 Hz), 3.96 (1H, d, J=2.7 Hz), 4.06 (1H, q, J=6.4 Hz), 4.10 (1H, dd, J=5.6, 10.2 Hz), 4.18 (1H, dd, J=6.3, 7.8 Hz), 4.24 (1H, d, J=7.8 Hz), 5.24 (1H, d, J=5.4 Hz).

MS (FAB) m/z 421 [M+H]$^+$.

Step (ix) of Example X1

Methyl 6-N-((2S,5S)-1-N-tert-butoxycarbonyl-5-propylazepane-2-carbonyl)-1-thio-α-lincosamide Lithium hydroxide monohydrate (16.5 mg, 0.393 mmol) was added to a solution of 110 mg (0.262 mmol) of the title compound in step (viii) of Example X1 in 1,4-dioxane:water=4:1 (5.5 ml), and the mixture was stirred at room temperature for 5 min. Tert-butyl dicarbonate was then added thereto, and the mixture was stirred at room temperature for one hr. A saturated aqueous sodium hydrogencarbonate solution was added thereto, and the mixture was then extracted with ethyl acetate. The extract was dried over anhydrous sodium sulfate and was then filtered. The filtrate was concentrated under the reduced pressure, and the residue was then dried to give the title compound as a crude product.

Step (x) of Example X1

Methyl 6-N-((2S,5S)-1-(N-tert-butoxycarbonyl)-5-propylazepane-2-carbonyl)-1-thio-2,3,4-tris-O-trimethylsilyl-α-lincosamide The title compound was produced in the same manner as in step (i) of Example S1, except that the title compound (whole quantity) in step (ix) of Example X1, 0.166 ml (1.31 mmol) of trimethylsilylchloride, 0.275 mol (1.31 mmol) of hexamethyldisilazane, pyridine (5.5 ml), methanol (5.5 ml), and 0.171 ml (0.341 mmol) of 2 N aqueous acetic acid solution were used.

Step (xi) of Example X1

6-N-((2S,5S)-1-(N-Tert-butoxycarbonyl)-5-propylazepane-2-carbonyl)-7-O-methanesulfonyl-1-thio-2,3,4-tris-O-trimethylsilyl-α-lincosamide The title compound was produced in the same manner as in step (ii) of Example S1, except that the title compound (whole quantity) in step (x) of Example X1, 0.182 ml (1.31 mmol) of triethylamine, 0.082 ml (1.05 mmol) of methanesulphonyl chloride, and chloroform (3.0 ml) were used.

Step (xii) of Example X1

Methyl 7-acetylthio-6-N-((2S,5S)-1-(N-tert-butoxycarbonyl)-5-propylazepane-2-carbonyl)-7-deoxy-7-epi-1-thio-2,3,4-tris-O-trimethylsilyl-α-lincosamide The title compound (five steps, 96 mg, yield 46%) was produced in the same manner as in step (iii) of Example S1, except that the title compound in step (xi) of Example X1, 181.3 mg (1.59 mmol) of potassium thioacetate and N,N-dimethylformamide (1.5 ml) were used.

$^1$H-NMR (400 MHz, CDCl$_3$) δ: −0.0043 (9H, s), 0.00 (9H, s), 0.042 (9H, s), 0.76 (3H, t, J=6.9 Hz), 1.06-1.23 (9H, m), 1.35-1.38 (1H, m), 1.38 (9H, s), 1.50-1.80 (4H, m), 1.85 (3H, s), 2.16 (3H, s), 2.70-2.95 (1H, m), 3.35-3.45 (2H, m), 3.58-4.20 (4H, m), 4.25-4.50 (2H, m), 5.02 (1H, d, J=5.6 Hz), 6.16 (1H, brd).

MS (FAB) m/z 795 [M+H]$^+$.

Step (xiii) of Example X1

Methyl7-acetylthio6-N-((2S,5S)-1-(N-tert-butoxycarbonyl)-5-propylazepane-2-carbonyl)-7-deoxy-7-epi-1-thio-α-lincosamide 1 N Hydrochloric acid (0.424 ml, 0.424 mmol) was added to a solution of 96 mg (0.121 mmol) of the title compound in step (xii) of Example X1 in methanol (2.0 ml), and the mixture was stirred at room temperature for 40 min. The reaction solution was then concentrated under the reduced pressure to give the title compound.

Step (xiv) of Example X1

Methyl 6-N-((2S,5S)-1-N-tert-butoxycarbonyl-5-propylazepane-2-carbonyl)-7-deoxy-7-epi-7-mercapto-1-thio-α-lincosamide A 4.1 N solution (0.03 ml) of sodium methoxide in methanol was added to a solution of the title compound (whole quantity) in step (xiii) of Example X1 in methanol (2 ml), and the mixture was stirred at room temperature for 30 min. A saturated aqueous sodium hydrogencarbonate solution was added to the reaction solution, and the mixture was extracted with ethyl acetate. The extract was dried over anhydrous sodium sulfate and was then filtered. The filtrate was concentrated under the reduced pressure. The residue was then purified by column chromatography on silica gel (chloroform:methanol:28% aqueous ammonia=20:1:0.1) to give the title compound (two steps, 40 mg, yield 62%).

$^1$H-NMR (400 MHz, CD$_3$OD) δ: 0.91 (3H, t, J=6.8 Hz), 1.24-1.35 (8H, m), 1.45-1.50 (1H, m), 1.48 (9H, s), 1.60-1.75 (3H, m), 1.90-2.05 (2H, m), 2.15 (3H, s), 3.45-3.59 (3H, m), 3.80-3.90 (1H, m), 4.02-4.15 (2H, m), 4.24-4.34 (1H, m), 4.36-4.32 (2H, m), 5.24 (1H, d, J=5.6 Hz).

MS (ESI) rink 537 [M+H]$^+$.

Step (xv) of Example X1

Methyl 6-N-((2S,5S)-1-(N-tert-butoxycarbonyl)-5-propylazepane-2-carbonyl)-7-deoxy-7-(4-(2-(dimethylamino)ethyl)phenylthio)-7-epi-1-thio-α-lincosamide The title compound (6.7 mg, yield 48%) was produced in the same manner as in step (vi) of Example S1, except that 11.0 mg (0.0204 mmol) of the title compound in step (xiv) of Example X1, 2.4 mg (0.0041 mmol) of 4,5-bis(diphenylphosphino)-9,9-dimethylsantene, 1.9 mg (0.00204 mmol) of tris(dibenzylideneacetone)dipalladium, 7.01 mg (0.0307 mmol) of 2-(4-bromophenyl)-N,N-dimethylethanamine, 0.0071 ml (0.0408 mmol) of diisopropylethylamine, and dioxane (0.2 ml) were used.

$^1$H-NMR (400 MHz, CD$_3$OD) δ: 0.91 (3H, t, J=6.7 Hz), 1.24-1.37 (9H, m), 1.48 (9H, s), 1.55-1.80 (3H, m), 1.97 (3H, s), 1.97-2.05 (2H, m), 2.45 (6H, s), 2.70-2.77 (2H, m), 2.79-2.85 (2H, m), 3.43-3.70 (4H, m), 3.70-3.85 (1H, m), 3.90-3.95 (1H, m), 4.04-4.10 (1H, m), 4.32-4.50 (2H, m), 5.25 (1H, d, J=5.3 Hz), 7.20 (2H, d, J=8.3 Hz), 7.36 (2H, d, J=8.3 Hz).

MS (FAB) m/z 684 [M+H]$^+$.

Step (xvi) of Example X1

Methyl 7-deoxy-7-(4-(2-(dimethylamino)ethyl)phenylthio)-7-epi-6-N-((2S,5S)-5-propylazepane-2-carbonyl)-1-thio-α-lincosamide (Compound 56)

The title compound (3.9 mg, yield 68%) was produced from 6.7 mg (0.0098 mmol) of the title compound in step (xv) of Example X1 in the same manner as in step (xi) of Example T1.

$^1$H-NMR (400 MHz, CD$_3$OD) δ: 0.91 (3H, t, J=7.2 Hz), 1.23-1.40 (9H, m), 1.40-1.54 (1H, m), 1.60-1.82 (1H, m), 1.84-1.94 (1H, m), 2.00 (3H, s), 2.00-2.06 (1H, m), 2.39 (6H, s), 2.63-2.70 (2H, m), 2.74-2.86 (3H, m), 3.05-3.16 (1H, m), 3.54-3.66 (2H, m), 3.73-3.86 (2H, m), 4.02-4.14 (2H, m), 4.36 (1H, d, J=9.8 Hz), 4.45 (1H, dd, J=9.8, 2.5 Hz), 5.26 (1H, d, J=5.4 Hz), 7.19 (2H, d, J=8.2 Hz), 7.36 (2H, d, J=8.2 Hz).

MS (FAB) m/z 584 [M+H]$^+$.

Step (i) of Example XA1

Benzyl 4-cyclopropyl-3-oxobutanoate

Triethylamine (13.7 ml, 98.28 mmol) was added to a solution of 4.92 g (49.14 mmol) of 2-cyclopropylacetic acid in dichloromethane (50.8 ml), and the mixture was then cooled to −50° C. Thionylchloride (5.35 ml, 73.71 mmol) was added dropwise thereto, and the temperature of the mixture was gradually raised to room temperature. The solution was gradually added to a mixed solution composed of 14.2 g (98.28 mmol) of 2,2-dimethyl-1,3-dioxane-4,6-dione and dichloromethane (101.5 ml): pyridine (50.8 ml), which had been cooled to 0° C. The temperature of the mixture was raised to room temperature, and the mixture was then stirred for 16 hr. The solvent was removed under the reduced pressure, and a saturated aqueous sodium hydrogencarbonate solution was added to the residue. The mixture was washed with ethyl acetate. The aqueous layer was adjusted to pH 4 by the addition of 1 N hydrochloric acid and was then extracted with ethyl acetate. The extract was dried over anhydrous sodium sulfate and was then filtered. The filtrate was concentrated under the reduced pressure, and the residue was then dried. N,N-Dimethylformamide (40 ml), 7.42 ml (196.6 mmol) of formic acid, and 6.62 ml (63.88 mmol) of benzylalcohol were added in that order, and the mixture was stirred at 120° C. for 1.5 hr. The mixture was cooled to room temperature. The cooled solution was then neutralized with a saturated aqueous sodium hydrogencarbonate solution. The neutralized solution was then extracted with ethyl acetate. The extract was then washed with an aqueous ammonium chloride solution, water, and brine in that order, was dried over anhydrous sodium sulfate, and was then filtered. The filtrate was concentrated under the reduced pressure, and the residue was purified by column chromatography on silica gel (hexane:ethyl acetate=20:1 to 14:1) to give 3.94 g (three steps, yield 35%) of the title compound.

$^1$H-NMR (400 MHz, CDCl$_3$) δ: 0.08-0.13 (2H, m), 0.51-0.59 (2H, m), 0.87-1.02 (1H, m), 2.39 (2H, d, J=7.1 Hz), 3.55 (2H, s), 5.17 (2H, s), 7.36 (5H, s).

MS (FAB) m/z 233 [M+H]$^+$.

Step (ii) of Example XA1

4-Cyclopropylbutane-1,3-diol

A solution of 3.23 g (13.91 mmol) of the title compound in step (i) of Example XA1 in tetrahydrofuran (31.3 ml) was cooled to 0° C. Lithiumaluminum hydride (2.11 g, 55.62 mmol) was then added thereto, and the mixture was stirred for 2.5 hr. Thereafter, the reaction solution was stirred at room temperature for one hr. Lithium aluminum hydride (0.528 g, 13.91 mmol) was added thereto, and the mixture was stirred at room temperature for one hr. A saturated aqueous sodium potassium tartrate solution was added thereto, and the mixture was extracted with diethyl ether. The extract was dried over anhydrous sodium sulfate and was then filtered. The filtrate was concentrated at a low temperature under the reduced pressure. The residue was purified by column chromatography on silica gel (hexane:diethyl ether=1:1 to 1:4) to give the title compound as a crude product.

$^1$H-NMR (400 MHz, CDCl$_3$) δ: 0.02-0.15 (2H, m), 0.42-0.53 (2H, m), 0.69-0.80 (1H, m), 1.31-1.40 (1H, m), 1.42-1.50 (1H, m), 1.65-1.75 (1H, m), 1.75-1.82 (1H, m), 3.78-3.92 (2H, m), 3.92-4.00 (1H, m).

MS (FAB) m/z 131 [M+H]$^+$.

Step (iii) of Example XA1

4-(Tert-butyldiphenylsilyloxy)-1-cyclopropylbutan-1-ol

Imidazole (0.697 g, 10.23 mmol) was added to a solution of 1.11 g (8.52 mmol) of the title compound in step (ii) of Example XA1 in N,N-dimethylformamide (5 ml), and the mixture was stirred for 5 min. Tert-butylchlorodiphenylsilane (1.25 ml) was gradually added dropwise thereto, and the mixture was stirred at room temperature for 15 min. A saturated aqueous sodium hydrogencarbonate solution was added to the reaction solution, and the mixture was extracted with ethyl acetate. The extract was dried over anhydrous sodium sulfate and was then filtered. The filtrate was concentrated under the reduced pressure, and the residue was purified by column chromatography on silica gel (hexane:ethyl acetate=20:1 to 15:1) to give 1.43 g (two steps, yield 28%) of the title compound.

$^1$H-NMR (400 MHz, CDCl$_3$) δ: 0.00-0.12 (2H, m), 0.40-0.50 (2H, m), 0.70-0.80 (1H, m), 1.05 (9H, s), 1.25-1.32 (1H, m), 1.48-1.56 (1H, m), 1.72-1.78 (2H, m), 3.28 (1H, d, J=2.0 Hz), 3.83-3.92 (2H, m), 3.96-4.04 (1H, m), 6.94-7.06 (6H, m), 7.24-7.33 (4H, m).

MS (FAB) m/z 369 [M+H]$^+$.

Step (iv) of Example XA1

4-(Tert-butyldiphenylsilyloxy)-1-cyclopropylbutan-2-one 1,1,1-Tris(acetyloxy)-1,1-dihydro-1,2-benziodoxol-3-(1H)-one (Dess-Martin periodinane) (6.07 g, 14.31 mmol) was added to a solution of 4.39 g (11.92 mmol) of the title compound in step (iii) of Example XA1 in dichloromethane (127 ml), and the mixture was stirred at room temperature for 20 min. A saturated aqueous sodium hydrogencarbonate solution was added to the reaction solution, and the mixture was filtered through Celite, and the filtrate was extracted with dichloromethane. The organic layer was washed with an aqueous thiosulfuric acid sodium solution and water in that order, was dried over anhydrous sodium sulfate and was then filtered. The filtrate was concentrated under the reduced pressure, and the residue was purified by column chromatography on silica gel (hexane:ethyl acetate=20:1) to give 2.98 g (yield 68%) of the title compound.

$^1$H-NMR (400 MHz, CDCl$_3$) δ: 0.05-0.14 (2H, m), 0.50-0.60 (2H, m), 0.95-1.05 (1H, m), 1.05 (9H, s), 2.35 (2H, d, J=6.8 Hz), 2.67 (2H, t, J=6.3 Hz), 3.94 (2H, t, J=6.3 Hz), 7.34-7.45 (6H, m), 7.60-7.70 (4H, m).

MS (FAB) m/z 367 [M+H]$^+$.

Step (v) of Example XA1

Tert-butyl(3-(cyclopropylmethyl)-3-butenyloxy)diphenylsilane

A 1.66 M hexane solution of butyllithium (5.88 ml, 9.76 mmol) was added to a solution of 4.36 g (12.21 mmol) of methyltriphenylphosphonium bromide in tetrahydrofuran (40 ml), and the mixture was stirred at room temperature for one hr. A solution of 2.98 g (8.14 mmol) of the title compound in step (iv) of Example XA1 in tetrahydrofuran (30 ml) was added thereto, and the mixture was stirred at room temperature for min. A saturated aqueous sodium hydrogencarbonate solution was added thereto, and the mixture was extracted with ethyl acetate. The extract was dried over anhydrous sodium sulfate and was then filtered. The filtrate was concentrated under the reduced pressure, and the residue was purified by column chromatography on silica gel (hexane:ethyl acetate=20:1) to give 2.23 g (yield 75%) of the title compound.

$^1$H-NMR (400 MHz, CDCl$_3$) δ: −0.02-0.03 (2H, m), 0.40-0.46 (2H, m), 0.67-0.76 (1H, m), 1.04 (9H, s), 1.85 (2H, d, J=7.1 Hz), 2.33 (2H, t, J=7.0 Hz), 3.76. (2H, t, J=6.9 Hz), 4.71-4.74 (1H, m), 4.89 (1H, brd, J=1.5 Hz), 7.34-7.44 (6H, m), 7.65-7.70 (4H, m).

MS (FAB) m/z 365 [M+H]$^+$.

Step (vi) of Example XA1

3-(Cyclopropylmethyl)-3-buten-1-ol

A 1 M tetrahydrofuran solution of tetrabutylammonium fluoride (6.44 ml, 6.44 mmol) was added to a solution of 2.13 g (5.85 mmol) of the title compound in step (v) of Example XA1 in diethyl ether (5 ml), and the mixture was stirred at room temperature for 10 min. Tetrahydrofuran (5 ml) was added to the reaction solution, and the mixture was stirred at room temperature for 2 hr. An aqueous ammonium chloride solution was added thereto, and the mixture was extracted with diethyl ether. The organic layer was washed with brine, was dried over anhydrous sodium sulfate and was then filtered. The filtrate was concentrated at a low temperature under the reduced pressure, and the residue was purified by distillation to give 545.4 mg (yield 74%) of the title compound.

$^1$H-NMR (400 MHz, CDCl$_3$) δ: 0.00-0.15 (2H, m), 0.43-0.56 (2H, m), 0.76-0.86 (1H, m), 1.85 (2H, d, J=6.9 Hz), 2.28 (2H, t, J=6.3 Hz), 3.63 (2H, t, J=6.3 Hz), 4.75 (1H, s), 4.94 (1H, d, J=1.4 Hz).

MS (GC) m/z 126 M$^+$.

Step (vii) of Example XA1

((S)-Methyl 2-(N-(3-(cyclopropylmethyl)-3-butenyl)-2-nitrophenylsulfonamide)-4-pentenoate The title compound (2.04 g, 6.48 mmol) in step (i) of Example X1 was added to a solution of 545.4 mg (4.32 mmol) of the title compound in step (vi) of Example XA1 in tetrahydrofuran (21.3 ml), and the mixture was stirred at 0° C. for 5 min. Triphenylphosphine (1.70 g, 6.48 mmol) was added to the reaction solution, and the mixture was stirred for 15 min. Diisopropyl azodicarboxylate (1.28 ml, 6.48 mmol) was then added thereto, and the mixture was stirred for 20 min. The temperature of the reaction solution was raised to room temperature, and the solution was further stirred for 30 min. A saturated aqueous sodium hydrogencarbonate solution was then added thereto, and the mixture was extracted with ethyl acetate. The extract was dried over anhydrous sodium sulfate and was then filtered. The filtrate was concentrated under the reduced pressure, and the residue was purified by column chromatography on silica gel (hexane:ethyl acetate=7:1) to give 1.72 g (yield 94%) of the title compound.

$^1$H-NMR (400 MHz, CDCl$_3$) δ: 0.03-0.14 (2H, m), 0.43-0.55 (2H, m), 0.74-0.83 (1H, m), 1.91 (2H, d, J=6.8 Hz), 2.33-2.43 (1H, m), 2.47-2.57 (2H, m), 2.78-2.87 (1H, m), 3.23-3.32 (1H, m), 3.49-3.58 (1H, m), 3.59 (3H, s), 4.73 (1H, dd, J=5.9, 9.3 Hz), 4.75 (1H, s), 4.94 (1H, brd, J=1.5 Hz), 5.12-5.23 (2H, m), 5.77-5.87 (1H, m), 7.57-7.62 (1H, m), 7.67-7.74 (2H, m), 8.02-8.08 (1H, m).

MS (FAB) m/z 423 [M+H]$^+$.

Step (viii) of Example XA1

(S,Z)-Methyl 5-(cyclopropylmethyl)-1-(2-nitrophenylsulfonyl)-2,3,6,7-tetrahydro-1H-azepine-2-carboxylate The title compound (1.60 g, yield 99%) was produced in the same manner as in step (iv) of Example X1, except that 1.72 g (4.08 mmol) of the title compound in step (vii) of Example XA1 was used.

$^1$H-NMR (400 MHz, CDCl$_3$) δ: −0.06-0.05 (2H, m), 0.36-0.47 (2H, m), 0.60-0.71 (1H, m), 1.79 (1H, dd, J=6.8, 15.1 Hz), 1.86 (1H, dd, J=6.8, 15.1 Hz), 2.36 (1H, ddd, J=2.2, 6.1, 16.6 Hz), 2.42-2.52 (1H, m), 2.58-2.66 (1H, m), 2.75-2.85 (1H, m), 3.51 (1H, ddd, J=2.4, 10.2, 12.0 Hz), 3.62 (3H, s), 3.84 (1H, ddd, J=3.1, 6.1, 11.3 Hz), 4.90 (1H, dd, J=3.4, 6.8 Hz), 5.54 (1H, m), 7.60-7.65 (1H, m), 7.66-7.71 (2H, m), 8.05-8.10 (1H, m).

MS (FAB) m/z 395 [M+H]$^+$.

Step (ix) of Example XA1

(S,Z)-Methyl 5-(cyclopropylmethyl)-2,3,6,7-tetrahydro-1H-azepine-2-carboxylate

The title compound (139.8 mg, yield 83%) was produced in the same manner as in step (vii) of Example X1, except that 317.1 mg (0.804 mmol) in step (viii) of Example XA1 was used.

$^1$H-NMR (400 MHz, CDCl$_3$) δ: 0.02-0.10 (2H, m), 0.42-0.50 (2H, m), 0.68-0.80 (1H, m), 1.89 (2H, d, J=6.9 Hz), 2.19-2.25 (1H, m), 2.32-2.37 (1H, m), 2.40 (1H, s), 2.45 (1H, dd, J=5.3, 9.4 Hz), 2.54-2.62 (1H, m), 2.70-2.78 (1H, m), 3.12 (1H, ddd, J=2.2, 6.7, 11.1 Hz), 3.48 (1H, dd, J=2.0, 9.3 Hz), 3.73 (3H, s), 5.61 (1H, t, J=6.3 Hz).

MS (FAB) m/z 210 [M+H]$^+$.

Step (x) of Example XA1

(2S)-Methyl 5-(cyclopropylmethyl)azepane-2-carboxylate

Rhodium-carbon (120 mg) was added to a solution of 139.8 mg (0.572 mmol) of the title compound in step (ix) of Example XA1 in methanol (6 ml), and the mixture was stirred in a hydrogen atmosphere (0.7 MPa) for 10 min. The reaction solution was filtered through Celite. The solvent was then removed from the filtrate under the reduced pressure, and the residue was dried.

MS (ESI) m/z 212 [M+H]$^+$.

Step (xi) of Example XA1

(2S)-1-Tert-butyl-2-methyl 5-(cyclopropylmethyl)azepane-1,2-dicarboxylate 1,3,4,6,7,8-Hexahydro-1-methyl-2H-pyrimido[1,2-a]pyrimidine (0.165 ml, 1.15 mmol) was added to a solution of the title compound in step (x) of Example XA1 in 1,4-dioxane:water=5:1 (3.72 ml), and the mixture was stirred at room temperature for 10 min. Tert-butyl dicarbonate (0.251 ml, 1.093 mmol) was then added to the reaction solution, and the mixture was stirred at room temperature for 14 hr. A saturated aqueous sodium hydrogencarbonate solution was added thereto, and the mixture was extracted with ethyl acetate. The extract was dried over anhydrous sodium sulfate and was then filtered. The filtrate was concentrated under the reduced pressure, and the residue was purified by column chromatography on silica gel (hexane:ethyl acetate=10:1) to give 98.8 mg (two steps, yield 48%) of the title compound.

MS (FAB) m/z 312 [M+H]$^+$.

Step (xii) of Example XA1

(2S)-1-(Tert-butoxycarbonyl)-5-(cyclopropylmethyl)azepane-2-carboxylic acid

The title compound was produced in the same manner as in step (v) of Example X1, except that 98.8 mg (0.317 mmol) of the title compound in step (xi) of Example XA1 was used.

MS (FAB) m/z 298 [M+H]$^+$.

Step (i) of Example Y1

Methyl 1-thio-6-N-trifluoroacetyl-α-lincosamide

The title compound was produced in the same manner as described in J. Med. Chem., 12, (1969), 780.

Step (ii) of Example Y1

Methyl 2,3,4,7-tetrakis-O-trimethylsilyl-1-thio-6-N-trifluoroacetyl-α-lincosamide Trimethylsilyl chloride (12.6 ml, 98.5 mmol) and 20.6 ml (98.5 mmol) of hexamethyldisilazane were added to a solution of 6.88 g (19.7 mmol) of the title compound in step (i) of Example Y1 in pyridine (40 ml) under ice cooling, and the mixture was stirred at room temperature for one hr. The reaction solution was added to a 10% aqueous sodium hydrogencarbonate solution, and the mixture was extracted with ethyl acetate. The extract was dried over anhydrous sodium sulfate. After filtration, the filtrate was concentrated. The residue was purified by column chromatography on silica gel (hexane:ethyl acetate=100:0 to 95:5) to give 8.87 g (yield 71%) of the title compound.

$^1$H-NMR (400 MHz, CDCl$_3$) δ: 0.13 (9H, s), 0.15 (18H, s), 0.20 (9H, s), 1.20 (3H, d, J=6.1 Hz), 2.01 (3H, s), 3.70 (1H, dd, J=2.5, 9.7 Hz), 3.84-3.93 (1H, m), 4.07 (1H, dd, J=5.6, 9.7 Hz), 4.10-4.18 (2H, m), 4.35 (1H, d, J=5.8 Hz), 5.19 (1H, d, J=5.4 Hz), 7.57 (1H, d, J=8.0 Hz).

Step (iii) of Example Y1

Methyl, 1-thio-6-N-trifluoroacetyl-2,3,4-tris-O-trimethylsilyl-α-lincosamide

6 N acetic acid (4.17 ml) was added to a solution of 8.87 g (13.9 mmol) of the title compound in step (ii) of Example Y1 in methanol (65 ml), and the mixture was stirred at room temperature for 15 min. A 10% aqueous sodium hydrogencarbonate solution was added to the reaction solution. The mixture was concentrated to about half amount, and the residue was extracted with ethyl acetate. The extract was dried over anhydrous sodium sulfate. After filtration, the filtrate was concentrated. The residue was purified by column chromatography on silica gel (hexane:ethyl acetate=95:5 to 80:20) to give 7.21 g (yield 91%) of the title compound.

$^1$H-NMR (400 MHz, CDCl$_3$) δ: 0.15 (18H, s), 0.20 (9H, s), 1.28 (3H, d, J=6.3 Hz), 2.02 (3H, s), 3.73 (1H, dd, J=2.7, 9.5 Hz), 3.84-3.94 (1H, m), 4.18 (1H, dd, J=5.4, 9.5 Hz), 4.14-4.22 (2H, m), 4.36 (1H, d, J=6.1 Hz), 5.19 (1H, d, J=5.4 Hz), 7.63 (1H, d, J=7.8 Hz).

MS (EI) m/z 566 [M+H]$^+$.

Step (iv) of Example Y1

Methyl 7-O-methanesulphonyl-1-thio-6-N-trifluoroacetyl-2,3,4-tris-O-trimethylsilyl-α-lincosamide Triethylamine (2.18 ml, 15.6 mmol) and 1.21 ml (15.6 mmol) of methanesulphonyl chloride were added to a solution of 4.42 g (7.82 mmol) of the title compound in step (iii) of Example Y1 in chloroform (20 ml), and the mixture was stirred at room temperature overnight. A saturated aqueous sodium hydrogencarbonate solution was added to the reaction solution, and the mixture was extracted with chloroform. The extract was dried over anhydrous sodium sulfate. After filtration, the filtrate was concentrated to give 5.46 g. (quant.) of the title compound.

$^1$H-NMR (400 MHz, CDCl$_3$) δ: 0.16 (9H, s), 0.17 (9H, s), 0.20 (9H, s), 1.49 (3H, d, J=6.3 Hz), 2.04 (3H, s), 3.07 (3H, s), 3.66 (1H, dd, J=9.8, 2.6 Hz), 4.08 (1H, dd, J=9.8, 5.4 Hz), 4.13-4.15 (1H, m), 4.29 (1H, d, J=6.6 Hz), 4.46 (1H, ddd, J=8.5, 6.6, 6.6 Hz), 4.90 (1H, td, J=6.3, 6.6 Hz), 5.18 (1H, d, J=5.4 Hz), 7.52 (1H, d, J=7.8 Hz).

Step (v) of Example Y1

Methyl 7-acetylthio-7-deoxy-7-epi-1-thio-6-N-trifluoroacetyl-2,3,4-tris-O-trimethylsilyl-α-lincosamide Potassium thioacetate (2.68 g, 23.4 mmol) was added to a solution of 5.46 g (7.82 mmol) of the title compound in step (iv) of Example Y1 in N,N-dimethylformamide (40 ml), and the mixture was stirred at 80° C. for 1.5 hr. The reaction solution was concentrated, and the residue was then diluted with ethyl acetate. The diluted solution was washed with a saturated aqueous sodium hydrogencarbonate solution. The washed solution was dried over anhydrous sodium sulfate. After filtration, the filtrate was then concentrated. Trimethylsilane chloride (6.35 ml, 50.0 mmol) and 10.5 ml (50.0 mmol) of hexamethyldisilazane were added to a solution of the residue in pyridine (16 ml), and the mixture was stirred at room temperature for 3 hr. A saturated aqueous sodium hydrogencarbonate solution was added to the reaction solution, and the mixture was extracted with ethyl acetate. The extract was dried over anhydrous sodium sulfate. After filtration, the filtrate was concentrated, and the residue was purified by column chromatography on silica gel (hexane:ethyl acetate=100:0 to 10:1) to give 2.88 g (yield 59%) of the title compound.

$^1$H-NMR (400 MHz, CDCl$_3$) δ: 0.15 (9H, s), 0.16 (9H, s), 0.22 (9H, s), 1.41 (3H, d, J=7.1 Hz), 2.01 (3H, s), 2.32 (3H, s), 3.65 (1H, dd, J=2.5, 9.5 Hz), 3.80 (1H, dq, J=7.1, 7.1 Hz), 3.99 (1H, d, J=2.5 Hz), 4.09 (1H, dd, J=5.6, 9.7 Hz), 4.17 (1H, d, J=7.1 Hz), 4.15-4.45 (1H, m), 5.18 (1H, d, J=5.6 Hz), 7.21 (1H, d, J=9.3 Hz).

MS (EI) m/z 624 [M+H]$^+$.

Step (vi) of Example Y1

Methyl 7-acetylthio-7-deoxy-7-epi-1-thio-6-N-trifluoroacetyl-α-lincosamide

1 N hydrochloric acid (18.1 ml) was added to a solution of 2.83 g (4.54 mmol) of the title compound in step (v) of Example Y1 in methanol (30 ml), and the mixture was stirred at room temperature for 10 min. A 10% aqueous sodium hydrogencarbonate solution was added to the reaction solution, and the mixture was concentrated to about half amount under the reduced pressure. The residue was extracted with ethyl acetate. The extract was dried over anhydrous sodium sulfate.

After filtration, the filtrate was concentrated to give the title compound.

Step (vii) of Example Y1

Methyl 7-deoxy-7-epi-7-mercapto-1-thio-6-N-trifluoroacetyl-α-lincosamide

The title compound (whole quantity) in step (vi) of Example Y1 was dissolved in 25 ml of methanol. Sodium methoxide (a 28% methanol solution) (2.63 ml) was added to the solution, and the mixture was stirred at room temperature for 15 min. A 10% aqueous ammonium chloride solution was added to the reaction solution, and the mixture was concentrated to about half amount under the reduced pressure. The residue was extracted with ethyl acetate. The extract was dried over anhydrous sodium sulfate. After filtration, the filtrate was concentrated, and the residue was purified by column chromatography on silica gel (hexane:ethyl acetate:methanol=50:50:0 to 0:95:5) to give 1.65 g (two steps, yield 99%) of the title compound.

$^1$H-NMR (400 MHz, CDCl$_3$) δ: 1.32 (3H, d, J=6.8 Hz), 1.58 (1H, d, J=4.4 Hz), 2.25 (3H, s), 2.52 (1H, br), 2.84 (1H, br), 3.51-3.60 (1H, br), 3.65-3.72 (1H, br), 3.74-3.84 (2H, m), 3.94 (1H, d, J=10.0 Hz), 4.08-4.17 (1H, m), 4.27-4.35 (1H, m), 5.33 (1H, d, J=5.6 Hz), 7.01 (1H, d, J=9.6 Hz)

MS (FAB) m/z: 366 [M+H]$^+$.

Step (viii) of Example Y1

Methyl 7-deoxy-7-(4-(2-(dimethylamino)ethyl)phenylthio)-7-epi-1-thio-6-N-trifluoroacetyl-α-lincosamide The title compound (1.45 g, yield 94%) was produced in the same manner as in step (vi) of Example S1, except that 1.10 g (3.0 mmol) synthesized in step (vii) of Example Y1, 172.8 mg (0.30 mmol) of 4,5-bis(diphenylphosphino)-9,9-dimethylsantene, 139.5 mg (0.15 mmol) of tris(dibenzylideneacetone)dipalladium, dioxane (15 ml), 769.6 mg (3.4 mmol) of 4-bromo(2-(dimethylamino)ethyl)benzene, and 1.03 ml (6.0 mmol) of diisopropylethylamine were used.

$^1$H-NMR (400 MHz, CD$_3$OD) δ: 1.26 (3H, d, J=6.8 Hz), 2.01 (3H, s), 2.43 (6H, s), 2.69-2.73 (2H, m), 2.80-2.84 (2H, m), 3.57-3.61 (1H, m), 3.74-3.79 (1H, m), 3.89 (1H, d, J=2.7 Hz), 4.09 (1H, dd, J=10.2, 5.6 Hz), 4.58-4.65 (2H, m), 5.28 (1H, d, J=5.6 Hz), 7.19 (2H, d, J=8.1 Hz), 7.35 (2H, d, J=8.1 Hz)

MS (FAB) m/z 513 [M+H]$^+$

Step (ix) of Example Y1

Methyl 7-deoxy-7-(4-(2-(dimethylamino)ethyl)phenylthio)-7-epi-1-thio-α-lincosamide Benzyltriethyl ammonium chloride (8.6 mg, 0.038 mmol) and 133 μl (0.47 mmol) of a 20% aqueous potassium hydroxide solution were added to a solution of 96.4 mg (0.19 mmol) of the compound synthesized in step (viii) of Example Y1 in methylene chloride (2 ml), and the mixture was stirred at room temperature for 4 hr. A saturated aqueous sodium hydrogencarbonate solution was added to the reaction solution, and the mixture was then extracted with ethyl acetate. The extract was dried over anhydrous sodium sulfate. The solvent was removed by distillation, and the residue was purified by gel filtration column chromatography (CM-Sephadex LH-20) to give 23.4 mg (yield 30%) of the title compound.

$^1$H-NMR (400 MHz, CD$_3$OD) δ: 1.40 (3H, d, J=7.1 Hz), 1.91 (3H, s), 2.31 (6H, s), 2.54-2.58 (2H, m), 2.74-2.79 (2H, m), 3.20 (1H, dd, J=8.8, 3.0 Hz), 3.56-3.66 (2H, m), 4.05-4.11 (2H, m), 4.23 (1H, dd, J=8.7, 0.9 Hz), 5.22 (1H, d, J=5.9 Hz), 7.16 (2H, d, J=8.3 Hz), 7.33 (2H, d, J=8.3 Hz)

Step (x) of Example Y1

Methyl 6-N-((2R,4S)-1-(tert-butoxycarbonyl)-4-cyclopropylmethylpiperidine-2-carbonyl)-7-deoxy-7-(4-(2-(dimethylamino)ethyl)phenylthio)-7-epi-1-thio-α-lincosamide 1-Ethyl-3-(3'-dimethylaminopropyl)carbodiimide (13.2 mg, 0.068 mmol) and 9.4 mg (0.070 mmol) of 1-hydroxybenzotriazole were added to a solution of 23.4 mg (0.0056 mmol) of the compound synthesized in step (ix) of Example Y1 and 18.4 mg (0.065 mmol) of 1-(tert-butoxycarbonyl)-4-cyclopropylmethylpyridine-2-carboxylic acid in N,N-dimethylformamide (1 ml), and the mixture was stirred at room temperature overnight. Water was added to the reaction solution, and the mixture was then extracted with ethyl acetate. The extract was dried over anhydrous sodium sulfate. The solvent was removed by distillation, and the residue was purified by preparative thin-layer chromatography (chloroform:methanol:28% aqueous ammonia=10:1:0.1) to give 8.3 mg (yield 22%) of the title compound and 8.9 mg (yield 23%) of the title compound in step (xiii) of Example W1.

$^1$H-NMR (400 MHz, CD$_3$OD) δ: 0.00-0.04 (2H, m), 0.40-0.46 (2H, m), 0.65-0.77 (1H, m), 1.14-1.32 (6H, m), 1.48 (9H, s), 1.60-1.75 (2H, m), 1.85-1.96 (1H, m), 1.99 (3H, s), 2.05-2.12 (1H, m), 2.30 (6H, s), 2.50-2.58 (2H, m), 2.72-2.80 (2H, m), 3.32-3.40 (1H, m), 3.51-3.58 (1H, m), 3.60-3.70 (1H, m), 3.75-3.83 (1H, m), 3.85-3.90 (1H, m), 4.08 (1H, dd, J=10.3, 5.6 Hz), 4.18-4.27 (1H, m), 4.36 (1H, d, J=9.3 Hz), 4.45-4.50 (1H, m), 5.25 (1H, d, J=5.4 Hz), 7.18 (2H, d, J=8.0 Hz), 7.34 (2H, d, J=8.0 Hz)

Step (xi) of Example Y1

Methyl 6-N-((2R,4S)-(4-cyclopropylmethyl)piperidine-2-carbonyl)-7-deoxy-7-(4-(2-(dimethylamino)ethyl)phenylthio)-7-epi-1-thio-α-lincosamide (Compound 57)

Trifluoroacetic acid (0.3 ml) was added at −20° C. to a solution of 47.4 mg (0.07 mmol) of the compound synthesized in step (x) of Example Y1 in methylene chloride (1 ml). The temperature of the mixture was gradually raised to room temperature, and the mixture was stirred at room temperature for 3 hr. The solvent was removed by distillation, and the residue was purified by preparative thin-layer chromatography (chloroform:methanol:28% aqueous ammonia=10:1:0.1) to give 31.8 mg (yield 78%) of the title compound.

$^1$H-NMR (400 MHz, CD$_3$OD) δ: 0.00-0.03 (2H, m), 0.4-0.46 (2H, m), 0.66-0.78 (1H, m), 0.93-1.18 (3H, m), 1.26 (3H, d, J=6.8 Hz), 1.27-1.36 (1H, m), 1.55-1.85 (2H, m), 2.01 (3H, s), 2.00-2.05 (1H, m), 2.30 (6H,. s), 2.53-2.58 (2H, m), 2.65 (1H, td, J=11.7, 2.7 Hz), 2.75-2.79 (2H, m), 3.11-3.16 (1H, m), 3.26 (1H, dd, J=11.7, 3.0 Hz), 3.57 (1H, dd, J=10.3, 3.4 Hz), 3.77-3.83 (2H, m), 3.57 (1H, dd, J=10.3, 3.2 Hz), 4.09 (1H, q, J=5.6 Hz), 4.39 (1H, d, J=10.5 Hz), 4.50 (1H, dd, J=9.9, 2.5 Hz), 5.26 (1H, d, J=5.6 Hz), 7.17 (2H, d, J=8.3 Hz), 7.36 (2H, d, J=8.3 Hz).

MS (FAB) m/z 582 [M+H]$^+$

Step (xii) of Example Y1

Methyl 6-N-((2R,4S)-(4-cyclopropylmethyl-1-methyl)piperidine-2-carbonyl)-7-deoxy-7-(4-(2-(dimethylamino)ethyl)phenylthio)-7-epi-1-thio-α-lincosamide (Compound 58)

The title compound (17.0 mg, yield 95%) was produced in the same manner as in step (x) of Example U1, except that 17.2 mg (0.03 mmol) of the compound synthesized in step (xi) of Example Y1, 24.0 μl (0.3 mmol) of a 37% formaldehyde solution, 167.1 mg (0.3 mmol) of sodium triacetoxy borohydride, 17 μl (0.3 mmol) of acetic acid, and 1 ml of methanol were used.

$^1$H-NMR (400 MHz, CD$_3$OD) δ: 0.00-0.03 (2H, m), 0.40-0.45 (2H, m), 0.63-0.75 (1H, m), 1.05-1.30 (7H, m), 1.78 (1H, d, J=13.1 Hz), 1.94 (1H, d, J=12.7 Hz), 2.01 (3H, s), 2.10 (1H, t, J=12.2 Hz), 2.23 (3H, s), 2.30 (6H, s), 2.52-2.56 (3H, m), 2.75 (1H, d, J=8.5 Hz), 2.77 (1H, d, J=10.7 Hz), 2.90-3.00 (2H, m), 3.58 (1H, dd, J=10.2, 3.3 Hz), 3.64 (1H, brs), 3.76 (1H, qd, J=7.0, 3.1 Hz), 3.83-3.84 (1H, m), 4.10 (1H, dd, J=10.3, 5.7 Hz), 4.41 (1H, d, J=9.5 Hz), 4.50 (1H, dd, J=9.5, 3.2 Hz), 5.26 (1H, d, J=5.7 Hz), 7.18 (2H, d, J=8.3 Hz), 7.36 (2H, d, J=8.3 Hz).

MS (FAB) m/z 596 [M+H]$^+$

Step (i) of Example Y2

Methyl 6-N-(1-(N-tert-butoxycarbonyl)-5-cyclopropylmethylazepane-2-carbonyl)-7-deoxy-7-(4-(2-(dimethylamino)ethyl)phenylthio)-7-epi-1-thio-α-lincosamide The title compound (two steps, 195 mg, yield 88%) was produced in the same manner as in step (vi) of Example Xl, except that the whole amount of the title compound in step (xii) of Example XA1 and 264.4 mg (0.635 mmol) of the title compound in step (ix) of Example Y1 were used.

MS (FAB) m/z 696 [M+H]$^+$

Step (ii) of Example Y2

Methyl 6-N-(5-cyclopropylmethylazepane-2-carbonyl)-7-deoxy-7-(4-(2-(dimethylamino)ethyl)phenylthio)-7-epi-1-thio-α-lincosamide (Isomer 1: Compound 122, Isomer 2; Compound 123)

The title compound (isomer 1) (12.2 mg, yield 12%) and 86 mg (yield 81%) of the title compound (isomer 2) were produced in the same manner as in step (xi) of Example T1, except that 124.0 mg (0.178 mmol) of the title compound in step (i) of Example Y2 was used.

(Isomer 1)
$^1$H-NMR (400 MHz, CD$_3$OD) δ: 0.00-0.04 (2H, m), 0.42-0.46 (2H, m), 0.66-0.75 (1H, m), 1.18-1.22 (2H, m), 1.24 (3H, d, J=6.9 Hz), 1.24-1.43 (2H, m), 1.57-1.73 (2H, m), 1.99 (3H, s), 1.96-2.05 (2H, m), 2.20-2.27 (1H, m), 2.46 (6H, s), 2.72-2.79 (2H, m), 2.81-2.87 (2H, m), 2.91-2.98 (1H, m), 3.06-3.13 (1H, m), 3.54-3.61 (2H, m), 3.75-3.85 (2H, m), 4.08 (1H, dd, J=5.6, 10.2 Hz), 4.36 (1H, d, J=9.7 Hz), 4.44 (1H, dd, J=2.3, 9.7 Hz), 5.26 (1H, d, J=5.6 Hz), 7.20 (2H, d, J=8.2 Hz), 7.37 (2H, d, J=8.2 Hz).
MS (FAB) m/z 596 [M+H]$^+$.

(Isomer 2)
$^1$H-NMR (400 MHz, CD$_3$OD) δ: −0.02-0.03 (2H, m), 0.41-0.45 (2H, m), 0.64-0.73 (1H, m), 1.17 (2H, t, J=6.8 Hz), 1.24 (3H, d, J=6.9 Hz), 1.24-1.42 (2H, m), 1.53-1.63 (1H, m), 1.74-1.82 (1H, m), 1.93-2.04 (3H, m), 2.10 (3H, s), 2.34 (6H, s), 2.57-2.63 (2H, m), 2.72-2.82 (3H, m), 3.08 (1H, ddd, J=2.6, 5.4, 14.2 Hz), 3.56 (1H, dd, J=3.3, 10.2 Hz), 3.61 (1H, t, J=5.6 Hz), 3.77-3.83 (2H, m), 4.08 (1H, dd, J=5.6, 10.2 Hz), 4.35 (1H, d, J=9.8 Hz), 4.43 (1H, dd, J=2.6, 9.8 Hz), 5.26 (1H, d, J=5.6 Hz), 7.18 (2H, d, J=8.1 Hz), 7.36 (2H, d, J=8.1 Hz).
MS (FAB) m/z 596 [M+H]$^+$.

Step (iii) of Example Y2

Methyl 6-N-((5-cyclopropylmethyl-1-methyl)azepan-2-carbonyl)-7-deoxy-7-(4-(2-(dimethylamino)ethyl)phenylthio)-7-epi-1-thio-α-lincosamide (Isomer 3: Compound 124, Isomer 4: Compound 125)

The title compound (isomer 3) (6.4 mg, yield 57%) was produced in the same manner as in step (xi) of Example U1, except that 11.0 mg (mmol) of the title compound (isomer 1) in step (ii) of Example Y2 was used.

(Isomer 3)
$^1$H-NMR (400 MHz, CD$_3$OD) δ: −0.02-0.03 (2H, m), 0.40-0.47 (2H, m), 0.64-0.75 (1H, m), 1.14-1.20 (2H, m), 1.26 (3H, d, J=6.8 Hz), 1.20-1.32 (1H, m), 1.45-1.60 (2H, m), 1.60-1.78 (2H, m), 2.03 (3H, s), 1.97-2.13 (2H, m), 2.36 (6H, s), 2.42 (3H, s), 2.59-2.65 (2H, m), 2.76-2.84 (2H, m), 2.89-2.99 (2H, m), 3.14-3.23 (1H, m), 3.58 (1H, dd, J=3.3, 10.2 Hz), 3.73 (1H, d, J=3.3 Hz), 3.78-3.88 (1H, m), 4.09 (1H, dd, J=5.6, 10.2 Hz), 4.30 (1H, d, J=10.0 Hz), 4.34 (1H, dd, J=2.3, 10.0 Hz), 5.26 (1H, d, J=5.6 Hz), 7.21 (2H, d, J=8.2 Hz), 7.37 (2H, d, J=8.2 Hz).
MS (FAB) m/z 610 [M+H]$^+$.

The title compound (isomer 4) (23.3 mg, yield 96%) was produced in the same manner as in step (iii) of Example Y2, except that 23.7 mg (0.0398 mmol) of the title compound (isomer 2) in step (ii) of Example Y2 was used.

(Isomer 4)
$^1$H-NMR (400 MHz, CD$_3$OD) δ: −0.03-0.06 (2H, m), 0.39-0.49 (2H, m), 0.62-0.74 (1H, m), 1.12-1.22 (2H, m), 1.27 (3H, d, J=7.1 Hz), 1.22-1.35 (1H, m), 1.39-1.55 (2H, m), 1.68-1.78 (1H, m), 1.87-2.13 (3H, m), 2.02 (3H, s), 2.38 (9H, s), 2.63-2.68 (2H, m), 2.71-2.91 (4H, m), 3.04 (1H, dd, J=3.8, 5.2 Hz), 3.54 (1H, dd, J=3.2, 10.2 Hz), 3.79-3.89 (2H, m), 4.08 (1H, dd, J=5.6, 10.2 Hz), 4.28 (1H, d, J=9.0 Hz), 4.33 (1H, dd, J=3.2, 9.0 Hz), 5.24 (1H, d, J=5.6 Hz), 7.21 (2H, d, J=8.3 Hz), 7.39 (2H, d, J=8.3 Hz).
MS (FAB) m/z 610 [M+H]$^+$.

Specific examples of compounds according to the present invention include compounds shown in Tables 10 to 18 and 28 to 31.

For representative compounds among lincomycin derivatives according to the present invention, the minimal inhibitory concentration (MIC, mg/ml) against various pneumococci was measured according to the method described in Clinical and Laboratory Standards Institute, M7-A7, 2006. The results are shown in Table 1. Sensitivity disk agar-N+5% horse aseptic defibranated blood was used as the medium for the measurement. The amount of bacteria inoculated was about 10$^4$ CFU/ml. In Table 1, CLDM represents clindamycin.

TABLE 1

| | Example No. | | | | |
| --- | --- | --- | --- | --- | --- |
| | 1 | 10 | 54 | 52 | CLDM |
| S. pneumoniae MSC10197 | ≦0.008 | 0.06 | 0.03 | 0.25 | 0.03 |
| S. pneumoniae MSC07571 | 0.015 | 0.06 | 0.03 | 0.25 | 0.06 |
| S. pneumoniae MSC17994 | 0.015 | 0.12 | 0.06 | 0.25 | 0.06 |
| S. pneumoniae MSC07337 | 4 | 16 | 2 | 32 | >128 |
| S. pneumoniae MSC07471 | 4 | 16 | 2 | 32 | >128 |
| S. pneumoniae MSC07365 | 8 | 32 | 4 | 64 | >128 |
| S. pneumoniae MSC07465 | ≦0.008 | 0.03 | 0.015 | 0.25 | 0.03 | lincomycin derivatives of formula (I) according to the present invention demonstrated potent antimicrobial activity against resistant pneumococci.

TABLE 2

| | | NMR data | | |
| --- | --- | --- | --- | --- |
| Compound No. | Compound name | δ (ppm) from TMS | Solvent/Hz | MS |
| 2 | 7-Deoxy-7-(4-(2-dimethylaminoacetyl)-phenylthio)-7-epilincomycin | 0.92 (3H, brs), 1.27-1.45 (7H, m), 1.78-2.22 (7H, m), 2.36 (6H, s), 2.40 (3H, s), 2.99 (1H, dd, J = 10.5, 4.8 Hz), 3.24 (1H, dd, J = 6.0, 8.3 Hz), 3.34 (2H, s), 3.57 (1H, dd, J = 10.2, 3.3 Hz), 3.75-3.80 (1H, | CD$_3$OD (400 MHz) | MS (FAB) m/z 584 [M + H]$^+$ |

TABLE 2-continued

| | | NMR data | | |
|---|---|---|---|---|
| Compound No. | Compound name | δ (ppm) from TMS | Solvent/Hz | MS |
| | | m), 4.04-4.11 (2H, m), 4.37 (1H, d, J = 10.5 Hz), 4.53 (1H, dd, J = 9.6, 2.6 Hz), 5.24 (1H, d, J = 5.6 Hz), 7.45 (2H, d, J = 8.6 Hz), 7.92 (2H, d, J = 8.6 Hz). | | |
| 3 | 7-Deoxy-7-(4-(3-(dimethylamino)-1-propynyl)phenylthio)-7-epilincomycin | 0.92 (3H, brs), 1.27-1.40 (7H, m), 1.79-1.88 (1H, m), 1.94 (3H, s), 1.94-2.20 (3H, m), 2.37 (6H, s), 2.38 (3H, s), 2.97 (1H, dd, J = 10.7, 4.8 Hz), 3.24 (1H, dd, J = 5.7, 8.2 Hz), 3.34 (2H, s), 3.57 (1H, dd, J = 10.3, 3.2 Hz), 3.75 (1H, d, J = 2.4 Hz), 3.89 (1H, qd, J = 7.0, 2.7 Hz), 4.10 (1H, d, J = 5.6 Hz), 4.35 (1H, d, J = 9.7 Hz), 4.45 (1H, dd, J = 9.8, 2.9 Hz), 5.25 (1H, d, J = 5.6 Hz), 7.90 (4H, s). | $CD_3OD$ (400 MHz) | MS (FAB) m/z 580 $[M + H]^+$ |
| 4 | 7-Deoxy-7-(4-(dimethylamino)methyl)phenylthio)-7-epilincomycin | 0.91-0.95 (3H, m), 1.29 (3H, d, J = 7.0 Hz), 1.35-1.36 (4H, m), 1.80-1.90 (1H, m), 1.97 (3H, s), 1.98-2.24 (3H, m), 2.26 (6H, s), 2.41 (3H, s), 3.00 (1H, dd, J = 10.5, 4.6 Hz), 3.23-3.29 (1H, m), 3.50 (2H, s), 3.57 (1H, dd, J = 10.3, 3.2 Hz), 3.74 (1H, d, J = 2.9 Hz), 3.87 (1H, qd, J = 6.9, 2.7 Hz), 4.10 (1H, dd, J = 10.3, 5.6 Hz), 4.34 (1H, d, J = 9.8 Hz), 4.42 (1H, dd, J = 9.8, 2.7 Hz), 5.25 (1H, d, J = 5.6 Hz), 7.28 (2H, d, J = 8.3 Hz), 7.40 (2H, d, J = 8.3 Hz). | $CD_3OD$ (400 MHz) | MS (FAB) m/z 556 $[M + H]^+$ |
| 5 | 7-Deoxy-7-(3-(3-(dimethylamino)-1-propynyl)phenylthio)-7-epilincomycin | 0.93 (3H, brs), 1.28-1.33 (7H, m), 1.80-1.88 (1H, m), 1.97 (3H, s), 1.97-2.34 (3H, m), 2.37 (6H, s), 2.38 (3H, s), 2.98 (1H, dd, J = 10.6, 4.7 Hz), 3.24 (1H, dd, J = 5.9, 8.1 Hz), 3.49 (2H, s), 3.57 (1H, dd, J = 10.3, 3.2 Hz), 3.75 (1H, d, J = 3.2 Hz), 3.85 (1H, qd, J = 6.8, 2.7 Hz), 4.10 (1H, dd, J = 10.1, 5.5 Hz), 4.34 (1H, d, J = 10.8 Hz), 4.43 (1H, dd, J = 9.6, 2.6 Hz), 5.26 (1H, d, J = 5.3 Hz), 7.28-7.33 (2H, m), 7.40-7.43 (1H, m), 7.47-7.90 (1H, m). | $CD_3OD$ (400 MHz) | MS (FAB) m/z 580 $[M + H]^+$ |
| 6 | 7-Deoxy-7-(4-(2-pyrrolidinoethyl)-phenylthio)-7-epilincomycin | 0.90-0.95 (3H, m), 1.26 (3H, d, J = 6.8 Hz), 1.30-1.40 (4H, m), 1.80-1.90 (5H, m), 1.89 (3H, s), 1.98-2.25 (3H, m), 2.39 (3H, s), 2.63 (4H, m), 2.65-2.75 (2H, m), 2.80-2.85 (2H, m), 2.98 (1H, m), 3.23 (1H, m), 3.57 (1H, m), 3.73 (1H, m), 3.81 (1H, m), 4.10 (1H, dd, J = 5.6, 10.3 Hz), 4.30-4.40 (2H, m), 5.26 (1H, d, J = 5.6 Hz), 7.19-7.25 (2H, m), 7.35-7.40 (2H, m). | $CD_3OD$ (400 MHz) | MS (FAB) m/z 596 $[M + H]^+$ |
| 7 | 7-Deoxy-7-(4-(2-(2-(dimethylamino)ethylamino)ethyl)-phenylthio)-7-epilincomycin | 0.90-0.97 (3H, m), 1.26 (3H, d, J = 6.8 Hz), 1.31-1.39 (4H, m), 1.85 (1H, dt, J = 10.0, 12.8 Hz), 1.99 (1H, ddd, J = 4.8, 8.4, 12.8 Hz), 2.01 (3H, s), 2.08 (1H, dd, J = 8.4, 10.4 Hz), 2.11-2.20 (1H, m), 2.24 (6H, s), 2.39 (3H, s), 2.47 (2H, t, J = 6.8 Hz), 2.74 (2H, t, J = 7.1 Hz), 2.77-2.89 (4H, m), 2.98 (1H, dd, J = 4.6, 10.5 Hz), 3.24 (1H, dd, J = 5.6, 8.3 Hz), 3.58 (1H, dd, J = 3.1, 10.2 Hz), 3.74 (1H, d, J = 3.1 Hz), 3.82 (1H, dq, J = 2.5, 6.8 Hz), 4.10 (1H, dd, J = 5.6, 10.2 Hz), 4.33 (1H, d, J = 9.8 Hz), 4.39 (1H, dd, J = 2.5, 10.8 Hz), 5.27 (1H, d, J = 5.3 Hz), 7.21 (2H, d, J = 8.1 Hz), 7.38 (2H, d, J = 8.2 Hz). | $CD_3OD$ (400 MHz) | MS (FAB) m/z 613 $[M + H]^+$ |
| 8 | 7-Deoxy-7-(4-(2-(dimethylamino)ethylcarbamoyl)-phenylthio)-7-epilincomycin | 0.90-0.96 (3H, m), 1.28-1.40 (4H, m), 1.37 (3H, d, J = 6.8 Hz), 1.84 (1H, dt, J = 10.0, 12.4 Hz), 1.87 (3H, s), 2.01 (1H, ddd, J = 4.8, 8.0, 12.8 Hz), 2.08 (1H, dd, J = 8.4, 10.4 Hz), 2.12-2.24 (1H, m), 2.33 (6H, s), 2.40 (3H, s), 2.59 (2H, t, J = 6.6 Hz), 3.00 (1H, dd, J = 4.6, 10.5 Hz), 3.24 (1H, dd, J = 5.8, 8.3 Hz), 3.53 (2H, t, J = 6.6 Hz), 3.58 (1H, dd, J = 3.0, 10.0 Hz), 3.77 (1H, d, J = 2.4 Hz), 4.00 (1H, dq, J = 2.7, 6.8 Hz), 4.11 (1H, dd, J = 5.6, 10.0 Hz), 4.37 (1H, d, J = 10.2 Hz), 4.51 (1H, dd, J = 2.7, 9.8 Hz), 5.26 (1H, d, J = 5.6 Hz), 7.45 (2H, d, J = 8.8 Hz), 7.79 (2H, d, J = 8.8 Hz). | $CD_3OD$ (400 MHz) | MS (FAB) m/z 613 $[M + H]^+$ |

TABLE 2-continued

| Compound No. | Compound name | NMR data δ (ppm) from TMS | Solvent/Hz | MS |
|---|---|---|---|---|
| 9 | 7-Deoxy-7-epi-7-(4-(4-methylpiperazino)-phenylthio)lincomycin | 0.90-0.95 (3H, m), 1.26 (3H, d, J = 7.0 Hz), 1.35-1.45 (4H, m), 1.85-2.30 (4H, m), 1.97 (3H, s), 2.41 (6H, m), 2.63 (4H, m), 2.60-2.85 (8H, m), 3.00-3.10 (1H, m), 3.20-3.30 (1H, m), 3.57 (1H, m), 3.74 (1H, m), 3.80 (1H, m), 4.10 (1H, dd, J = 5.6 Hz, 10.0 Hz), 4.30-4.45 (2H, m), 5.26 (1H, d, J = 5.6 Hz), 7.20 (2H, d, J = 8.3 Hz), 7.36 (2H, d, J = 8.3 Hz). | CD$_3$OD (400 MHz) | MS (FAB) m/z 625 [M + H]$^+$ |
| 10 | 7-Deoxy-7-(4-(2-((2-(dimethylamino)ethyl)-(methyl)amino)ethyl)-phenylthio)-7-epilincomycin | 0.90-0.96 (3H, m), 1.26 (3H, d, J = 6.8 Hz), 1.31-1.38 (4H, m), 1.85 (1H, dt, J = 10.4, 12.8 Hz), 1.99 (1H, ddd, J = 4.8, 7.6, 12.8 Hz), 2.01 (3H, s), 2.08 (1H, dd, J = 8.4, 10.4 Hz), 2.11-2.21 (1H, m), 2.29 (6H, s), 2.34 (3H, s), 2.39 (3H, s), 2.49-2.56 (2H, m), 2.57-2.68 (4H, m), 2.75-2.82 (2H, m), 2.98 (1H, dd, J = 4.6, 10.5 Hz), 3.23 (1H, dd, J = 5.6, 8.0 Hz), 3.58 (1H, dd, J = 3.2, 10.2 Hz), 3.73 (1H, d, J = 3.2 Hz), 3.81 (1H, dq, J = 2.4, 6.8 Hz), 4.10 (1H, dd, J = 5.6, 10.2 Hz), 4.36 (1H, d, J = 10.2 Hz), 4.38 (1H, dd, J = 2.4, 9.8 Hz), 5.27 (1H, d, J = 5.6 Hz), 7.20 (2H, d, J = 8.3 Hz), 7.37 (2H, d, J = 8.3 Hz). | CD$_3$OD (400 MHz) | MS (FAB) m/z 627 [M + H]$^+$ |
| 11 | 7-(4-(2-(Cyclopropylamino)-ethyl)phenylthio)-7-deoxy-7-epilincomycin | 0.33-0.39 (2H, m), 0.46-0.51 (2H, m), 0.90-0.97 (3H, m), 1.27 (3H, d, J = 7.1 Hz), 1.31-1.39 (4H, m), 1.85 (1H, dt, J = 10.8, 12.8 Hz), 1.99 (1H, ddd, J = 4.8, 8.0, 12.8 Hz), 2.01 (3H, s), 2.08 (1H, dd, J = 8.0, 10.0 Hz), 2.12-2.22 (1H, m), 2.39 (3H, s), 2.76-2.83 (2H, m), 2.85-2.92 (2H, m), 2.98 (1H, dd, J = 4.7, 10.7 Hz), 3.23 (1H, dd, J = 5.6, 8.0 Hz), 3.58 (1H, dd, J = 3.1, 10.2 Hz), 3.74 (1H, d, J = 2.6 Hz), 3.81 (1H, dq, J = 2.4, 7.1 Hz), 4.10 (1H, dd, J = 5.6, 10.2 Hz), 4.34 (1H, d, J = 10.5 Hz), 4.39 (1H, dd, J = 2.4, 9.8 Hz), 5.27 (1H, d, J = 5.6 Hz), 7.20 (2H, d, J = 8.3 Hz), 7.38 (2H, d, J = 8.2 Hz). | CD$_3$OD (400 MHz) | MS (FAB) m/z 582 [M + H]$^+$ |
| 12 | 7-Deoxy-7-(4-(2-dimethylaminoethyl)-2-nitrophenylthio)-7-epilincomycin | 0.90-0.95 (3H, m), 1.30-1.40 (7H, m), 1.80-2.20 (3H, m), 1.81 (3H, s), 2.31 (6H, s), 2.41 (3H, s), 2.60 (2H, m), 2.88 (2H, m), 2.99 (1H, m), 3.27 (1H, m), 3.56 (1H, m), 3.60 (1H, m), 3.78 (1H, m), 4.03 (1H, m), 4.08 (1H, dd, J = 5.6, 10.2 Hz), 4.35 (1H, m), 4.55 (1H, m), 5.21 (1H, d, J = 5.6 Hz), 7.53 (1H, m), 7.61 (1H, m), 7.93 (1H, m). | CD$_3$OD (400 MHz) | MS (FAB) m/z 615 [M + H]$^+$ |
| 13 | 7-Deoxy-7-epi-7-(4-(4-methylpiperazin-1-ylmethyl)phenylthio)-lincomycin | 0.88-0.97 (3H, m), 1.28 (3H, d, J = 6.9 Hz), 1.30-1.39 (4H, m), 1.85 (1H, dt, J = 10.2, 12.6 Hz), 1.93-2.23 (3H, m), 1.98 (3H, s), 2.28 (3H, s), 2.36-2.62 (8H, m), 2.40 (3H, s), 2.99 (1H, dd, J = 4.8, 10.5 Hz), 3.25 (1H, dd, J = 5.1, 7.8 Hz), 3.51 (2H, s), 3.57 (1H, dd, J = 3.3, 10.2 Hz), 3.74 (1H, d, J = 3.3 Hz), 3.85 (1H, dq, J = 2.4, 6.9 Hz), 4.10 (1H, dd, J = 5.7, 10.2 Hz), 4.32 (1H, d, J = 9.9 Hz), 4.40 (1H, dd, J = 2.4, 9.9 Hz), 5.26 (1H, d, J = 5.4 Hz), 7.29 (2H, d, J = 8.4 Hz), 7.39 (2H, d, J = 8.1 Hz). | CD$_3$OD (300 MHz) | MS (FAB) m/z 611 [M + H]$^+$ |

TABLE 3

| Compound No. | Compound name | NMR data δ (ppm) from TMS | Solvent/Hz | Mb |
|---|---|---|---|---|
| 14 | 7-Deoxy-7-epi-7-(4-(piperidin-1-ylmethyl)phenylthio)-lincomycin | 0.90-0.96 (3H, m), 1.29 (3H, d, J = 6.9 Hz), 1.30-1.39 (4H, m), 1.42-1.50 (2H, m), 1.54-1.64 (4H, m), 1.85 (1H, dt, J = 10.5, 12.6 Hz), 1.97 (3H, s), 1.98-2.22 (3H, m), 2.40 (3H, s), 2.40-2.46 (4H, m), 2.99 (1H, dd, J = 4.5, 10.5 Hz), 3.25 (1H, dd, J = 5.1, 7.8 Hz), 3.49 (2H, s), 3.57 (1H, dd, J = 3.3, 10.2 Hz), 3.74 (1H, d, J = 3.3 Hz), 3.86 (1H, dq, J = 2.4, 6.9 Hz), 4.10 (1H, dd, J = 5.4, 10.2 Hz), 4.33 (1H, d, J = 9.9 Hz), 4.41 (1H, dd, J = 2.7, 9.6 Hz), 5.26 (1H, d, J = 5.4 Hz), 7.29 (2H, d, J = 8.4 Hz), 7.39 (2H, d, J = 8.1 Hz). | CD$_3$OD (300 MHz) | MS (FAB) m/z 596 [M + H]$^+$ |
| 15 | 7-Deoxy-7-epi-7-(4-(2-(ethylmethylamino)-ethyl)phenylthio)-lincomycin | 0.90-0.95 (3H, m), 1.11 (3H, t, J = 7.2 Hz), 1.26 (3H, d, J = 7.2 Hz), 1.30-1.38 (4H, m), 1.84 (1H, dt, J = 10.2, 12.6 Hz), 1.94-2.11 (2H, m), 2.01 (3H, s), 2.10-2.21 (1H, m), 2.33 (3H, s), 2.39 (3H, s), 2.56 (2H, q, J = 7.2 Hz), 2.60-2.66 (2H, m), 2.76-2.82 (2H, m), 2.98 (1H, dd, J = 4.8, 10.5 Hz), 3.23 (1H, dd, J = 4.8, 8.1 Hz), 3.58 (1H, dd, J = 3.3, 10.2 Hz), 3.73 (1H, d, J = 3.0 Hz), 3.81 (1H, dq, J = 2.4, 6.9 Hz), 4.10 (1H, dd, J = 5.4, 10.2 Hz), 4.33 (1H, d, J = 9.9 Hz), 4.39 (1H, dd, J = 2.4, 9.9 Hz), 5.27 (1H, d, J = 5.7 Hz), 7.19 (2H, d, J = 8.1 Hz), 7.37 (2H, d, J = 8.1 Hz). | CD$_3$OD (300 MHz) | MS (FAB) m/z 584 [M + H]$^+$ |
| 16 | 7-Deoxy-7-epi-7-(4-(pyrrolidin-1-ylmethyl)phenylthio)-lincomycin | 0.88-0.96 (3H, m), 1.28 (3H, d, J = 6.9 Hz), 1.30-1.38 (4H, m), 1.76-1.84 (4H, m), 1.79-2.23 (4H, m), 1.98 (3H, s), 2.40 (3H, s), 2.52-2.58 (4H, m), 2.99 (1H, dd, J = 4.8, 10.5 Hz), 3.25 (1H, dd, J = 5.4, 7.8 Hz), 3.58 (1H, dd, J = 3.3, 10.2 Hz), 3.63 (2H, s), 3.74 (1H, d, J = 3.3 Hz), 3.86 (1H, dq, J = 2.4. 6.9 Hz), 4.10 (1H, dd, J = 5.4, 10.2 Hz), 4.33 (1H, d, J = 9.9 Hz), 4.42 (1H, dd, J = 2.4, 9.9 Hz), 5.27 (1H, d, J = 5.7 Hz), 7.31 (2H, d, J = 8.4 Hz), 7.39 (2H, d, J = 8.1 Hz). | CD$_3$OD (300 MHz) | MS (FAB) m/z 582 [M + H]$^+$ |
| 17 | 7-Deoxy-7-epi-7-(4-(2-((2-hydroxyethyl)(methyl)-amino)ethyl)-phenylthio)lincomycin | 0.89-0.97 (3H, m), 1.26 (3H, d, J = 6.8 Hz), 1.31-1.38 (4H, m), 1.85 (1H, dt, J = 10.8, 12.8 Hz), 1.99 (1H, ddd, J = 4.8, 8.0, 12.8 Hz), 2.01 (3H, s), 2.05-2.11 (1H, m), 2.12-2.21 (1H, m), 2.39 (6H, s), 2.65 (2H, t, J = 6.1 Hz), 2.68-2.73 (2H, m), 2.78-2.84 (2H, m), 2.98 (1H, dd, J = 4.7, 10.5 Hz), 3.24 (1H, dd, J = 5.6, 8.7 Hz), 3.58 (1H, dd, J = 3.1, 10.0 Hz), 3.67 (2H, t, J = 6.1 Hz), 3.73 (1H, d, J = 3.4 Hz), 3.81(1H, dq, J = 2.5, 6.8 Hz), 4.10 (1H, dd, J = 5.6, 10.2 Hz), 4.33 (1H, d, J = 10.2 Hz), 4.38 (1H, dd, J = 2.4, 9.7 Hz), 5.26 (1H, d, J = 5.6 Hz), 7.20 (2H, d, J = 8.3 Hz), 7.37 (2H, d, J = 8.3 Hz). | CD$_3$OD (400 MHz) | MS (FAB) m/z 600 [M + H]$^+$ |
| 18 | 7-Deoxy-7-(6-(2-(dimethylamino)ethyl)-pyridin-3-ylthio)-7-epilincomycin | 0.90-0.95 (3H, m), 1.22-1.35 (7H, m), 1.81-1.90 (1H, m), 1.98-2.30 (6H, m), 2.41 (3H, s), 2.61 (6H, s), 3.01 (1H, dd, J = 10.6, 4.7 Hz), 3.10 (4H, s), 3.24-3.28 (1H, m), 3.57 (1H, dd, J = 10.2, 3.2 Hz), 3.77-3.79 (1H, m), 3.85 (1H, qd, J = 6.8, 2.9 Hz), 4.10 (1H, dd, J = 10.2, 5.6 Hz), 4.35 (1H, d, J = 9.3 Hz), 4.45 (1H, dd, J = 9.5, 2.9 Hz), 5.25 (1H, d, J = 5.6 Hz), 7.34 (1H, d, J = 8.2 Hz), 7.86 (1H, dd, J = 8.2, 2.5 Hz), 8.52 (1H, d, J = 2.5 Hz). | CD$_3$OD (400 MHz) | MS (FAB) m/z 571 [M + H]$^+$ |
| 19 | 7-Deoxy-7-((E)-4-(1-(dimethylamino)-3-oxoprop-1-ene-2-yl)phenylthio)-7-epilincomycin | 0.89-0.96 (3H, m), 1.30 (3H, d, J = 6.8 Hz), 1.31-1.39 (4H, m), 1.86 (1H, dt, J = 10.5, 12.9 Hz), 1.95-2.05 (1H, m), 2.01 (3H, s), 2.10 (1H, dd, J = 8.5, 10.3 Hz), 2.10-2.25 (1H, m), 2.43 (3H, s), 2.47-3.34 (6H, br), 3.02 (1H, dd, J = 4.9, 10.5 Hz), 3.27 (1H, dd, J = 5.8, 8.2 Hz), 3.59 (1H, dd, J = 3.4, 10.0 Hz), 3.75 (1H, d, J = 3.2 Hz), 3.89 (1H, dq, J = 2.7, 6.8 Hz), 4.11 (1H, dd, J = 5.6, 10.2 Hz), 4.35 (1H, d, J = | CD$_3$OD (400 MHz) | MS (FAB) m/z 596 [M + H]$^+$ |

TABLE 3-continued

| Compound No. | Compound name | NMR data δ (ppm) from TMS | Solvent/Hz | Mb |
|---|---|---|---|---|
| | | 9.8 Hz), 4.44 (1H, dd, J = 2.7, 9.7 Hz), 5.28 (1H, d, J = 5.6 Hz), 7.12 (2H, d, J = 8.3 Hz), 7.16-7.21 (1H, br), 7.39 (2H, d, J = 8.2 Hz), 8.87 (1H, s). | | |
| 20 | 7-Deoxy-7-(4-(2-dimethylaminoethyl-aminomethyl)phenyl-thio)-7-epilincomycin | 0.90-0.95 (3H, m), 1.26 (3H, d, J = 6.6 Hz), 1.30-1.38 (4H, m), 1.85 (1H, dt, J = 10.2, 12.3 Hz), 1.94-2.21 (3H, m), 2.00 (3H, s), 2.26 (6H, s), 2.40 (3H, s), 2.52 (2H, t, J = 6.6 Hz), 2.72 (2H, t, J = 6.6 Hz), 2.99 (1H, dd, J = 4.8, 10.2 Hz), 3.24 (1H, dd, J = 5.1, 7.8 Hz), 3.58 (1H, dd, J = 3.3, 10.2 Hz), 3.74 (1H, d, J = 3.3 Hz), 3.77 (2H, s), 3.86 (1H, dq, J = 2.7, 6.9 Hz), 4.11 (1H, dd, J = 5.4, 10.2 Hz), 4.33 (1H, d, J = 9.6 Hz), 4.42 (1H, dd, J = 2.7, 9.9 Hz), 5.28 (1H, d, J = 5.4 Hz), 7.32 (2H, d, J = 8.1 Hz), 7.40 (2H, d, J = 8.1 Hz). | $CD_3OD$ (300 MHz) | MS (FAB) m/z 599 $[M + H]^+$ |
| 21 | 7-Deoxy-7-epi-7-(4-((3-pyrrolin-1-yl)methyl)phenylthio)-lincomycin | 0.86 (3H, m), 1.29 (3H, d, J = 6.9 Hz), 1.30-1.40 (4H, m), 1.85 (1H, dt, J = 10.2, 12.3 Hz), 1.93-2.24 (3H, m), 1.97 (3H, s), 2.41 (3H, s), 3.00 (1H, dd, J = 4.8, 10.5 Hz), 3.25 (1H, dd, J = 5.1, 7.8 Hz), 3.48 (4H, s), 3.59 (1H, dd, J = 3.3, 10.2 Hz), 3.75 (1H, d, J = 3.3 Hz), 3.81 (2H, s), 3.86 (1H, dq, J = 2.4, 6.9 Hz), 4.11 (1H, dd, J = 5.7, 10.2 Hz), 4.34 (1H, d, J = 9.6 Hz), 4.42 (1H, dd, J = 2.4, 9.6 Hz), 5.27 (1H, d, J = 5.4 Hz), 5.81 (2H, s), 7.33 (2H, d, J = 8.1 Hz), 7.40 (2H, d, J = 8.4 Hz). | $CD_3OD$ (300 MHz) | MS (FAB) m/z 580 $[M + H]^+$ |
| 22 | 7-Deoxy-7-(4-(2-dimethylaminoethyl)-3-nitrophenylthio)-7-epilincomycin | 0.90-0.95 (3H, m), 1.30-1.40 (7H, m), 1.80-2.20 (4H, m), 1.94 (3H, s), 2.33 (6H, s), 2.40 (3H, s), 2.62 (2H, m), 2.95-3.05 (3H, m), 3.24 (1H, m), 3.56 (1H, m), 3.78 (1H, m), 3.93 (1H, m), 4.09 (1H, dd, J = 5.6, 10.2 Hz), 4.34 (1H, m), 4.48 (1H, m), 5.25 (1H, d, J = 5.6 Hz), 7.44 (1H, m), 7.65 (1H, m), 7.92 (1H, m). | $CD_3OD$ (400 MHz) | MS (FAB) m/z 615 $[M + H]^+$ |
| 23 | 7-(4-(Azetidin-1-yl methyl)phenylthio)-7-deoxy-7-epilincomycin | 0.89-0.97 (3H, m), 1.28 (3H, d, J = 6.9 Hz), 1.30-1.38 (4H, m), 1.85 (1H, dt, J = 10.2, 12.9 Hz), 1.96 (3H, s), 1.96-2.22 (3H, m), 2.12 (2H, t, J = 7.2 Hz), 2.40 (3H, s), 2.99 (1H, dd, J = 4.8, 10.2 Hz), 3.24 (1H, dd, J = 5.4, 8.1 Hz), 3.31 (4H, t, J = 7.2 Hz), 3.58 (1H, dd, J = 2.7, 10.2 Hz), 3.61 (2H, s), 3.74 (1H, d, J = 3.0 Hz), 3.85 (1H, dq, J = 2.4, 6.9 Hz), 4.10 (1H, dd, J = 5.4, 10.2 Hz), 4.33 (1H, d, J = 9.9 Hz), 4.42 (1H, dd, J = 2.4, 9.6 Hz), 5.26 (1H, d, J = 5.4 Hz), 7.25 (2H, d, J = 8.1 Hz), 7.38 (2H, d, J = 8.1 Hz). | $CD_3OD$ (300 MHz) | MS (FAB) m/z 568 $[M + H]^+$ |
| 24 | 7-Deoxy-7-(3-dimethylamino-4-(2-dimethylaminoethyl)-phenylthio)-7-epilincomycin | 0.90-1.00 (3H, m), 1.29 (3H, d, J = 6.8 Hz), 1.30-1.40 (4H, m), 1.80-2.25 (4H, m), 1.90 (3H, s), 2.40 (6H, s), 2.41 (3H, s), 2.60-2.75 (2H, m), 2.67 (6H, m), 2.88 (2H, m), 2.99 (1H, m), 3.24 (1H, m), 3.57 (1H, m), 3.74 (1H, m), 3.81 (1H, m), 4.10 (1H, dd, J = 5.6, 10.3 Hz), 4.32 (1H, m), 4.39 (1H, m), 5.26 (1H, d, J = 5.6 Hz), 7.05-7.20 (3H, m). | $CD_3OD$ (400 MHz) | MS (FAB) m/z 613 $[M + H]^+$ |

TABLE 4

| Compound No. | Compound name | NMR data δ (ppm) from TMS | Solvent/Hz | MS |
|---|---|---|---|---|
| 28 | 7-Deoxy-7-(4-(((2-(dimethylamino)ethyl)-(methyl)amino)methyl)-phenylthio)-7-epilincomycin | 0.90-0.95 (3H, m), 1.27 (3H, d, J = 6.9 Hz), 1.31-1.38 (4H, m), 1.85 (1H, dt, J = 9.9, 12.6 Hz), 1.94-2.24 (7H, m), 1.99 (3H, s), 2.22 (6H, s), 2.41 (3H, s), 2.50 (3H, s), 2.99 (1H, dd, J = 4.8, 10.5 Hz), 3.25 (1H, dd, J = 5.4, 8.1 Hz), 3.51 (2H, s), 3.58 (1H, dd, J = 3.0, 10.2 Hz), 3.74 (1H, d, J = 3.0 Hz), 3.86 (1H, dq, J = 2.4, 6.9 Hz), 4.10 (1H, dd, J = 5.7, 10.2 Hz), 4.33 (1H, d, J = 9.9 Hz), 4.41 (1H, dd, J = 2.4, 9.9 Hz), 5.27 (1H, d, J = 5.7 Hz), 7.30 (2H, d, J = 8.4 Hz), 7.39 (2H, d, J = 8.4 Hz). | CD$_3$OD (300 MHz) | MS (FAB) m/z 613 [M + H]$^+$ |

TABLE 5

| Compound No. | Compound name | NMR data δ (ppm) from TMS | Solvent/Hz | MS |
|---|---|---|---|---|
| 30 | 7-Deoxy-7-epi-7-(4-(2-(methylamino)-ethyl)phenylthio)-lincomycin | 0.89-0.98 (3H, m), 1.27 (3H, d, J = 7.1 Hz), 1.30-1.40 (4H, m), 2.01 (3H, s), 1.80-1.90 (1H, m), 1.95-2.24 (6H, m), 2.38 (3H, s), 2.39 (3H, s), 2.74-2.81 (4H, m), 2.98 (1H, dd, J = 4.6, 10.7 Hz), 3.23 (1H, dd, J = 5.4, 7.8 Hz), 3.58 (1H, dd, J = 3.2, 10.2 Hz), 3.74 (1H, d, J = 3.2 Hz), 3.82 (1H, dq, J = 2.4, 7.1 Hz), 4.10 (1H, dd, J = 5.6, 10.2 Hz), 4.33 (1H, d, J = 10.2 Hz), 4.38 (1H, dd, J = 2.4, 10.2 Hz), 5.27 (1H, d, J = 5.6 Hz), 7.19 (2H, d, J = 8.3 Hz), 7.38 (2H, d, J = 8.3 Hz). | CD$_3$OD (400 MHz) | MS (FAB) 556 [M + H]$^+$ |

TABLE 6

| Compound No. | Compound name | NMR data δ (ppm) from TMS | Solvent/Hz | MS |
|---|---|---|---|---|
| 34 | 7-Deoxy-7-(3-(3-(dimethylamino)-propyl)phenylthio)-7-epilincomycin | 0.93 (3H, brs), 1.28-1.35 (7H, m), 1.76-1.88 (3H, m), 1.96 (3H, s), 1.96-2.23 (3H, m), 2.27 (6H, s), 2.35-2.40 (5H, m), 2.62 (2H, t, J = 7.5 Hz), 2.98 (1H, dd, J = 10.6, 4.8 Hz), 3.22-3.26 (1H, m), 3.57 (1H, dd, J = 10.3, 3.2 Hz), 3.74 (1H, d, J = 3.0 Hz), 3.86 (1H, qd, J = 7.0, 2.6 Hz), 4.10 (1H, dd, J = 10.2, 5.6 Hz), 4.34 (1H, d, J = 9.7 Hz), 4.41 (1H, dd, J = 9.7, 2.6 Hz), 5.26 (1H, d, J = 5.6 Hz), 7.09-7.11 (1H, m), 7.21-7.26 (3H, m). | CD$_3$OD (400 MHz) | MS (FAB) m/z 584 [M + H]$^+$ |

TABLE 7

| Compound No. | Compound name | NMR data δ (ppm) from TMS | Solvent/Hz | MS |
|---|---|---|---|---|
| 37 | 7-(3-Amino-4-(2-dimethylaminoethyl)phenylthio)-7-deoxy-7-epilincomycin | 0.90-0.95 (3H, m), 1.29 (3H, d, J = 7.1 Hz), 1.25-1.40 (4H, m), 1.80-2.25 (4H, m), 2.04 (3H, s), 2.35-2.45 (9H, m), 2.55 (2H, m), 2.67 (2H, m), 2.96 (1H, m), 3.22 (1H, m), 3.58 (1H, m), 3.70-3.80 (2H, m), 4.09 (1H, dd, J = 5.6, 10.2 Hz), 4.35 (2H, m), 5.26 (1H, d, J = 5.6 Hz), 6.70 (1H, m), 6.83 (1H, m), 6.93 (1H, m). | CD$_3$OD (400 MHz) | MS (FAB) m/z 585 [M + H]$^+$ |

TABLE 8

| Compound | | NMR data | | |
|---|---|---|---|---|
| No. | Compound name | δ (ppm) from TMS | Solvent/Hz | MS |
| 42 | 7-Deoxy-7-(5-(3-(dimethylamino)-propyl)-1,3,4-thiadiazol-2-ylthio)-7-epilincomycin | 0.87-0.97 (3H, m), 1.26-1.39 (4H, m), 1.51 (3H, d, J = 7.1 Hz), 1.77-1.89 (1H, m), 1.90-2.09 (7H, m), 2.12-2.27 (7H, m), 2.33-2.45 (5H, m), 2.98 (1H, dd, J = 5.1, 10.5 Hz), 3.10 (2H, t, J = 7.6 Hz), 3.23 (1H, dd, J = 6.3, 8.5 Hz), 3.56 (1H, dd, J = 3.4, 10.2 Hz), 3.77-3.82 (1H, m), 4.10 (1H, dd, J = 5.6, 10.2 Hz), 4.30-4.42 (2H, m), 4.56 (1H, dd, J = 3.2, 9.7 Hz), 5.25 (1H, d, J = 5.6 Hz). | $CD_3OD$ (400 MHz) | MS (FAB) m/z 592 $[M + H]^+$ |

TABLE 9

| Compound | | NMR data | | |
|---|---|---|---|---|
| No. | Compound name | δ (ppm) from TMS | Solvent/Hz | MS |
| 47 | Methyl 6-N-((2S,4R)-(4-cyclopropylmethyl)-piperidine-2-carbonyl)-7-deoxy-7-(6-(2-(dimethylamino)ethyl)-pyridin-3-ylthio)-7-epi-1-thio-α-lincosamide | 0.02-0.04 (2H, m), 0.43-0.48 (2H, m), 0.68-0.78 (1H, m), 1.08-1.25 (3H, m), 1.25-1.36 (4H, m), 1.70 (1H, brs), 1.81 (1H, d, J = 12.8 Hz), 2.00 (3H, s), 2.07-2.15 (1H, m), 2.35 (6H, s), 2.65-2.80 (3H, m), 2.93-3.00 (2H, m), 3.19 (1H, d, J = 12.8 Hz), 3.36-3.42 (1H, m), 3.55 (1H, dd, J = 10.2, 3.2 Hz), 3.79 (1H, qd, J = 7.0, 2.2 Hz), 3.84-3.88 (1H, m), 4.08 (1H, dd, J = 10.2, 5.6 Hz), 4.40 (1H, d, J = 10.0 Hz), 4.57 (1H, dd, J = 10.0, 2.4 Hz), 5.25 (1H, d, J = 5.6 Hz), 7.31 (1H, d, J = 8.3 Hz), 7.82 (2H, d, J = 8.3, 2.4 Hz), 8.45-8.48 (1H, m). | $CD_3OD$ (400 MHz) | MS (FAB) m/z 583 $[M + H]^+$ |
| 48 | Methyl 6-N-(((2S,4R)-4-cyclopropylmethyl)-piperidine-2-carbonyl)-7-deoxy-7-epi-7-(4-(2-Ethylmethylamino-ethyl)phenylthio)-1-thio-α-lincosamide | −0.02-0.04 (2H, m), 0.40-0.47 (2H, m), 0.64-0.77 (1H, m), 1.03-1.26 (4H, m), 1.09 (3H, t, J = 6.9 Hz), 1.24 (3H, d, J = 6.9 Hz), 1.59-1.74 (1H, m), 1.74-1.82 (1H, m), 1.95 (3H, s), 2.03-2.12 (1H, m), 2.33 (3H, s), 2.56 (2H, q, J = 6.9 Hz), 2.60-2.80 (5H, m), 3.12-3.20 (1H, m), 3.36 (1H, dd, J = 2.7, 12.0 Hz), 3.56 (1H, dd, J = 3.0, 10.5 Hz), 3.74 (1H, dq, J = 3.0, 10.5 Hz), 3.85 (1H, d, J = 2.1 Hz), 4.07 (1H, dd, J = 5.7, 10.2 Hz), 4.39 (1H, d, J = 10.2 Hz), 4.52 (1H, dd, J = 2.4, 10.2 Hz), 5.25 (1H, d, J = 5.4 Hz), 7.15 (2H, d, J = 7.8 Hz), 7.32 (2H, d, J = 8.4 Hz). | $CD_3OD$ (300 MHz) | MS (FAB) m/z 596 $[M + H]^+$ |
| 49 | Methyl 7-(4-(2-(cyclopropyl(methyl)-amino)ethyl)phenyl-thio)-6-N-((2S,4R)-4-(cyclopropylmethyl)-piperidine-2-carbonyl)-7-deoxy-7-epi-1-thio-α-lincosamide | −0.03-0.07 (2H, m), 0.37-0.58 (6H, m), 0.67-0.79 (1H, m), 1.01-1.32 (8H, m), 1.56-1.73 (3H, m), 1.98 (3H, s), 2.02-2.10 (1H, m), 2.41 (3H, s), 2.65 (1H, dt, J = 2.4, 12.7 Hz), 2.70-2.86 (4H, m), 3.10-3.20 (1H, m), 3.58 (1H, dd, J = 3.2, 10.2 Hz), 3.76 (1H, dq, J = 1.9, 7.1 Hz), 3.86 (1H, d, J = 3.2 Hz), 4.08 (1H, dd, J = 5.6, 10.2 Hz), 4.42 (1H, d, J = 10.0 Hz), 4.52 (1H, dd, J = 1.9, 10.0 Hz), 5.26 (1H, d, J = 5.6 Hz), 7.17 (2H, d, J = 8.0 Hz), 8.34 (2H, d, J = 8.0 Hz). | $CD_3OD$ (400 MHz) | MS (FAB) m/z 608 $[M + H]^+$ |
| 50 | Methyl 6-N-(((2S,4R)-4-cyclopropylmethyl)-piperidine-2-carbonyl)-7-deoxy-7-epi-7-(4-(pyrrolidin-1-ylmethyl)phenylthio)-1-thio-α-lincosamide | −0.03-0.02 (2H, m), 0.40-0.45 (2H, m), 0.65-0.75 (1H, m), 1.02-1.23 (4H, m), 1.25 (3H, d, J = 6.8 Hz), 1.60-1.84 (6H, m), 1.91 (3H, s), 2.04-2.11 (1H, m), 2.51-2.58 (4H, m), 2.65 (1H, dt, J = 2.7, 12.9 Hz), 3.12-3.18 (1H, m), 3.34 (1H, dd, J = 2.7, 11.7 Hz), 3.54 (1H, dd, J = 3.4, 10.3 Hz), 3.60 (2H, s), 3.78 (1H, dq, J = 2.4, 6.8 Hz), 3.84 (1H, d, J = 3.2 Hz), 4.06 (1H, dd, J = 5.6, 10.2 Hz), 4.39 (1H, d, J = 10.0 Hz), 4.53 (1H, dd, J = 2.4, 10.0 Hz), 5.23 (1H, d, J = 5.6 Hz), 7.26 (2H, d, J = 8.2 Hz), 7.34 (2H, d, J = 8.3 Hz). | $CD_3OD$ (400 MHz) | MS (FAB) m/z 594 $[M + H]^+$ |

TABLE 9-continued

| Compound No. | Compound name | NMR data δ (ppm) from TMS | Solvent/Hz | MS |
|---|---|---|---|---|
| 52 | Methyl 6-N-((2S,4R)-(4-cyclopropylmethyl-1-methyl)piperidine-2-carbonyl)-7-deoxy-7-(6-(2-(dimethylamino)ethyl)-pyridin-3-ylthio)-7-epi-1-thio-α-lincosamide | 0.00-0.02 (2H, m), 0.42-0.45 (2H, m), 0.65-0.75 (1H, m), 1.17 (2H, dd, J = 6.8, 2.7 Hz), 1.28-1.38 (5H, m), 1.44-1.56 (1H, m), 1.80 (1H, brd, J = 12.9 Hz), 1.96 (1H, brd, J = 12.9 Hz), 2.01 (3H, s), 2.10-2.20 (1H, m), 2.26 (3H, s), 2.35 (6H, s), 2.62 (1H, dd, J = 11.5, 2.7 Hz), 2.74-2.78 (2H, m), 2.95-2.99 (3H, m), 3.57 (1H, dd, J = 10.2, 3.1 Hz), 3.79-3.81 (2H, m), 4.10 (1H, dd, J = 10.2, 5.6 Hz), 4.39 (1H, d, J = 10.5 Hz), 4.58 (1H, dd, J = 9.8, 2.7 Hz), 5.26 (1H, d, J = 5.6 Hz), 7.31 (1H, d, J = 8.3 Hz), 7.83 (1H, dd, J = 8.3, 2.2 Hz), 8.48 (1H, d, J = 2.2 Hz). | CD$_3$OD (400 MHz) | MS (FAB) m/z 597 [M + H]$^+$ |
| 53 | Methyl 6-N-(((2S,4R)-4-cyclopropylmethyl)-piperidine-2-carbonyl)-7-deoxy-7-epi-7-(4-(2-ethylmethylamino-ethyl)phenylthio)-1-methyl-1-thio-α-lincosamide | −0.02-0.04 (2H, m), 0.40-0.47 (2H, m), 0.64-0.76 (1H, m), 1.11 (3H, t, J = 7.2 Hz), 1.17 (2H, t, J = 6.6 Hz), 1.20-1.38 (2H, m), 1.27 (3H, d, J = 6.9 Hz), 1.41-1.56 (1H, m), 1.75-1.84 (1H, m), 1.92-2.02 (1H, m), 1.99 (3H, s), 2.07-2.18 (1H, m), 2.25 (3H, s), 2.34 (3H, s), 2.58 (2H, q, J = 7.2 Hz), 2.61-2.68 (3H, m), 2.76-2.82 (2H, m), 2.92-2.99 (1H, m), 3.58 (1H, dd, J = 3.0, 10.2 Hz), 3.79 (1H, dq, J = 2.7, 6.9 Hz), 3.82 (1H, d, J = 3.3 Hz), 4.10 (1H, dd, J = 5.4, 10.2 Hz), 4.39 (1H, d, J = 9.9 Hz), 4.54 (1H, dd, J = 3.0, 9.9 Hz), 5.27 (1H, d, J = 5.4 Hz), 7.18 (2H, d, J = 8.4 Hz), 7.36 (2H, d, J = 8.4 Hz). | CD$_3$OD (300 MHz) | MS (FAB) m/z 610 [M + H]$^+$ |
| 54 | Methyl 7-(4-(2-(cyclopropyl(methyl)-amino)ethyl)phenyl-thio)-6-N-((2S,4R)-4-(cyclopropylmethyl)-1-methylpiperidine-2-carbonyl)-7-deoxy-7-epi-1-thio-α-lincosamide | −0.03-0.06 (2H, m), 0.38-0.47 (4H, m), 0.49-0.58 (2H, m), 0.65-0.76 (1H, m), 1.12-1.38 (7H, m), 1.41-1.55 (1H, m), 1.72-1.83 (2H, m), 1.92-2.03 (4H, m), 2.07-2.18 (1H, m), 2.25 (3H, s), 2.41 (3H, s), 2.60 (1H, dd, J = 2.9, 11.4 Hz), 2.71-2.84 (4H, m), 2.91-3.00 (1H, m), 3.59 (1H, dd, J = 3.2, 10.2 Hz), 3.73-3.85 (2H, m), 4.10 (1H, dd, J = 5.6, 10.2 Hz), 4.40 (1H, d, J = 10.0 Hz), 4.54 (1H, dd, J = 2.7, 10.0 Hz), 5.27 (1H, d, J = 5.6 Hz), 7.18 (2H, d, J = 8.3 Hz), 8.36 (2H, d, J = 8.3 Hz). | CD$_3$OD (400 MHz) | MS (FAB) m/z 622 [M + H]$^+$ |
| 55 | Methyl 6-N-((2S,4R)-4-cyclopropylmethyl-1-methyl)piperidine-2-carbonyl)-7-deoxy-7-epi-7-(4-(pyrrolidin-1-ylmethyl)phenylthio)-1-thio-α-lincosamide | −0.03-0.02 (2H, m), 0.39-0.45 (2H, m), 0.64-0.74 (1H, m), 1.15 (2H, dt, J = 2.4, 6.6 Hz), 1.24-1.36 (2H, m), 1.29 (3H, d, J = 6.8 Hz), 1.42-1.55 (1H, m), 1.74-1.85 (5H, m), 1.90-1.99 (1H, m), 1.94 (3H, s), 2.07-2.16 (1H, m), 2.24 (3H, s), 2.54-2.63 (5H, m), 2.91-2.99 (1H, m), 3.56 (1H, dd, J = 3.2, 10.2 Hz), 3.64 (2H, s), 3.81 (1H, d, J = 2.9 Hz), 3.83 (1H, dq, J = 2.7, 6.8 Hz), 4.09 (1H, dd, J = 5.6, 10.2 Hz), 4.39 (1H, d, J = 9.7 Hz), 4.55 (1H, dd, J = 2.7, 9.7 Hz), 5.25 (1H, d, J = 5.6 Hz), 7.28 (2H, d, J = 8.1 Hz), 7.36 (2H, d, J = 8.3 Hz). | CD$_3$OD (400 MHz) | MS (FAB) m/z 608 [M + H]$^+$ |

TABLE 10
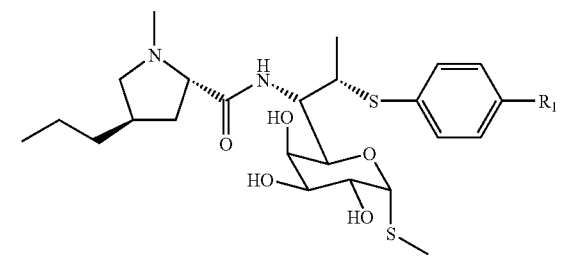
| Compound No. | R₁ |
|---|---|
| 25 | -CH₂CH₂-NH₂ |
| 1 | -CH₂CH₂-N(CH₃)₂ |
| 26 | -C(O)CH₂-NH₂ |
| 2 | -C(O)CH₂-N(CH₃)₂ |
| 3 | -C≡C-CH₂-N(CH₃)₂ |
| 4 | -CH₂-N(CH₃)₂ |
| 33 | -CH₂CH₂CH₂-N(CH₃)₂ |
| 6 | -CH₂CH₂-pyrrolidinyl |
| 7 | -CH₂CH₂-NH-CH₂CH₂-N(CH₃)₂ |
TABLE 10-continued
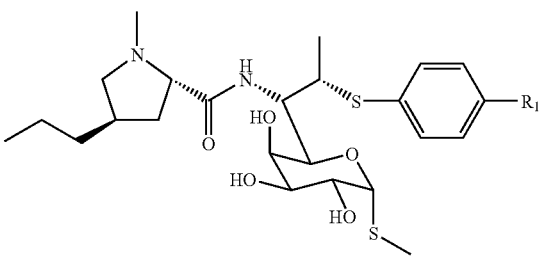
| Compound No. | R₁ |
|---|---|
| 8 | -C(O)NH-CH₂CH₂-N(CH₃)₂ |
| 9 | -CH₂CH₂-N(piperazinyl)-N-CH₃ |
| 32 | -CH₂CH₂-NH-CH₂CH₂-OH |
| 10 | -CH₂CH₂-N(CH₃)-CH₂CH₂-N(CH₃)₂ |
| 11 | -CH₂-NH-cyclopropyl |
| 27 | -CH₂CH₂-N(CH₃)-cyclopropyl |
| 30 | -CH₂CH₂-NH-CH₃ |
| 29 | -CH₂CH₂-NH-CH₂CH₂CH₃ |

TABLE 10-continued
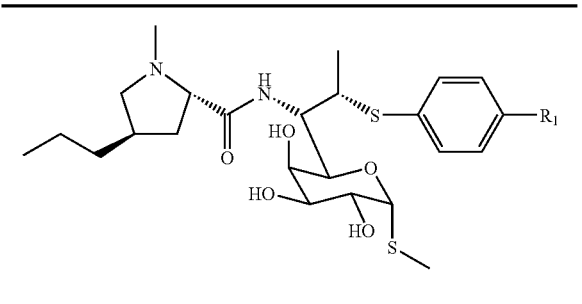
| Compound No. | R₁ |
|---|---|
| 31 | 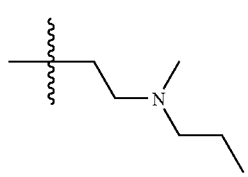 |
| 13 | 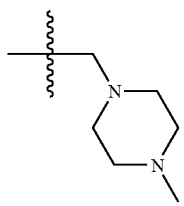 |
| 14 | 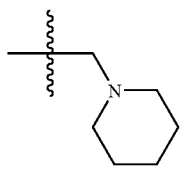 |
| 15 | 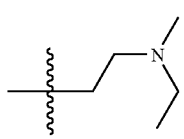 |
| 16 | 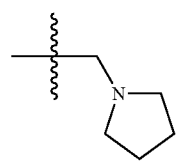 |
| 17 | 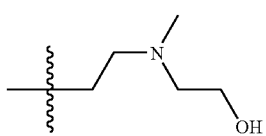 |
| 19 | 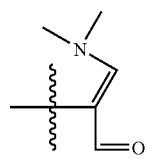 |
TABLE 10-continued
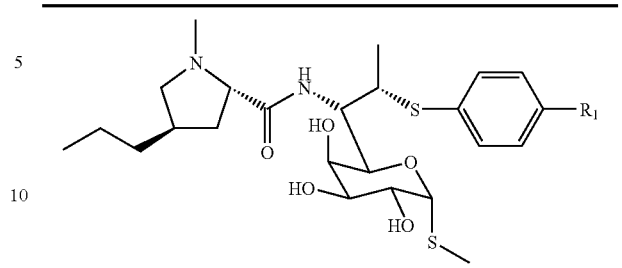
| Compound No. | R₁ |
|---|---|
| 20 | 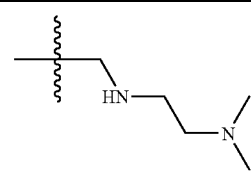 |
| 28 | 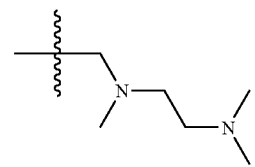 |
| 21 | 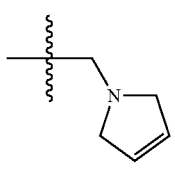 |
| 23 | 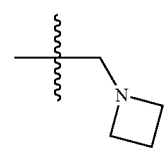 |
TABLE 11
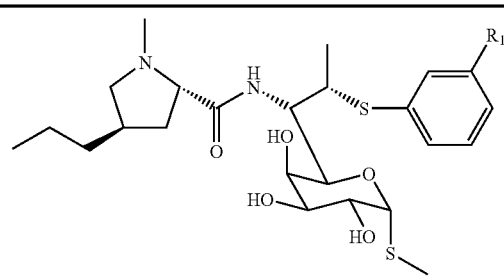
| Compound No. | R₁ |
|---|---|
| 5 | 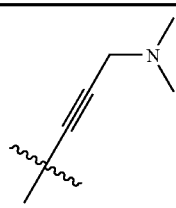 |

TABLE 11-continued
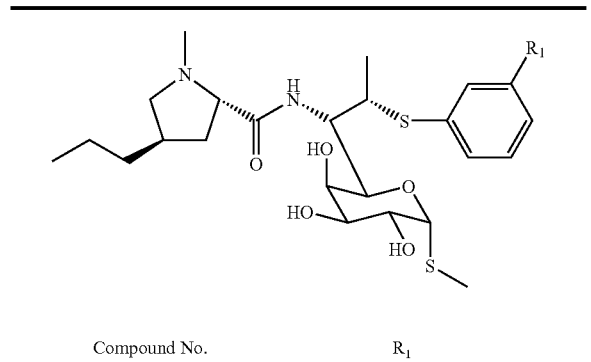
| Compound No. | $R_1$ |
|---|---|
| 35 | 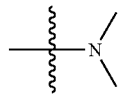 |
| 34 | 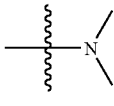 |
TABLE 12
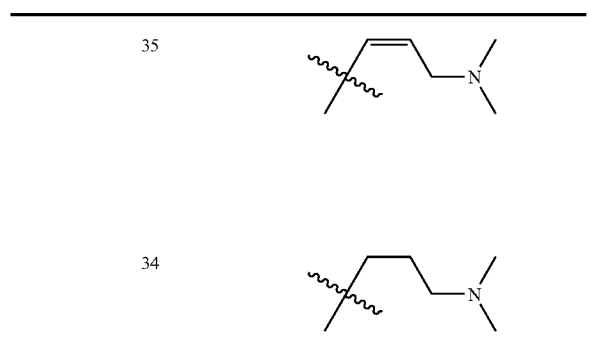
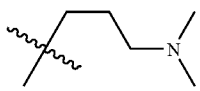
| Compound No. | $R_{1a'}$ | $R_{1b'}$ |
|---|---|---|
| 12 | NO | H |
| 36 | NH | H |
| 38 | 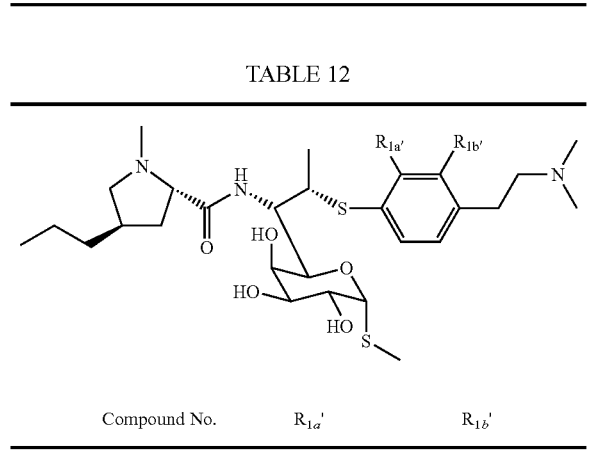 | H |
| 22 | H | NO |
| 37 | H | NH |
| 24 | H | 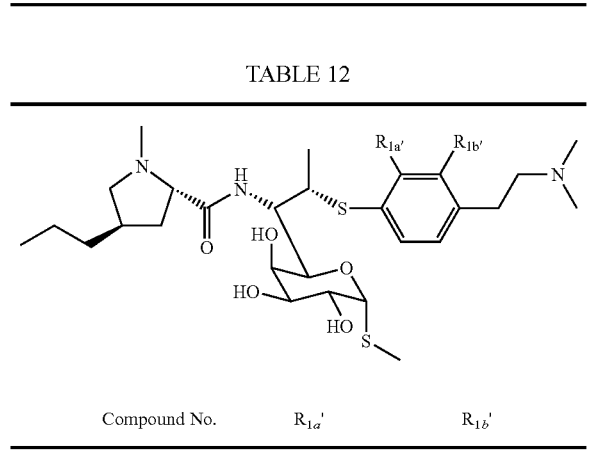 |
TABLE 13
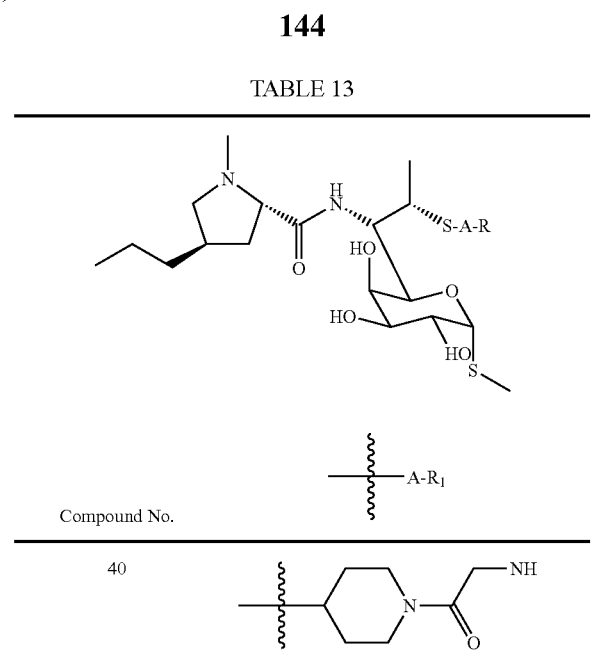
| Compound No. | —A-$R_1$ |
|---|---|
| 40 | 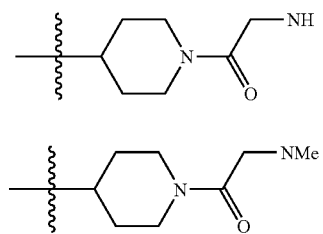 |
| 39 | 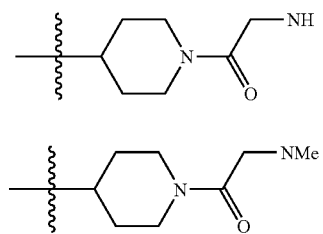 |
| 18 | 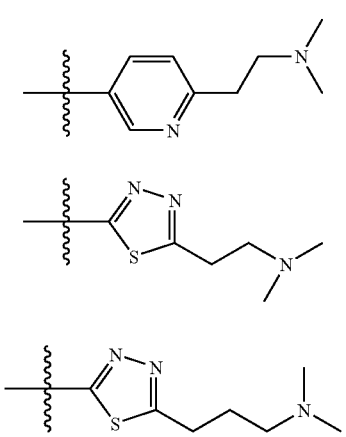 |
| 41 | 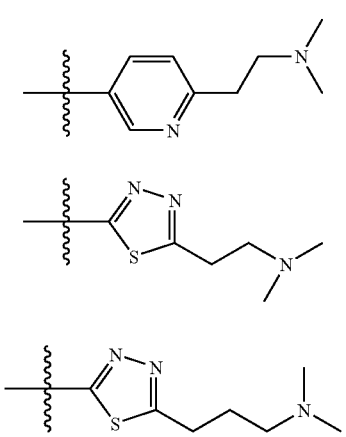 |
| 42 | 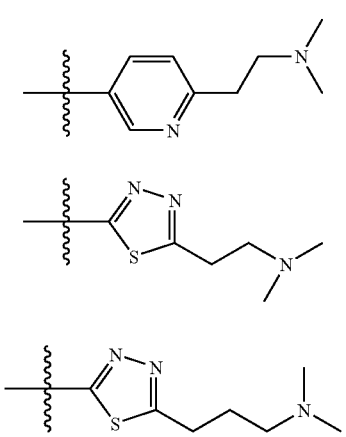 |
TABLE 14
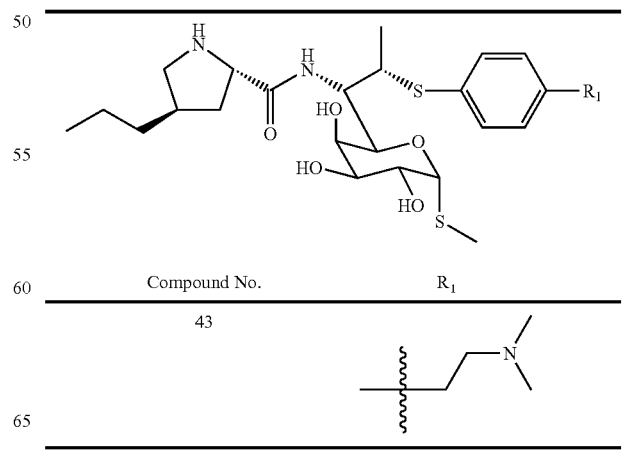
| Compound No. | $R_1$ |
|---|---|
| 43 | 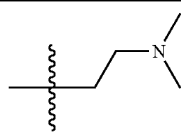 |

TABLE 15
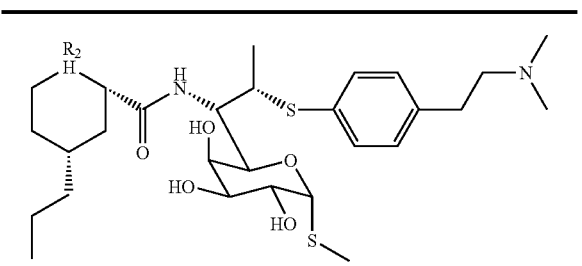
| Compound No. | R₂ |
|---|---|
| 44 | H |
| 45 | Me |
TABLE 16
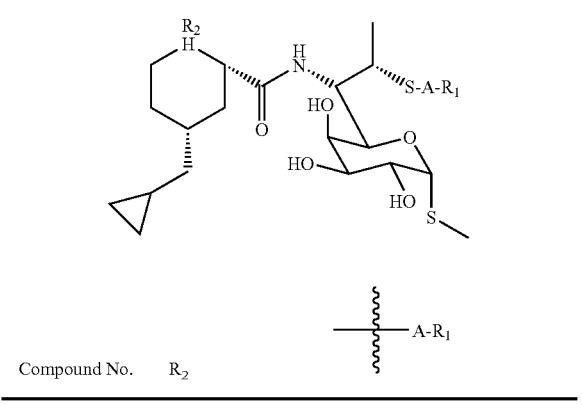
| Compound No. | R₂ | A-R₁ |
|---|---|---|
| 46 | H | 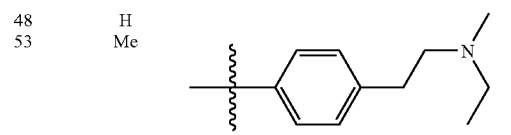 |
| 51 | Me | |
| 48 | H | 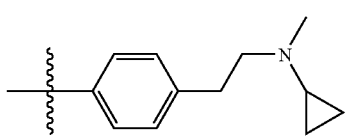 |
| 53 | Me | |
| 49 | H | 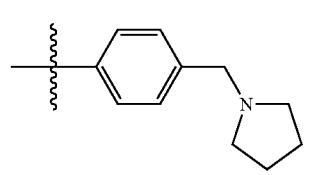 |
| 54 | Me | |
| 50 | H | |
| 55 | Me | |
TABLE 16-continued
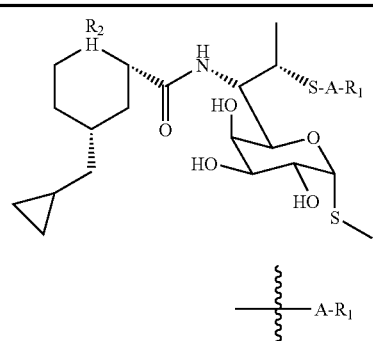
| Compound No. | R₂ | A-R₁ |
|---|---|---|
| 47 | H | |
| 52 | Me | |
TABLE 17
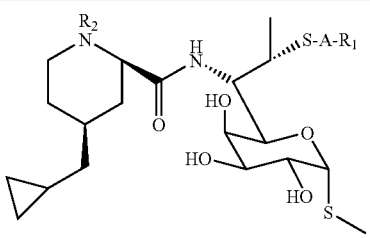
| Compound No. | R₂ | A-R₁ |
|---|---|---|
| 57 | H | |
| 58 | Me | |
TABLE 18
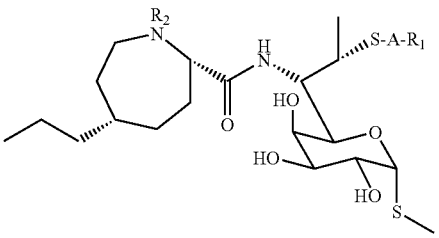
| Compound No. | R₂ | A-R₁ |
|---|---|---|
| 56 | H | 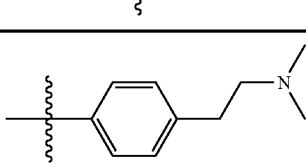 |

TABLE 19

| Compound No. | Compound name | NMR data δ (ppm) from TMS | Solvent/Hz | MS |
|---|---|---|---|---|
| 59 | 7-Deoxy-7-(5-(1-(dimethylamino)ethyl)-pyridin-2-ylthio)-7-epilincomycin | 0.9-0.95 (3H, m), 1.30-1.50 (4H, m), 1.40 (3H, d, J = 6.8 Hz), 1.44 (3H, d, J = 6.8 Hz), 1.79 (3H, s), 1.80-2.30 (4H, m), 2.20 (6H, s), 2.37 (3H, s), 2.90-3.00 (1H, m), 3.20-3.30 (1H, m), 3.40-3.50 (1H, m), 3.55 (1H, m), 3.76 (1H, m), 4.10 (1H, dd, J = 5.6 Hz, 10.2 Hz), 4.20-4.40 (2H, m), 4.40-4.50 (1H, m), 5.22 (1H, d, J = 5.6 Hz), 7.30 (1H, d, J = 8.1 Hz), 7.59 (1H, m), 8.34 (1H, s) | CD$_3$OD (400 MHz) | MS (FAB) m/z 571 [M + H]$^+$ |
| 60 | 7-Deoxy-7-(4-((ethyl(methyl)amino)-methyl)phenylthio)-7-epilincomycin | 0.89-0.97 (3H, m), 1.12 (3H, t, J = 7.3 Hz), 1.29 (3H, d, J = 7.1 Hz), 1.32-1.38 (4H, m), 1.87 (1H, dt, J = 10.2 Hz, 12.9 Hz), 1.97 (3H, s), 1.97-2.11 (3H, m), 2.19 (3H, s), 2.41 (3H, s), 2.47 (2H, q, J = 7.1 Hz), 3.00 (1H, dd, J = 4.9 Hz, 10.7 Hz), 3.25 (1H, dd, J = 5.8 Hz, 7.8 Hz), 3.51 (2H, s), 3.58 (1H, dd, J = 3.4 Hz, 10.2 Hz), 3.74 (1H, d, J = 2.4 Hz), 3.86 (1H, dq, J = 2.7 Hz, 6.8 Hz), 4.10 (1H, dd, J = 5.6 Hz, 10.2 Hz), 4.34 (1H, d, J = 10.0 Hz), 4.41 (1H, dd, J = 2.7 Hz, 9.7 Hz), 5.26 (1H, d, J = 5.6 Hz), 7.29 (2H, d, J = 8.3 Hz), 7.39 (2H, d, J = 8.3 Hz) | CD$_3$OD (400 MHz) | MS (FAB) m/z 570 [M + H]$^+$ |
| 61 | 7-Deoxy-7-epi-7-(4-((1H-pyrrol-1-yl)methyl)phenylthio)-lincomycin | 0.89-0.97 (3H, m), 1.28 (3H, d, J = 6.8 Hz), 1.30-1.36 (4H, m), 1.92 (3H, s), 1.80-2.21 (4H, m), 2.35 (3H, s), 2.97 (1H, dd, J = 3.9 Hz, 10.5 Hz), 3.20 (1H, m), 3.56 (1H, dd, J = 2.9 Hz, 10.2 Hz), 3.72 (1H, br s), 3.83 (1H, m), 4.08 (1H, dd, J = 5.6 Hz, 10.0 Hz), 4.28-4.40 (2H, m), 5.07 (2H, s), 5.23 (1H, d, J = 5.6 Hz), 6.07 (2H, s), 6.70 (2H, s), 7.09 (2H, d, J = 7.7 Hz), 7.37 (2H, d, J = 8.0 Hz) | CD$_3$OD (400 MHz) | MS (FAB) m/z 578 [M + H]$^+$ |
| 62 | 7-(4-((Cyclopropyl(methyl)-amino)methyl)phenyl-thio)-7-deoxy-7-epilincomycin | 0.35-0.40 (2H, m), 0.44-0.50 (2H, m), 0.90-0.97 (3H, m), 1.27 (3H, d, J = 7.0 Hz), 1.31-1.37 (4H, m), 1.67-1.79 (1H, m), 1.79-1.90 (1H, m), 1.98 (3H, s), 1.94-2.20 (3H, m), 2.25 (3H, s), 2.40 (3H, s), 2.98 (1H, dd, J = 4.6 Hz, 10.7 Hz), 3.24 (1H, dd, J = 5.6 Hz, 8.1 Hz), 3.57 (1H, dd, J = 3.5 Hz, 10.2 Hz), 3.65 (2H, s), 3.73 (1H, d, J = 3.4 Hz), 3.85 (1H, dq, J = 2.4 Hz, 6.8 Hz), 4.09 (1H, dd, J = 5.6 Hz, 10.2 Hz), 4.33 (1H, d, J = 10.0 Hz), 4.40 (1H, dd, J = 2.5 Hz, 9.8 Hz), 5.26 (1H, d, J = 5.6 Hz), 7.26 (2H, d, J = 8.2 Hz), 7.37 (2H, d, J = 8.2 Hz) | CD$_3$OD (400 MHz) | MS (FAB) m/z 582 [M + H]$^+$ |
| 63 | 7-(4-((Butyl(methyl)amino)-methyl)phenylthio)-7-deoxy-7-epilincomycin | 0.89-0.97 (6H, m), 1.28 (3H, d, J = 6.8 Hz), 1.30-1.37 (6H, m), 1.42-1.57 (2H, m), 1.80-1.90 (1H, m), 1.97 (3H, s), 1.93-2.23 (3H, m), 2.22 (3H, s), 2.40 (3H, s), 2.37-2.44 (2H, q), 2.99 (1H, dd, J = 4.6 Hz, 10.7 Hz), 3.26 (1H, m), 3.54 (2H, s), 3.57 (1H, dd, J = 3.2 Hz, 10.3 Hz), 3.74 (1H, d, J = 3.4 Hz), 3.86 (1H, dq, J = 2.7 Hz, 6.9 Hz), 4.09 (1H, dd, J = 5.6 Hz, 10.2 Hz), 4.34 (1H, d, J = 9.5 Hz), 4.41 (1H, dd, J = 2.7 Hz, 9.7 Hz), 5.25 (1H, d, J = 5.6 Hz), 7.29 (2H, d, J = 8.3 Hz), 7.39 (2H, d, J = 8.3 Hz) | CD$_3$OD (400 MHz) | MS (FAB) m/z 598 [M + H]$^+$ |
| 64 | 7-Deoxy-7-epi-7-(4-(((R)-3-hydroxypyrrolidin-1-yl)methyl)phenylthio)-lincomycin | 0.88-0.98 (3H, m), 1.27 (3H, d, J = 6.8 Hz), 1.30-1.40 (4H, m), 1.66-1.75 (1H, m), 1.80-1.92 (1H, m), 1.96-2.25 (7H, m), 2.40 (3H, s), 2.46 (1H, dd, J = 10.2, 3.4 Hz), 2.49-2.57 (1H, m), 2.67-2.81 (2H, m), 2.99 (1H, dd, J = 10.7, 4.6 Hz), 3.22-3.28 (1H, m), 3.57 (1H, dd, J = 10.2, 2.7 Hz), 3.58 (1H, d, J = 12.7 Hz), 3.64 (1H, d, J = 12.7 Hz), 3.74 (1H, d, J = 2.7 Hz), 3.86 (1H, dq, J = 2.4, 6.8 Hz), 4.10 (1H, dd, J = 10.2, 5.6 Hz), 4.30-4.38 (2H, m), 4.41 (1H, dd, J = 9.7, 2.4 Hz), 5.27 (1H, d, J = 5.6 Hz), 7.31 (2H, d, J = 8.3 Hz), 7.39 (2H, d, J = 8.3 Hz) | CD$_3$OD (400 MHz) | MS (FAB) m/z 598 [M + H]$^+$ |

TABLE 19-continued

| Compound No. | Compound name | NMR data δ (ppm) from TMS | Solvent/Hz | MS |
|---|---|---|---|---|
| 65 | 7-Deoxy-7-epi-7-(4-(((R)-3-methoxypyrrolidin-1-yl)methyl)phenylthio)-lincomycin | 0.89-0.95 (3H, m), 1.28 (3H, d, J = 6.8 Hz), 1.30-1.40 (4H, m), 1.74-1.90 (2H, m), 1.95-2.25 (7H, m), 2.40 (3H, s), 2.44-2.52 (1H, m), 2.58 (1H, dd, J = 10.5, 3.4 Hz), 2.65-2.74 (2H, m), 2.99 (1H, dd, J = 10.5, 4.6 Hz), 3.22-3.28 (4H, m), 3.56 (1H, d, J = 12.9 Hz), 3.57 (1H, dd, J = 10.0, 3.4 Hz), 3.64 (1H, d, J = 12.9 Hz), 3.74 (1H, d, J = 3.4 Hz), 3.86 (1H, dq, J = 2.7, 6.8 Hz), 3.91-3.98 (1H, m), 4.10 (1H, dd, J = 10.0, 5.6 Hz), 4.34 (1H, d, J = 10.0 Hz), 4.41 (1H, dd, J = 10.0, 2.7 Hz), 5.26 (1H, d, J = 5.6 Hz), 7.31 (2H, d, J = 8.3 Hz), 7.39 (2H, d, J = 8.3 Hz) | $CD_3OD$ (400 MHz) | MS (FAB) m/z 612 [M + H]$^+$ |
| 66 | 7-Deoxy-7-(5-(2-(dimethylamino)ethyl)-pyridin-2-ylthio)-7-epilincomycin | 0.90-0.95 (3H, m), 1.25-1.40 (4H, m), 1.41 (3H, d, J = 6.8 Hz), 1.80-2.30 (4H, m), 1.82 (3H, s), 2.30-2.40 (9H, m), 2.64 (2H, m), 2.82 (2H, m), 3.00 (1H, m), 3.25 (1H, m), 3.57 (1H, m), 3.76 (1H, m), 4.09 (1H, dd, J = 5.6 Hz, 10.2 Hz), 4.26 (1H, m), 4.33 (1H, m), 4.45 (1H, m), 5.22 (1H, d, J = 5.6 Hz), 7.26 (1H, d, J = 8.3 Hz), 7.53 (1H, m), 8.30 (1H, m) | $CD_3OD$ (400 MHz) | MS (FAB) m/z 571 [M + H]$^+$ |

TABLE 20

| Compound No. | Compound name | NMR data δ (ppm) from TMS | Solvent/Hz | MS |
|---|---|---|---|---|
| 67 | 7-Deoxy-7-(4-(((R)-2-(hydroxymethyl)-pyrrolidin-1-yl)methyl)phenylthio)-7-epilincomycin | 0.91-0.95 (3H, m), 1.28 (3H, d, J = 7.1 Hz), 1.31-1.38 (4H, m), 1.74-1.72 (3H, m), 1.80-1.90 (1H, m), 1.98-2.00 (4H, m), 2.06-2.20 (2H, m), 2.25-2.30 (1H, m), 2.40 (3H, s), 2.64-2.72 (1H, m), 2.85-2.95 (1H, m), 2.95-3.01 (1H, m), 3.25 (1H, dd, J = 8.5, 5.8 Hz), 3.39-3.49 (3H, m), 3.54-3.59 (2H, m), 3.74 (1H, d, J = 3.2 Hz), 3.81-3.88 (1H, m), 4.06 (1H, d, J = 14.1 Hz), 4.10 (1H, dd, J = 10.0, 5.6 Hz), 4.34 (1H, d, J = 10.3 Hz), 4.40 (1H, dd, J = 9.8, 2.5 Hz), 5.26 (1H, d, J = 5.6 Hz), 7.31 (2H, d, J = 8.3 Hz), 7.38 (2H, d, J = 8.3 Hz). | $CD_3OD$ (400 MHz) | MS (FAB) m/z 612 [M + H]$^+$ |
| 68 | 7-Deoxy-7-(4-(((S)-2-(hydroxymethyl)-pyrrolidin-1-yl)methyl)phenylthio)-7-epilincomycin | 0.89-0.93 (3H, m), 1.23-1.35 (7H, m), 1.66-1.76 (3H, m), 1.80-1.90 (1H, m), 1.96-2.02 (4H, m), 2.06-2.12 (1H, m), 2.12-2.22 (1H, m), 2.30-2.39 (1H, m), 2.40 (3H, s), 2.68-2.77 (1H, m), 2.89-2.96 (1H, m), 2.99 (1H, dd, J = 10.7, 4.6 Hz), 3.22-3.28 (1H, m), 3.33-3.36 (1H, m), 3.42-3.52 (2H, m), 3.55-3.60 (2H, m), 3.74 (1H, d, J = 2.9 Hz), 3.83-3.89 (1H, m), 4.05-4.13 (2H, m), 4.34 (1H, d, J = 9.7 Hz), 4.41 (1H, dd, J = 9.8, 2.5 Hz), 5.26 (1H, d, J = 5.6 Hz), 7.32 (2H, d, J = 8.2 Hz), 7.39 (2H, d, J = 8.2 Hz). | $CD_3OD$ (400 MHz) | MS (FAB) m/z 612 [M + H]$^+$ |
| 69 | 7-(4-(1,3-Bis(dimethylamino)-propan-2-yl)phenylthio)-7-deoxy-7-epilincomycin | 0.89-0.99 (3H, m), 1.27 (3H, d, J = 7.1 Hz), 1.31-1.44 (4H, m), 1.80-1.94 (1H, m), 2.02 (3H, s), 1.97-2.07 (1H, m), 2.07-2.14 (1H, m), 2.20 (12H, s), 2.14-2.28 (1H, m), 2.42 (3H, s), 2.50 (2H, dd, J = 7.8, 12.6 Hz), 2.66 (2H, dd, J = 6.4, 12.6 Hz), 3.00 (1H, dd, J = 4.6, 10.7 Hz), 3.04-3.10 (1H, m), 3.27 (1H, dd, J = 5.6, 8.1 Hz), 3.58 (1H, dd, J = 3.3, 10.3 Hz), 3.74 (1H, d, J = 3.3 Hz), 3.85 (1H, dq, J = 2.7, 7.1 Hz), 4.10 (1H, dd, J = 5.6, 10.3 Hz), 4.33 (1H, d, J = 9.7 Hz), 4.40 (1H, dd, J = 2.7, 9.7 Hz), 5.27 (1H, d, J = 5.6 Hz), 7.24 (2H, d, J = 8.3 Hz), 7.39 (2H, d, J = 8.3 Hz) | $CD_3OD$ (400 MHz) | MS (FAB) m/z 627 [M + H]$^+$ |

TABLE 20-continued

| Compound No. | Compound name | NMR data δ (ppm) from TMS | Solvent/Hz | MS |
|---|---|---|---|---|
| 70 | 7-Deoxy-7-epi-7-(4-((propyl(methyl)-amino)methyl)-phenylthio)linocomycin | 0.87-0.97 (6H, m), 1.28 (3H, d, J = 7.1 Hz), 1.31-1.37 (4H, m), 1.46-1.60 (2H, m), 1.82-1.90 (1H, m), 1.97 (3H, s), 1.97-2.20 (3H, m), 2.19 (3H, s), 2.34 (3H, t, J = 7.5 Hz), 2.40 (3H, s), 2.99 (1H, dd, J = 4.7 Hz, 10.8 Hz), 3.22-3.27 (1H, m), 3.50 (2H, s), 3.57 (1H, dd, J = 3.4 Hz, 10.5 Hz), 3.74 (1H, d), 3.85 (1H, dq, J = 2.0 Hz, 6.8 Hz), 4.09 (1H, dd, J = 5.6 Hz, 10.2 Hz), 4.33 (1H, d, J = 9.5 Hz), 4.40 (1H, dd, J = 2.5 Hz, 10.0 Hz), 5.25 (1H, d, J = 5.4 Hz), 7.28 (2H, d, J = 8.0 Hz), 7.38 (2H, d, J = 8.0 Hz) | CD$_3$OD (400 MHz) | MS (FAB) m/z 584 [M + H]$^+$ |
| 71 | 7-Deoxy-7-epi-7-(4-((methoxyethyl-(methyl)amino-methyl)-phenylthio)lincomycin | 0.90-0.95 (3H, m), 1.28 (3H, d, J = 6.9 Hz), 1.31-1.37 (4H, m), 1.80-1.95 (1H, m), 1.97 (3H, s), 1.95-2.20 (3H, m), 2.24 (3H, s), 2.40 (3H, s), 2.59 (2H, t, J = 5.6 Hz), 2.99 (1H, dd, J = 4.6 Hz, 10.7 Hz), 3.22-3.28 (1H, m), 3.30 (3H, s), 3.52 (2H, t, J = 5.6 Hz), 3.54-3.59 (3H, m), 3.74 (1H, d, J = 3.2 Hz), 3.85 (1H, dq, J = 2.6 Hz, 6.8 Hz), 4.09 (1H, dd, J = 5.6 Hz, 10.3 Hz), 4.30 (1H, d, J = 9.7 Hz), 4.40 (1H, dd, J = 2.5 Hz, 9.8 Hz), 5.25 (1H, d, J = 5.6 Hz), 7.29 (2H, d, J = 8.2 Hz), 7.39 (2H, d, J = 8.3 Hz) | CD$_3$OD (400 MHz) | MS (FAB) m/z 600 [M + H]$^+$ |
| 72 | 7-Deoxy-7-epi-7-(4-(((S)-3-hydroxypyrrolidin-1-yl)methyl)phenylthio)-lincomycin | 0.89-0.96 (3H, m), 1.28 (3H, d, J = 6.8 Hz), 1.30-1.39 (4H, m), 1.65-1.74 (1H, m), 1.79-1.90 (1H, m), 1.93-2.24 (7H, m), 2.40 (3H, s), 2.46 (1H, dd, J = 10.2, 6.1 Hz), 2.48-2.55 (1H, m), 2.62-2.75 (1H, m), 2.77 (1H, dd, J = 10.2, 6.1 Hz), 2.98 (1H, dd, J = 10.7, 4.6 Hz), 3.22-3.28 (1H, m), 3.54-3.60 (2H, m), 3.64 (1H, d, J = 12.9 Hz), 3.74 (1H, d, J = 2.7 Hz), 3.85 (1H, dq, J = 2.7, 6.8 Hz), 4.09 (1H, dd, J = 10.2, 5.6 Hz), 4.29-4.36 (2H, m), 4.40 (1H, dd, J = 9.7, 2.7 Hz), 5.26 (1H, d, J = 5.6 Hz), 7.31 (2H, d, J = 8.3 Hz), 7.39 (2H, d, J = 8.3 Hz) | CD$_3$OD (400 MHz) | MS (FAB) m/z 598 [M + H]$^+$ |
| 73 | 7-Deoxy-7-(4-((2-(dimethylamino)-1-hydroxy)ethyl)-phenylthio)-7-epilincomycin | 0.89-0.98 (3H, m), 1.27 (3H, d, J = 6.9 Hz), 1.31-1.40 (4H, m), 1.80-1.91 (1H, m), 1.96-2.05 (4H, m), 2.09 (1H, dd, J = 8.5, 10.2 Hz), 2.13-2.23 (1H, m), 2.35 (6H, s), 2.40 (3H, s), 2.43 (1H, dd, J = 3.7, 12.9 Hz), 2.62 (1H, dd, J = 9.2, 12.9 Hz), 2.99 (1H, dd, J = 4.6, 10.7 Hz), 3.23-3.29 (1H, m), 3.58 (1H, m), 3.74 (1H, d, J = 3.2 Hz), 3.85 (1H, dq, J = 2.6, 6.9 Hz), 4.10 (1H, dd, J = 5.6, 10.3 Hz), 4.34 (1H, d, J = 9.7 Hz), 4.41 (1H, dd, J = 2.6, 9.7 Hz), 4.78 (1H, dd, J = 3.7, 9.2 Hz), 5.26 (1H, d, J = 5.6 Hz), 7.34 (2H, d, J = 8.3 Hz), 7.40 (2H, d, J = 8.3 Hz) | CD$_3$OD (400 MHz) | MS (FAB) m/z 586 [M + H]$^+$ |
| 74 | 7-Deoxy-7-epi-7-(4-(((S)-3-methoxypyrrolidin-1-yl)methyl)phenylthio)-lincomycin | 0.88-0.97 (3H, m), 1.28 (3H, d, J = 6.8 Hz), 1.30-1.40 (4H, m), 1.74-1.91 (2H, m), 1.95-2.24 (7H, m), 2.41 (3H, s), 2.44-2.52 (1H, m), 2.58 (1H, dd, J = 10.5, 3.2 Hz), 2.65-2.74 (2H, m), 2.99 (1H, dd, J = 10.5, 4.6 Hz), 3.22-3.28 (4H, m), 3.56 (1H, d, J = 12.7 Hz), 3.58 (1H, dd, J = 10.0, 3.4 Hz), 3.64 (1H, d, J = 12.7 Hz), 3.74 (1H, d, J = 3.4 Hz), 3.86 (1H, dq, J = 2.4, 6.8 Hz), 3.92-3.96 (1H, m), 4.10 (1H, dd, J = 10.0, 5.6 Hz), 4.34 (1H, d, J = 9.7 Hz), 4.41 (1H, dd, J = 9.7, 2.4 Hz), 5.26 (1H, d, J = 5.6 Hz), 7.31 (2H, d, J = 8.3 Hz), 7.39 (2H, d, J = 8.3 Hz) | CD$_3$OD (400 MHz) | MS (FAB) m/z 612 [M + H]$^+$ |

TABLE 21

| Compound No. | Compound name | NMR data δ (ppm) from TMS | Solvent/Hz | MS |
|---|---|---|---|---|
| 76 | 7-Deoxy-7-(4-(((S)-3-(dimethylamino)-pyrrolidin-1-yl)methyl)phenylthio)-7-epilincomycin | 0.89-0.93 (3H, m), 1.28 (3H, d, J = 6.8 Hz), 1.30-1.40 (4H, m), 1.67-1.77 (1H, m), 1.79-1.91 (1H, m), 1.95-2.25 (13H, m), 2.27-2.35 (1H, m), 2.40 (3H, s), 2.47-2.55 (1H, m), 2.68-2.76 (1H, m), 2.69-2.88 (2H, m), 2.98 (1H, dd, J = 10.7, 4.6 Hz), 3.24 (1H, dd, J = 8.0, 5.6 Hz), 3.53-3.66 (3H, m), 3.74 (1H, d, J = 3.2 Hz), 3.85 (1H, dq, J = 2.4, 6.8 Hz), 4.10 (1H, dd, J = 10.2, 5.6 Hz), 4.34 (1H, d, J = 9.7 Hz), 4.40 (1H, dd, J = 10.0, 2.4 Hz), 5.26 (1H, d, J = 5.6 Hz), 7.30 (2H, d, J = 8.3 Hz), 7.39 (2H, d, J = 8.3 Hz) | CD$_3$OD (400 MHz) | MS (FAB) m/z 625 [M + H]$^+$ |
| 77 | 7-Deoxy-7-epi-7-(4-(((R)-2-(methoxymethyl)-pyrrolidin-1-yl)methyl)phenylthio)-lincomycin | 0.85-0.96 (3H, m), 1.28 (3H, d, J = 6.8 Hz), 1.30-1.39 (4H, m), 1.52-1.75 (3H, m), 1.80-2.04 (6H, m), 2.08 (1H, dd, J = 10.2, 8.3 Hz), 2.17 (1H, br), 2.20-2.29 (1H, m), 2.40 (3H, s), 2.67-2.77 (1H, m), 2.84-2.90 (1H, m), 2.98 (1H, dd, J = 10.5, 4.6 Hz), 3.21-3.26 (1H, m), 3.28-3.35 (4H, m), 3.37-3.44 (2H, m), 3.58 (1H, dd, J = 10.2, 3.2 Hz), 3.74 (1H, d, J = 3.2 Hz), 3.85 (1H, dq, J = 2.4, 6.8 Hz), 4.04-4.14 (2H, m), 4.34 (1H, d, J = 10.2 Hz), 4.40 (1H, dd, J = 10.2, 2.4 Hz), 5.27 (1H, d, J = 5.6 Hz), 7.30 (2H, d, J = 8.3 Hz), 7.38 (2H, d, J = 8.3 Hz) | CD$_3$OD (400 MHz) | MS (FAB) m/z 626 [M + H]$^+$ |
| 78 | 7-Deoxy-7-epi-7-(4-(((S)-2-(methoxymethyl)-pyrrolidin-1-yl)methyl)phenylthio)-lincomycin | 0.87-0.95 (3H, m), 1.25 (3H, d, J = 7.1 Hz), 1.27-1.38 (4H, m), 1.51-1.74 (3H, m), 1.77-2.02 (6H, m), 2.07 (1H, dd, J = 10.2, 8.5 Hz), 2.14 (1H, br), 2.18-2.27 (1H, m), 2.37 (3H, s), 2.67-2.75 (1H, m), 2.81-2.88 (1H, m), 2.96 (1H, dd, J = 10.7, 4.6 Hz), 3.19-3.24 (1H, m), 3.28-3.34 (4H, m), 3.35-3.42 (2H, m), 3.51 (1H, dd, J = 10.2, 3.4 Hz), 3.71 (1H, d, J = 3.2 Hz), 3.82 (1H, dq, J = 2.7, 7.1 Hz), 4.02-4.10 (2H, m), 4.32 (1H, d, J = 10.0 Hz), 4.37 (1H, dd, J = 10.0, 2.7 Hz), 5.24 (1H, d, J = 5.6 Hz), 7.28 (2H, d, J = 8.3 Hz), 7.36 (2H, d, J = 8.3 Hz) | CD$_3$OD (400 MHz) | MS (FAB) m/z 626 [M + H]$^+$ |

TABLE 22

| Compound No. | Compound name | NMR data δ (ppm) from TMS | Solvent/Hz | MS |
|---|---|---|---|---|
| 79 | 7-(4-(3-Aminopropen-2-yl)phenylthio)-7-deoxy-7-epilincomycin | 0.88-0.98 (3H, m), 1.33 (3H, d, J = 6.9 Hz), 1.34-1.40 (4H, m), 1.80-1.93 (1H, m), 1.98 (3H, s), 1.93-2.04 (1H, m), 2.04-2.13 (1H, m), 2.13-2.22 (1H, m), 2.39 (3H, s), 2.99 (1H, dd, J = 4.8, 10.6 Hz), 3.24 (1H, dd, J = 5.6, 8.3 Hz), 3.59 (1H, dd, J = 3.3, 10.2 Hz), 3.73 (2H, s), 3.76 (1H, d, J = 3.3 Hz), 3.89 (1H, dq, J = 2.7, 6.9 Hz), 4.11 (1H, dd, J = 5.6, 10.2 Hz), 4.35 (1H, d, J = 9.8 Hz), 4.44 (1H, dd, J = 2.7, 9.8 Hz), 5.27 (1H, d, J = 5.6 Hz), 5.30 (1H, s), 5.48 (1H, s), 7.42 (4H, s). | CD$_3$OD (400 MHz) | MS (FAB) m/z 554 [M + H]$^+$ |

TABLE 23

| Compound No. | Compound name | NMR data δ (ppm) from TMS | Solvent/Hz | MS |
|---|---|---|---|---|
| 81 | 7-Deoxy-7-(5-((dimethylamino)-methyl)-1,3,4-thiadiazol-2-ylthio)-7-epilincomycin | 0.88-0.97 (3H, m), 1.30-1.40 (4H, m), 1.52 (3H, d, J = 6.8 Hz), 1.78-1.88 1H, m), 1.93-2.19 (5H, m), 2.13-2.25 (1H, br), 2.32 (6H, s), 2.37 (3H, s), 2.98 (1H, dd, J = 10.5, 5.1 Hz), 3.25 (1H, dd, J = 8.3, 6.1 Hz), 3.56 (1H, dd, J = 10.2, 3.2 Hz), 3.80 (1H, d, J = 3.2 Hz), 3.88 (2H, s), 4.10 (1H, dd, J = 10.2, 5.6 Hz), 4.73 (1H, dq, J = 2.9, 6.8 Hz), 4.38 (1H, d, J = 10.0 Hz), 4.57 (1H, dd, J = 10.0, 2.9 Hz), 5.26 (1H, d, J = 5.6 Hz) | CD$_3$OD (400 MHz) | MS (FAB) m/z 564 [M + H]$^+$ |

TABLE 24a

| Compound No. | Compound name | NMR data δ (ppm) from TMS | Solvent/Hz | MS |
|---|---|---|---|---|
| 83 | 7-Deoxy-7-(4-(2-(pyrrolidin-1-yl)ethyl)-phenylthio)-7-epi-6-N-((2S,4R)-4-(cyclopropylmethyl)-piperidine-2-carbonyl)-1-thio-α-lincosamide | −0.10-0.10 (2H, m), 0.4-0.5 (2H, m), 0.65-0.8 (1H, m), 1.10-1.60 (7H, m), 1.70-2.30 (7H, m), 1.94 (3H, s), 2.55-3.00 (10H, m), 3.13 (1H, m) 3.50-3.70 (1H, m), 3.70 -3.90 (2H, m), 4.05 (1H, dd, J = 5.5 Hz, 10.4 Hz), 4.30-4.60 (2H, m), 5.22 (1H, d, J = 5.6 Hz), 7.23 (2H, d, J = 8.2 Hz), 7.31 (2H, d, J = 8.2 Hz) | CD$_3$OD (400 MHz) | MS (FAB) m/z 608 [M + H]$^+$ |
| 84 | Methyl 6-N-((2S,4R)-(4-cyclopropylmethyl)piperidine-2-carbonyl-7-deoxy-7-epi-7-(4-(piperidin-1-ylmethyl)phenylthio)-1-thio-α-lincosamide | 0.05-0.08 (2H, m), 0.49-0.52 (2H, m), 0.70-0.80 (1H, m), 1.16-1.23 (1H, m), 1.29-1.45 (7H, m), 1.58-1.68 (2H, m), 1.75-1.82 (4H, m), 1.84-1.90 (4H, m), 2.01 (1H, d, J = 13.7 Hz), 2.42 (1H, d, J = 13.1 Hz),, 3.07-3.13 (4H, m), 3.43 (1H, d, J = 11.0 Hz), 3.57 (1H, dd, J = 10.3, 3.2 Hz), 3.84-3.95 (3H, m), 4.07-4.11 (3H, m), 4.44 (1H, d, J = 10.0 Hz), 4.66 (1H, d, J = 10.0 Hz), 5.26 (1H, d, J = 5.6 Hz), 7.39 (2H, d, J = 8.4 Hz), 7.43 (2H, d, J = 8.4 Hz). | CD$_3$OD (400 MHz) | MS (FAB) m/z 608 [M + H]$^+$ |
| 85 | Methyl 7-(4-(azetidin-1-ylmethyl)phenylthio)-7-deoxy-7-epi-6-N-((2S,4R)-4-(cyclopropylmethyl)-piperidine-2-carbonyl)-1-thio-α-lincosamide | 0.00-0.10 (2H, m), 0.42-0.48 (2H, m), 0.70-0.80 (1H, m), 1.08-1.22 (4H, m), 1.28 (3H, d, J = 6.8 Hz), 1.60-1.81 (2H, m), 1.93 (3H, s), 2.05-2.16 (3H, m), 2.60-2.70 (1H, m), 3.10-3.20 (1H, m), 3.21-3.38 (5H, m), 3.55 (1H, dd, J = 3.2 Hz, 10.2 Hz), 3.58 (2H, s), 3.79-3.86 (2H, m), 4.08 (1H, dd, J = 5.6 Hz, 10.5 Hz), 4.40 (1H, d, J = 10.5 Hz) 4.54 (1H, dd, J = 2.2 Hz, 10.0 Hz), 5.25 (1H, d, J = 5.6 Hz), 7.22 (2H, d, J = 8.2 Hz), 7.35 (2H, d, J = 8.3 Hz) | CD$_3$OD (400 MHz) | MS (FAB) m/z 580 [M + H]$^+$ |
| 86 | Methyl 6-N-((2S,4R)-(4-cyclopropylmethyl)-piperidine-2-carbonyl)-7-deoxy-7-epi-7-(4-(((R)-3-hydroxypyrrolidin-1-yl)methyl)phenylthio)-1-thio-α-lincosamide | −0.02-0.05 (2H, m), 0.42-0.48 (2H, m), 0.67-0.78 (1H, m), 1.02-1.25 (5H, m), 1.28 (3H, d, J = 6.8 Hz), 1.60-1.72 (3H, m), 1.95 (3H, s), 2.03-2.19 (3H, m), 2.45 (1H, dd, J = 10.2, 3.4 Hz), 2.48-2.56 (1H, m), 2.60-2.80 (3H, m), 3.11-3.19 (1H, m), 3.53-3.62 (3H, m), 3.81 (1H, dq, J = 2.4, 6.8 Hz), 3.85 (1H, d, J = 2.7 Hz), 4.08 (1H, d, J = 10.2, 5.6 Hz), 4.29-4.36 (1H, m), 4.41 (1H, d, J = 10.2 Hz), 4.53 (1H, dd, J = 10.2, 2.4 Hz), 5.25 (1H, d, J = 5.6 Hz), 7.29 (2H, d, J = 8.3 Hz), 7.36 (2H, d, J = 8.3 Hz) | CD$_3$OD (400 MHz) | MS (FAB) m/z 610 [M + H]$^+$ |

TABLE 24a-continued

| Compound No. | Compound name | NMR data δ (ppm) from TMS | Solvent/Hz | MS |
|---|---|---|---|---|
| 87 | Methyl 6-N-(((2S,4R)-(4-cyclopropylmethyl)-piperidine-2-carbonyl)-7-deoxy-7-epi-7-(4-((cyclopropyl(methyl)-amino)methyl)phenyl-thio)-1-thio-α-lincosamide | 0.01-0.05 (2H, m), 0.35-0.40 (1H, m), 0.42-0.51 (4H, m), 0.69-0.77 (1H, m), 1.08-1.32 (8H, m), 1.65-1.75 (2H, m), 1.78-1.83 (1H, m), 1.96 (3H, s), 2.08-2.13 (1H, m), 2.25 (3H, s), 2.69 (1H, td, J = 12.9, 2.7 Hz), 3.18 (1H, d, J = 13.2 Hz), 3.37 (1H, dd, J = 11.6, 2.6 Hz), 3.57 (1H, dd, J = 10.3, 3.5 Hz), 3.64 (2H, s), 3.81 (1H, qd, J = 6.7, 2.1 Hz), 3.86 (1H, d, J = 3.4 Hz), 4.09 (1H, dd, J = 10.3, 5.6 Hz), 4.42, (1H, d, J = 10.0 Hz), 4.54 (1H, dd, J = 10.0, 2.2 Hz), 5.26 (1H, d, J = 5.6 Hz), 7.22-7.41 (4H, m). | $CD_3OD$ (400 MHz) | MS (FAB) m/z 594 [M + H]$^+$ |
| 88 | Methyl 7-(4-(1,3-bis(dimethylamino)-propan-2-yl)phenylthio)-7-deoxy-7-epi-6-N-((2S,4R)-4-(cyclopropylmethyl)-piperidine-2-carbonyl)-1-thio-α-lincosamide | −0.03-0.03 (2H, m), 0.38-0.48 (2H, m), 0.65-0.78 (1H, m), 1.03-1.32 (4H, m), 1.24 (3H, d, J = 7.0 Hz), 1.60-1.73 (1H, m), 1.73-1.82 (1H, m), 1.94 (3H, s), 2.07-2.14 (1H, m), 2.26 (12H, s), 2.56 (2H, dd, J = 7.1, 12.4 Hz), 2.61-2.71 (1H, m), 2.76 (2H, dd, J = 7.3, 12.4 Hz), 3.07-3.21 (2H, m), 3.34 (1H, dd, J = 2.9, 11.8 Hz), 3.53 (1H, dd, J = 3.4, 10.2 Hz), 3.77 (1H, dq, J = 2.5, 7.0 Hz), 3.82 (1H, d, J = 3.4 Hz), 4.05 (1H, dd, J = 5.6, 10.2 Hz), 4.38 (1H, d, J = 10.0 Hz), 4.51 (1H, dd, J = 2.5, 10.0 Hz), 5.23 (1H, d, J = 5.6 Hz), 7.20 (2H, d, J = 8.3 Hz), 7.34 (2H, d, J = 8.3 Hz) | $CD_3OD$ (400 MHz) | MS (FAB) m/z 639 [M + H]$^+$ |
| 89 | Methyl 6-N-((2S,4R)-(4-cyclopropylmethyl)-piperidine-2-carbonyl-7-deoxy-7-epi-7-(4-((2,5-dihydro-1H-pyrrol-1-yl)methyl)phenylthio)-1-thio-α-lincosamide | 0.03-0.07 (2H, m), 0.47-0.51 (2H, m), 0.70-0.80 (1H, m), 1.15-1.23 (1H, m), 1.25-1.35 (7H, m), 1.78-1.86 (1H, m), 1.90-1.98 (4H, m), 2.32 (1H, d, J = 13.4 Hz), 2.87-2.97 (1H, m), 3.32-3.37 (1H, m), 3.53-3.60 (4H, m), 3.71 (1H, dd, J = 12.4, 3.2 Hz), 3.81-3.88 (4H, m), 4.09 (1H, dd, J = 10.2, 5.6 Hz), 4.44 (1H, d, J = 9.9 Hz), 4.59 (1H, dd, J = 10.0, 2.4 Hz), 5.26 (1H, d, J = 5.6 Hz), 5.83 (2H, s), 7.32 (2H, d, J = 8.5 Hz), 7.37 (2H, d, J = 8.5 Hz). | $CD_3OD$ (400 MHz) | MS (FAB) m/z 592 [M + H]$^+$ |

TABLE 24b

| Compound No. | Compound name | NMR data δ (ppm) from TMS | Solvent/Hz | MS |
|---|---|---|---|---|
| 90 | Methyl 6-N-((2S,4R)-(4-cyclopropylmethyl)-piperidine-2-carbonyl)-7-deoxy-7-epi-7-(4-(((R)-2-(hydroxymethyl)pyrrolidin-1-yl)methyl)phenylthio)-1-thio-α-lincosamide | 0.04-0.07 (2H, m), 0.46-0.51 (2H, m), 0.70-0.77 (1H, m), 1.15-1.35 (9H, m), 1.70-1.86 (4H, m), 1.93 (3H, s), 1.98-2.08 (1H, m), 2.27 (1H, d, J = 13.4 Hz), 2.50-2.58 (1H, m), 2.83-3.05 (2H, m), 3.57-3.65 (5H, m), 3.80-3.88 (2H, m), 4.09 (1H, dd, J = 10.3, 5.4 Hz), 4.18 (1H, d, J = 12.7 Hz), 4.43 (1H, d, J = 10.0 Hz), 4.59 (1H, dd, J = 10.0, 2.2 Hz), 5.26 (1H, d, J = 5.6 Hz), 7.34 (2H, d, J = 8.6 Hz), 7.37 (2H, d, J = 8.6 Hz). | $CD_3OD$ (400 MHz) | MS (FAB) m/z 624 [M + H]$^+$ |

TABLE 24b-continued

| Compound | | NMR data | | |
|---|---|---|---|---|
| No. | Compound name | δ (ppm) from TMS | Solvent/Hz | MS |
| 91 | Methyl 6-N-((2S,4R)-(4-cyclopropylmethyl)-piperidine-2-carbonyl-7-deoxy-7-epi-7-(4-(((S)-2-(hydroxymethyl)pyrrolidin-1-yl)methyl)phenylthio)-1-thio-α-lincosamide | 0.03-0.08 (2H, m), 0.45-0.51 (2H, m), 0.69-0.79 (1H, m), 1.15-1.35 (9H, m), 1.72-1.88 (4H, m), 1.90-1.94 (4H, m), 2.00-2.10 (1H, m), 2.30 (1H, d, J = 12.5 Hz), 2.57-2.65 (1H, m), 2.91 (1H, td, J = 13.0, 2.9 Hz), 2.97-3.10 (1H, m), 3.55-3.63 (3H, m), 3.65-3.92 (2H, m), 3.81-3.90 (2H, m), 4.09 (1H, dd, J = 10.3, 5.6 Hz), 4.22 (1H, d, J = 12.9 Hz), 4.44 (1H, d, J = 10.0 Hz), 4.60 (1H, dd, J = 10.0, 2.2 Hz), 5.27 (1H, d, J = 5.6 Hz), 7.35 (2H, d, J = 8.7 Hz), 7.38 (2H, d, J = 8.7 Hz). | CD$_3$OD (400 MHz) | MS (FAB) m/z 624 [M + H]$^+$ |

TABLE 25a

| Compound | | NMR data | | |
|---|---|---|---|---|
| No. | Compound name | δ (ppm) from TMS | Solvent/Hz | MS |
| 92 | Methyl 6-N-((2S,4R)-(4-cyclopropylmethyl)-piperidine-2-carbonyl)-7-deoxy-7-epi-7-(4-(((S)-2-(methoxymethyl)-pyrrolidin-1-yl)methyl)phenylthio)-1-thio-α-lincosamide | −0.00-0.06 (2H, m), 0.42-0.49 (2H, m), 0.68-0.79 (1H, m), 1.01-1.24 (5H, m), 1.27 (3H, d, J = 7.1 Hz), 1.54-1.82 (5H, m), 1.88-2.00 (4H, m), 2.04-2.11 (1H, m), 2.21-2.30 (1H, m), 2.60-2.77 (2H, m), 2.84-2.90 (1H, m), 3.13-3.19 (1H, m), 3.30-3.44 (6H, m), 3.57 (1H, dd, J = 10.2, 3.4 Hz), 3.81 (1H, dq, J = 3.4, 7.1 Hz), 3.86 (1H, d, J = 3.4 Hz), 4.05 (1H, d, J = 12.7 Hz), 4.08 (1H, dd, J = 10.2, 5.6 Hz), 4.42 (1H, d, J = 10.0 Hz), 4.54 (1H, dd, J = 10.0, 2.4 Hz), 5.26 (1H, d, J = 5.6 Hz), 7.28 (2H, d, J = 8.3 Hz), 7.36 (2H, d, J = 8.3 Hz) | CD$_3$OD (400 MHz) | MS (FAB) m/z 638 [M + H]$^+$ |
| 93 | Methyl 6-N-((2S,4R)-4-(cyclopropylmethyl)-piperidine-2-carbonyl)-7-deoxy-7-(4-(2-diethylaminoethyl)-phenylthio)-7-epi-1-thio-α-lincosamide | −0.01-0.06 (2H, m), 0.40-0.49 (2H, m), 0.69-0.79 (1H, m), 1.05-1.30 (4H, m), 1.09 (6H, t), 1.25 (3H, d, J = 6.8 Hz), 1.60-1.80 (2H, m), 1.98 (3H, s), 2.01-2.10 (1H, m), 2.61-2.77 (9H, m), 3.12-3.18 (1H, m), 3.20-3.29 (1H, m), 3.56 (1H, dd, J = 3.4 Hz, 10.2 Hz), 3.76 (1H, dq, J = 2.4 Hz, 6.8 Hz), 3.85 (1H, d, J = 2.2 Hz), 4.08 (1H, dd, J = 5.4 Hz, 10.2 Hz), 4.41 (1H, d, J = 10.0 Hz), 4.52 (1H, dd, J = 2.5 Hz, 10.0 Hz), 5.26 (1H, d, J = 5.6 Hz), 7.17 (2H, d, J = 8.0 Hz), 7.34 (2H, d, J = 8.3 Hz) | CD$_3$OD (400 MHz) | MS (FAB) m/z 610 [M + H]$^+$ |
| 94 | Methyl 6-N-((2S,4R)-4-(cyclopropylmethyl)-piperidine-2-carbonyl)-7-deoxy-7-epi-7-(4-((ethyl(methyl)amino)-methyl)phenylthio)-1-thio-α-lincosamide | −0.01-0.05 (2H, m), 0.42-0.49 (2H, m), 0.70-0.78 (1H, m), 1.05-1.24 (4H, m), 1.11 (3H, t, J = 7.1 Hz), 1.29 (3H, d, J = 7.1 Hz), 1.60-1.81 (2H, m), 1.96 (3H, s), 2.04-2.12 (1H, m), 2.18 (3H, s), 2.46 (2H, q, J = 7.3 Hz), 2.60-2.71 (1H, m), 3.11-3.20 (1H, m), 3.22-3.30 (1H, m), 3.49 (2H, s), 3.56 (1H, dd, J = 3.4 Hz, 10.2 Hz), 3.82 (1H, dq, J = 2.4 Hz, 6.8 Hz), 3.85 (1H, d, J = 3.4 Hz), 4.08 (1H, dd, J = 5.6 Hz, 10.2 Hz), 4.41 (1H, d, J = 10.0 Hz), 4.54 (1H, dd, J = 2.4 Hz, 10.0 Hz), 5.25 (1H, d, J = 5.6 Hz), 7.26 (2H, d, J = 8.3 Hz), 7.37 (2H, d, J = 8.3 Hz) | CD$_3$OD (400 MHz) | MS (FAB) m/z 582 [M + H]$^+$ |
| 95 | Methyl 6-N-((2S,4R)-4-(cyclopropylmethyl)-piperidine-2-carbonyl)-7-deoxy-7-(4-(diethylaminomethyl)-phenylthio)-7-epi-1-thio-α-lincosamide | −0.01-0.05 (2H, m), 0.41-0.49 (2H, m), 0.70-0.80 (1H, m), 1.01-1.22 (4H, m), 1.07 (6H, t, J = 7.1 Hz), 1.29 (3H, d, J = 6.8 Hz), 1.60-1.81 (2H, m), 1.94 (3H, s), 2.05-2.12 (1H, m), 2.55 (4H, q, J = 7.1 Hz), 2.61-2.71 (1H, m), 3.11-3.20 (1H, m), 3.20-3.30 (1H, m), 3.56 (1H, dd, J = 3.2 Hz, 10.2 Hz), 3.58 (2H, s), 3.81 (1H, dq, J = 2.4 Hz, 7.1 Hz), 3.85 (1H, d, J = 2.2 Hz), 4.08 (1H, dd, J = 5.6 Hz, 10.2 Hz), 4.41 (1H, d, J = 10.0 Hz), | CD$_3$OD (400 MHz) | MS (FAB) m/z 596 [M + H]$^+$ |

TABLE 25a-continued

| Compound No. | Compound name | NMR data δ (ppm) from TMS | Solvent/Hz | MS |
|---|---|---|---|---|
| | | 4.54 (1H, dd, J = 2.4 Hz, 10.0 Hz), 5.25 (1H, d, J = 5.6 Hz), 7.28 (2H, d, J = 8.3 Hz), 7.36 (2H, d, J = 8.3 Hz) | | |
| 96 | Methyl 6-N-((2S,4R)-(4-cyclopropylmethyl)-piperidine-2-carbonyl)-7-deoxy-7-epi-7-(4-(((S)-2-(dimethylaminomethyl)-pyrrolidin-1-yl)methyl)phenylthio)-1-thio-α-lincosamide | −0.02-0.05 (2H, m), 0.42-0.48 (2H, m), 0.68-0.79 (1H, m), 1.05-1.25 (5H, m), 1.32 (3H, d, J = 6.8 Hz), 1.55-1.82 (5H, m), 1.97 (3H, s), 2.02-2.14 (2H, m), 2.19-2.34 (8H, m), 2.45 (1H, dd, J = 12.2, 3.4 Hz), 2.57-2.70 (2H, m), 2.84-2.92 (1H, m), 3.11-3.19 (1H, m), 3.30-3.35 (1H, m), 3.57 (1H dd, J = 10.2, 3.2 Hz), 3.82 (1H, dq, J = 2.4, 6.8 Hz), 3.86 (1H, d, J = 3.2 Hz), 4.02 (1H, d, J = 12.9 Hz), 4.08 (1H, dd, J = 10.2, 5.6 Hz), 4.42 (1H, d, J = 10.5 Hz), 4.54 (1H, dd, J = 10.5, 2.4 Hz), 5.26 (1H, d, J = 5.6 Hz), 7.29 (2H, d, J = 8.3 Hz), 7.37 (2H, d, J = 8.3 Hz) | CD$_3$OD (400 MHz) | MS (FAB) m/z 651 [M + H]$^+$ |
| 97 | Methyl 6-N-((2S,4R)-4-(cyclopropylmethyl)-piperidine-2-carbonyl)-7-deoxy-7-(4-((2-(dimethylamino)-1-hydroxy)ethyl)-phenylthio)-7-epi-1-thio-α-lincosamide | −0.04-0.03 (2H, m), 0.38-0.48 (2H, m), 0.62-0.73 (1H, m), 1.05-1.34 (7H, m), 1.69-1.83 (1H, m), 1.83-1.94 (4H, m), 2.26 (1H, m), 2.68 (6H, s), 2.80-3.03 (3H, m), 3.28-3.35 (1H, m), 3.52 (1H, dd, J = 3.4, 10.2 Hz), 3.63 (1H, dd, J = 2.7, 12.4 Hz), 3.72-3.86 (2H, m), 4.03 (1H, dd, J = 5.6, 10.2 Hz), 4.37 (1H, d, J = 10.2), 4.54 (1H, dd, J = 2.2, 10.2 Hz), 4.88 (1H, dd, J = 3.4, 10.0 Hz), 5.21 (1H, d, J = 5.6 Hz), 7.31 (2H, d, J = 8.7 Hz), 7.34 (2H, d, J = 8.7 Hz) | CD$_3$OD (400 MHz) | MS (FAB) m/z 598 [M + H]$^+$ |
| 98 | Methyl 6-N-((2S,4R)-4-(cyclopropylmethyl)-piperidine-2-carbonyl)-7-deoxy-7-(4-(1-(dimethylamino)-3-hydroxypropan-2-yl)phenylthio)-7-epi-1-thio-α-lincosamide | 0.05-0.10 (2H, m), 0.48-0.55 (2H, m), 0.70-0.80 (1H, m), 1.29 (3H, d, J = 6.9 Hz), 1.15-1.44 (4H, m), 1.80-1.91 (1H, m), 1.95 (3H, s), 1.93-2.05 (1H, m), 2.36-2.44 (1H, m), 2.68 (6H, s), 2.95-3.05 (1H, m), 3.18 (1H, dd, J = 6.8, 12.4 Hz), 3.20-3.29 (1H, m), 3.35-3.44 (2H, m), 3.58 (1H, dd, J = 3.5, 10.3 Hz), 3.71-3.89 (5H, m), 4.09 (1H, dd, J = 5.6, 10.3 Hz), 4.44 (1H, d, J = 10.1 Hz), 4.61 (1H, dd, J = 2.3, 10.1 Hz), 5.27 (1H, d, J = 5.6 Hz), 7.27 (2H, d, J = 8.3 Hz), 7.38 (2H, d, J = 8.3 Hz) | CD$_3$OD (400 MHz) | MS (FAB) m/z 612 [M + H]$^+$ |

TABLE 25b

| Compound No. | Compound name | NMR data δ (ppm) from TMS | Solvent/Hz | MS |
|---|---|---|---|---|
| 99 | Methyl 6-N-((2S,4R)-4-(cyclopropylmethyl)-piperidine-2-carbonyl)-7-(4-(((cyclopropylmethyl)-(methyl)amino)methyl)-phenylthio)-7-deoxy-7-epi-1-thio-α-lincosamide | −0.03-0.02 (2H, m), 0.04-0.11 (2H, m), 0.39-0.45 (2H, m), 0.47-0.54 (2H, m), 0.65-0.75 (1H, m), 0.85-0.94 (1H, m), 1.02-1.35 (4H, m), 1.26 (3H, d, J = 6.8 Hz), 1.60-1.72 (1H, m), 1.77 (1H, d, J = 8.2 Hz), 1.90 (3H, s), 2.02-2.11 (1H, m), 2.24 (3H, s), 2.26 (2H, d, J = 6.6 Hz), 2.60-2.70 (1H, m), 3.11-3.18 (1H, m), 3.34 (1H, dd, J = 2.9, 11.9 Hz), 3.53 (2H, s), 3.53-3.57 (1H, m), 3.79 (1H, dq, J = 2.3, 6.8 Hz), 3.84 (1H, dd, J = 0.73, 3.3 Hz), 4.06 (1H, dd, J = 5.6, 10.2 Hz), 4.39 (1H, dd, J = 0.73, 10.0 Hz), 4.52 (1H, dd, J = 2.3, 10.0 Hz), 5.23 (1H, d, J = 5.6 Hz), 7.24 (2H, d, J = 8.3 Hz), 7.34 (2H, d, J = 8.3 Hz) | CD$_3$OD (400 MHz) | MS (FAB) m/z 608 [M + H]$^+$ |

TABLE 25b-continued

| Compound | | NMR data | | |
|---|---|---|---|---|
| No. | Compound name | δ (ppm) from TMS | Solvent/Hz | MS |
| 100 | 6-N-((2S,4R)-4-(Cyclopropylmethyl)-piperidine-2-carbonyl)-7-deoxy-7-(4-(dimethylaminomethyl)-phenylthio)-7-epi-1-thio-α-lincosamide | −0.05-0.10 (2H, m), 0.4-0.5 (2H, m), 0.7-0.8 (1H, m), 1.10-1.60 (4H, m), 1.29 (3H, d, J = 7.1 Hz), 1.60-1.80 (2H, m), 1.96 (3H, s), 2.05-2.15 (1H, m), 2.23 (6H, s), 2.66 (1H, m), 3.15 (1H, m), 3.30-3.40 (1H, m), 3.43 (2H, s), 3.56 (1H, m), 3.75-3.90 (2H, m), 4.08 (1H, dd, J = 5.6 Hz, 10.2 Hz), 4.41 (1H, m), 4.54 (1H, m), 5.25 (1H, d, J = 5.6 Hz), 7.25 (2H, d, J = 8.3 Hz), 7.37 (2H, d, J = 8.3 Hz) | CD$_3$OD (400 MHz) | MS (FAB) m/z 568 [M + H]$^+$ |

TABLE 26a

| Compound | | NMR data | | |
|---|---|---|---|---|
| No. | Compound name | δ (ppm) from TMS | Solvent/Hz | MS |
| 101 | Methyl 7-deoxy-7-(4-(2-(pyrrolidin-1-yl)ethyl)phenylthio)-7-epi-6-N-((2S,4R)-4-(cyclopropylmethyl)-piperidine-2-carbonyl-1-thio-α-lincosamide | −0.10-0.10 (2H, m), 0.4-0.5 (2H, m), 0.7-0.8 (1H, m), 1.10-1.60 (7H, m), 1.70-2.40 (7H, m), 1.85 (3H, s), 2.25 (3H, s), 2.55-3.00 (10H, m), 2.40-3.60 (3H, m), 3.81 (1H, m), 4.10 (1H, dd, J = 5.5 Hz, 10.4 Hz), 4.39 (1H, m), 4.53 (1H, m), 5.26 (1H, d, J = 5.4 Hz), 7.19 (2H, d, J = 8.4 Hz), 7.35 (2H, d, J = 8.4 Hz) | CD$_3$OD (400 MHz) | MS (FAB) m/z 622 [M + H]$^+$ |
| 102 | Methyl 6-N-((2S,4R)-(4-cyclopropylmethyl-1-methyl)piperidine-2-carbonyl)-7-deoxy-7-epi-7-(4-(piperidin-1-ylmethyl)phenylthio)-1-thio-α-lincosamide | 0.00-0.04 (2H, m), 0.41-0.46 (2H, m), 0.68-0.72 (1H, m), 1.13-1.22 (1H, m), 1.29-1.39 (6H, m), 1.50-1.55 (3H, m), 1.65-1.70 (4H, m), 1.83 (1H, d, J = 12.9 Hz), 1.92 (3H, s), 2.02 (1H, d, J = 11.0 Hz), 2.21-2.28 (1H, m), 2.33 (3H, s), 2.70-2.78 (4H, m), 3.03 (1H, d, J = 11.4 Hz), 3.57 (1H, dd, J = 10.3, 3.2 Hz), 3.76-3.90 (4H, m), 4.10 (1H, dd, J = 10.3, 5.6 Hz), 4.41 (H, d, J = 9.8 Hz), 4.60 (1H, dd, J = 9.9, 2.6 Hz), 5.26 (1H, d, J = 5.6 Hz), 7.33 (2H, d, J = 8.4 Hz), 7.41 (2H, d, J = 8.4 Hz). | CD$_3$OD (400 MHz) | MS (FAB) m/z 622 [M + H]$^+$ |
| 103 | Methyl 7-(4-(azetidin-1-ylmethyl)phenylthio)-7-deoxy-7-epi-6-N-((2S,4R)-(4-cyclopropylmethyl-1-methyl)piperidine-2-carbonyl)-1-thio-α-lincosamide | −0.02-0.04 (2H, m), 0.40-0.48 (2H, m), 0.65-0.75 (1H, m), 1.17 (2H, dt, J = 2.7 Hz, 6.8 Hz), 1.29 (3H, d, J = 7.1 Hz), 1.25-1.34 (2H, m), 1.40-1.55 (1H, m), 1.76-1.84 (1H, m), 1.95 (3H, s), 1.93-2.02 (1H, m), 2.08-2.16 (3H, m), 2.25 (3H, s), 2.61 (1H, dd, J = 2.9 Hz, 11.4 Hz), 2.90-3.00 (1H, m), 3.21-3.38 (4H, m), 3.57 (1H, dd, J = 3.4 Hz, 10.2 Hz), 3.58 (2H, s), 3.79-3.89 (2H, m), 4.10 (1H, dd, J = 5.6 Hz, 10.2 Hz), 4.39 (1H, d, J = 9.8 Hz), 4.56 (1H, dd, J = 2.6 Hz, 9.9 Hz), 5.25 (1H, d, J = 5.9 Hz), 7.23 (2H, d, J = 8.3 Hz), 7.36 (2H, d, J = 8.3 Hz) | CD$_3$OD (400 MHz) | MS (FAB) m/z 594 [M + H]$^+$ |
| 104 | Methyl 6-N-((2S,4R)-(4-cyclopropylmethyl-1-methyl)piperidine-2-carbonyl)-7-deoxy-7-epi-7-(4-(((R)-3-hydroxypyrrolidin-1-yl)methyl)phenylthio)-1-thio-α-lincosamide | −0.02-0.05 (2H, m), 0.40-0.47 (2H, m), 0.65-0.76 (1H, m), 1.10-1.21 (2H, m), 1.23-1.37 (5H, m), 1.49 (1H, br), 1.65-1.75 (1H, m), 1.76-1.84 (1H, m), 1.93-2.02 (4H, m), 2.08-2.19 (2H, m), 2.26 (3H, s), 2.47 (1H, dd, J = 10.5, 3.7 Hz), 2.50-2.58 (1H, m), 2.62 (1H, dd, 11.7, 2.9 Hz), 2.69-2.77 (1H, m), 2.79 (1H, dd, 10.2, 6.1 Hz), 2.84-3.00 (1H, m), 3.55-3.62 (2H, m), 3.64 (1H, d, J = 12.9 Hz), 3.80-3.87 (2H, m), 4.11 (1H, dd, J = 10.2, 5.6 Hz), 4.30-4.37 (1H, m), 4.41 (1H, d, J = 9.7 Hz), 4.56 (1H, dd, J = 9.7, 2.4 Hz), 5.26 (1H, d, J = 5.6 Hz), 7.30 (2H, d, J = 8.3 Hz), 7.38 (2H, d, J = 8.3 Hz) | CD$_3$OD (400 MHz) | MS (FAB) m/z 624 [M + H]$^+$ |

TABLE 26a-continued

| Compound No. | Compound name | NMR data δ (ppm) from TMS | Solvent/Hz | MS |
|---|---|---|---|---|
| 105 | Methyl 6-N-((2S,4R)-(4-cyclopropylmethyl-1-methyl)piperidine-2-carbonyl)-7-deoxy-7-epi-7-(4-((cyclopropyl(methyl)amino)methyl)phenylthio)-1-thio-α-lincosamide | 0.00-0.03 (2H, m), 0.39-0.50 (5H, m), 0.64-0.75 (1H, m), 1.15-1.40 (8H, m), 1.50-1.60 (1H, m), 1.70-1.76 (1H, m), 1.76-1.83 (1H, m), 1.83-1.88 (1H, m), 1.97 (3H, s), 2.23-2.30 (4H, m), 2.34 (3H, s), 2.75-2.82 (1H, m), 3.02-3.07 (1H, m), 3.59 (1H, dd, J = 10.0, 3.2 Hz), 3.66 (2H, s), 3.80-3.86 (3H, m), 4.10 (1H, dd, J = 10.2, 5.6 Hz), 4.42 (1H, d, J = 9.7 Hz), 4.57 (1H, dd, J = 9.9, 2.4 Hz), 5.27 (1H, d, J = 5.6 Hz), 7.21-7.42 (4H, m). | CD$_3$OD (400 MHz) | MS (FAB) m/z 608 [M + H]$^+$ |
| 106 | Methyl 7-(4-(1,3-bis(dimethylamino)propane-2-yl)phenylthio)-7-deoxy-7-epi-6-N-((2S,4R)-(4-cyclopropylmethyl-1-methyl)piperidine-2-carbanyl)-1-thio-α-lincosamide | −0.02-0.04 (2H, m), 0.40-0.47 (2H, m), 0.67-0.76 (1H, m), 1.13-1.40 (4H, m), 1.29 (3H, d, J = 6.8 Hz), 1.46-1.58 (1H, m), 1.77-1.85 (1H, m), 1.97 (3H, s), 1.96-2.07 (1H, m), 2.12-2.21 (1H, m), 2.28 (3H, s), 2.47 (12H, s), 2.65 (2H, dd, J = 2.9, 12.1 Hz), 2.75 (2H, dd, J = 5.5, 12.1 Hz), 2.95-3.02 (1H, m), 3.02-3.12 (2H, m), 3.59 (1H, dd, J = 3.2, 10.2 Hz), 3.80-3.90 (2H, m) 4.10 (1H, dd, J = 5.6, 10.2 Hz), 4.39 (1H, d, J = 9.9 Hz), 4.58 (1H, dd, J = 2.7, 9.9 Hz), 5.26 (1H, d, J = 5.6 Hz), 7.25 (2H, d, J = 8.3 Hz), 7.39 (2H, d, J = 8.3 Hz) | CD$_3$OD (400 MHz) | MS (FAB) m/z 653 [M + H]$^+$ |
| 107 | Methyl 6-N-((2S,4R)-(4-cyclopropylmethyl-1-methyl)piperidine-2-carbanyl)-7-deoxy-7-epi-7-(4-((2,5-dihydro-1H-pyrrol-1-yl)methyl)phenylthio)-1-thio-α-lincosamide | 0.01-0.03 (2H, m), 0.43-0.47 (2H, m), 0.67-0.75 (1H, m), 1.12-1.40 (8H, m), 1.55-1.65 (1H, m), 1.92 (3H, s), 2.02-2.08 (1H, m), 2.35-2.45 (4H, m), 2.95 (1H, dd, J = 11.7, 5.0 Hz), 3.12 (1H, d, J = 10.5 Hz), 3.59 (1H, dd, J = 10.1, 3.3 Hz), 3.70 (4H, s), 3.83-3.88 (2H, m), 4.02 (2H, s), 4.10 (1H, dd, J = 10.3, 5.6 Hz), 4.43 (1H, d, J = 10.0 Hz), 4.60 (1H, dd, J = 10.0, 2.4 Hz), 5.26 (1H, d, J = 5.6 Hz), 5.86 (2H, s), 7.37 (2H, d, J = 8.5 Hz), 7.40 (2H, d, J = 8.5 Hz). | CD$_3$OD (400 MHz) | MS (FAB) m/z 606 [M + H]$^+$ |

TABLE 26b

| Compound No. | Compound name | NMR data δ (ppm) from TMS | Solvent/Hz | MS |
|---|---|---|---|---|
| 108 | Methyl 6-N-((2S,4R)-(4-cyclopropylmethyl-1-methyl)piperidine-2-carbonyl)-7-deoxy-7-epi-7-(4-(((R)-2-(hydroxymethyl)-pyrrolidin-1-yl)methyl)phenylthio)-1-thio-α-lincosamide | 0.00-0.04 (2H, m), 0.42-0.46 (2H, m), 0.66-0.75 (1H, m), 1.14-1.20 (2H, m), 1.24-1.38 (7H, m), 1.48-1.52 (2H, m), 1.65-1.85 (2H, m), 1.95-2.00 (4H, m), 2.10-2.18 (1H, m), 2.26 (3H, s), 2.30-2.35 (1H, m), 2.62 (1H, dd, J = 11.5, 2.9 Hz), 2.68-2.75 (1H, m), 2.88-3.00 (2H, m), 3.42-3.50 (2H, m), 3.55-3.60 (2H, m), 3.81-3.86 (2H, m), 4.07 (1H, d, J = 12.9 Hz), 4.10 (1H, dd, J = 10.2, 5.6 Hz), 4.40 (1H, d, J = 10.0 Hz), 4.56 (1H, dd, J = 9.9, 2.6 Hz), 5.26 (1H, d, J = 5.7 Hz), 7.30 (2H, d, J = 8.3 Hz), 7.37 (2H, d, J = 8.3 Hz). | CD$_3$OD (400 MHz) | MS (FAB) m/z 638 [M + H]$^+$ |
| 109 | Methyl 6-N-((2S,4R)-(4-cyclopropylmethyl-1-methyl)piperidine-2-carbonyl)-7-deoxy-7-epi-7-(4-(((S)-2-(hydroxymethyl)-pyrrolidin- | 0.00-0.03 (2H, m), 0.41-0.46 (2H, m), 0.66-0.75 (1H, m), 1.15-1.20 (2H, m), 1.23-1.34 (6H, m), 1.46-1.52 (2H, m), 1.62-1.84 (3H, m), 1.94-2.00 (4H, m), 2.08-2.16 (1H, m), 2.23-2.30 (4H, m), 2.59 (1H, dd, J = 11.7, 2.9 Hz), | CD$_3$OD (400 MHz) | MS (FAB) m/z 638 [M + H]$^+$ |

TABLE 26b-continued

| Compound | | NMR data | | |
|---|---|---|---|---|
| No. | Compound name | δ (ppm) from TMS | Solvent/Hz | MS |
| | 1-yl)methyl)phenylthio)-1-thio-α-lincosamide | 2.61-2.69 (1H, m), 2.85-2.91 (1H, m), 2.93-2.99 (1H, m), 3.38 (1H, d, J = 13.0 Hz), 3.46 (1H, dd, J = 10.9, 6.1 Hz), 3.54-3.60 (2H, m), 3.80-3.87 (2H, m), 4.03 (1H, d, J = 13.0 Hz), 4.10 (1H, dd, J = 10.2, 5.6 Hz), 4.40 (1H, d, J = 10.0 Hz), 4.55 (1H, dd, J = 10.0, 2.7 Hz), 5.26 (1H, d, J = 5.6 Hz), 7.29 (2H, d, J = 8.3 Hz), 7.36 (2H, d, J = 8.3 Hz). | | |

TABLE 27a

| Compound | | NMR data | | |
|---|---|---|---|---|
| No. | Compound name | δ (ppm) from TMS | Solvent/Hz | MS |
| 110 | Methyl 6-N-((2S,4R)-(4-cyclopropylmethyl-1-methyl)piperidine-2-carbonyl)-7-deoxy-7-epi-7-(4-(((S)-2-(methoxymethyl)-pyrrolidin-1-yl)methyl)phenylthio)-1-thio-α-lincosamide | −0.02-0.05 (2H, m), 0.40-0.48 (2H, m), 0.66-0.76 (1H, m), 1.10-1.36 (7H, m), 1.44-1.84 (5H, m), 1.89-2.02 (5H, m), 2.07-2.17 (1H, m), 2.22-2.32 (4H, m), 2.61 (1H, dd, J = 11.7, 2.9 Hz), 2.69-2.78 (1H, m), 2.84-2.92 (1H, m), 2.93-3.00 (1H, m), 3.30-3.37 (4H, m), 3.38-3.45 (2H, m), 3.58 (1H, dd, J = 10.2, 3.2 Hz), 3.80-3.88 (2H, m), 4.04-4.14 (2H, m), 4.41 (1H, d, J = 10.0 Hz), 4.56 (1H, dd, J = 10.0, 2.4 Hz), 5.27 (1H, d, J = 5.6 Hz), 7.29 (2H, d, J = 8.3 Hz), 7.37 (2H, d, J = 8.3 Hz) | CD$_3$OD (400 MHz) | MS (FAB) m/z 652 [M + H]$^+$ |
| 111 | Methyl 6-N-((2S,4R)-(4-cyclopropylmethyl-1-methyl)piperidine-2-carbonyl)-7-deoxy-7-(4-(2-diethylaminoethyl)-phenylthio)-7-epi-1-thio-α-lincosamide | −0.01-0.07 (2H, m), 0.40-0.48 (2H, m), 0.66-0.76 (1H, m), 1.10 (6H, t, J = 7.1 Hz), 1.13-1.20 (2H, m), 1.24-1.34 (2H, m), 1.28 (3H, d, J = 7.1 Hz), 1.42-1.54 (1H, m), 1.70-1.82 (1H, m), 1.92-2.02 (1H, m), 2.00 (3H, s), 2.12 (1H, dt, J = 2.2 Hz, 12.0 Hz), 2.24 (3H, s), 2.59 (1H, dd, J = 3.0 Hz, 11.5 Hz), 2.67 (4H, q, J = 7.1 Hz), 2.71-2.78 (4H, m), 2.90-3.00 (1H, m), 3.58 (1H, dd, J = 3.2 Hz, 10.2 Hz), 3.78 (1H, dq, J = 2.6 Hz, 6.8 Hz), 3.81 (1H, d, J = 2.2 Hz), 4.10 (1H, dd, J = 5.6 Hz, 10.2 Hz), 4.39 (1H, d, J = 10.0 Hz), 4.53 (1H, dd, J = 2.4 Hz, 9.8 Hz), 5.26 (1H, d, J = 5.6 Hz), 7.18 (2H, d, J = 8.3 Hz), 7.36 (2H, d, J = 8.3 Hz) | CD$_3$OD (400 MHz) | MS (FAB) m/z 624 [M + H]$^+$ |
| 112 | Methyl 6-N-((2S,4R)-(4-cyclopropylmethyl-1-methyl)piperidine-2-carbonyl)-7-deoxy-7-(4-((ethyl(methyl)amino)-methyl)phenylthio)-7-epi-1-thio-α-lincosamide | −0.04-0.02 (2H, m), 0.38-0.47 (2H, m), 0.65-0.74 (1H, m), 1.11 (3H, t, J = 7.3 Hz), 1.13-1.20 (2H, m), 1.30 (3H, d, J = 7.1 Hz), 1.25-1.34 (2H, m), 1.42-1.54 (1H, m), 1.74-1.81 (1H, m), 1.96 (3H, s), 1.90-2.00 (1H, m), 2.08-2.19 (1H, m), 2.18 (3H, s), 2.25 (3H, s), 2.47 (2H, q, J = 7.1 Hz), 2.57-2.64 (1H, m), 2.91-2.99 (1H, m), 3.50 (2H, s), 3.58 (1H, dd, J = 2.9 Hz, 10.2 Hz), 3.80-3.86 (2H, m), 4.10 (1H, dd, J = 5.6 Hz, 10.2 Hz), 4.40 (1H, d, J = 10.0 Hz), 4.56 (1H, dd, J = 2.7 Hz, 10.0 Hz), 5.26 (1H, d, J = 5.4 Hz), 7.27 (2H, d, J = 8.3 Hz), 7.38 (2H, d, J = 8.3 Hz) | CD$_3$OD (400 MHz) | MS (FAB) m/z 596 [M + H]$^+$ |
| 113 | Methyl 6-N-((2S,4R)-(4-cyclopropylmethyl-1-methyl)piperidine-2-carbonyl)-7-deoxy-7-(4-(diethylaminomethyl)-phenylthio)-7-epi-1-thio-α-lincosamide | −0.02-0.03 (2H, m), 0.40-0.46 (2H, m), 0.65-0.75 (1H, m), 1.08 (6H, t, J = 7.3 Hz), 1.09 (3H, d, J = 7.3 Hz), 1.12-1.20 (2H, m), 1.23-1.37 (2H, m), 1.41-1.52 (1H, m), 1.75-1.82 (1H, m), 1.93-2.00 (1H, m), 1.96 (3H, s), 2.10-2.19 (1H, m), 2.26 (3H, s), 2.54-2.63 (5H, m), 2.92-3.00 (1H, m), 3.57 (1H, dd, J = 3.2 Hz, 10.3 Hz), 3.61 (2H, s), 3.80-3.85 (2H, m), 4.10 (1H, dd, J = 5.6 Hz, 10.2 Hz), 4.40 (1H, d, J = 9.7 Hz), | CD$_3$OD (400 MHz) | MS (FAB) m/z 610 [M + H]$^+$ |

TABLE 27a-continued

| Compound No. | Compound name | NMR data δ (ppm) from TMS | Solvent/Hz | MS |
|---|---|---|---|---|
| | | 4.56 (1H, dd, J = 2.7 Hz, 10.0 Hz), 5.26 (1H, d, J = 5.6 Hz), 7.29 (2H, d, J = 8.3 Hz), 7.38 (2H, d, J = 8.3 Hz) | | |
| 114 | Methyl 6-N-((2S,4R)-(4-cyclopropylmethyl-1-methyl)piperidine-2-carbonyl)-7-deoxy-7-epi-7-(4-(((S)-2-(dimethylaminomethyl)-pyrrolidin-1-yl)methyl)phenylthio)-1-thio-α-lincosamide | −0.02-0.05 (2H, m), 0.39-0.48 (2H, m), 0.65-0.76 (1H, m), 1.14-1.20 (2H, m), 1.25-1.48 (5H, m), 1.48 (1H, br), 1.55-1.84 (5H, m), 1.93-2.17 (6H, m), 2.20-2.35 (11H, m), 2.46 (1H, dd, J = 12.2, 3.4 Hz), 2.57-2.61 (2H, m), 2.74-2.91 (1H, m), 2.92-2.99 (1H, m), 3.30-3.35 (1H, m), 3.58 (1H, dd, J = 10.2, 3.4 Hz), 3.79-3.87 (2H, m), 4.05 (1H, d, J = 12.7 Hz), 4.10 (1H, dd, J = 10.2, 5.6 Hz), 4.40 (1H, d, J = 9.9 Hz), 5.27 (1H, d, J = 5.6 Hz), 7.29 (2H, d, J = 8.3 Hz), 7.38 (2H, d, J = 8.3 Hz) | CD$_3$OD (400 MHz) | MS (FAB) m/z 665 [M + H]$^+$ |
| 115 | Methyl 6-N-((2S,4R)-(4-cyclopropylmethyl-1-methyl)piperidine-2-carbonyl)-7-deaxy-7-(4-((2-(dimethylamino)-1-hydroxy)ethyl)phenylthio)-7-epi-1-thio-α-lincosamide | −0.04-0.04 (2H, m), 0.38-0.48 (2H, m), 0.63-0.75 (1H, m), 1.09-1.38 (7H, m), 1.42-1.53 (1H, m), 1.74-1.82 (1H, m), 1.93-2.10 (4H, m), 2.07-2.17 (1H, m), 2.45 (3H, s), 2.44 (6H, s), 2.53-2.65 (2H, m), 2.68-2.78 (1H, m), 2.92-2.99 (1H, m), 3.56 (1H, dd, J = 3.3, 10.2 Hz), 3.80 (1H, d, J = 3.3 Hz), 3.82 (1H, dq, J = 2.7, 7.1 Hz), 4.08 (1H, dd, J = 5.6, 10.2 Hz), 4.38 (1H, d, J = 9.9 Hz), 4.55 (1H, dd, J = 2.7, 9.9 Hz), 4.80 (1H, dd, J = 3.4, 9.5 Hz), 5.24 (1H, d, J = 5.6 Hz), 7.32 (2H, d, J = 8.1 Hz), 7.38 (2H, d, J = 8.1 Hz) | CD$_3$OD (400 MHz) | MS (FAB) m/z 612 [M + H]$^+$ |
| 116 | Methyl 6-N-((2S,4R)-(4-cyclopropylmethyl-1-methyl)piperidine-2-carbonyl)-7-deoxy-7-(4-(1-(dimethylamino)-3-hydroxypropan-2-yl)phenylthio)-7-epi-1-thio-α-lincosamide | −0.01-0.04 (2H, m), 0.41-0.48 (2H, m), 0.66-0.68 (1H, m), 1.13-1.40 (4H, m), 1.29 (3H, d, J = 6.8 Hz), 1.47-1.60 (1H, m), 1.78-1.87 (1H, m), 1.98 (3H, s), 1.98-2.07 (1H, m), 2.18-2.27 (1H, m), 2.31 (3H, s), 2.50 (6H, s), 2.69-2.75 (1H, m), 2.88-2.98 (1H, m), 2.98-3.05 (1H, m), 3.10-3.20 (2H, m), 3.58 (1H, dd, J = 3.5, 10.2 Hz), 3.66-3.88 (4H, m), 4.10 (1H, dd, J = 5.6, 10.2 Hz), 4.40 (1H, d, J = 9.9 Hz), 4.57 (1H, dd, J = 2.7, 9.9 Hz), 5.26 (1H, d, J = 5.6 Hz), 7.24 (2H, d, J = 8.4 Hz), 7.38 (2H, d, J = 8.4 Hz) | CD$_3$OD (400 MHz) | MS (FAB) m/z 626 [M + H]$^+$ |

TABLE 27b

| Compound No. | Compound name | NMR data δ (ppm) from TMS | Solvent/Hz | MS |
|---|---|---|---|---|
| 117 | Methyl 6-N-((2S,4R)-(4-cyclopropylmethyl-1-methyl)piperidine-2-carbonyl)-7-deoxy-7-(4-(((cyclopropylmethyl)(methyl)amino)methyl)-phenylthio)-7-epi-1-thio-α-lincosamide | −0.03-0.03 (2H, m), 0.10-0.17 (2H, m), 0.38-0.48 (2H, m), 0.52-0.59 (2H, m), 0.63-0.75 (1H, m), 0.85-0.99 (1H, m), 1.10-1.20 (2H, m), 1.23-1.37 (2H, m), 1.29 (3H, d, J = 6.9 Hz), 1.43-1.55 (1H, m), 1.74-1.82 (1H, m), 1.93 (3H, s), 1.94-2.00 (1H, m), 2.09-2.18 (1H, m), 2.26 (3H, s), 2.31 (3H, s), 2.34 (2H, d, J = 6.5 Hz), 2.63 (1H, dd, J = 2.9, 11.4 Hz), 2.93-2.99 (1H, m), 3.56 (1H, dd, J = 3.2, 10.2 Hz), 3.61 (2H, s), 3.81 (1H, d, J = 3.2 Hz), 3.83 (1H, dq, J = 2.7, 6.9 Hz), 4.09 (1H, dd, J = 5.6, 10.2 Hz), 4.39 (1H, d, J = 10.0 Hz), 4.56 (1H, dd, J = 2.7, 10.0 Hz), 5.25 (1H, d, J = 5.6 Hz), 7.28 (2H, d, J = 8.2 Hz), 7.37 (2H, d, J = 8.2 Hz) | CD$_3$OD (400 MHz) | MS (FAB) m/z 622 [M + H]$^+$ |

TABLE 27b-continued
| Compound | | NMR data | | |
|---|---|---|---|---|
| No. | Compound name | δ (ppm) from TMS | Solvent/Hz | MS |
| 118 | Methyl 7-deoxy-7-(4-(dimethylaminomethyl)phenylthio)-7-epi-6-N-((2S,4R)-4-(cyclopropylmethyl)-piperidine-2-carbonyl)-1-thio-α-lincosamide | −0.10-0.10 (2H, m), 0.4-0.5 (2H, m), 0.7-0.8 (1H, m), 1.10-1.60 (4H, m), 1.28 (3H, m), 1.70-2.30 (3H, m), 1.95 (3H, s), 2.23 (6H, s), 2.26 (3H, s), 2.61 (1H, m), 2.96 (1H, m), 3.30-3.40 (1H, m), 3.47 (2H, s), 3.58 (1H, m), 3.75-3.90 (2H, m), 4.10 (1H, dd, J = 5.6 Hz, 10.2 Hz), 4.40 (1H, m), 4.55 (1H, m), 5.26 (1H, d, J = 5.6 Hz), 7.26 (2H, d, J = 8.3 Hz), 7.38 (2H, d, J = 8.3 Hz) | CD$_3$OD (400 MHz) | MS (FAB) m/z 582 [M + H]$^+$ |
TABLE 28
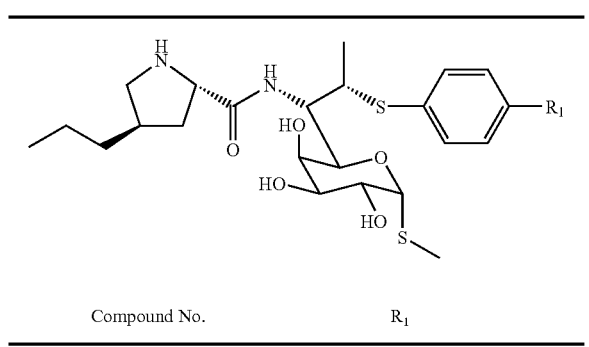
| Compound No. | R$_1$ |
|---|---|
| 60 | 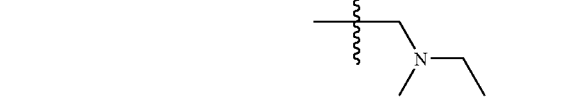 |
| 61 |  |
| 62 |  |
| 63 |  |
| 64 | 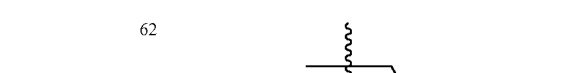 |
TABLE 28-continued
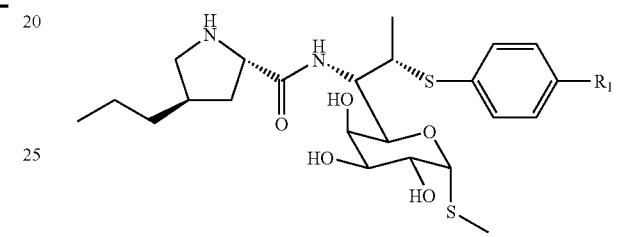
| Compound No. | R$_1$ |
|---|---|
| 65 |  |
| 75 |  |
| 76 |  |
| 67 |  |
| 68 |  |

TABLE 28-continued

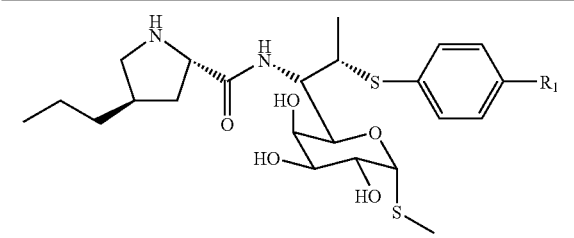

| Compound No. | $R_1$ |
|---|---|
| 79 | ⁃C(=CH₂)CH₂NH₂ |
| 69 | ⁃CH(CH₂N(CH₃)₂)₂ |
| 70 | ⁃CH₂N(CH₃)(n-Pr) |
| 71 | ⁃CH₂N(CH₃)CH₂CH₂OCH₃ |
| 77 | ⁃CH₂-(2-methoxymethyl-pyrrolidin-1-yl) |
| 78 | ⁃CH₂-(2-methoxymethyl-pyrrolidin-1-yl) |
| 80 | ⁃C(=CH₂)CH₂N(CH₃)₂ |
| 72 | ⁃CH₂-(3-hydroxy-pyrrolidin-1-yl) |

TABLE 28-continued

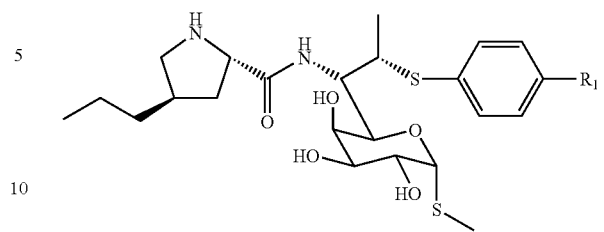

| Compound No. | $R_1$ |
|---|---|
| 73 | ⁃CH₂CH(OH)CH₂N(CH₃)₂ |
| 74 | ⁃CH₂-(3-methoxy-pyrrolidin-1-yl) |

TABLE 29

| Compound No. | —A—$R_1$ |
|---|---|
| 81 | 5-((dimethylamino)methyl)-1,3,4-thiadiazol-2-yl |
| 59 | 6-(1-(dimethylamino)ethyl)pyridin-3-yl |
| 66 | 6-(2-(dimethylamino)ethyl)pyridin-3-yl |
| 82 | 2-(2-(dimethylamino)ethyl)-1H-imidazol-5-yl |

TABLE 30
| Compound | R2 | |
|---|---|---|
| 83 101 | H Me | 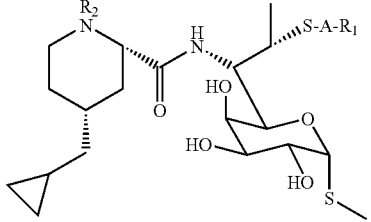 |
| 84 102 | H Me | 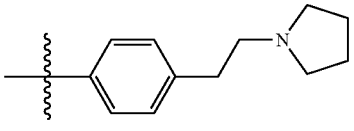 |
| 85 103 | H Me | 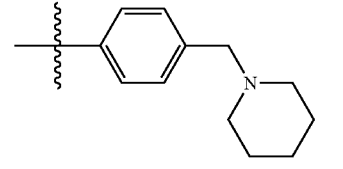 |
| 86 104 | H Me | 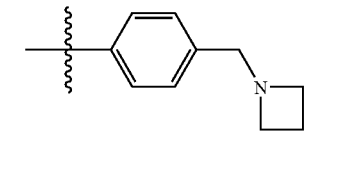 |
| 87 105 | H Me | 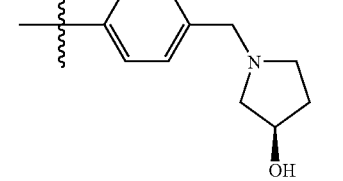 |
| 88 106 | H Me | 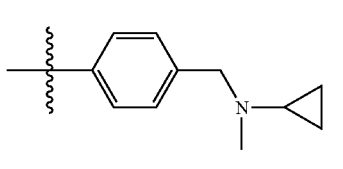 |
| 89 107 | H Me | 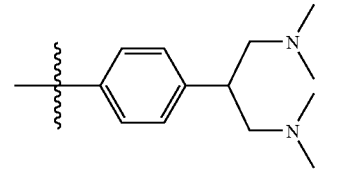 |
TABLE 30-continued
| Compound | R2 | |
|---|---|---|
| 90 108 | H Me | 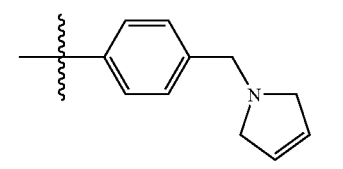 |
| 91 109 | H Me | 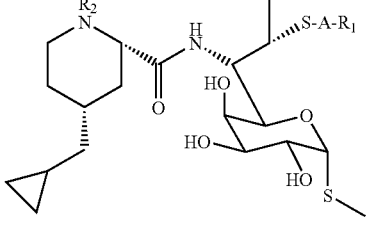 |
| 121 | Et | 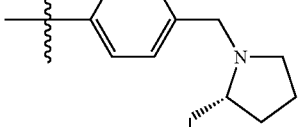 |
| 92 110 | H Me | 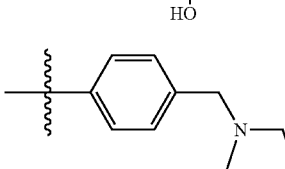 |
| 93 111 | H Me | 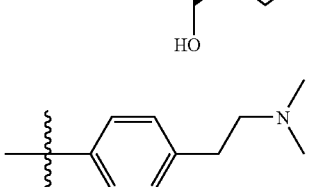 |
| 94 112 | H Me | 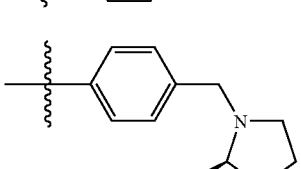 |
| 95 113 | H Me | 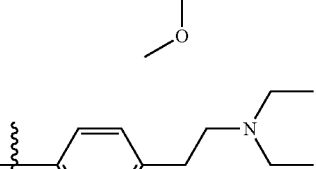 |

TABLE 30-continued

[Structure diagram: piperidine-based compound with R₂ substituent, cyclopropylmethyl group, amide linkage to sugar with S-A-R₁]

| Compound | R₂ | —A-R₁ |
|---|---|---|
| 96 | H | [4-((pyrrolidin-2-ylmethyl)(methyl)amino)methyl)phenyl with N,N-dimethyl] |
| 114 | Me | |
| 97 | H | [4-(1-hydroxy-2-(dimethylamino)ethyl)phenyl] |
| 115 | Me | |
| 98 | H | [4-(1-(dimethylaminomethyl)-2-hydroxyethyl)phenyl] |
| 116 | Me | |
| 99 | H | [4-((N-methyl-N-cyclopropylmethyl)aminomethyl)phenyl] |
| 117 | Me | |
| 100 | H | [4-((dimethylamino)methyl)phenyl] |
| 118 | Me | |
| 119 | H | [5-(2-(dimethylamino)ethyl)-1,3,4-thiadiazol-2-yl] |
| 120 | Me | |

TABLE 31

[Structure diagram: azepane-based compound with R₂ substituent, cyclopropylmethyl group, amide linkage to sugar with S-A-R₁]

| Compound No. | R₂ | —A-R₁ |
|---|---|---|
| 122 isomer 1 | H | [4-(2-(dimethylamino)ethyl)phenyl] |
| 124 isomer 3 | Me | |
| 123 isomer 2 | H | [4-(2-(dimethylamino)ethyl)phenyl] |
| 125 isomer 4 | Me | |

The invention claimed is:

1. A compound of formula (1) or its pharmacologically acceptable salt:

(1)

[Structure of formula (1) with substituents R₂, R₃, R₄, R₅, R₆, R₇, R₁, R₁', A, n, m, p]

wherein
A represents
   aryl;
   cyclohexyl; or
   a four- to seven-membered heterocyclic group
      wherein the heterocyclic group is selected from the group consisting of pyridyl, piperidyl, pyridazyl, pyrimidinyl, pyrazinyl, thienyl, thiazolyl, 1,3,4-thiadiazolyl, azetidinyl, pyrrolidinyl, azepanyl, tetrahydropyridyl, dihydropyrrolyl, imidazolyl, 1,3,4-triazinyl, furyl, oxazolyl, 1,3,4-oxadiazolyl, and tetrahydroazepanyl,
$R_1'$ represents
   a halide;
   nitro;
   amino;
   cyano;
   hydroxyl;
   $C_{1-6}$ alkyl;
   $C_{1-6}$ alkyloxy;
   $C_{1-6}$ alkylthio;

$C_{1-6}$ alkylamino;
di-$C_{1-6}$ alkylamino;
$C_{i-6}$ alkyloxycarbonyl; or
N,N-dialkyl substituted carbamoyl, and, when p is 2, $R_1$'s may be the same or different, $R_1$ represents
amino-$C_{1-6}$ alkyl;
N-(optionally substituted $C_{1-6}$ alkyl) amino-$C_{1-6}$ alkyl
wherein the $C_{1-6}$ alkyl group in the optionally substituted $C_{1-6}$ alkyl group is optionally substituted by one or more groups, which may be the same or different, selected from the group consisting of hydroxyl, $C_{1-6}$ alkyloxy, and di- and $C_{1-6}$ alkylamino;
N—$C_{3-6}$ cycloalkylamino-$C_{1-6}$ alkyl;
N-optionally substituted $C_{1-6}$ alkyl-N-optionally substituted $C_{1-6}$ alkylamino-$C_{1-6}$ alkyl,
Wherein
the $C_{1-6}$ alkyl group in the optionally substituted $C_{1-6}$ alkyl group is optionally substituted by one or more groups, which may be the same or different, selected from the group consisting of hydroxyl, $C_{1-6}$ alkyloxy, and di-$C_{1-6}$ alkylamino;
N—$C_{1-6}$ alkyl-N—$C_{3-6}$ cycloalkylamino-$C_{1-6}$ alkyl;
tri-$C_{1-6}$ alkylammonio-$C_{1-6}$ alkyl;
1-(di-$C_{1-6}$ alkylamino-$C_{1-6}$ alkyl)vinyl;
1-(amino-$C_{1-6}$ alkyl)vinyl;
N—($C_{3-6}$ cycloalkyl-$C_{1-4}$ alkyl)-N—$C_{1-6}$ alkylamino-$C_{1-6}$ alkyl;
1-formyl-2-di-$C_{1-6}$ alkylaminovinyl;
amino-$C_{1-6}$ alkylamino-$C_{1-6}$ alkyl;
N—$C_{1-6}$ alkyl-N—(N',N'-di-$C_{1-6}$ alkylamino-$C_{1-6}$ alkyl)-amino-$C_{1-6}$ alkyl;
$C_{1-6}$ alkylamino-$C_{1-6}$ alkylamino-$C_{1-6}$ alkyl;
di-$C_{1-6}$ alkylamino-$C_{1-6}$ alkylamino-$C_{1-6}$ alkyl;
$C_{1-6}$ alkyl substituted by cyclic amino,
wherein the cyclic amino group is selected from the group consisting of (1-, 2-, or 3-)pyrrolidinyl, (1-, 2-, or 3-)dihydropyrrolyl, 1-piperazinyl, 1-(4-methylpiperazinyl), 1-piperidino, 1-azetidinyl, 3-(1-methylazetidinyl), 3-azetidinyl, (1-, 2-, or 3-)azepanyl, (1-, 2-, or 3-)azepinyl, and 1H-pyrrolyl, and
the cyclic amino group is optionally substituted by one or more groups, which may be the same or different, selected from the group consisting of $C_{1-6}$ alkyloxy, $C_{1-6}$ alkylamino, di-$C_{1-6}$ alkylamino, hydroxyl, $C_{2-6}$ alkenyloxy, hydroxy-$C_{1-6}$ alkyl, $C_{1-6}$ alkyloxy-$C_{1-6}$ alkyl, and di-$C_{1-6}$ alkylamino-$C_{1-6}$ alkyl;
amino-$C_{1-6}$ alkylcarbonyl;
N,N-di-$C_{1-6}$ alkylamino-$C_{1-6}$ alkylcarbonyl;
N,N-di-$C_{1-6}$ alkylamino-$C_{2-6}$ alkenyl;
N,N-di-$C_{1-6}$ alkylamino-$C_{2-6}$ alkynyl;
N,N-di-$C_{1-6}$ alkylamino-$C_{1-6}$ alkylamino;
N,N-di-$C_{1-6}$ alkylamino-$C_{1-6}$ alkoxy;
a group of formula (g-1):

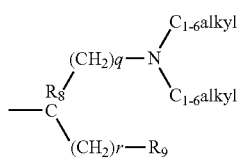

(g-1)

wherein
$R_8$ represents a hydrogen atom, a halide, or $C_{1-6}$ alkyl,
$R_9$ represents a hydrogen atom, hydroxyl, a halide, or $C_{1-6}$ alkyl optionally substituted by one or more halides, $C_{1-6}$ alkyloxy, $C_{1-6}$ alkyloxycarbonyl, or di-$C_{1-6}$ alkylamino, or, when r is 2 to 4, $R_8$ and $R_9$ may combine with each other and, together with the carbon atom to which $R_8$ is attached, represent $C_{3-6}$ cycloalkyl, and
q and r, which may be the same or different, are an integer of 0 to 4; or
a group of formula (g-2):

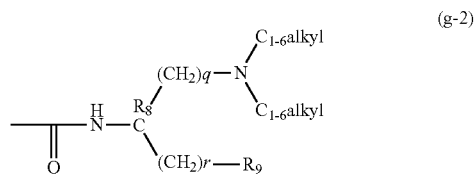

(g-2)

wherein $R_8$, $R_9$, q, and r are as defined in formula (g-1),
$R_2$ represents
a hydrogen atom;
optionally substituted $C_{1-6}$ alkyl;
optionally substituted $C_{2-6}$ alkenyl;
optionally substituted acyl; or
optionally substituted $C_{1-6}$ alkyloxycarbonyl
wherein the $C_{1-6}$ alkyl group, the $C_{2-6}$ alkenyl group, the acyl group, and the $C_{1-6}$ alkyloxycarbonyl group are optionally substituted by one or more groups that may be the same or different and are selected from the group consisting of heterocyclic rings, amino, hydroxy, and cyano that are optionally substituted by $C_{1-6}$ alkyl,
$R_3$ represents
optionally substituted $C_{1-6}$ alkyl
wherein the $C_{1-6}$ alkyl group is optionally substituted by one or more groups that are selected from the group consisting of halides; nitro; hydroxy; amino; $C_{1-6}$ alkyloxycarbonyl; carbamoyl; cyano; $C_{1-6}$ alkyloxy; oxo; heterocyclic rings; azide; $C_{1-6}$ alkylaminocarbonyl; di-$C_{1-6}$ alkylaminocarbonyl; and aryl optionally substituted by a halide, hydroxy, or $C_{1-4}$ alkyl;
$C_{3-6}$ cycloalkyl-$C_{1-4}$ alkyl; or
$C_{2-6}$ alkenyl,
$R_4$, $R_5$, and $R_6$, which may be the same or different, represent
a hydrogen atom;
optionally substituted $C_{1-6}$ alkyl; or
optionally substituted acyl
wherein the $C_{1-6}$ alkyl group and hydrogen atoms on the acyl group are optionally substituted by one or more groups selected from the group consisting of halides;
nitro; hydroxy; amino; $C_{1-6}$ alkyloxycarbonyl; carbamoyl; cyano; nitro halide; $C_{1-6}$ alkyloxy; oxo; heterocyclic rings; azide; $C_{1-6}$ alkylaminocarbonyl; di-$C_{1-6}$ alkylaminocarbonyl; and aryl optionally substituted by a halide, hydroxy or $C_{1-4}$ alkyl, $R_7$ represents
$C_{1-6}$ alkyl optionally substituted by one or more groups selected from the group consisting of halides and hydroxy,
m is 1 to 3,
n is 0 or 1, and
p is 0 to 2.

2. The compound according to claim 1 or its pharmacologically acceptable salt, wherein, when $R_1$ represents $C_{1-6}$ alkyl substituted by cyclic amino, $R_3$ represents $C_{3-6}$ cycloalkyl-$C_{1-4}$ alkyl.

3. The compound according to claim 1 or its pharmacologically acceptable salt, wherein n is 0.

4. The compound according to claim 1 or its pharmacologically acceptable salt, wherein A represents aryl.

5. The compound according to claim 1 or its pharmacologically acceptable salt, wherein
A represents aryl,
$R_3$ represents $C_{3-6}$ cycloalkyl-$C_{1-4}$ alkyl, and
n is 0.

6. The compound according to claim 1 or its pharmacologically acceptable salt, wherein
A represents aryl,
$R_1$ represents
N-optionally substituted $C_{1-6}$ alkyl-N-optionally substituted $C_{1-6}$ alkylamino-$C_{1-6}$ alkyl or
a group of formula (g-1)
$R_2$ represents
a hydrogen atom or
optionally substituted $C_{1-6}$ alkyl,
$R_3$ represents
optionally substituted $C_{1-6}$ alkyl or
$C_{3-6}$ cycloalkyl-$C_{1-4}$ alkyl,
m is 1 to 3,
n is 0, and
p is 0 to 2.

7. The compound according to claim 1 or its pharmacologically acceptable salt, wherein
A represents
aryl or
a four- to seven-membered heterocyclic group,
$R_1$ represents
amino-$C_{1-6}$ alkyl;
N-(optionally substituted $C_{1-6}$ alkyl)amino-$C_{1-6}$ alkyl;
N—$C_{3-6}$ cycloalkylamino-$C_{1-6}$ alkyl;
N-optionally substituted $C_{1-6}$ alkyl-N-optionally substituted $C_{1-6}$ alkylamino-$C_{1-6}$ alkyl;
N—$C_{1-6}$ alkyl-N—$C_{3-6}$ cycloalkylamino-$C_{1-6}$ alkyl;
1-(di-$C_{1-6}$ alkylamino-$C_{1-6}$ alkyl)vinyl;
1-formyl-2-di-$C_{1-6}$ alkylaminovinyl;
di-$C_{1-6}$ alkylamino-$C_{1-6}$ alkylamino-$C_{1-6}$ alkyl;
$C_{1-6}$ alkyl substituted by cylic amino;
amino-$C_{1-6}$ alkylcarbonyl;
N,N-di-$C_{1-6}$ alkylamino-$C_{1-6}$ alkylcarbonyl;
N,N-di-$C_{1-6}$ alkylamino-$C_{2-6}$ alkenyl;
N,N-di-$C_{1-6}$ alkylamino-$C_{2-6}$ alkynyl;
a group of formula (g-1); or
a group of formula (g-2),
$R_2$ represents
a hydrogen atom or
optionally substituted $C_{1-6}$ alkyl,
$R_3$ represents
optionally substituted $C_{1-6}$ alkyl or
$C_{3-6}$ cycloalkyl-$C_{1-4}$ alkyl,
$R_4$, $R_5$, and $R_6$ each represent a hydrogen atom,
$R_7$ represents $C_{1-6}$ alkyl,
m is 1 to 3,
n is 0, and
p is 0 to 2.

8. The compound according to claim 1 or its pharmacologically acceptable salt, wherein A represents phenyl.

9. The compound according to claim 1 or its pharmacologically acceptable salt, wherein
A represents
phenyl or
a five- or six-membered heterocyclic group
$R_1'$ represents
a halide;
nitro;
amino; or
di-$C_{1-6}$ alkylamino,
$R_1$ represents
amino-$C_{1-6}$ alkyl;
N-(optionally substituted $C_{1-6}$ alkyl)amino-$C_{1-6}$ alkyl;
N—$C_{3-6}$ cycloalkylamino-$C_{1-6}$ alkyl;
N-optionally substituted $C_{1-6}$ alkyl-N-optionally substituted $C_{1-6}$ alkylamino-$C_{1-6}$ alkyl;
N—$C_{1-6}$ alkyl-N—$C_{3-6}$ cycloalkylamino-$C_{1-6}$ alkyl;
1-(di-$C_{1-6}$ alkylamino-$C_{1-6}$ alkyl)vinyl;
1-formyl-2-di-$C_{1-6}$ alkylaminovinyl;
di-$C_{1-6}$ alkylamino-$C_{1-6}$ alkylamino-$C_{1-6}$ alkyl;
$C_{1-6}$ alkyl substituted by cyclic amino
wherein $R_3$ represents $C_{3-6}$ cycloalkyl-$C_{1-4}$ alkyl;
amino-$C_{1-6}$ alkylcarbonyl;
N,N-di-$C_{1-6}$ alkylamino-$C_{1-6}$ alkylcarbonyl;
N,N-di-$C_{1-6}$ alkylamino-$C_{2-6}$ alkenyl;
N,N-di-$C_{1-6}$ alkylamino-$C_{2-6}$ alkynyl;
a group of formula (g-1); or
a group of formula (g-2),
$R_2$ represents
a hydrogen atom, or
$C_{1-6}$ alkyl,
$R_3$ represents
$C_{1-6}$ alkyl or
$C_{3-6}$ cycloalkyl-$C_{1-4}$ alkyl
$R_4$, $R_5$, and $R_6$ each represent a hydrogen atom,
$R_7$ represents $C_{1-6}$ alkyl,
m is 1 to 3,
n is 0, and
p is 0 to 2.

10. A pharmaceutical composition, comprising a compound according to claim 1 or its pharmacologically acceptable salt and a pharmaceutically acceptable carrier.

11. The pharmaceutical composition according to claim 10, which further comprises an additive for a pharmaceutical preparation.

12. A method for treating a bacterial infectious disease, comprising administering a therapeutically effective amount of a compound according to claim 1 or its pharmacologically acceptable salt together with a pharmaceutically acceptable carrier to a mammal or a domestic fowl having a bacterial infectious disease.

13. The method according to claim 12, wherein the bacterial infectious disease is in a respiratory organ.

* * * * *